United States Patent
Nicolaou et al.

(10) Patent No.: US 10,874,646 B2
(45) Date of Patent: Dec. 29, 2020

(54) EPOTHILONE ANALOGS, METHODS OF SYNTHESIS, METHODS OF TREATMENT, AND DRUG CONJUGATES THEREOF

(71) Applicant: WILLIAM MARSH RICE UNIVERSITY, Houston, TX (US)

(72) Inventors: Kyriacos C Nicolaou, Houston, TX (US); Derek Rhoades, Houston, TX (US); Yanping Wang, Houston, TX (US); Sotirios Totokotsopoulos, Chicago, IL (US)

(73) Assignee: William Marsh Rice University, Houston, TX (US)

( * ) Notice: Subject to any disclaimer, the term of this patent is extended or adjusted under 35 U.S.C. 154(b) by 0 days.

(21) Appl. No.: 15/768,800

(22) PCT Filed: Oct. 14, 2016

(86) PCT No.: PCT/US2016/057093
§ 371 (c)(1),
(2) Date: Apr. 16, 2018

(87) PCT Pub. No.: WO2017/066606
PCT Pub. Date: Apr. 20, 2017

(65) Prior Publication Data
US 2019/0022069 A1 Jan. 24, 2019

Related U.S. Application Data

(60) Provisional application No. 62/242,702, filed on Oct. 16, 2015.

(51) Int. Cl.
| | |
|---|---|
| *A61K 31/427* | (2006.01) |
| *A61K 31/4155* | (2006.01) |
| *A61K 47/68* | (2017.01) |
| *A61P 35/02* | (2006.01) |
| *A61K 31/428* | (2006.01) |
| *A61K 39/395* | (2006.01) |
| *A61K 31/4427* | (2006.01) |
| *C07D 407/06* | (2006.01) |
| *A61K 45/06* | (2006.01) |
| *C07D 405/06* | (2006.01) |
| *C07D 491/08* | (2006.01) |
| *C07D 493/08* | (2006.01) |

(52) U.S. Cl.
CPC ........ *A61K 31/427* (2013.01); *A61K 31/4155* (2013.01); *A61K 31/428* (2013.01); *A61K 31/4427* (2013.01); *A61K 39/395* (2013.01); *A61K 45/06* (2013.01); *A61K 47/6869* (2017.08); *A61P 35/02* (2018.01); *C07D 405/06* (2013.01); *C07D 407/06* (2013.01); *C07D 491/08* (2013.01); *C07D 493/08* (2013.01)

(58) Field of Classification Search
None
See application file for complete search history.

(56) References Cited

U.S. PATENT DOCUMENTS

| | | | |
|---|---|---|---|
| 2003/0203938 A1* | 10/2003 | Nicolaou | C07D 313/00 514/338 |
| 2010/0168179 A1 | 7/2010 | Klar et al. | |
| 2011/0112149 A1 | 5/2011 | Li et al. | |
| 2014/0323533 A1* | 10/2014 | Jure-Kunkel | A61K 45/06 514/365 |

FOREIGN PATENT DOCUMENTS

| | | |
|---|---|---|
| EP | 1930004 A1 | 6/2008 |
| EP | 2009114 A1 | 12/2008 |
| JP | 2001-504856 | 4/2001 |
| JP | 2009-516753 | 4/2009 |
| JP | 2009-538350 | 11/2009 |
| WO | WO 1998-025929 | 6/1998 |
| WO | WO 99/54319 | 10/1999 |

(Continued)

OTHER PUBLICATIONS

Chemical Abstract Registry No. 1348540-91-9, indexed in the Registry File on STN CAS Online Dec. 4, 2011.*

(Continued)

*Primary Examiner* — Kamal A Saeed
(74) *Attorney, Agent, or Firm* — Parker Highlander PLLC

(57) ABSTRACT

In one aspect, the present disclosure provides epothilone analogs of the formula (I) wherein the variables are as defined herein. In another aspect, the present disclosure also provides methods of preparing the compounds disclosed herein. In another aspect, the present disclosure also provides pharmaceutical compositions and methods of use of the compounds disclosed herein. Additionally, drug conjugates with cell targeting moieties of the compounds are also provided.

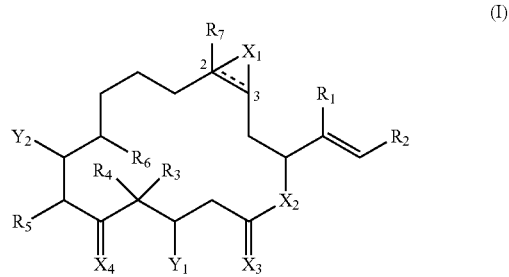

(I)

17 Claims, 45 Drawing Sheets

(56) References Cited

FOREIGN PATENT DOCUMENTS

| WO | WO 00/47584 | 8/2000 |
| WO | WO 2007-062288 | 5/2007 |
| WO | WO 2007-140298 | 12/2007 |
| WO | WO2014096551 | * 6/2014 |

OTHER PUBLICATIONS

Alhamadsheh, Mamoun M., et al. "Total synthesis and selective activity of a new class of conformationally restrained epothilones." *Chemistry—A European Journal* 14.2 (2008): 570-581.

Bode, Jeffrey W., and Erick M. Carreira. "Stereoselective syntheses of epothilones A and B via directed nitrile oxide cycloaddition1." *Journal of the American Chemical Society* 123.15 (2001): 3611-3612.

Carlomagno, Teresa, et al. "The High-Resolution Solution Structure of Epothilone A Bound to Tubulin: An Understanding of the Structure-Activity Relationships for a Powerful Class of Antitumor Agents." *Angewandte Chemie International Edition* 42.22 (2003): 2511-2515.

Ermolenko, Mikhail S., and Pierre Potier. "Synthesis of epothilones B and D from D-glucose." *Tetrahedron letters* 43.16 (2002): 2895-2898.

Heinz, Dirk W., Wolf-Dieter Schubert, and Gerhard Hoefle. "Much anticipated—the bioactive conformation of epothilone and its binding to tubulin." *Angewandte Chemie International Edition* 44.9 (2005): 1298-1301.

Hofle, G., et al., "Epothilone A and B-Novel 16-Mem-bered Macrolides with Cytotoxic Activity: Isolation, Crystal Structure, and Conformation in Solution", *Angew. Chem. Int. Ed.*, vol. 35, 1567-1569, 1996.

Keck, Gary E., et al. "Total synthesis of epothilones B and D: Stannane equivalents for β-keto ester dianions." *The Journal of organic chemistry* 73.24 (2008): 9675-9691.

Manallack, David T. "The p K a distribution of drugs: application to drug discovery." *Perspectives in medicinal chemistry* 1 (2007): 25-38.

Martin and Thomas, Tet. Lett., 42:8378-8377, 2001.

Nicolaou, K. C., et al. "Designed Epoihilones: Combinatorial Synthesis, Tubulin Assembly Properties, and Cytotoxic Action against Taxol-Resistant Tumor Cells." *Angewandte Chemie International Edition in English* 36.19 (1997): 2097-2103.

Nicolaou, K. C., et al. "Synthesis and Biological Evaluation of Novel Epothilone B Side Chain Analogues," *ChemMedChem* 10.12 (2015): 1974-1979.

Nicolaou, K. C., et al. "Chemical synthesis and biological properties of pyridine epothilones." *Chemistry & biology* 7.8 (2000): 593-599.

Nicolaou, K. C., et al. "Molecular design and chemical synthesis of a highly potent epothilone." *ChemMedChem: Chemistry Enabling Drug Discovery* 1.1 (2006): 41-44.

Nicolaou, K. C., et al. "The olefin metathesis approach to epothilone A and its analogues," *Journal of the American Chemical Society* 119.34 (1997): 7960-7973.

Nicolaou, K. C., et al. "Total syntheses of epothilones A and B via a macrolactonization-based strategy." *Journal of the American Chemical Society* 119.34 (1997): 7974-7991.

Nicolaou, K. C., et al. "Total syntheses of epothilones E and related Side-chain Modified Analogues via a Stille Coupling Based Strategy." *Bioorganic & Medicinal Chemistry*, vol. 7, No. 5 (1999), 665-697.

Nicolaou, K. C., et al. "Total Synthesis of 16-Desmethylepothilone B, Epothilone B10, Epothilone F, and Related Side Chain Modified Epothilone B Analogues," *Chemistry—A European Journal* 6.15 (2000): 2783-2800.

Partial European Search Report dated May 2, 2019, issued in European Application No. 16856299 filed May 15, 2018.

PCT Search Report and Written Opinion dated Feb. 1, 2017 issued in PCT/US2016/057093 filed Oct. 14, 2016.

Reese, Marcel, et al. "Structural basis of the activity of the microtubule-stabilizing agent epothilone A studied by NMR spectroscopy in solution." *Angewandte Chemie International Edition* 46.11 (2007): 1864-1868.

Sawada, Daisuke, Motomu Kanai, and Masakatsu Shibasaki. "Enantioselective total synthesis of epothilones A and B using multifunctional asymmetric catalysis." *Journal of the American Chemical Society* 122.43 (2000): 10521-10532.

Schinzer, et al., Synlett, 861-863, 1998.

Shoemaker, Robert H. "The NCI60 human tumour cell line anticancer drug screen." *Nature Reviews Cancer* 6.10 (2006): 813.

Sinha, Subhash C., Carlos F. Barbas, and Richard A. Lerner, "The antibody catalysis route to the total synthesis of epothilones." *Proceedings of the National Academy of Sciences* 95.25 (1998): 14603-14608.

Taylor, Richard E., and Yue Chen. "Total synthesis of epothilones B and D." *Organic letters* 3.14 (2001): 2221-2224.

Valluri, Muralikrishna, et al. "Total synthesis of epothilone B." *Organic letters* 3.23 (2001): 3607-3609.

Wang, Jie, et al. "An Efficient Total Synthesis of (−)-Epothilone B." *Organic letters* 14.24 (2012): 6354-6357.

White, James D., Rich G. Carter, and Kurt F. Sundermann "A highly stereoselective synthesis of epothilone B." *The Journal of organic chemistry* 64.3 (1999): 684-685.

Office Action issued in Japanese Application No. 2018-519372, dated Oct. 7, 2020, and English translation thereof.

* cited by examiner

National Cancer Institute Development Therapeutics Program
In-Vitro Testing Results NSC: D - 781077 / 1  Experimental ID: 1408NS31  Test Type: 08  Units: Molar
Report Date: August 28, 2014  Test Date: August 11, 2014  QNS:  MC:
COMI: KCDR_5A  Stain Reagent: SRB Dual-Pass Related  SSPL: OZAS Log10 Concentration

| Panel/Cell Line | Time Zero | Ctrl | Mean Optical Densities | | | | | Percent Growth | | | | | GI50 | TGI | LC50 |
|---|---|---|---|---|---|---|---|---|---|---|---|---|---|---|---|
| | | | -8.3 | -7.3 | -6.3 | -5.3 | -4.3 | -8.3 | -7.3 | -6.3 | -5.3 | -4.3 | | | |
| Leukemia | | | | | | | | | | | | | | | |
| CCRF-CEM | 0.532 | 2.315 | 2.326 | 1.243 | 0.889 | 0.876 | 0.731 | 101 | 40 | 20 | 19 | 11 | 3.41E-08 | >5.00E-5 | >5.00E-5 |
| HL-60(TB) | 0.953 | 2.815 | 2.712 | 1.059 | 0.891 | 0.974 | 1.070 | 94 | 6 | -7 | 1 | 6 | 1.58E-08 | >5.00E-5 | >5.00E-5 |
| K-562 | 0.270 | 1.982 | 1.960 | 0.758 | 0.518 | 0.477 | 0.503 | 99 | 28 | 14 | 12 | 14 | 2.47E-08 | >5.00E5-5 | >5.00E-5 |
| MOLT-4 | 0.789 | 2.789 | 2.761 | 1.671 | 1.360 | 1.354 | 1.392 | 99 | 44 | 29 | 28 | 30 | 3.89E-08 | >5.00E-5 | >5.00E-5 |
| RPMI-8226 | 0.955 | 2.649 | 2.739 | 1.250 | 1.258 | 1.220 | 1.144 | 105 | 17 | 18 | 16 | 11 | 2.13E-08 | >5.00E-5 | >5.00E-5 |
| SR | 0.632 | 2.556 | 2.411 | 1.366 | 1.283 | 1.401 | 1.211 | 92 | 38 | 34 | 40 | 30 | 3.03E-08 | >5.00E-5 | >5.00E-5 |
| Non-Small Cell Lung Cancer | | | | | | | | | | | | | | | |
| A549/ATCC | 0.482 | 2.243 | 2.182 | 1.239 | 1.002 | 0.919 | 1.016 | 97 | 43 | 30 | 25 | 30 | 3.69E-08 | >5.00E-5 | >5.00E-5 |
| EKVX | 0.786 | 1.659 | 1.526 | 1.427 | 1.268 | 1.170 | 1.230 | 85 | 73 | 55 | 44 | 51 | | >5.00E-5 | >5.00E-5 |
| HOP-62 | 0.578 | 1.970 | 1.907 | 1.346 | 1.141 | 1.081 | 1.063 | 95 | 55 | 40 | 36 | 35 | 1.12E-07 | >5.00E-5 | >5.00E-5 |
| HOP-92 | 1.431 | 1.845 | 1.821 | 1.703 | 1.564 | 1.578 | 1.522 | 94 | 66 | 32 | 35 | 22 | 1.46E-07 | >5.00E-5 | >5.00E-5 |
| NCI-H226 | 0.545 | 1.731 | 1.775 | 1.501 | 1.285 | 1.206 | 1.149 | 104 | 81 | 62 | 56 | 51 | >5.00E-5 | >5.00E-5 | >5.00E-5 |
| NCI-H23 | 0.675 | 2.424 | 2.332 | 1.219 | 0.995 | 0.884 | 1.009 | 95 | 3.1 | 18 | 12 | 19 | 2.52E-08 | >5.00E-5 | >5.00E-5 |
| NCI-H322M | 1.153 | 2.671 | 2.541 | 1.728 | 1.425 | 1.431 | 1.572 | 91 | 38 | 18 | 18 | 28 | 2.97E-08 | >5.00E-5 | >5.00E-5 |
| NCI-H460 | 0.417 | 3.173 | 3.205 | 0.908 | 0.764 | 0.758 | 0.751 | 101 | 18 | 13 | 12 | 12 | 2.05E-08 | >5.00E-5 | >5.00E-5 |
| NCI-H522 | 1.063 | 2.678 | 2.568 | 1.916 | 1.052 | 0.902 | 0.989 | 93 | 53 | -1 | -15 | -7 | 5.64E-08 | 4.78E-07 | >5.00E-5 |
| Colon Cancer | | | | | | | | | | | | | | | |
| COLO 205 | 0.434 | 1.892 | 1.776 | 0.702 | 0.490 | 0.403 | 0.359 | 92 | 18 | 4 | -7 | -17 | 1.86E-08 | 1.11E-06 | >5.00E-5 |
| HCC-2998 | 0.694 | 2.079 | 2.015 | 1.282 | 0.902 | 0.750 | 0.847 | 95 | 42 | 15 | 4 | 11 | 3.60E-08 | >5.00E-5 | >5.00E-5 |
| HCT-116 | 0.311 | 2.423 | 2.372 | 0.616 | 0.487 | 0.456 | 0.502 | 68 | 14 | 8 | 7 | 9 | 1.87E-08 | >5.00E-5 | >5.00E-5 |
| HCT-15 | 0.378 | 2.639 | 2.389 | 1.179 | 0.861 | 0.622 | 0.777 | 89 | 35 | 21 | 11 | 18 | 2.67E-08 | >5.00E-5 | >5.00E-5 |
| HT29 | 0.303 | 1.645 | 1.617 | 0.533 | 0.440 | 0.405 | 0.436 | 98 | 17 | 10 | 8 | 10 | 1.96E-08 | >5.00E-5 | >5.00E-5 |
| KM12 | 0.609 | 2.902 | 2.787 | 1.025 | 0.857 | 0.904 | 1.001 | 95 | 18 | 11 | 13 | 17 | 1.92E-08 | >5.00E-5 | >5.00E-5 |
| SW-620 | 0.358 | 2.278 | 2.215 | 0.931 | 0.891 | 0.992 | 1.092 | 97 | 30 | 28 | 33 | 38 | 2.50E-08 | >5.00E-5 | >5.00E-5 |

FIG. 6A

| | | | | | | | | | | | | |
|---|---|---|---|---|---|---|---|---|---|---|---|---|
| CNS Cancer | | | | | | | | | | | | |
| SF-268 | 0.741 | 2.078 | 1.923 | 1.493 | 1.237 | 1.144 | 1.120 | 88 | 56 | 37 | 30 | 28 | 1.06E-07 | >5.00E-5 |
| SF-295 | 0.977 | 3.016 | 2.762 | 2.177 | 1.272 | 1.135 | 1.241 | 88 | 59 | 14 | 8 | 13 | 7.91E-08 | >5.00E-5 |
| SF-539 | 0.914 | 2.414 | 2.189 | 1.285 | 0.533 | 0.370 | 0.472 | 85 | 25 | -42 | -60 | -48 | 1.90E-08 | 1.18E-07 |
| SNB-19 | 0.847 | 2.415 | 2.349 | 1.897 | 1.556 | 1.448 | 1.495 | 96 | 67 | 45 | 38 | 41 | 3.01E-07 | >5.00E-5 |
| SNB-75 | 0.784 | 1.486 | 1.224 | 0.976 | 0.727 | 0.607 | 0.627 | 63 | 27 | -7 | -23 | -20 | 1.14E-08 | 3.08E-07 |
| U251 | 0.492 | 2.402 | 2.358 | 1.289 | 0.810 | 0.753 | 0.813 | 98 | 42 | 17 | 14 | 17 | 3.56E-08 | >5.00E-5 |
| Melanoma | | | | | | | | | | | | |
| LOX IMVI | 0.406 | 2.360 | 2.219 | 0.978 | 0.817 | 0.675 | 0.830 | 93 | 29 | 21 | 14 | 22 | 2.36E-08 | >5.00E-5 |
| MALME-3M | 0.674 | 1.174 | 1.114 | 0.985 | 0.832 | 0.834 | 0.919 | 88 | 62 | 32 | 32 | 49 | 1.26E-07 | >5.00E-5 |
| M14 | 0.396 | 1.598 | 1.578 | 0.586 | 0.291 | 0.347 | 0.745 | 98 | 16 | -27 | -12 | 29 | 1.92E-08 | >5.00E-5 |
| MDA-MB-435 | 0.594 | 2.550 | 2.178 | 0.193 | 0.210 | 0.168 | 0.478 | 81 | -68 | -65 | -72 | -20 | 8.09E-09 | 1.75E-08 |
| SK-MEL-2 | 0.944 | 1.859 | 1.861 | 1.469 | 1.091 | 1.074 | 1.144 | 100 | 57 | 16 | 14 | 22 | 7.55E-08 | >5.00E-5 |
| SK-MEL-28 | 0.736 | 2.192 | 2.066 | 1.631 | 1.455 | 1.407 | 1.635 | 91 | 61 | 49 | 46 | 62 | | >5.00E-5 |
| SK-MEL-5 | 0.728 | 2.822 | 2.700 | 1.164 | 0.779 | 0.676 | 0.888 | 94 | 21 | 2 | -7 | 8 | 2.00E-08 | >5.00E-5 |
| UACC-257 | 1.091 | 2.302 | 2.327 | 1.946 | 1.748 | 1.671 | 1.888 | 102 | 71 | 54 | 48 | 66 | | >5.00E-5 |
| UACC-62 | 1.034 | 2.855 | 2.913 | 2.163 | 1.975 | 1.746 | 1.899 | 103 | 62 | 52 | 39 | 48 | 6.76E-07 | >5.00E-5 |
| Ovarian Cancer | | | | | | | | | | | | |
| IGROV1 | 0.630 | 2.300 | 2.198 | 1.520 | 1.567 | 1.322 | 1.334 | 94 | 53 | 56 | 41 | 42 | 1.30E-06 | >5.00E-5 |
| OVCAR-3 | 0.486 | 1.558 | 1.566 | 0.594 | 0.521 | 0.482 | 0.448 | 101 | 10 | 3 | -1 | -8 | 1.81E-08 | 3.01E-06 |
| OVCAR-4 | 0.688 | 1.433 | 1.352 | 1.176 | 1.048 | 0.969 | 0.969 | 89 | 65 | 48 | 38 | 38 | 3.97E-07 | >5.00E-5 |
| OVCAR-5 | 0.693 | 1.659 | 1.415 | 1.180 | 1.004 | 0.938 | 0.805 | 75 | 50 | 32 | 25 | 12 | 5.25E-08 | >5.00E-5 |
| OVCAR-8 | 0.588 | 2.355 | 2.436 | 1.456 | 1.194 | 1.029 | 1.128 | 105 | 49 | 34 | 25 | 31 | 4.82E-08 | >5.00E-5 |
| NCI/ADR-RES | 0.663 | 2.285 | 2.249 | 1.593 | 0.632 | 0.463 | 0.503 | 98 | 57 | -5 | -30 | -24 | 6.56E-08 | 4.19E-07 |
| SK-OV-3 | 0.635 | 1.617 | 1.605 | 1.387 | 1.053 | 0.962 | 1.007 | 99 | 77 | 43 | 33 | 38 | 3.01E-07 | >5.00E-5 |
| Renal Cancer | | | | | | | | | | | | |
| 786-0 | 0.700 | 2.204 | 2.208 | 1.878 | 1.234 | 0.991 | 0.973 | 93 | 72 | 33 | 18 | 17 | 1.84E-07 | >5.00E-5 |
| A498 | 1.366 | 1.982 | 1.897 | 1.743 | 1.521 | 1.312 | 1.347 | 86 | 61 | 25 | -4 | -1 | 1.02E-07 | 3.66E-06 |
| ACHN | 0.508 | 2.220 | 2.005 | 1.455 | 1.239 | 1.084 | 1.281 | 87 | 55 | 43 | 34 | 45 | 1.32E-07 | >5.00E-5 |
| CAKI-1 | 1.025 | 3.146 | 2.854 | 2.414 | 1.947 | 1.706 | 1.817 | 86 | 65 | 43 | 32 | 37 | 2.52E-07 | >5.00E-5 |
| RXF 393 | 0.755 | 1.409 | 1.340 | 1.042 | 0.847 | 0.720 | 0.792 | 98 | 44 | 14 | -5 | 6 | 3.84E-08 | >5.00E-5 |

FIG. 6A, Continued

|  |  |  |  |  |  |  |  |  |  |  |  |
|---|---|---|---|---|---|---|---|---|---|---|---|
| SN12C | 0.743 | 2.790 | 2.780 | 1.869 | 1.640 | 1.499 | 1.491 | 100 | 55 | 44 | 37 | 37 | 1.40E-07 | >5.00E-5 |
| TK-10 | 1.103 | 1.909 | 1.859 | 1.652 | 1.431 | 1.415 | 1.490 | 94 | 68 | 41 | 39 | 48 | 2.28E-07 | >5.00E-5 |
| UO-31 | 0.963 | 2.517 | 2.282 | 1.998 | 1.627 | 1.651 | 1.596 | 85 | 67 | 43 | 44 | 41 | 2.48E-07 | >5.00E-5 |
| Prostate Cancer | | | | | | | | | | | | | | |
| PC-3 | 0.765 | 2.474 | 2.327 | 1.425 | 1.175 | 1.207 | 1.259 | 91 | 39 | 24 | 26 | 29 | 3.04E-08 | >5.00E-5 |
| DU-145 | 0.398 | 1.571 | 1.550 | 0.833 | 0.426 | 0.350 | 0.335 | 98 | 37 | 2 | -12 | -16 | 3.07E-08 | 7.32E-07 |
| Breast Cancer | | | | | | | | | | | | | | |
| MCF7 | 0.371 | 2.071 | 1.751 | 0.652 | 0.588 | 0.528 | 0.596 | 81 | 17 | 13 | 9 | 13 | 1.52E-08 | >5.00E-5 |
| MDA-MB-231/ATCC | 0.689 | 1.622 | 1.643 | 1.306 | 1.117 | 1.062 | 0.883 | 102 | 66 | 46 | 40 | 21 | 3.12E-07 | >5.00E-5 |
| HS 578T | 1.018 | 2.004 | 1.833 | 1.492 | 1.140 | 1.045 | 0.945 | 83 | 48 | 12 | 3 | -7 | 4.40E-08 | 9.37E-06 |
| BT-549 | 1.310 | 2.572 | 2.477 | 2.135 | 1.750 | 1.759 | 1.682 | 92 | 65 | 35 | 36 | 29 | 1.60E-07 | >5.00E-5 |
| T-47D | 0.669 | 1.421 | 1.367 | 1.081 | 1.002 | 1.054 | 1.086 | 93 | 55 | 44 | 51 | 55 | >5.00E-5 | >5.00E-5 |
| MDA-MB-468 | 0.923 | 2.040 | 1.977 | 1.423 | 0.998 | 0.908 | 0.891 | 94 | 45 | 7 | -2 | -3 | 3.92E-08 | 3.15E-06 |

FIG. 6A, Continued

National Cancer Institute Development Therapeutics Program
In-Vitro Testing Results NSC: D-781491/1  
Report Date: September 17, 2014  
COMI: KCDR_2A  
Experimental ID: 1409NS43  
Test Date: September 2, 2014  
Stain Reagent: SRB Dual-Pass Related  
Test Type: 08  
QNS:  
SSPL: OZAS  
Units: Molar  
MC:

Log10 Concentration

| Panel/Cell Line | Time Zero | Ctrl | -8.3 | -7.3 | -6.3 | -5.3 | -4.3 | -8.3 | -7.3 | -6.3 | -5.3 | -4.3 | GI50 | TGI | LC50 |
|---|---|---|---|---|---|---|---|---|---|---|---|---|---|---|---|
| | | | Mean Optical Densities | | | | | Percent Growth | | | | | | | |
| Leukemia | | | | | | | | | | | | | | | |
| CCRF-CEM | 0.640 | 2.965 | 3.040 | 2.683 | 1.291 | 1.065 | 0.856 | 103 | 88 | 28 | 18 | 9 | 4.76E-08 | >1.11E-5 | >1.11E-5 |
| HL-60(TB) | 0.615 | 2.785 | 2.639 | 1.536 | 0.702 | 0.674 | 0.605 | 93 | 42 | 4 | 3 | -2 | 7.88E-09 | 4.55E-06 | >1.11E-5 |
| K-562 | 0.230 | 2.136 | 2.177 | 1.288 | 0.585 | 0.467 | 0.405 | 102 | 56 | 19 | 12 | 9 | 1.57E-08 | >1.11E-5 | >1.11E-5 |
| MOLT-4 | 0.782 | 3.174 | 3.195 | 2.690 | 1.572 | 1.323 | 1.030 | 104 | 50 | 17 | 14 | 4 | 1.11E-08 | >1.11E-5 | >1.11E-5 |
| RPMI-8226 | 0.766 | 2.393 | 2.457 | 1.580 | 1.043 | 1.000 | 0.831 | 104 | 50 | 17 | 14 | 4 | 1.11E-08 | >1.11E-5 | >1.11E-5 |
| Non-Small Cell Lung Cancer | | | | | | | | | | | | | | | |
| A549/ATCC | 0.502 | 2.169 | 2.211 | 1.650 | 1.161 | 0.907 | 0.681 | 103 | 69 | 40 | 24 | 11 | 4.88E-08 | >1.11E-5 | >1.11E-5 |
| EKVX | 0.676 | 1.960 | 1.757 | 1.823 | 1.327 | 1.140 | 0.956 | 84 | 89 | 51 | 36 | 22 | 1.23E-07 | >1.11E-5 | >1.11E-5 |
| HOP-62 | 0.715 | 1.482 | 1.292 | 1.259 | 1.084 | 0.937 | 0.871 | 75 | 71 | 48 | 29 | 20 | 9.15E-08 | >1.11E-5 | >1.11E-5 |
| HOP-92 | 1.280 | 1.615 | 1.604 | 1.594 | 1.459 | 1.408 | 1.308 | 97 | 94 | 53 | 38 | 8 | 1.83E-07 | >1.11E-5 | >1.11E-5 |
| NCI-H226 | 0.773 | 2.093 | 2.131 | 2.065 | 1.892 | 1.661 | 1.295 | 103 | 98 | 85 | 67 | 40 | 4.64E-06 | >1.11E-5 | >1.11E-5 |
| NCI-H23 | 0.450 | 1.445 | 1.434 | 1.254 | 0.914 | 0.805 | 0.711 | 99 | 81 | 47 | 36 | 26 | 8.85E-08 | >1.11E-5 | >1.11E-5 |
| NCI-H322M | 0.752 | 1.781 | 1.760 | 1.499 | 1.126 | 1.025 | 1.017 | 98 | 73 | 36 | 27 | 26 | 4.65E-08 | >1.11E-5 | >1.11E-5 |
| NCI-H460 | 0.308 | 2.884 | 2.975 | 1.170 | 0.605 | 0.580 | 0.357 | 104 | 33 | 12 | 11 | 2 | 6.45E-09 | >1.11E-5 | >1.11E-5 |
| NCI-H522 | 0.828 | 2.206 | 2.136 | 1.829 | 0.496 | 0.341 | 0.282 | 95 | 73 | -40 | -59 | -66 | 1.76E-08 | 4.89E-08 | >1.11E-5 |
| Colon Cancer | | | | | | | | | | | | | | | |
| COLO 205 | 0.454 | 1.910 | 1.780 | 1.265 | 0.584 | 0.467 | 0.282 | 91 | 56 | 9 | 1 | -38 | 1.47E-08 | 1.17E-06 | >1.11E-5 |
| HCC-2998 | 0.488 | 1.608 | 1.605 | 1.142 | 0.660 | 0.527 | 0.367 | 100 | 58 | 15 | 3 | -25 | 1.74E-08 | 1.47E-06 | >1.11E-5 |
| HCT-116 | 0.271 | 2.206 | 2.101 | 0.833 | 0.510 | 0.395 | 0.327 | 95 | 29 | 12 | 6 | 3 | 5.31E-09 | >1.11E-5 | >1.11E-5 |
| HCT-15 | 0.236 | 1.609 | 1.450 | 1.136 | 0.418 | 0.295 | 0.259 | 88 | 66 | 13 | 4 | 2 | 2.20E-08 | >1.11E-5 | >1.11E-5 |
| HT29 | 0.256 | 1.442 | 1.378 | 0.598 | 0.235 | 0.199 | 0.100 | 95 | 29 | -8 | -22 | -61 | 5.29E-09 | 6.60E-08 | >1.11E-5 |
| KM12 | 0.400 | 2.316 | 2.221 | 0.942 | 0.655 | 0.605 | 0.448 | 95 | 28 | 13 | 11 | 3 | 5.25E-09 | >1.11E-5 | >1.11E-5 |
| SW-620 | 0.273 | 2.028 | 2.017 | 0.756 | 0.772 | 0.780 | 0.671 | 99 | 28 | 28 | 29 | 23 | 5.40E-09 | >1.11E-5 | >1.11E-5 |

FIG. 6B

| | | | | | | | | | | | |
|---|---|---|---|---|---|---|---|---|---|---|---|
| CNS Cancer | | | | | | | | | | | |
| SF-268 | 0.614 | 2.056 | 1.963 | 1.671 | 1.147 | 0.902 | 0.691 | 94 | 73 | 37 | 20 | 5 | 4.85E-08 | >1.11E-5 | >1.11E-5 |
| SF-295 | 0.541 | 2.447 | 2.202 | 1.961 | 0.785 | 0.546 | 0.528 | 87 | 74 | 13 | | -2 | 2.77E-08 | 1.39E-06 | >1.11E-5 |
| SF-539 | 0.972 | 2.706 | 2.462 | 2.139 | 1.281 | 0.796 | 0.645 | 86 | 67 | 18 | -18 | -34 | 2.48E-08 | 3.47E-07 | >1.11E-5 |
| SNB-19 | 0.559 | 1.879 | 1.909 | 1.761 | 1.117 | 0.976 | 0.817 | 102 | 91 | 42 | 32 | 20 | 7.71E-08 | >1.11E-5 | >1.11E-5 |
| U251 | 0.518 | 2.416 | 2.471 | 1.020 | 1.089 | 0.780 | 0.669 | 103 | 73 | 30 | 14 | 8 | 3.81E-08 | >1.11E-5 | >1.11E-5 |
| Melanoma | | | | | | | | | | | |
| LOX IMVI | 0.333 | 2.199 | 2.165 | 1.498 | 0.840 | 0.780 | 0.507 | 98 | 62 | 27 | 24 | 9 | 2.50E-08 | >1.11E-5 | >1.11E-5 |
| MALME-3M | 0.795 | 1.355 | 1.299 | 1.177 | 1.061 | 1.058 | 1.031 | 90 | 68 | 47 | 47 | 42 | 8.34E-08 | >1.11E-5 | >1.11E-5 |
| M14 | 0.356 | 1.569 | 1.469 | 1.023 | 0.367 | 0.276 | 0.331 | 92 | 55 | 1 | -22 | -7 | 1.37E-08 | 1.21E-07 | >1.11E-5 |
| MDA-MB-435 | 0.293 | 1.616 | 1.438 | 0.154 | 0.123 | 0.075 | 0.129 | 87 | -48 | -58 | -74 | -56 | 2.08E-09 | 4.90E-09 | >1.11E-5 |
| SK-MEL-2 | 1.169 | 2.243 | 2.285 | 1.958 | 1.063 | 1.004 | 0.777 | 104 | 73 | -9 | -14 | -34 | 2.13E-08 | 8.61E-08 | >1.11E-5 |
| SK-MEL-28 | 0.607 | 2.024 | 1.914 | 1.734 | 1.342 | 1.260 | 1.043 | 92 | 80 | 52 | 46 | 31 | 2.35E-07 | >1.11E-5 | >1.11E-5 |
| SK-MEL-5 | 0.788 | 3.186 | 3.179 | 2.378 | 1.069 | 0.909 | 0.832 | 100 | 66 | 12 | 5 | 2 | 2.21E-08 | >1.11E-5 | >1.11E-5 |
| UACC-257 | 0.952 | 2.062 | 2.020 | 1.909 | 1.552 | 1.456 | 1.388 | 96 | 86 | 54 | 45 | 39 | 3.22E-07 | >1.11E-5 | >1.11E-5 |
| UACC-62 | 0.890 | 2.804 | 2.795 | 2.157 | 1.484 | 1.309 | 1.124 | 100 | 66 | 31 | 22 | 12 | 3.20E-08 | >1.11E-5 | >1.11E-5 |
| Ovarian Cancer | | | | | | | | | | | |
| IGROV1 | 0.594 | 2.312 | 2.363 | 1.654 | 1.348 | 1.266 | 1.052 | 103 | 62 | 44 | 39 | 27 | 5.01E-08 | >1.11E-5 | >1.11E-5 |
| OVCAR-3 | 0.470 | 1.634 | 1.666 | 1.151 | 0.509 | 0.532 | 0.431 | 103 | 58 | 3 | 5 | -8 | 1.58E-08 | 2.73E-06 | >1.11E-5 |
| OVCAR-4 | 1.146 | 2.180 | 2.039 | 2.016 | 1.850 | 1.843 | 1.632 | 86 | 84 | 68 | 67 | 47 | 7.89E-06 | >1.11E-5 | >1.11E-5 |
| OVCAR-5 | 0.709 | 1.835 | 1.827 | 1.470 | 1.138 | 0.903 | 0.767 | 99 | 68 | 38 | 17 | 5 | 4.36E-08 | >1.11E-5 | >1.11E-5 |
| OVCAR-8 | 0.480 | 1.998 | 2.109 | 1.847 | 0.951 | 0.718 | 0.613 | 107 | 90 | 31 | 16 | 9 | 5.29E-08 | >1.11E-5 | >1.11E-5 |
| NCI/ADR-RES | 0.474 | 1.574 | 1.597 | 1.498 | 1.185 | 0.720 | 0.612 | 102 | 93 | 65 | 22 | 13 | 2.46E-07 | >1.11E-5 | >1.11E-5 |
| SK-OV-3 | 0.782 | 1.996 | 1.900 | 1.744 | 1.193 | 1.130 | 1.067 | 92 | 79 | 34 | 29 | 23 | 4.90E-08 | >1.11E-5 | >1.11E-5 |
| Renal Cancer | | | | | | | | | | | |
| 786-0 | 0.577 | 2.088 | 1.876 | 1.826 | 1.221 | 0.824 | 0.672 | 86 | 83 | 43 | 16 | 6 | 7.25E-08 | >1.11E-5 | >1.11E-5 |
| A498 | 1.270 | 2.132 | 2.086 | 2.035 | 1.604 | 1.288 | 1.362 | 95 | 89 | 39 | 2 | 11 | 6.60E-08 | >1.11E-5 | >1.11E-5 |
| ACHN | 0.440 | 1.819 | 1.701 | 1.535 | 1.000 | 0.864 | 0.750 | 91 | 79 | 41 | 31 | 22 | 6.35E-08 | >1.11E-5 | >1.11E-5 |
| CAKI-1 | 1.251 | 3.349 | 3.182 | 3.025 | 2.442 | 2.280 | 1.929 | 92 | 85 | 57 | 49 | 32 | 8.38E-07 | >1.11E-5 | >1.11E-5 |
| RXF 393 | 0.622 | 1.263 | 1.280 | 1.181 | 0.759 | 0.620 | 0.476 | 103 | 87 | 21 | | -23 | 4.07E-08 | 1.06E-06 | >1.11E-5 |
| SN12C | 1.165 | 3.295 | 3.288 | 3.260 | 2.482 | 2.414 | 1.908 | 100 | 98 | 62 | 59 | 35 | 2.56E-06 | >1.11E-5 | >1.11E-5 |
| TK-10 | 0.796 | 1.743 | 1.701 | 1.558 | 1.148 | 0.966 | 0.778 | 96 | 80 | 37 | 18 | -2 | 5.59E-08 | 8.53E-06 | >1.11E-5 |

FIG. 6B, Continued

| | | | | | | | | | | |
|---|---|---|---|---|---|---|---|---|---|---|
| UO-31 | 0.709 | 2.405 | 2.210 | 2.049 | 1.468 | 1.371 | 1.148 | 88 | 79 | 45 | 39 | 26 | 7.81E-08 | >1.11E-5 | >1.11E-5 |
| Prostate Cancer | | | | | | | | | | | |
| PC-3 | 0.611 | 2.401 | 2.389 | 1.931 | 1.012 | 1.004 | 0.808 | 99 | 74 | 22 | 22 | 11 | 3.22E-08 | >1.11E-5 | >1.11E-5 |
| DU-145 | 0.339 | 1.559 | 1.550 | 1.416 | 0.540 | 0.307 | 0.193 | 99 | 88 | 16 | -10 | -43 | 3.79E-08 | 4.76E-07 | >1.11E-5 |
| Breast Cancer | | | | | | | | | | | |
| MCF7 | 0.232 | 1.400 | 1.168 | 0.487 | 0.386 | 0.330 | 0.259 | 80 | 22 | 13 | 8 | 2 | 3.65E-09 | >1.11E-5 | >1.11E-5 |
| MDA-MB-231/ATCC | 0.732 | 1.750 | 1.795 | 1.564 | 1.276 | 1.118 | 0.743 | 104 | 82 | 53 | 38 | 1 | 1.84E-07 | >1.11E-5 | >1.11E-5 |
| HS 578T | 1.208 | 2.375 | 2.317 | 2.048 | 1.550 | 1.229 | 0.980 | 95 | 72 | 29 | 2 | -19 | 3.64E-08 | 1.35E-06 | >1.11E-5 |
| BT-549 | 0.991 | 2.218 | 2.015 | 1.930 | 1.474 | 1.151 | 0.914 | 83 | 76 | 39 | 13 | -8 | 5.73E-08 | 4.70E-06 | >1.11E-5 |
| T-47D | 0.773 | 1.630 | 1.467 | 1.353 | 1.125 | 1.099 | 0.991 | 81 | 68 | 41 | 38 | 25 | 5.10E-08 | >1.11E-5 | >1.11E-5 |
| MDA-MB-468 | 0.780 | 1.382 | 1.418 | 1.234 | 0.746 | 0.604 | 0.490 | 106 | 75 | -4 | -23 | -37 | 2.31E-08 | 9.79E-08 | >1.11E-5 |

FIG. 6B, Continued

National Cancer Institute Development Therapeutics Program
In-Vitro Testing Results NSC: D - 781076 / 1     Experimental ID: 1408NS31     Test Type: 08     Units: Molar
Report Date: September 22, 2014     Test Date: August 11, 2014     QNS:     MC:
COMI: KCDR_4A     Stain Reagent: SRB Dual-Pass Related     SSPL: OZAS Log10 Concentration

| Panel/Cell Line | Time Zero | Ctrl | -8.3 | -7.3 | -6.3 | -5.3 | -4.3 | -8.3 | -7.3 | -6.3 | -5.3 | -4.3 | GI50 | TGI | LC50 |
|---|---|---|---|---|---|---|---|---|---|---|---|---|---|---|---|
| | | | Mean Optical Densities | | | | | Percent Growth | | | | | | | |
| Leukemia | | | | | | | | | | | | | | | |
| CCRF-CEM | 0.532 | 2.409 | 2.325 | 1.020 | 0.805 | 0.762 | 0.704 | 96 | 26 | 15 | 12 | 9 | 2.26E-08 | >5.00E-5 | >5.00E-5 |
| HL-60(TB) | 0.953 | 2.812 | 2.839 | 1.059 | 0.873 | 0.834 | 0.807 | 101 | 6 | -8 | -12 | -15 | 1.72E-08 | 1.27E-07 | >5.00E-5 |
| K-562 | 0.270 | 2.092 | 1.987 | 0.817 | 0.486 | 0.425 | 0.394 | 94 | 30 | 12 | 8 | 7 | 2.44E-08 | >5.00E-5 | >5.00E-5 |
| MOLT-4 | 0.789 | 2.754 | 2.705 | 1.447 | 1.248 | 0.927 | 0.846 | 97 | 33 | 23 | 7 | 3 | 2.76E-08 | >5.00E-5 | >5.00E-5 |
| RPMI-8226 | 0.955 | 2.691 | 2.578 | 1.212 | 1.291 | 1.170 | 0.962 | 93 | 15 | 19 | 12 | | 1.78E-08 | >5.00E-5 | >5.00E-5 |
| SR | 0.632 | 2.651 | 2.421 | 1.367 | 1.178 | 1.044 | 0.783 | 89 | 36 | 27 | 20 | 7 | 2.74E-08 | >5.00E-5 | >5.00E-5 |
| Non-Small Cell Lung Cancer | | | | | | | | | | | | | | | |
| A549/ATCC | 0.482 | 2.215 | 2.168 | 1.191 | 0.876 | 0.843 | 0.795 | 97 | 41 | 23 | 21 | 18 | 3.45E-08 | >5.00E-5 | >5.00E-5 |
| EKVX | 0.786 | 1.623 | 1.567 | 1.397 | 1.280 | 1.129 | 1.072 | 93 | 73 | 59 | 41 | 34 | 1.57E-06 | >5.00E-5 | >5.00E-5 |
| HOP-62 | 0.578 | 1.912 | 1.905 | 1.348 | 1.116 | 0.944 | 0.929 | 99 | 58 | 40 | 27 | 26 | 1.38E-07 | >5.00E-5 | >5.00E-5 |
| HOP-92 | 1.431 | 1.934 | 1.816 | 1.699 | 1.622 | 1.522 | 1.436 | 76 | 53 | 38 | 18 | 1 | 8.07E-08 | >5.00E-5 | >5.00E-5 |
| NCI-H226 | 0.545 | 1.787 | 1.735 | 1.485 | 1.319 | 1.206 | 0.948 | 96 | 76 | 62 | 53 | 32 | 7.14E-06 | >5.00E-5 | >5.00E-5 |
| NCI-H23 | 0.675 | 2.510 | 2.465 | 1.444 | 1.117 | 0.994 | 0.963 | 98 | 42 | 24 | 17 | 16 | 3.58E-08 | >5.00E-5 | >5.00E-5 |
| NCI-H322M | 1.153 | 2.661 | 2.600 | 1.820 | 1.540 | 1.393 | 1.508 | 96 | 44 | 26 | 16 | 24 | 3.86E-08 | >5.00E-5 | >5.00E-5 |
| NCI-H460 | 0.417 | 3.141 | 3.164 | 0.885 | 0.711 | 0.674 | 0.576 | 101 | 17 | 11 | 9 | 6 | 2.03E-08 | >5.00E-5 | >5.00E-5 |
| NCI-H522 | 1.063 | 2.615 | 2.523 | 1.838 | 0.985 | 0.932 | 0.790 | 94 | 50 | -7 | -12 | -26 | 4.98E-08 | 3.72E-07 | >5.00E-5 |
| Colon Cancer | | | | | | | | | | | | | | | |
| COLO 205 | 0.434 | 1.798 | 1.758 | 0.708 | 0.458 | 0.334 | 0.229 | 97 | 20 | 2 | -23 | -47 | 2.04E-08 | 5.86E-07 | >5.00E-5 |
| HCC-2998 | 0.694 | 2.121 | 2.033 | 1.416 | 0.881 | 0.792 | 0.846 | 94 | 51 | 13 | 7 | 11 | 5.18E-08 | >5.00E-5 | >5.00E-5 |
| HCT-116 | 0.311 | 2.264 | 2.247 | 0.547 | 0.502 | 0.449 | 0.415 | 99 | 12 | 10 | 7 | 5 | 5.18E-08 | >5.00E-5 | >5.00E-5 |
| HCT-15 | 0.378 | 2.609 | 2.647 | 1.229 | 0.756 | 0.636 | 0.623 | 102 | 38 | 17 | 12 | 11 | 3.25E-08 | >5.00E-5 | >5.00E-5 |
| HT29 | 0.303 | 1.713 | 1.637 | 0.545 | 0.408 | 0.411 | 0.355 | 95 | 17 | 7 | 8 | 4 | 1.88E-08 | >5.00E-5 | >5.00E-5 |
| KM12 | 0.609 | 2.905 | 2.889 | 1.046 | 0.856 | 0.871 | 0.974 | 99 | 19 | 11 | 11 | 16 | 2.06E-08 | >5.00E-5 | >5.00E-5 |
| SW-620 | 0.358 | 2.283 | 2.238 | 0.909 | 0.884 | 0.932 | 1.042 | 98 | 29 | 27 | 30 | 36 | 2.45E-08 | >5.00E-5 | >5.00E-5 |

FIG. 6C

| | | | | | | | | | | | | |
|---|---|---|---|---|---|---|---|---|---|---|---|---|
| CNS Cancer | | | | | | | | | | | | |
| SF-268 | 0.741 | 2.185 | 2.077 | 1.629 | 1.176 | 1.086 | 0.979 | 93 | 61 | 30 | 24 | 16 | 1.16E-07 | >5.00E-5 |
| SF-295 | 0.977 | 3.058 | 3.021 | 2.166 | 1.285 | 1.012 | 1.098 | 98 | 57 | 15 | 2 | 6 | 7.37E-08 | >5.00E-5 |
| SF-539 | 0.914 | 2.509 | 2.332 | 1.091 | 0.822 | 0.698 | 0.626 | 89 | 11 | -10 | -24 | -32 | 1.58E-08 | 1.67E-07 |
| SNB-19 | 0.847 | 2.369 | 2.286 | 1.744 | 1.432 | 1.348 | 1.299 | 95 | 59 | 38 | 33 | 30 | 1.37E-07 | >5.00E-5 |
| SNB-75 | 0.784 | 1.503 | 1.313 | 0.985 | 0.700 | 0.563 | 0.517 | 74 | 28 | -11 | -28 | -34 | 1.64E-08 | 2.63E-07 |
| U251 | 0.492 | 2.333 | 2.260 | 1.187 | 0.736 | 0.686 | 0.628 | 96 | 38 | 13 | 11 | 7 | 3.08E-08 | >5.00E-5 |
| Melanoma | | | | | | | | | | | | |
| LOX IMVI | 0.406 | 2.345 | 2.303 | 1.140 | 0.957 | 0.783 | 0.618 | 98 | 38 | 28 | 19 | 11 | 3.30E-08 | >5.00E-5 |
| MALME-3M | 0.674 | 1.168 | 1.166 | 0.989 | 0.877 | 0.855 | 0.919 | 100 | 64 | 41 | 37 | 50 | 2.01E-07 | >5.00E-5 |
| M14 | 0.396 | 1.530 | 1.531 | 0.509 | 0.278 | 0.410 | 0.645 | 100 | 10 | -30 | 1 | 22 | 1.80E-08 | >5.00E-5 |
| MDA-MB-435 | 0.594 | 2.587 | 2.518 | 0.186 | 0.153 | 0.166 | 0.383 | 97 | -69 | -74 | -72 | -36 | 9.56E-09 | 1.92E-08 |
| SK-MEL-2 | 0.944 | 1.807 | 1.845 | 1.394 | 1.072 | 1.016 | 1.086 | 104 | 52 | 15 | 8 | 16 | 5.69E-08 | >5.00E-5 |
| SK-MEL-28 | 0.736 | 2.244 | 2.139 | 1.595 | 1.518 | 1.487 | 1.321 | 93 | 57 | 52 | 50 | 39 | 3.86E-06 | >5.00E-5 |
| SK-MEL-5 | 0.728 | 2.857 | 2.771 | 1.246 | 0.858 | 0.795 | 0.827 | 96 | 24 | 6 | 3 | 5 | 2.19E-08 | >5.00E-5 |
| UACC-257 | 1.091 | 2.300 | 2.206 | 1.749 | 1.644 | 1.625 | 1.603 | 92 | 54 | 46 | 44 | 42 | 1.61E-07 | >5.00E-5 |
| UACC-62 | 1.034 | 2.866 | 2.815 | 2.102 | 1.921 | 1.790 | 1.570 | 97 | 58 | 48 | 41 | 29 | 3.45E-07 | >5.00E-5 |
| Ovarian Cancer | | | | | | | | | | | | |
| IGROV1 | 0.630 | 2.241 | 2.223 | 1.531 | 1.449 | 1.199 | 1.216 | 99 | 56 | 51 | 35 | 36 | 5.65E-07 | >5.00E-5 |
| OVCAR-3 | 0.486 | 1.642 | 1.657 | 0.628 | 0.509 | 0.482 | 0.450 | 101 | 12 | 2 | -1 | -8 | 1.88E-08 | 2.55E-06 |
| OVCAR-4 | 0.688 | 1.444 | 1.440 | 1.145 | 1.074 | 0.906 | 0.818 | 100 | 60 | 51 | 29 | 17 | 5.59E-07 | >5.00E-5 |
| OVCAR-5 | 0.693 | 1.651 | 1.502 | 1.211 | 1.029 | 0.898 | 0.662 | 84 | 54 | 35 | 21 | -5 | 8.19E-08 | 3.34E-05 |
| OVCAR-8 | 0.588 | 2.280 | 2.221 | 1.333 | 1.114 | 0.908 | 0.891 | 96 | 44 | 31 | 19 | 18 | 3.85E-08 | >5.00E-5 |
| NCI/ADR-RES | 0.663 | 2.442 | 2.429 | 2.016 | 0.935 | 0.671 | 0.630 | 99 | 76 | 15 | | -5 | 1.34E-07 | 6.04E-06 |
| SK-OV-3 | 0.635 | 1.660 | 1.655 | 1.149 | 0.955 | 0.897 | 0.893 | 99 | 50 | 31 | 24 | 25 | 5.08E-08 | >5.00E-5 |
| Renal Cancer | | | | | | | | | | | | |
| 786-0 | 0.700 | 2.340 | 2.121 | 1.656 | 0.849 | 0.824 | 0.692 | 87 | 58 | 9 | 8 | -1 | 7.36E-08 | 3.63E-05 |
| A498 | 1.366 | 1.960 | 1.800 | 1.562 | 1.342 | 1.254 | 1.290 | 73 | 33 | -2 | -8 | -6 | 1.88E-08 | 4.45E-07 |
| ACHN | 0.508 | 2.281 | 2.312 | 1.513 | 1.332 | 1.202 | 1.125 | 102 | 57 | 46 | 39 | 35 | 2.26E-07 | >5.00E-5 |
| CAKI-1 | 1.025 | 3.134 | 3.013 | 2.352 | 2.020 | 1.536 | 1.558 | 94 | 63 | 47 | 24 | 25 | 3.30E-07 | >5.00E-5 |
| RXF 393 | 0.755 | 1.438 | 1.367 | 1.066 | 0.788 | 0.670 | 0.608 | 90 | 46 | 5 | -11 | -19 | 3.96E-08 | 9.88E-07 |

FIG. 6C, Continued

| | | | | | | | | | | | | |
|---|---|---|---|---|---|---|---|---|---|---|---|---|
| SN12C | 0.743 | 2.789 | 2.622 | 1.824 | 1.504 | 1.315 | 1.212 | 92 | 53 | 37 | 28 | 23 | 7.56E-08 | >5.00E-5 |
| TK-10 | 1.103 | 1.898 | 1.829 | 1.623 | 1.425 | 1.356 | 1.319 | 91 | 65 | 40 | 32 | 27 | 2.07E-07 | >5.00E-5 |
| UO-31 | 0.963 | 2.488 | 2.406 | 2.018 | 1.648 | 1.543 | 1.441 | 95 | 69 | 45 | 38 | 31 | 3.09E-07 | >5.00E-5 |
| Prostate Cancer | | | | | | | | | | | | | |
| PC-3 | 0.765 | 2.441 | 2.370 | 1.453 | 1.089 | 1.143 | 1.088 | 96 | 41 | 19 | 23 | 19 | 3.43E-08 | >5.00E-5 |
| DU-145 | 0.398 | 1.604 | 1.664 | 0.947 | 0.385 | 0.337 | 0.329 | 105 | 46 | -3 | -15 | -17 | 4.28E-07 | 4.29E-07 |
| Breast Cancer | | | | | | | | | | | | | |
| MCF7 | 0.371 | 2.116 | 1.969 | 0.649 | 0.659 | 0.573 | 0.463 | 92 | 16 | 17 | 12 | 5 | 1.77E-08 | >5.00E-5 |
| MDA-MB-231/ATCC | 0.689 | 1.553 | 1.595 | 1.286 | 1.079 | 0.848 | 0.746 | 105 | 69 | 45 | 18 | 7 | 3.12E-07 | >5.00E-5 |
| HS 578T | 1.018 | 2.019 | 1.853 | 1.435 | 1.121 | 0.976 | 0.887 | 83 | 42 | 10 | -4 | -13 | 3.16E-08 | 2.57E-06 |
| BT-549 | 1.310 | 2.492 | 2.352 | 2.023 | 1.751 | 1.604 | 1.445 | 88 | 60 | 37 | 25 | 11 | 1.40E-07 | >5.00E-5 |
| T-47D | 0.669 | 1.396 | 1.366 | 1.068 | 0.960 | 0.949 | 0.842 | 96 | 55 | 40 | 39 | 24 | 1.06E-07 | >5.00E-5 |
| MDA-MB-468 | 0.923 | 2.021 | 1.908 | 1.258 | 0.965 | 0.858 | 0.778 | 90 | 30 | 4 | -7 | -16 | 2.34E-08 | 1.12E-06 |

FIG. 6C, Continued

National Cancer Institute Development Therapeutics Program
In-Vitro Testing Results NSC: D-781079/1  
Report Date: September 22, 2014  
COMI: KCDR_8A Experimental ID: 1408NS31  
Test Date: August 11, 2014  
Stain Reagent: SRB Dual-Pass Related  
Log10 Concentration Test Type: 08  
QNS:  
SSPL: OZAS Units: Molar  
MC:

| Panel/Cell Line | Time Zero | Ctrl | Mean Optical Densities |  |  |  |  | Percent Growth |  |  |  |  | GI50 | TGI | LC50 |
|---|---|---|---|---|---|---|---|---|---|---|---|---|---|---|---|
| | | | -8.3 | -7.3 | -6.3 | -5.3 | -4.3 | -8.3 | -7.3 | -6.3 | -5.3 | -4.3 | | | |
| Leukemia | | | | | | | | | | | | | | | |
| CCRF-CEM | 0.532 | 2.325 | 2.237 | 0.836 | 0.854 | 0.778 | 0.635 | 95 | 17 | 18 | 14 | 6 | 1.23E-08 | >3.25E-5 | >3.25E-5 |
| HL-60(TB) | 0.953 | 2.660 | 2.497 | 0.729 | 0.726 | 0.812 | 0.677 | 90 | -24 | -24 | -15 | -29 | 7.36E-09 | 2.02E-08 | >3.25E-5 |
| K-562 | 0.270 | 1.681 | 1.386 | 0.561 | 0.401 | 0.390 | 0.322 | 79 | 21 | 9 | 9 | 4 | 1.02E-08 | >3.25E-5 | >3.25E-5 |
| MOLT-4 | 0.789 | 2.569 | 2.330 | 1.312 | 1.078 | 1.079 | 0.758 | 87 | 29 | 16 | 16 | -4 | 1.42E-08 | 2.06E-05 | >3.25E-5 |
| RPMI-8226 | 0.955 | 2.580 | 2.329 | 1.177 | 1.271 | 1.245 | 0.839 | 85 | 14 | 19 | 18 | -12 | 9.98E-09 | 1.28E-05 | >3.25E-5 |
| SR | 0.632 | 2.320 | 1.697 | 1.069 | 1.143 | 1.003 | 0.551 | 63 | 26 | 30 | 22 | -13 | 7.29E-09 | 1.39E-05 | >3.25E-5 |
| Non-Small Cell Lung Cancer | | | | | | | | | | | | | | | |
| A549/ATCC | 0.482 | 2.234 | 1.883 | 1.029 | 0.942 | 0.940 | 0.606 | 80 | 31 | 26 | 26 | 7 | 1.34E-08 | >3.25E-5 | >3.25E-5 |
| EKVX | 0.786 | 1.674 | 1.622 | 1.359 | 1.311 | 1.254 | 0.904 | 94 | 64 | 59 | 53 | 13 | 3.80E-06 | >3.25E-5 | >3.25E-5 |
| HOP-62 | 0.578 | 1.917 | 1.821 | 1.223 | 1.083 | 0.955 | 0.796 | 93 | 48 | 38 | 28 | 16 | 2.95E-08 | >3.25E-5 | >3.25E-5 |
| HOP-92 | 1.431 | 1.827 | 1.746 | 1.578 | 1.622 | 1.619 | 1.327 | 80 | 37 | 48 | 48 | -7 | 1.61E-08 | 2.39E-05 | >3.25E-5 |
| NCI-H226 | 0.545 | 1.732 | 1.608 | 1.260 | 1.247 | 1.205 | 0.579 | 89 | 60 | 59 | 56 | 3 | 4.14E-06 | >3.25E-5 | >3.25E-5 |
| NCI-H23 | 0.675 | 2.369 | 2.280 | 1.269 | 1.155 | 1.192 | 0.872 | 95 | 35 | 28 | 30 | 12 | 1.83E-08 | >3.25E-5 | >3.25E-5 |
| NCI-H322M | 1.153 | 2.710 | 2.564 | 1.723 | 1.537 | 1.530 | 1.558 | 91 | 37 | 25 | 24 | 26 | 1.84E-08 | >3.25E-5 | >3.25E-5 |
| NCI-H460 | 0.417 | 3.117 | 2.535 | 0.746 | 0.726 | 0.714 | 0.300 | 78 | 12 | 11 | 11 | -28 | 8.73E-09 | 6.20E-06 | >3.25E-5 |
| NCI-H522 | 1.063 | 2.660 | 2.480 | 1.450 | 0.983 | 0.986 | 1.000 | 89 | 24 | -8 | -7 | -6 | 1.29E-08 | 1.88E-07 | >3.25E-5 |
| Colon Cancer | | | | | | | | | | | | | | | |
| COLO 205 | 0.434 | 1.822 | 1.579 | 0.497 | 0.443 | 0.377 | 0.155 | 82 | 5 | 1 | -13 | -64 | 8.48E-09 | 3.60E-07 | >3.25E-5 |
| HCC-2998 | 0.694 | 2.426 | 2.260 | 1.669 | 1.209 | 1.344 | 0.807 | 90 | 56 | 30 | 38 | 6 | 5.60E-08 | >3.25E-5 | >3.25E-5 |
| HCT-116 | 0.311 | 2.169 | 1.397 | 0.480 | 0.453 | 0.463 | 0.311 | 58 | 9 | 8 | 8 | | 4.82E-09 | >3.25E-5 | >3.25E-5 |
| HCT-15 | 0.378 | 2.649 | 2.099 | 0.994 | 0.846 | 0.759 | 0.443 | 76 | 27 | 21 | 17 | 3 | 1.10E-08 | >3.25E-5 | >3.25E-5 |
| HT29 | 0.303 | 1.713 | 1.184 | 0.470 | 0.433 | 0.416 | 0.281 | 62 | 19 | 9 | 8 | -7 | 5.74E-09 | 1.07E-05 | >3.25E-5 |
| KM12 | 0.609 | 2.831 | 2.327 | 0.978 | 0.919 | 0.958 | 0.722 | 77 | 17 | 14 | 16 | 5 | 9.16E-09 | >3.25E-5 | >3.25E-5 |
| SW-620 | 0.358 | 2.229 | 1.463 | 0.864 | 0.952 | 1.058 | 0.624 | 59 | 27 | 32 | 37 | 14 | 6.23E-09 | >3.25E-5 | >3.25E-5 |

FIG. 6D

| | | | | | | | | | | | | |
|---|---|---|---|---|---|---|---|---|---|---|---|---|
| CNS Cancer | | | | | | | | | | | | |
| SF-268 | 0.741 | 2.096 | 1.917 | 1.454 | 1.242 | 1.151 | 0.888 | 87 | 53 | 37 | 30 | 11 | 4.75E-08 | >3.25E-5 |
| SF-295 | 0.977 | 3.039 | 2.761 | 1.739 | 1.242 | 1.168 | 0.788 | 87 | 37 | 13 | 9 | -10 | 1.77E-08 | 9.72E-06 |
| SF-539 | 0.914 | 2.486 | 2.317 | 0.999 | 0.883 | 0.906 | 0.595 | 89 | 5 | -3 | -1 | -35 | 9.55E-09 | 1.33E-07 |
| SNB-19 | 0.847 | 2.472 | 2.235 | 1.690 | 1.482 | 1.412 | 1.071 | 85 | 52 | 39 | 35 | 14 | 4.55E-08 | >3.25E-5 |
| SNB-75 | 0.784 | 1.550 | 1.242 | 0.883 | 0.751 | 0.746 | 0.598 | 60 | 13 | -4 | -5 | -24 | 5.25E-09 | 1.84E-07 |
| U251 | 0.492 | 2.409 | 2.169 | 1.068 | 0.773 | 0.829 | 0.450 | 87 | 30 | 15 | 18 | -9 | 1.46E-08 | 1.52E-05 |
| Melanoma | | | | | | | | | | | | |
| LOX IMVI | 0.406 | 2.300 | 1.724 | 0.983 | 0.870 | 0.784 | 0.355 | 70 | 30 | 24 | 20 | -13 | 1.03E-08 | 1.33E-05 |
| MALME-3M | 0.674 | 1.198 | 1.187 | 0.900 | 0.872 | 0.942 | 0.824 | 98 | 43 | 38 | 51 | 29 | | >3.25E-5 |
| M14 | 0.396 | 1.498 | 1.103 | 0.333 | 0.310 | 0.581 | 0.369 | 64 | -16 | -22 | 17 | -7 | 4.88E-09 | |
| MDA-MB-435 | 0.594 | 2.595 | 0.955 | 0.172 | 0.276 | 0.296 | 0.489 | 20 | -71 | -54 | -50 | -18 | <3.25E-9 | 5.39E-09 |
| SK-MEL-2 | 0.944 | 1.907 | 1.918 | 1.352 | 1.071 | 1.158 | 0.740 | 101 | 42 | 13 | 22 | -22 | 2.41E-08 | 1.04E-05 |
| SK-MEL-28 | 0.736 | 2.242 | 2.229 | 1.508 | 1.516 | 1.554 | 0.811 | 99 | 51 | 52 | 54 | 5 | 3.98E-06 | >3.25E-5 |
| SK-MEL-5 | 0.728 | 2.717 | 2.474 | 0.949 | 0.813 | 0.771 | 0.091 | 88 | 11 | 4 | 2 | -88 | 1.01E-08 | 3.43E-06 |
| UACC-257 | 1.091 | 2.352 | 2.201 | 1.754 | 1.758 | 1.787 | 1.234 | 88 | 53 | 53 | 55 | 11 | 4.27E-06 | >3.25E-5 |
| UACC-62 | 1.034 | 2.904 | 2.707 | 2.024 | 1.970 | 1.721 | 1.042 | 89 | 53 | 50 | 37 | | 3.28E-07 | >3.25E-5 |
| Ovarian Cancer | | | | | | | | | | | | |
| IGROV1 | 0.630 | 2.311 | 1.972 | 1.588 | 1.461 | 1.360 | 1.024 | 80 | 57 | 49 | 43 | 23 | 2.75E-07 | >3.25E-5 |
| OVCAR-3 | 0.486 | 1.621 | 1.509 | 0.594 | 0.540 | 0.502 | 0.375 | 90 | 9 | 5 | 1 | -23 | 1.02E-08 | 3.72E-06 |
| OVCAR-4 | 0.688 | 1.400 | 1.319 | 1.065 | 1.042 | 0.961 | 0.704 | 89 | 53 | 50 | 38 | 2 | 2.66E-07 | >3.25E-5 |
| OVCAR-5 | 0.693 | 1.668 | 1.647 | 1.100 | 1.150 | 0.935 | 0.653 | 98 | 42 | 47 | 25 | -6 | 2.31E-08 | 2.09E-05 |
| OVCAR-8 | 0.588 | 2.411 | 2.279 | 1.311 | 1.142 | 1.131 | 0.706 | 93 | 40 | 30 | 30 | 6 | 2.07E-08 | >3.25E-5 |
| NCI/ADR-RES | 0.663 | 2.212 | 2.195 | 1.624 | 0.857 | 0.751 | 0.635 | 99 | 62 | 13 | 6 | -4 | 5.69E-08 | 1.20E-05 |
| SK-OV-3 | 0.635 | 1.632 | 1.621 | 1.325 | 0.975 | 0.907 | 0.713 | 99 | 69 | 34 | 27 | 8 | 1.15E-07 | >3.25E-5 |
| Renal Cancer | | | | | | | | | | | | |
| 786-0 | 0.700 | 2.273 | 2.040 | 1.311 | 1.071 | 1.016 | 0.637 | 85 | 39 | 24 | 20 | -9 | 1.86E-08 | 1.59E-05 |
| A498 | 1.366 | 1.984 | 1.775 | 1.590 | 1.261 | 1.271 | 1.160 | 66 | 36 | -8 | -7 | -15 | 1.13E-08 | 2.17E-07 |
| ACHN | 0.508 | 2.268 | 2.083 | 1.380 | 1.309 | 1.237 | 0.521 | 90 | 50 | 46 | 41 | 1 | 3.17E-08 | >3.25E-5 |
| CAKI-1 | 1.025 | 3.167 | 2.894 | 2.179 | 1.990 | 1.787 | 1.219 | 87 | 54 | 45 | 36 | 9 | 8.92E-08 | >3.25E-5 |
| RXF 393 | 0.755 | 1.400 | 1.318 | 0.939 | 0.806 | 0.773 | 0.573 | 87 | 29 | 8 | 3 | -24 | 1.40E-08 | 4.12E-06 |

FIG. 6D, Continued

| | | | | | | | | | | |
|---|---|---|---|---|---|---|---|---|---|---|
| SN12C | 0.743 | 2.727 | 2.629 | 1.704 | 1.537 | 1.550 | 1.109 | 95 | 48 | 40 | 41 | 18 | 3.01E-08 | >3.25E-5 |
| TK-10 | 1.103 | 1.906 | 1.843 | 1.656 | 1.466 | 1.410 | 1.057 | 92 | 69 | 45 | 38 | -4 | 2.03E-07 | 2.59E-05 | >3.25E-5 |
| UO-31 | 0.963 | 2.580 | 2.400 | 1.935 | 1.695 | 1.556 | 1.002 | 89 | 60 | 45 | 37 | 2 | 1.56E-07 | >3.25E-5 | >3.25E-5 |
| Prostate Cancer | | | | | | | | | | | |
| PC-3 | 0.765 | 2.305 | 2.101 | 1.148 | 1.127 | 1.103 | 0.796 | 87 | 25 | 24 | 22 | 2 | 1.27E-08 | >3.25E-5 | >3.25E-5 |
| DU-145 | 0.398 | 1.531 | 1.492 | 0.562 | 0.365 | 0.329 | 0.348 | 97 | 14 | -8 | -17 | -13 | 1.20E-08 | 1.41E-07 | >3.25E-5 |
| Breast Cancer | | | | | | | | | | | |
| MCF7 | 0.371 | 2.100 | 1.123 | 0.610 | 0.582 | 0.573 | 0.390 | 43 | 14 | 12 | 12 | 1 | <3.25E-9 | >3.25E-5 | >3.25E-5 |
| MDA-MB-231/ATCC | 0.689 | 1.619 | 1.621 | 1.320 | 1.218 | 1.016 | 0.704 | 100 | 68 | 57 | 35 | 2 | 6.72E-07 | >3.25E-5 | >3.25E-5 |
| HS 578T | 1.018 | 2.075 | 1.678 | 1.292 | 1.138 | 1.093 | 0.843 | 62 | 26 | 11 | 7 | -17 | 7.10E-09 | 6.35E-06 | >3.25E-5 |
| BT-549 | 1.310 | 2.462 | 2.233 | 1.863 | 1.648 | 1.713 | 1.301 | 80 | 48 | 29 | 35 | -1 | 2.81E-08 | 3.10E-05 | >3.25E-5 |
| T-47D | 0.669 | 1.404 | 1.257 | 0.982 | 0.991 | 1.031 | 0.649 | 80 | 43 | 44 | 49 | -3 | 2.06E-08 | 2.85E-05 | >3.25E-5 |
| MDA-MB-468 | 0.923 | 1.962 | 1.718 | 1.184 | 1.026 | 1.047 | 0.861 | 77 | 25 | 10 | 12 | -7 | 1.06E-08 | 1.42E-05 | >3.25E-5 |

FIG. 6D, Continued

National Cancer Institute Development Therapeutics Program
In-Vitro Testing Results NSC: D - 781080 / 1  Experimental ID: 1408NS31  Test Type: 08  Units: Molar
Report Date: September 22, 2014  Test Date: August 11, 2014  QNS:  MC:
COMI: KCDR_9A  Stain Reagent: SRB Dual-Pass Related  SSPL: OZAS Log10 Concentration

| Panel/Cell Line | Time Zero | Ctrl | -8.3 | -7.3 | -6.3 | -5.3 | -4.3 | -8.3 | -7.3 | -6.3 | -5.3 | -4.3 | GI50 | TGI | LC50 |
|---|---|---|---|---|---|---|---|---|---|---|---|---|---|---|---|
| | | | Mean Optical Densities | | | | | Percent Growth | | | | | | | |
| Leukemia | | | | | | | | | | | | | | | | |
| CCRF-CEM | 0.532 | 2.238 | 1.431 | 0.891 | 0.795 | 0.744 | 0.791 | 53 | 21 | 15 | 12 | 15 | 6.09E-09 | >5.00E-5 | >5.00E-5 |
| HL-60(TB) | 0.953 | 2.880 | 1.364 | 0.741 | 0.711 | 0.753 | 0.761 | 21 | -22 | -25 | -21 | -20 | <5.00E-9 | 1.54E-08 | >5.00E-5 |
| K-562 | 0.270 | 1.856 | 0.777 | 0.527 | 0.392 | 0.355 | 0.352 | 32 | 16 | 8 | 5 | 5 | <5.00E-9 | >5.00E-5 | >5.00E-5 |
| MOLT-4 | 0.789 | 2.736 | 1.704 | 1.308 | 1.028 | 0.886 | 0.985 | 47 | 27 | 12 | 5 | 10 | <5.00E-9 | >5.00E-5 | >5.00E-5 |
| RPMI-8226 | 0.955 | 2.628 | 1.238 | 1.162 | 1.203 | 1.137 | 1.045 | 17 | 12 | 15 | 11 | 5 | <5.00E-9 | >5.00E-5 | >5.00E-5 |
| SR | 0.632 | 2.491 | 1.382 | 1.166 | 1.103 | 1.021 | 0.829 | 40 | 29 | 25 | 21 | 11 | <5.00E-9 | >5.00E-5 | >5.00E-5 |
| Non-Small Cell Lung Cancer | | | | | | | | | | | | | | | | |
| A549/ATCC | 0.482 | 2.269 | 1.406 | 1.038 | 0.875 | 0.829 | 0.922 | 52 | 31 | 22 | 19 | 25 | 6.05E-09 | >5.00E-5 | >5.00E-5 |
| EKVX | 0.786 | 1.673 | 1.504 | 1.348 | 1.222 | 1.202 | 1.116 | 81 | 63 | 49 | 47 | 37 | 4.32E-07 | >5.00E-5 | >5.00E-5 |
| HOP-62 | 0.578 | 1.994 | 1.602 | 1.215 | 0.953 | 0.911 | 0.972 | 72 | 45 | 26 | 24 | 28 | 3.27E-08 | >5.00E-5 | >5.00E-5 |
| HOP-92 | 1.431 | 1.827 | 1.591 | 1.557 | 1.484 | 1.506 | 1.400 | 40 | 32 | 13 | 19 | -2 | <5.00E-9 | 3.94E-05 | >5.00E-5 |
| NCI-H226 | 0.545 | 1.702 | 1.541 | 1.270 | 1.235 | 1.170 | 0.943 | 86 | 63 | 60 | 54 | 34 | 7.99E-06 | >5.00E-5 | >5.00E-5 |
| NCI-H23 | 0.675 | 2.436 | 1.578 | 1.190 | 0.977 | 1.009 | 1.125 | 51 | 29 | 17 | 19 | 26 | 5.72E-09 | >5.00E-5 | >5.00E-5 |
| NCI-H322M | 1.153 | 2.685 | 2.106 | 1.687 | 1.445 | 1.477 | 1.674 | 62 | 35 | 19 | 21 | 34 | 1.39E-08 | >5.00E-5 | >5.00E-5 |
| NCI-H460 | 0.417 | 3.113 | 0.872 | 0.756 | 0.686 | 0.681 | 0.644 | 17 | 13 | 10 | 10 | 8 | <5.00E-9 | >5.00E-5 | >5.00E-5 |
| NCI-H522 | 1.063 | 2.694 | 2.234 | 1.645 | 0.915 | 1.005 | 1.164 | 72 | 36 | -14 | -5 | 6 | 2.01E-08 | | >5.00E-5 |
| Colon Cancer | | | | | | | | | | | | | | | | |
| COLO 205 | 0.434 | 1.751 | 0.906 | 0.562 | 0.366 | 0.342 | 0.270 | 36 | 10 | -16 | -21 | -38 | <5.00E-9 | 1.20E-07 | >5.00E-5 |
| HCC-2998 | 0.694 | 2.331 | 1.750 | 1.452 | 0.993 | 1.078 | 1.228 | 64 | 46 | 18 | 23 | 33 | 3.12E-08 | >5.00E-5 | >5.00E-5 |
| HCT-116 | 0.311 | 2.126 | 0.624 | 0.381 | 0.403 | 0.322 | 0.514 | 17 | 4 | 5 | 1 | 11 | <5.00E-9 | >5.00E-5 | >5.00E-5 |
| HCT-15 | 0.378 | 2.584 | 1.356 | 0.978 | 0.686 | 0.612 | 0.706 | 44 | 27 | 14 | 11 | 15 | <5.00E-9 | >5.00E-5 | >5.00E-5 |
| HT29 | 0.303 | 1.718 | 0.616 | 0.455 | 0.414 | 0.406 | 0.360 | 22 | 11 | 8 | 7 | 4 | <5.00E-9 | >5.00E-5 | >5.00E-5 |
| KM12 | 0.609 | 2.849 | 1.301 | 0.908 | 0.815 | 0.877 | 1.117 | 31 | 13 | 9 | 12 | 23 | <5.00E-9 | >5.00E-5 | >5.00E-5 |

FIG. 6E

| | | | | | | | | | | | | |
|---|---|---|---|---|---|---|---|---|---|---|---|---|
| SW-620 | 0.358 | 2.186 | 0.823 | 0.820 | 0.838 | 0.966 | 1.122 | 25 | 25 | 26 | 33 | 42 | <5.00E-9 | >5.00E-5 | >5.00E-5 |
| CNS Cancer | | | | | | | | | | | | |
| SF-268 | 0.741 | 2.162 | 1.715 | 1.457 | 1.107 | 1.044 | 1.030 | 69 | 50 | 26 | 21 | 20 | 5.17E-08 | >5.00E-5 | >5.00E-5 |
| SF-295 | 0.977 | 3.016 | 2.484 | 1.639 | 1.021 | 1.080 | 1.287 | 74 | 32 | 2 | 5 | 15 | 1.89E-08 | >5.00E-5 | >5.00E-5 |
| SF-539 | 0.914 | 2.394 | 1.867 | 1.092 | 0.753 | 0.722 | 0.779 | 64 | 12 | -18 | -21 | -15 | 9.41E-09 | 1.27E-07 | >5.00E-5 |
| SNB-19 | 0.847 | 2.396 | 1.982 | 1.590 | 1.501 | 1.338 | 1.319 | 73 | 48 | 42 | 32 | 30 | 4.15E-08 | >5.00E-5 | >5.00E-5 |
| SNB-75 | 0.784 | 1.555 | 1.115 | 0.853 | 0.638 | 0.555 | 0.598 | 43 | 9 | -19 | -29 | -24 | <5.00E-9 | 1.05E-07 | >5.00E-5 |
| U251 | 0.492 | 2.478 | 1.452 | 1.065 | 0.717 | 0.739 | 0.733 | 48 | 29 | 11 | 12 | 12 | <5.00E-9 | >5.00E-5 | >5.00E-5 |
| Melanoma | | | | | | | | | | | | |
| LOX IMVI | 0.406 | 2.288 | 1.174 | 0.987 | 0.816 | 0.835 | 0.704 | 41 | 31 | 22 | 23 | 16 | <5.00E-9 | >5.00E-5 | >5.00E-5 |
| MALME-3M | 0.674 | 1.166 | 0.998 | 0.910 | 0.853 | 0.867 | 0.937 | 66 | 48 | 36 | 39 | 53 | | >5.00E-5 | >5.00E-5 |
| M14 | 0.396 | 1.494 | 0.602 | 0.294 | 0.260 | 0.549 | 0.599 | 19 | -26 | -34 | 14 | 18 | <5.00E-9 | | >5.00E-5 |
| MDA-MB-435 | 0.594 | 2.616 | 0.224 | 0.158 | 0.219 | 0.247 | 0.465 | -62 | -73 | -63 | -58 | -22 | <5.00E-9 | <5.00E-9 | >5.00E-5 |
| SK-MEL-2 | 0.944 | 1.968 | 1.757 | 1.384 | 1.217 | 1.100 | 1.247 | 79 | 43 | 27 | 15 | 30 | 3.21E-08 | >5.00E-5 | >5.00E-5 |
| SK-MEL-28 | 0.736 | 2.234 | 1.873 | 1.525 | 1.499 | 1.611 | 1.400 | 76 | 53 | 51 | 58 | 44 | 1.98E-05 | >5.00E-5 | >5.00E-5 |
| SK-MEL-5 | 0.728 | 2.873 | 1.457 | 0.970 | 0.875 | 0.755 | 0.653 | 34 | 11 | 7 | 1 | -10 | <5.00E-9 | 6.40E-06 | >5.00E-5 |
| UACC-257 | 1.091 | 2.418 | 2.043 | 1.743 | 1.732 | 1.742 | 1.690 | 72 | 49 | 48 | 49 | 45 | 4.58E-08 | >5.00E-5 | >5.00E-5 |
| UACC-62 | 1.034 | 2.869 | 2.303 | 2.016 | 1.823 | 1.833 | 1.674 | 69 | 54 | 43 | 44 | 35 | 1.08E-07 | >5.00E-5 | >5.00E-5 |
| Ovarian Cancer | | | | | | | | | | | | |
| IGROV1 | 0.630 | 2.316 | 1.613 | 1.506 | 1.407 | 1.218 | 1.123 | 58 | 52 | 46 | 35 | 29 | 1.06E-07 | >5.00E-5 | >5.00E-5 |
| OVCAR-3 | 0.486 | 1.602 | 0.731 | 0.547 | 0.451 | 0.417 | 0.426 | 22 | 5 | -7 | -14 | -12 | <5.00E-9 | 1.35E-07 | >5.00E-5 |
| OVCAR-4 | 0.688 | 1.412 | 1.209 | 1.062 | 0.985 | 0.898 | 0.827 | 72 | 52 | 41 | 29 | 19 | 7.17E-08 | >5.00E-5 | >5.00E-5 |
| OVCAR-5 | 0.693 | 1.694 | 1.574 | 1.214 | 1.026 | 0.965 | 0.867 | 88 | 52 | 33 | 27 | 17 | 6.38E-08 | >5.00E-5 | >5.00E-5 |
| OVCAR-8 | 0.588 | 2.431 | 1.803 | 1.337 | 1.104 | 1.027 | 1.240 | 66 | 41 | 28 | 24 | 35 | 2.13E-08 | >5.00E-5 | >5.00E-5 |
| NCI/ADR-RES | 0.663 | 2.267 | 1.938 | 1.618 | 0.795 | 0.740 | 0.699 | 79 | 60 | 8 | 5 | 2 | 7.67E-08 | >5.00E-5 | >5.00E-5 |
| SK-OV-3 | 0.635 | 1.656 | 1.346 | 1.061 | 0.864 | 0.832 | 0.911 | 70 | 42 | 22 | 19 | 27 | 2.52E-08 | >5.00E-5 | >5.00E-5 |
| Renal Cancer | | | | | | | | | | | | |
| 786-0 | 0.700 | 2.255 | 1.823 | 1.289 | 0.789 | 0.873 | 1.213 | 72 | 38 | 6 | 11 | 33 | 2.22E-08 | >5.00E-5 | >5.00E-5 |
| A498 | 1.366 | 2.008 | 1.637 | 1.506 | 1.255 | 1.324 | 1.320 | 42 | 22 | -8 | -3 | -3 | <5.00E-9 | 2.67E-07 | >5.00E-5 |
| ACHN | 0.508 | 2.226 | 1.833 | 1.472 | 1.386 | 1.185 | 1.149 | 77 | 56 | 51 | 39 | 37 | 6.18E-07 | >5.00E-5 | >5.00E-5 |

FIG. 6E, Continued

| | | | | | | | | | | | |
|---|---|---|---|---|---|---|---|---|---|---|---|
| CAKI-1 | 1.025 | 3.171 | 2.570 | 2.179 | 1.980 | 1.668 | 1.699 | 72 | 54 | 45 | 30 | 31 | 1.28E-07 | >5.00E-5 |
| RXF 393 | 0.755 | 1.316 | 1.098 | 0.870 | 0.694 | 0.689 | 0.724 | 61 | 20 | -8 | -9 | -4 | 9.39E-09 | 2.61E-07 | >5.00E-5 |
| SN12C | 0.743 | 2.700 | 2.216 | 1.646 | 1.399 | 1.346 | 1.353 | 75 | 46 | 33 | 31 | 31 | 3.68E-08 | >5.00E-5 |
| TK-10 | 1.103 | 1.920 | 1.815 | 1.626 | 1.416 | 1.351 | 1.336 | 87 | 64 | 38 | 30 | 28 | 1.75E-07 | >5.00E-5 |
| UO-31 | 0.963 | 2.560 | 2.122 | 1.907 | 1.685 | 1.555 | 1.318 | 73 | 59 | 45 | 37 | 22 | 2.26E-07 | >5.00E-5 |
| Prostate Cancer | | | | | | | | | | | | |
| PC-3 | 0.765 | 2.297 | 1.692 | 1.137 | 1.080 | 1.087 | 1.120 | 61 | 24 | 21 | 21 | 23 | 9.75E-09 | >5.00E-5 |
| DU-145 | 0.398 | 1.595 | 1.303 | 0.608 | 0.335 | 0.294 | 0.362 | 76 | 18 | -16 | -26 | -9 | 1.38E-08 | 1.68E-07 | >5.00E-5 |
| Breast Cancer | | | | | | | | | | | | |
| MCF7 | 0.371 | 2.050 | 0.611 | 0.563 | 0.564 | 0.483 | 0.414 | 14 | 11 | 11 | 7 | 3 | <5.00E-9 | >5.00E-5 |
| MDA-MB-231/ATCC | 0.689 | 1.630 | 1.376 | 1.255 | 0.999 | 0.893 | 0.888 | 73 | 60 | 33 | 22 | 21 | 1.17E-07 | >5.00E-5 |
| HS 578T | 1.018 | 2.021 | 1.531 | 1.264 | 0.997 | 0.904 | 0.874 | 51 | 24 | -2 | -11 | -14 | 5.51E-09 | 4.18E-07 | >5.00E-5 |
| BT-549 | 1.310 | 2.436 | 2.071 | 1.903 | 1.538 | 1.482 | 1.237 | 68 | 53 | 20 | 15 | -6 | 6.03E-08 | 2.70E-05 | >5.00E-5 |
| T-47D | 0.669 | 1.364 | 1.132 | 0.995 | 0.913 | 0.897 | 0.834 | 67 | 47 | 35 | 33 | 24 | 3.49E-08 | >5.00E-5 |
| MDA-MB-468 | 0.923 | 1.983 | 1.491 | 1.254 | 1.086 | 1.033 | 0.997 | 54 | 31 | 15 | 10 | 7 | 7.22E-09 | >5.00E-5 |

FIG. 6E, Continued

National Cancer Institute Development Therapeutics Program
In-Vitro Testing Results NSC: D - 781492 / 1  Experimental ID: 1409NS43  Test Type: 08  Units: Molar
Report Date: September 17, 2014  Test Date: September 2, 2014  QNS:  MC:
COMI: KCDR_6A  Stain Reagent: SRB Dual-Pass Related  SSPL: OZAS Log10 Concentration

| Panel/Cell Line | Time Zero | Ctrl | -8.3 | -7.3 | -6.3 | -5.3 | -4.3 | -8.3 | -7.3 | -6.3 | -5.3 | -4.3 | GI50 | TGI | LC50 |
|---|---|---|---|---|---|---|---|---|---|---|---|---|---|---|---|
| Leukemia | | | Mean Optical Densities | | | | | Percent Growth | | | | | | | |
| CCRF-CEM | 0.640 | 2.915 | 2.866 | 2.874 | 2.857 | 0.966 | 0.912 | 98 | 98 | 97 | 14 | 12 | 4.13E-07 | >1.11E-5 | >1.11E-5 |
| HL-60(TB) | 0.615 | 2.778 | 2.708 | 2.643 | 2.518 | 0.607 | 0.596 | 97 | 94 | 88 | -1 | -3 | 2.96E-07 | 1.07E-06 | >1.11E-5 |
| K-562 | 0.230 | 2.107 | 2.085 | 2.012 | 1.916 | 0.439 | 0.375 | 99 | 95 | 90 | 11 | 8 | 3.56E-07 | >1.11E-5 | >1.11E-5 |
| MOLT-4 | 0.782 | 3.159 | 3.154 | 3.175 | 3.123 | 1.432 | 1.144 | 100 | 101 | 98 | 27 | 15 | 5.33E-07 | >1.11E-5 | >1.11E-5 |
| RPMI-8226 | 0.766 | 2.422 | 2.333 | 2.320 | 2.299 | 0.962 | 0.939 | 95 | 94 | 93 | 12 | 10 | 3.74E-07 | >1.11E-5 | >1.11E-5 |
| Non-Small Cell Lung Cancer | | | | | | | | | | | | | | | |
| A549/ATCC | 0.502 | 2.294 | 2.267 | 2.174 | 2.132 | 1.020 | 0.811 | 99 | 93 | 91 | 29 | 17 | 5.08E-07 | >1.11E-5 | >1.11E-5 |
| EKVX | 0.676 | 1.923 | 1.840 | 1.775 | 1.864 | 1.182 | 0.972 | 93 | 88 | 95 | 41 | 24 | 7.47E-07 | >1.11E-5 | >1.11E-5 |
| HOP-62 | 0.715 | 1.405 | 1.359 | 1.262 | 1.234 | 0.965 | 0.703 | 93 | 79 | 75 | 36 | -2 | 4.90E-07 | 9.98E-06 | >1.11E-5 |
| HOP-92 | 1.280 | 1.660 | 1.561 | 1.566 | 1.638 | 1.478 | 1.337 | 74 | 75 | 94 | 52 | 15 | 1.27E-06 | >1.11E-5 | >1.11E-5 |
| NCI-H226 | 0.773 | 2.046 | 1.964 | 1.947 | 2.035 | 1.463 | 1.393 | 94 | 92 | 99 | 54 | 49 | 6.35E-06 | >1.11E-5 | >1.11E-5 |
| NCI-H23 | 0.450 | 1.385 | 1.392 | 1.456 | 1.323 | 0.738 | 0.680 | 101 | 108 | 93 | 31 | 25 | 5.48E-07 | >1.11E-5 | >1.11E-5 |
| NCI-H322M | 0.752 | 1.790 | 1.746 | 1.759 | 1.706 | 1.154 | 1.053 | 96 | 97 | 92 | 39 | 29 | 6.81E-07 | >1.11E-5 | >1.11E-5 |
| NCI-H460 | 0.308 | 2.895 | 2.898 | 2.888 | 2.394 | 0.571 | 0.429 | 100 | 100 | 81 | 10 | 5 | 3.02E-07 | >1.11E-5 | >1.11E-5 |
| NCI-H522 | 0.828 | 2.258 | 2.128 | 2.157 | 1.925 | 0.380 | 0.289 | 91 | 93 | 77 | -54 | -65 | 1.78E-07 | 4.28E-07 | 1.03E-06 |
| Colon Cancer | | | | | | | | | | | | | | | |
| COLO 205 | 0.454 | 1.772 | 1.758 | 1.630 | 1.585 | 0.382 | 2.400 | 99 | 89 | 86 | -16 | -47 | 2.50E-07 | 7.73E-07 | >1.11E-5 |
| HCC-2998 | 0.488 | 1.665 | 1.577 | 1.569 | 1.426 | 0.632 | 0.468 | 93 | 92 | 80 | 12 | -4 | 3.06E-07 | 6.23E-06 | >1.11E-5 |
| HCT-116 | 0.271 | 2.093 | 2.103 | 1.971 | 1.437 | 0.447 | 0.375 | 101 | 93 | 64 | 10 | 6 | 2.01E-07 | >1.11E-5 | >1.11E-5 |
| HCT-15 | 0.236 | 1.495 | 1.525 | 1.416 | 1.374 | 0.508 | 0.252 | 102 | 94 | 90 | 22 | 1 | 4.29E-07 | >1.11E-5 | >1.11E-5 |
| HT29 | 0.256 | 1.454 | 1.465 | 1.388 | 0.870 | 0.250 | 0.183 | 101 | 95 | 51 | -3 | -29 | 1.17E-07 | 9.96E-07 | >1.11E-5 |
| KM12 | 0.400 | 2.110 | 2.161 | 2.109 | 1.648 | 0.552 | 0.498 | 103 | 100 | 73 | 9 | 6 | 2.54E-07 | >1.11E-5 | >1.11E-5 |
| SW-620 | 0.273 | 2.038 | 2.019 | 1.973 | 1.439 | 0.784 | 0.680 | 99 | 96 | 66 | 29 | 23 | 3.01E-07 | >1.11E-5 | >1.11E-5 |

FIG. 6F

| | | | | | | | | | | |
|---|---|---|---|---|---|---|---|---|---|---|
| CNS Cancer | | | | | | | | | | |
| SF-268 | 0.614 | 2.076 | 1.984 | 1.908 | 1.828 | 1.070 | 0.802 | 94 | 88 | 83 | 31 | 13 | 4.81E-07 | >1.11E-5 |
| SF-295 | 0.541 | 2.383 | 2.306 | 2.164 | 2.144 | 0.633 | 0.477 | 96 | 88 | 87 | 5 | -12 | 3.14E-07 | 2.91E-06 |
| SF-539 | 0.972 | 2.628 | 2.618 | 2.424 | 2.406 | 1.025 | 0.866 | 99 | 88 | 87 | 3 | -11 | 3.05E-07 | 1.86E-06 |
| SNB-19 | 0.559 | 1.913 | 1.865 | 1.903 | 1.818 | 0.984 | 0.839 | 96 | 99 | 93 | 31 | 21 | 5.53E-07 | >1.11E-5 |
| U251 | 0.518 | 2.421 | 2.350 | 2.313 | 2.182 | 0.865 | 0.678 | 96 | 94 | 87 | 18 | 8 | 3.86E-07 | >1.11E-5 |
| Melanoma | | | | | | | | | | |
| LOX IMVI | 0.333 | 2.159 | 2.094 | 2.099 | 1.911 | 0.859 | 0.769 | 96 | 97 | 86 | 29 | 24 | 4.75E-07 | >1.11E-5 |
| MALME-3M | 0.795 | 1.359 | 1.357 | 1.321 | 1.310 | 1.027 | 0.978 | 100 | 93 | 91 | 41 | 32 | 7.36E-07 | >1.11E-5 |
| M14 | 0.356 | 1.656 | 1.611 | 1.495 | 1.325 | 0.384 | 0.313 | 97 | 88 | 75 | 2 | -12 | 2.42E-07 | 1.56E-06 |
| MDA-MB-435 | 0.293 | 1.624 | 1.552 | 1.386 | 0.802 | 0.132 | 0.086 | 95 | 82 | 38 | -55 | -71 | 5.99E-08 | 2.86E-07 |
| SK-MEL-2 | 1.169 | 2.257 | 2.297 | 2.269 | 2.216 | 1.058 | 0.885 | 104 | 101 | 96 | -10 | -24 | 3.03E-07 | 9.02E-07 |
| SK-MEL-28 | 0.607 | 1.973 | 1.950 | 1.864 | 1.827 | 1.280 | 1.125 | 98 | 92 | 89 | 49 | 38 | 1.06E-06 | >1.11E-5 |
| SK-MEL-5 | 0.788 | 3.030 | 2.845 | 2.973 | 2.955 | 0.888 | 0.806 | 92 | 97 | 97 | 4 | 1 | 3.56E-07 | >1.11E-5 |
| UACC-257 | 0.952 | 2.119 | 2.077 | 1.946 | 2.101 | 1.516 | 1.425 | 96 | 85 | 98 | 48 | 41 | 1.03E-06 | >1.11E-5 |
| UACC-62 | 0.890 | 2.749 | 2.684 | 2.610 | 2.568 | 1.404 | 1.267 | 97 | 93 | 90 | 28 | 20 | 4.88E-07 | >1.11E-5 |
| Ovarian Cancer | | | | | | | | | | |
| IGROV1 | 0.594 | 2.382 | 2.345 | 2.319 | 2.137 | 1.370 | 1.127 | 98 | 97 | 86 | 43 | 30 | 7.78E-07 | >1.11E-5 |
| OVCAR-3 | 0.470 | 1.644 | 1.646 | 1.633 | 1.545 | 0.552 | 0.417 | 100 | 99 | 92 | 7 | -11 | 3.44E-07 | 2.66E-06 |
| OVCAR-4 | 1.146 | 2.244 | 2.153 | 2.091 | 2.136 | 1.821 | 1.748 | 92 | 86 | 90 | 61 | 55 | | >1.11E-5 |
| OVCAR-5 | 0.709 | 1.847 | 1.823 | 1.775 | 1.735 | 1.054 | 0.875 | 98 | 94 | 90 | 30 | 15 | 5.19E-07 | >1.11E-5 |
| OVCAR-8 | 0.480 | 1.941 | 1.984 | 1.915 | 2.072 | 0.764 | 0.532 | 103 | 98 | 109 | 19 | 4 | 5.06E-07 | >1.11E-5 |
| NCI/ADR-RES | 0.474 | 1.561 | 1.553 | 1.572 | 1.567 | 1.374 | 0.776 | 99 | 101 | 101 | 83 | 28 | 4.38E-06 | >1.11E-5 |
| SK-OV-3 | 0.782 | 1.835 | 1.828 | 1.729 | 1.694 | 1.027 | 0.930 | 99 | 90 | 87 | 23 | 14 | 4.20E-07 | >1.11E-5 |
| Renal Cancer | | | | | | | | | | |
| 786-0 | 0.577 | 2.089 | 1.983 | 1.838 | 1.889 | 1.106 | 0.779 | 93 | 83 | 87 | 35 | 13 | 5.69E-07 | >1.11E-5 |
| A498 | 1.270 | 2.114 | 1.920 | 1.954 | 1.985 | 1.314 | 1.125 | 77 | 81 | 85 | 5 | -11 | 3.03E-07 | 2.27E-06 |
| ACHN | 0.440 | 1.871 | 1.820 | 1.734 | 1.635 | 0.913 | 0.795 | 96 | 90 | 83 | 33 | 25 | 5.12E-07 | >1.11E-5 |
| CAKI-1 | 1.251 | 3.364 | 3.328 | 3.220 | 3.184 | 2.661 | 2.244 | 98 | 93 | 91 | 67 | 47 | 7.81E-06 | >1.11E-5 |
| RXF 393 | 0.622 | 1.316 | 1.271 | 1.356 | 1.255 | 0.736 | 0.548 | 94 | 106 | 91 | 16 | -12 | 3.95E-07 | 4.21E-06 |
| SN12C | 1.165 | 3.211 | 3.177 | 3.185 | 3.281 | 2.231 | 1.948 | 98 | 99 | 103 | 52 | 38 | 1.57E-06 | >1.11E-5 |
| TK-10 | 0.796 | 1.784 | 1.694 | 1.673 | 1.694 | 1.150 | 0.930 | 91 | 89 | 91 | 36 | 14 | 6.12E-07 | >1.11E-5 |

FIG. 6F, Continued

| | | | | | | | | | | |
|---|---|---|---|---|---|---|---|---|---|---|
| UO-31 | 0.709 | 2.397 | 2.256 | 2.256 | 2.173 | 1.509 | 1.372 | 92 | 87 | 47 | 39 | 9.54E-07 | >1.11E-5 |
| Prostate Cancer | | | | | | | | | | |
| PC-3 | 0.611 | 2.453 | 2.291 | 2.285 | 2.242 | 0.982 | 0.917 | 91 | 91 | 89 | 20 | 17 | 4.06E-07 | >1.11E-5 |
| DU-145 | 0.339 | 1.506 | 1.583 | 1.586 | 1.565 | 0.414 | 0.308 | 107 | 107 | 105 | 6 | -9 | 4.01E-07 | 2.87E-06 >1.11E-5 |
| Breast Cancer | | | | | | | | | | |
| MCF7 | 0.232 | 1.327 | 1.260 | 1.181 | 0.729 | 0.340 | 0.315 | 94 | 87 | 45 | 10 | 8 | 8.59E-08 >1.11E-5 |
| MDA-MB-231/ATCC | 0.732 | 1.671 | 1.687 | 1.704 | 1.704 | 1.248 | 0.901 | 102 | 104 | 104 | 55 | 18 | 1.51E-06 >1.11E-5 |
| HS 578T | 1.208 | 2.361 | 2.268 | 2.208 | 2.201 | 1.451 | 1.030 | 92 | 87 | 86 | 21 | -15 | 3.99E-07 | 4.30E-06 >1.11E-5 |
| BT-549 | 0.991 | 2.175 | 2.124 | 1.966 | 1.963 | 1.419 | 1.081 | 96 | 82 | 82 | 36 | 8 | 5.53E-07 >1.11E-5 |
| T-47D | 0.773 | 1.431 | 1.421 | 1.368 | 1.391 | 1.017 | 0.982 | 98 | 90 | 94 | 37 | 32 | 6.58E-07 >1.11E-5 |
| MDA-MB-468 | 0.780 | 1.360 | 1.346 | 1.360 | 1.321 | 0.696 | 0.644 | 98 | 100 | 93 | -11 | -18 | 2.89E-07 | 8.73E-07 >1.11E-5 |

FIG. 6F, Continued

National Cancer Institute Development Therapeutics Program
In-Vitro Testing Results NSC: D-781078/1  
Experimental ID: 1408NS31  
Test Type: 08  
Units: Molar  
Report Date: September 22, 2014  
Test Date: August 11, 2014  
QNS:  
MC:  
COMI: KCDR_7A  
Stain Reagent: SRB Dual-Pass Related  
SSPL: OZAS Log10 Concentration

| Panel/Cell Line | Time Zero | Ctrl | -8.3 | -7.3 | -6.3 | -5.3 | -4.3 | -8.3 | -7.3 | -6.3 | -5.3 | -4.3 | GI50 | TGI | LC50 |
|---|---|---|---|---|---|---|---|---|---|---|---|---|---|---|---|
| | | | Mean Optical Densities | | | | | Percent Growth | | | | | | | |
| Leukemia | | | | | | | | | | | | | | | |
| CCRF-CEM | 0.532 | 2.189 | 1.544 | 1.123 | 0.794 | 0.783 | 0.737 | 61 | 36 | 16 | 15 | 12 | 1.36E-08 | >5.00E-5 | >5.00E-5 |
| HL-60(TB) | 0.953 | 2.628 | 2.428 | 1.011 | 0.830 | 0.912 | 0.925 | 88 | 3 | -13 | -4 | -3 | 1.41E-08 | 8.14E-08 | >5.00E-5 |
| K-562 | 0.270 | 1.894 | 1.769 | 0.654 | 0.480 | 0.474 | 0.409 | 92 | 24 | 13 | 13 | 9 | 2.07E-08 | >5.00E-5 | >5.00E-5 |
| MOLT-4 | 0.769 | 2.720 | 2.598 | 1.479 | 1.252 | 1.175 | 1.101 | 94 | 36 | 24 | 20 | 16 | 2.83E-08 | >5.00E-5 | >5.00E-5 |
| RPMI-8226 | 0.955 | 2.571 | 2.599 | 1.190 | 1.134 | 1.142 | 1.020 | 102 | 15 | 11 | 12 | 4 | 1.96E-08 | >5.00E-5 | >5.00E-5 |
| SR | 0.620 | 2.508 | 2.435 | 1.305 | 1.193 | 1.262 | 0.735 | 96 | 36 | 30 | 34 | 5 | 2.92E-08 | >5.00E-5 | >5.00E-5 |
| Non-Small Cell Lung Cancer | | | | | | | | | | | | | | | |
| A549/ATCC | 0.482 | 2.197 | 2.217 | 1.216 | 0.974 | 0.917 | 0.997 | 101 | 43 | 29 | 25 | 30 | 3.76E-08 | >5.00E-5 | >5.00E-5 |
| EKVX | 0.786 | 1.601 | 1.481 | 1.347 | 1.202 | 1.145 | 1.065 | 85 | 69 | 51 | 44 | 34 | 7.05E-07 | >5.00E-5 | >5.00E-5 |
| HOP-62 | 0.578 | 1.925 | 1.878 | 1.232 | 1.060 | 0.937 | 1.037 | 96 | 49 | 36 | 27 | 34 | 4.67E-08 | >5.00E-5 | >5.00E-5 |
| HOP-92 | 1.431 | 1.821 | 1.767 | 1.637 | 1.659 | 1.644 | 1.560 | 86 | 53 | 58 | 55 | 33 | 8.19E-06 | >5.00E-5 | >5.00E-5 |
| NCI-H226 | 0.545 | 1.678 | 1.651 | 1.386 | 1.221 | 1.154 | 0.940 | 98 | 74 | 60 | 54 | 35 | 7.87E-06 | >5.00E-5 | >5.00E-5 |
| NCI-H23 | 0.675 | 2.303 | 2.242 | 1.144 | 0.945 | 0.852 | 1.033 | 96 | 29 | 17 | 11 | 22 | 2.42E-08 | >5.00E-5 | >5.00E-5 |
| NCI-H322M | 1.153 | 2.676 | 2.556 | 1.704 | 1.429 | 1.426 | 1.593 | 92 | 36 | 18 | 18 | 29 | 2.83E-08 | >5.00E-5 | >5.00E-5 |
| NCI-H460 | 0.417 | 3.089 | 3.142 | 0.900 | 0.699 | 0.725 | 0.682 | 102 | 18 | 11 | 12 | 10 | 2.08E-08 | >5.00E-5 | >5.00E-5 |
| NCI-H522 | 1.063 | 2.563 | 2.496 | 1.628 | 0.968 | 0.817 | 1.155 | 96 | 38 | -9 | -23 | 6 | 3.06E-08 | | >5.00E-5 |
| Colon Cancer | | | | | | | | | | | | | | | |
| COLO 205 | 0.434 | 1.806 | 1.725 | 0.646 | 0.441 | 0.386 | 0.323 | 94 | 15 | 1 | -11 | -26 | 1.82E-08 | 5.53E-07 | >5.00E-5 |
| HCC-2998 | 0.694 | 1.999 | 1.885 | 1.213 | 0.759 | 0.676 | 0.689 | 91 | 40 | 5 | -3 | -1 | 3.17E-08 | 2.23E-06 | >5.00E-5 |
| HCT-116 | 0.311 | 2.077 | 1.967 | 0.519 | 0.407 | 0.409 | 0.483 | 94 | 12 | 5 | 6 | 10 | 1.71E-08 | >5.00E-5 | >5.00E-5 |
| HCT-15 | 0.378 | 2.447 | 2.243 | 0.975 | 0.723 | 0.545 | 0.599 | 90 | 29 | 17 | 8 | 11 | 2.26E-08 | >5.00E-5 | >5.00E-5 |
| HT29 | 0.303 | 1.557 | 1.534 | 0.466 | 0.398 | 0.393 | 0.346 | 98 | 13 | 8 | 7 | 3 | 1.84E-08 | >5.00E-5 | >5.00E-5 |
| KM12 | 0.609 | 2.834 | 2.634 | 0.971 | 0.806 | 0.906 | 1.019 | 91 | 16 | 9 | 13 | 18 | 1.77E-08 | >5.00E-5 | >5.00E-5 |

FIG. 6G

| | | | | | | | | | | | | |
|---|---|---|---|---|---|---|---|---|---|---|---|---|
| SW-620 | 0.358 | 2.295 | 2.239 | 0.883 | 0.938 | 1.040 | 1.101 | 97 | 27 | 30 | 35 | 38 | 2.36E-08 | >5.00E-5 |
| CNS Cancer | | | | | | | | | | | | | |
| SF-268 | 0.741 | 2.128 | 2.007 | 1.506 | 1.262 | 1.113 | 1.054 | 91 | 55 | 38 | 27 | 23 | 9.79E-08 | >5.00E-5 |
| SF-295 | 0.977 | 2.913 | 2.647 | 1.989 | 1.074 | 0.988 | 1.133 | 86 | 52 | 5 | 1 | 8 | 5.58E-08 | >5.00E-5 |
| SF-539 | 0.914 | 2.554 | 2.209 | 1.550 | 0.808 | 0.684 | 0.680 | 79 | 39 | -12 | -25 | -26 | 2.62E-08 | >5.00E-5 |
| SNB-19 | 0.847 | 2.392 | 2.345 | 1.866 | 1.546 | 1.375 | 1.428 | 97 | 66 | 45 | 34 | 38 | 2.94E-07 | >5.00E-5 |
| SNB-75 | 0.784 | 1.472 | 1.222 | 0.969 | 0.674 | 0.615 | 0.611 | 64 | 27 | -14 | -22 | -22 | 1.17E-08 | 2.26E-07 |
| U251 | 0.492 | 2.324 | 2.312 | 1.261 | 0.812 | 0.738 | 0.784 | 99 | 42 | 17 | 13 | 16 | 3.62E-08 | >5.00E-5 |
| Melanoma | | | | | | | | | | | | | |
| LOX IMVI | 0.406 | 2.331 | 2.184 | 0.958 | 0.778 | 0.695 | 0.724 | 92 | 29 | 19 | 15 | 16 | 2.31E-08 | >5.00E-5 |
| MALME-3M | 0.674 | 1.162 | 1.099 | 0.941 | 0.810 | 0.879 | 0.957 | 87 | 55 | 28 | 42 | 58 | | >5.00E-5 |
| M14 | 0.396 | 1.480 | 1.471 | 0.540 | 0.263 | 0.379 | 0.628 | 99 | 13 | -34 | -4 | 21 | 1.87E-08 | >5.00E-5 |
| MDA-MB-435 | 0.594 | 2.513 | 2.200 | 0.193 | 0.088 | 0.188 | 0.466 | 84 | -68 | -85 | -68 | -22 | 8.35E-09 | 1.79E-08 |
| SK-MEL-2 | 0.944 | 1.789 | 1.802 | 1.331 | 1.084 | 1.104 | 1.252 | 102 | 46 | 17 | 19 | 36 | 4.19E-08 | >5.00E-5 |
| SK-MEL-28 | 0.736 | 2.201 | 2.108 | 1.726 | 1.469 | 1.457 | 1.287 | 94 | 68 | 50 | 49 | 38 | 5.36E-07 | >5.00E-5 |
| SK-MEL-5 | 0.728 | 2.759 | 2.735 | 0.949 | 0.616 | 0.639 | 0.706 | 99 | 11 | -15 | -12 | -3 | 1.80E-08 | 1.29E-07 |
| UACC-257 | 1.091 | 2.320 | 2.341 | 1.896 | 1.723 | 1.765 | 1.947 | 102 | 65 | 51 | 55 | 70 | >5.00E-5 | >5.00E-5 |
| UACC-62 | 1.034 | 2.909 | 2.915 | 2.125 | 1.939 | 1.754 | 1.762 | 100 | 58 | 48 | 38 | 39 | 3.33E-07 | >5.00E-5 |
| Ovarian Cancer | | | | | | | | | | | | | |
| IGROV1 | 0.630 | 2.283 | 2.111 | 1.433 | 1.370 | 1.253 | 1.227 | 90 | 49 | 45 | 38 | 36 | 4.61E-08 | >5.00E-5 |
| OVCAR-3 | 0.486 | 1.583 | 1.587 | 0.577 | 0.472 | 0.475 | 0.418 | 100 | 8 | -3 | -2 | -14 | 1.76E-08 | 2.76E-07 |
| OVCAR-4 | 0.688 | 1.397 | 1.299 | 1.117 | 1.053 | 0.962 | 0.890 | 86 | 60 | 51 | 39 | 28 | 6.44E-07 | >5.00E-5 |
| OVCAR-5 | 0.693 | 1.694 | 1.469 | 1.228 | 1.009 | 0.899 | 0.208 | 77 | 53 | 32 | 21 | 11 | 7.18E-08 | >5.00E-5 |
| OVCAR-8 | 0.588 | 2.348 | 2.419 | 1.383 | 1.059 | 0.979 | 1.126 | 104 | 45 | 27 | 22 | 31 | 4.14E-08 | >5.00E-5 |
| NCI/ADR-RES | 0.663 | 2.187 | 2.213 | 1.529 | 0.557 | 0.429 | 0.472 | 102 | 57 | -16 | -35 | -29 | 6.20E-08 | 3.01E-07 |
| SK-OV-3 | 0.635 | 1.630 | 1.627 | 1.368 | 0.974 | 0.955 | 0.971 | 100 | 74 | 34 | 32 | 34 | 1.98E-07 | >5.00E-5 |
| Renal Cancer | | | | | | | | | | | | | |
| 786-0 | 0.700 | 2.228 | 2.113 | 1.631 | 1.138 | 0.951 | 1.122 | 92 | 61 | 29 | 16 | 28 | 1.09E-07 | >5.00E-5 |
| A498 | 1.366 | 2.025 | 1.853 | 1.741 | 1.520 | 1.344 | 1.449 | 74 | 57 | 23 | -2 | 13 | 8.02E-08 | >5.00E-5 |
| ACHN | 0.508 | 2.097 | 2.042 | 1.486 | 1.183 | 1.075 | 1.075 | 97 | 62 | 42 | 36 | 36 | 2.01E-07 | >5.00E-5 |

FIG. 6G, Continued

| | | | | | | | | | | | | | |
|---|---|---|---|---|---|---|---|---|---|---|---|---|---|
| CAKI-1 | 1.025 | 3.114 | 2.820 | 2.242 | 1.790 | 1.678 | 1.757 | 86 | 58 | 37 | 31 | 35 | 1.20E-07 | >5.00E-5 |
| RXF 393 | 0.755 | 1.370 | 1.360 | 0.982 | 0.742 | 0.679 | 0.697 | 98 | 37 | -2 | -10 | -8 | 3.06E-08 | 4.51E-07 |
| SN12C | 0.743 | 2.714 | 2.712 | 1.763 | 1.495 | 1.441 | 1.429 | 100 | 52 | 38 | 35 | 35 | 6.74E-08 | >5.00E-5 |
| TK-10 | 1.103 | 1.888 | 1.846 | 1.626 | 1.440 | 1.364 | 1.331 | 95 | 67 | 43 | 33 | 29 | 2.53E-07 | >5.00E-5 |
| UO-31 | 0.963 | 2.490 | 2.260 | 1.894 | 1.600 | 1.527 | 1.269 | 85 | 61 | 42 | 37 | 20 | 1.85E-07 | >5.00E-5 |
| Prostate Cancer | | | | | | | | | | | | | | |
| PC-3 | 0.765 | 2.327 | 2.157 | 1.301 | 1.166 | 1.221 | 1.185 | 89 | 34 | 26 | 29 | 27 | 2.58E-08 | >5.00E-5 |
| DU-145 | 0.398 | 1.573 | 1.554 | 0.742 | 0.365 | 0.319 | 0.272 | 98 | 29 | -8 | -20 | -32 | 2.51E-08 | 3.01E-07 |
| Breast Cancer | | | | | | | | | | | | | | |
| MCF7 | 0.371 | 1.989 | 1.640 | 0.608 | 0.558 | 0.501 | 0.509 | 78 | 15 | 12 | 8 | 9 | 1.40E-08 | >5.00E-5 |
| MDA-MB-231/ATCC | 0.689 | 1.609 | 1.661 | 1.315 | 1.059 | 0.976 | 0.767 | 106 | 68 | 40 | 31 | 8 | 2.22E-07 | >5.00E-5 |
| HS 578T | 1.018 | 2.052 | 1.851 | 1.488 | 1.211 | 1.021 | 0.951 | 81 | 45 | 19 | | -7 | 3.72E-08 | 5.51E-06 |
| BT-549 | 1.310 | 2.471 | 2.388 | 2.064 | 1.666 | 1.675 | 1.586 | 93 | 65 | 31 | 31 | 24 | 1.36E-07 | >5.00E-5 |
| T-47D | 0.669 | 1.395 | 1.336 | 1.061 | 0.987 | 1.010 | 0.943 | 92 | 54 | 44 | 47 | 38 | 1.23E-07 | >5.00E-5 |
| MDA-MB-468 | 0.923 | 1.892 | 1.842 | 1.143 | 0.781 | 0.773 | 0.848 | 95 | 23 | -15 | -16 | -8 | 2.09E-08 | 1.97E-07 |

FIG. 6G, Continued

EPOTHILONE ANALOGS, METHODS OF SYNTHESIS, METHODS OF TREATMENT, AND DRUG CONJUGATES THEREOF

The present application is a national phase application under 35 U.S.C. § 371 of International Application No. PCT/US2016/057093 filed on Oct. 14, 2016 and claims the benefit of priority to U.S. Provisional Application Ser. No. 62/242,702 filed on Oct. 16, 2015, the entire contents of which is incorporated herein by reference.

The development of this disclosure was funded in part by the Welch Foundation under Grant No. C-1819.

BACKGROUND

1. Field

This disclosure relates to the fields of medicine, pharmacology, chemistry, and oncology. In particular, new compounds, compositions, methods of treatment, and methods of synthesis relating to analogs of epothilone are disclosed.

2. Related Art

The discovery of epothilones A and B (1, FIG. 1) stimulated intense research activities in chemistry, biology, and medicine, culminating in numerous total syntheses of these naturally occurring molecules and their analogues, as well as the development of several drug candidates (Altmann, et al., 2004; Höfle, et al., 1996; Nicolaou, et al., 1997a; Nicolaou, et al., 1997b; Meng, et al., 1997; Schinzer, et al, 1998; Sinha, et al., 1998; Mulzer, et al., 1998; May and Grieco, 1999; White, et al., 1999; Sawada, et al., 2000; Bode and Carreira, 2001; Martin and Thomas, 2001; Taylor and Chen, 2001; Valluri, et al., 2001; Ermolenko and Potier, 2002; Keck, et al., 2008; Wang, et al., 2012). Compounds, such as Ixempra® (2, ixabepilone, FIG. 1), have received approval by the FDA but toxicity issues has limited the compound's usefulness. One way to modulate the activity of the compounds is to use the compounds as a payload conjugated to a cell targeting moiety such as an antibody-drug conjugates (ADCs) (3). By targeting the cytotoxic compound to specific locations these conjugates reduces the negative side effects experienced when the payload alone is administered. Unfortunately, current potent epothilone analogs lack side chains which are amenable to conjugation to these complexes. Therefore the introduction of a suitable side chain which allows for conjugation to a cell targeting agent without negatively compromising biological activity such as cytotoxicity and pharmacokinetics is needed.

SUMMARY

The present disclosure provides compounds of the formula:

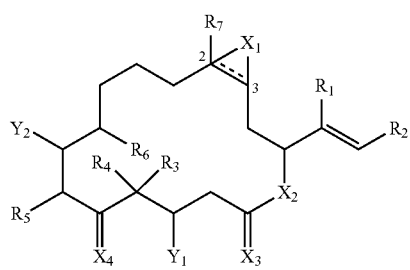

(I)

wherein:
$X_1$ is absent, —O— or —$NR_a$—; wherein
$R_a$ is hydrogen or alkyl$_{(C≤8)}$, cycloalkyl$_{(C≤8)}$, -alkanediyl$_{(C≤6)}$-cycloalkyl$_{(C≤8)}$, or a substituted version of either of these groups;
provided that when $X_1$ is absent, that the atoms to which it is attached are a part of a double bond; and provided that when the atoms to which it is attached are a part of a double bond, then $X_1$ is absent;
$X_2$, $X_3$, and $X_4$ are each independently —O— or —$NR_b$—; wherein
$R_b$ is hydrogen or alkyl$_{(C≤8)}$, cycloalkyl$_{(C≤8)}$, -alkanediyl$_{(C≤6)}$-cycloalkyl$_{(C≤8)}$, aralkyl$_{(C≤8)}$, or a substituted version of either of these groups;
$Y_1$ and $Y_2$ are each independently amino, hydroxy, or alkoxy$_{(C≤8)}$, aralkoxy$_{(C≤8)}$, acyloxy$_{(C≤8)}$, alkylamino$_{(C≤8)}$, dialkylamino$_{(C≤8)}$, amido$_{(C≤8)}$, or a substituted version of any of these groups, or —$OR_c$, wherein:
$R_c$ is a hydroxy protecting group;
$R_1$, $R_3$, $R_4$, $R_5$, $R_6$ and $R_7$ are each independently hydrogen or alkyl$_{(C≤12)}$, cycloalkyl$_{(C≤12)}$, alkenyl$_{(C≤12)}$, alkynyl$_{(C≤12)}$, aryl$_{(C≤12)}$, or a substituted version of any of these groups; and
$R_2$ is heteroaryl$_{(C≤12)}$, -heteroarenediyl$_{(C≤8)}$-$R_d$, or a substituted version of either of these groups; wherein:
$R_d$ is alkyl$_{(C≤12)}$, aryl$_{(C≤12)}$, aralkyl$_{(C≤12)}$, heteroaryl$_{(C≤12)}$, heteroaralkyl$_{(C≤12)}$, or a substituted version of either of these groups;
provided that $R_2$ is not 2-methyl-thiazolyl, 2-hydroxymethyl-thiazolyl, N-2-methyl-3-methylthiopyrazolyl, or 2-methylthio-thiazolyl;
or a pharmaceutically acceptable salt thereof.

In some embodiments, the compounds are further defined as:

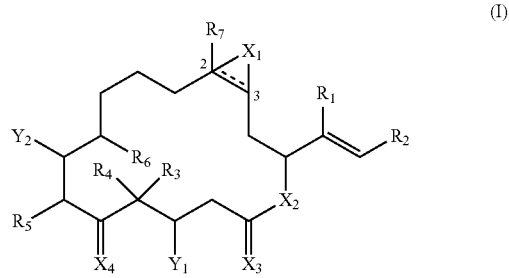

(I)

wherein:
$X_1$ is absent, —O— or —$NR_a$—; wherein
$R_a$ is hydrogen or alkyl$_{(C≤8)}$, cycloalkyl$_{(C≤8)}$, -alkanediyl$_{(C≤6)}$-cycloalkyl$_{(C≤8)}$, or a substituted version of either of these groups;
provided that when $X_1$ is absent, that the atoms to which it is attached are a part of a double bond; and provided that when the atoms to which it is attached are a part of a double bond, then $X_1$ is absent;
$X_2$, $X_3$, and $X_4$ are each independently —O— or —$NR_b$—; wherein
$R_b$ is hydrogen or alkyl$_{(C≤8)}$, cycloalkyl$_{(C≤8)}$, -alkanediyl$_{(C≤6)}$-cycloalkyl$_{(C≤8)}$, aralkyl$_{(C≤8)}$, or a substituted version of either of these groups;
$Y_1$ and $Y_2$ are each independently amino, hydroxy, or alkoxy$_{(C≤8)}$, aralkoxy$_{(C≤8)}$, acyloxy$_{(C≤8)}$, alkylamino$_{(C≤8)}$, dialkylamino$_{(C≤8)}$, amido$_{(C≤8)}$, or a substituted version of any of these groups, or —$OR_c$, wherein:
  $R_c$ is a hydroxy protecting group;
  $R_1$, $R_3$, $R_4$, $R_5$, $R_6$ and $R_7$ are each independently hydrogen or alkyl$_{(C\leq12)}$, cycloalkyl$_{(C\leq12)}$, alkenyl$_{(C\leq12)}$, alkynyl$_{(C\leq12)}$, aryl$_{(C\leq12)}$, or a substituted version of any of these groups; and
  $R_2$ is heteroaryl$_{(C\leq12)}$, -heteroarenediyl$_{(C\leq8)}$-$R_d$, or a substituted version of either of these groups; wherein:
    $R_d$ is alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, or a substituted version of either of these groups;
  provided that $R_2$ is not 2-methyl-thiazolyl, 2-hydroxymethyl-thiazolyl, N-2-methyl-3-methylthiopyrazolyl, or 2-methylthio-thiazolyl;
or a pharmaceutically acceptable salt thereof.

In some embodiments, the compounds are further defined as:

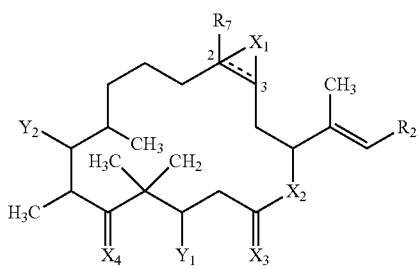

(II)

wherein:
  $X_1$ is absent, —O— or —NR$_a$—; wherein
    $R_a$ is hydrogen or alkyl$_{(C\leq8)}$, cycloalkyl$_{(C\leq8)}$, -alkanediyl$_{(C\leq6)}$-cycloalkyl$_{(C\leq8)}$, or a substituted version of either of these groups;
  provided that when $X_1$ is absent, that the atoms to which it is attached are a part of a double bond; and provided that when the atoms to which it is attached are a part of a double bond, then $X_1$ is absent;
  $X_2$, $X_3$, and $X_4$ are each independently —O— or —NR$_b$—; wherein
    $R_b$ is hydrogen or alkyl$_{(C\leq8)}$, cycloalkyl$_{(C\leq8)}$, -alkanediyl$_{(C\leq6)}$-cycloalkyl$_{(C\leq8)}$, aralkyl$_{(C\leq8)}$, or a substituted version of either of these groups;
  $Y_1$ and $Y_2$ are each independently amino, hydroxy, or alkoxy$_{(C\leq8)}$, aralkoxy$_{(C\leq8)}$, acyloxy$_{(C\leq8)}$, alkylamino$_{(C\leq8)}$, dialkylamino$_{(C\leq8)}$, amido$_{(C\leq8)}$, or a substituted version of any of these groups, or —OR$_c$, wherein:
    $R_c$ is a hydroxy protecting group;
  $R_7$ is hydrogen or alkyl$_{(C\leq12)}$, cycloalkyl$_{(C\leq12)}$, alkenyl$_{(C\leq12)}$, alkynyl$_{(C\leq12)}$, aryl$_{(C\leq12)}$, or a substituted version of any of these groups; and
  $R_2$ is heteroaryl$_{(C\leq12)}$, -heteroarenediyl$_{(C\leq8)}$-$R_d$, or a substituted version of either of these groups; wherein:
    $R_d$ is alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, or a substituted version of either of these groups;
  provided that $R_2$ is not 2-methyl-thiazolyl, 2-hydroxymethyl-thiazolyl, N-2-methyl-3-methylthiopyrazolyl, or 2-methylthio-thiazolyl;
or a pharmaceutically acceptable salt thereof. In some embodiments, the compounds are further defined as:

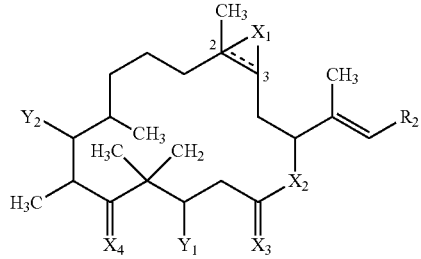

(III)

wherein:
  $X_1$ is absent, —O— or —NR$_a$—; wherein
    $R_a$ is hydrogen or alkyl$_{(C\leq8)}$, cycloalkyl$_{(C\leq8)}$, -alkanediyl$_{(C\leq6)}$-cycloalkyl$_{(C\leq8)}$, or a substituted version of either of these groups;
  provided that when $X_1$ is absent, that the atoms to which it is attached are a part of a double bond; and provided that when the atoms to which it is attached are a part of a double bond, then $X_1$ is absent;
  $X_2$, $X_3$, and $X_4$ are each independently —O— or —NR$_b$—; wherein
    $R_b$ is hydrogen or alkyl$_{(C\leq8)}$, cycloalkyl$_{(C\leq8)}$, -alkanediyl$_{(C\leq6)}$-cycloalkyl$_{(C\leq8)}$, aralkyl$_{(C\leq8)}$, or a substituted version of either of these groups;
  $Y_1$ and $Y_2$ are each independently amino, hydroxy, or alkoxy$_{(C\leq8)}$, aralkoxy$_{(C\leq8)}$, acyloxy$_{(C\leq8)}$, alkylamino$_{(C\leq8)}$, dialkylamino$_{(C\leq8)}$, amido$_{(C\leq8)}$, or a substituted version of any of these groups, or —OR$_c$, wherein:
    $R_c$ is a hydroxy protecting group; and
  $R_2$ is heteroaryl$_{(C\leq12)}$, -heteroarenediyl$_{(C\leq8)}$-$R_d$, or a substituted version of either of these groups; wherein:
    $R_d$ is alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, or a substituted version of either of these groups;
  provided that $R_2$ is not 2-methyl-thiazolyl, 2-hydroxymethyl-thiazolyl, N-2-methyl-3-methylthiopyrazolyl, or 2-methylthio-thiazolyl;
or a pharmaceutically acceptable salt thereof. In some embodiments, the compounds are further defined as:

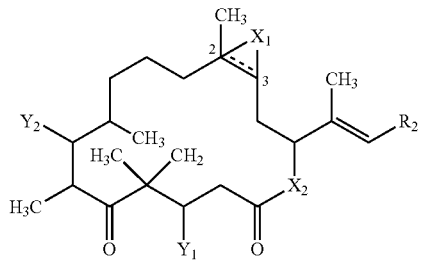

(IV)

wherein:
  $X_1$ is absent, —O— or —NR$_a$—; wherein
    $R_a$ is hydrogen or alkyl$_{(C\leq8)}$, cycloalkyl$_{(C\leq8)}$, -alkanediyl$_{(C\leq6)}$-cycloalkyl$_{(C\leq8)}$, or a substituted version of either of these groups;
  provided that when $X_1$ is absent, that the atoms to which it is attached are a part of a double bond; and provided that when the atoms to which it is attached are a part of a double bond, then $X_1$ is absent;

$X_2$ is —O— or —$NR_b$—; wherein $R_b$ is hydrogen or alkyl$_{(C \leq 8)}$, cycloalkyl$_{(C \leq 8)}$, -alkanediyl$_{(C \leq 6)}$-cycloalkyl$_{(C \leq 8)}$, aralkyl$_{(C \leq 8)}$, or a substituted version of either of these groups;

$Y_1$ and $Y_2$ are each independently amino, hydroxy, or alkoxy$_{(C \leq 8)}$, aralkoxy$_{(C \leq 8)}$, acyloxy$_{(C \leq 8)}$, alkylamino$_{(C \leq 8)}$, dialkylamino$_{(C \leq 8)}$, amido$_{(C \leq 8)}$, or a substituted version of any of these groups, or —$OR_c$, wherein:

$R_c$ is a hydroxy protecting group; and $R_2$ is heteroaryl$_{(C \leq 12)}$, -heteroarenediyl$_{(C \leq 8)}$-$R_d$, or a substituted version of either of these groups; wherein:

$R_d$ is alkyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, or a substituted version of either of these groups;

provided that $R_2$ is not 2-methyl-thiazolyl, 2-hydroxymethyl-thiazolyl, N-2-methyl-3-methylthiopyrazolyl, or 2-methylthio-thiazolyl;

or a pharmaceutically acceptable salt thereof. In some embodiments, the compounds are further defined as:

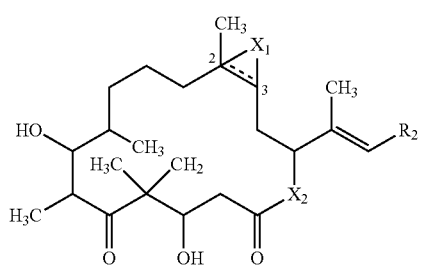

(V)

wherein:

$X_1$ is absent, —O— or —$NR_a$—; wherein $R_a$ is hydrogen or alkyl$_{(C \leq 8)}$, cycloalkyl$_{(C \leq 8)}$, -alkanediyl$_{(C \leq 6)}$-cycloalkyl$_{(C \leq 8)}$, or a substituted version of either of these groups;

provided that when $X_1$ is absent, that the atoms to which it is attached are a part of a double bond; and provided that when the atoms to which it is attached are a part of a double bond, then $X_1$ is absent;

$X_2$ is —O— or —$NR_b$—; wherein $R_b$ is hydrogen or alkyl$_{(C \leq 8)}$, cycloalkyl$_{(C \leq 8)}$, -alkanediyl$_{(C \leq 6)}$-cycloalkyl$_{(C \leq 8)}$, aralkyl$_{(C \leq 8)}$, or a substituted version of either of these groups; and $R_2$ is heteroaryl$_{(C \leq 12)}$, -heteroarenediyl$_{(C \leq 12)}$-$R_d$, or a substituted version of either of these groups; wherein:

$R_d$ is alkyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, or a substituted version of either of these groups;

provided that $R_2$ is not 2-methyl-thiazolyl, 2-hydroxymethyl-thiazolyl, N-2-methyl-3-methylthiopyrazolyl, or 2-methylthio-thiazolyl;

or a pharmaceutically acceptable salt thereof. In some embodiments, the compounds are further defined as:

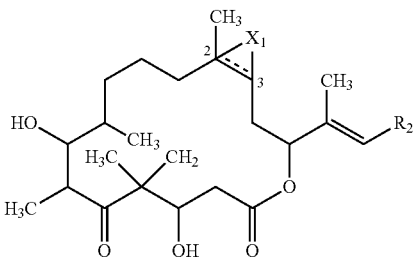

(VI)

wherein:

$X_1$ is absent, —O— or —$NR_a$—; wherein $R_a$ is hydrogen or alkyl$_{(C \leq 8)}$, cycloalkyl$_{(C \leq 8)}$, -alkanediyl$_{(C \leq 6)}$-cycloalkyl$_{(C \leq 8)}$, or a substituted version of either of these groups;

provided that when $X_1$ is absent, that the atoms to which it is attached are a part of a double bond; and provided that when the atoms to which it is attached are a part of a double bond, then $X_1$ is absent;

$R_2$ is heteroaryl$_{(C \leq 12)}$, -heteroarenediyl$_{(C \leq 8)}$-$R_d$, or a substituted version of either of these groups; wherein:

$R_d$ is alkyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, or a substituted version of either of these groups;

provided that $R_2$ is not 2-methyl-thiazolyl, 2-hydroxymethyl-thiazolyl, N-2-methyl-3-methylthiopyrazolyl, or 2-methylthio-thiazolyl;

or a pharmaceutically acceptable salt thereof. In some embodiments, the compounds are further defined as:

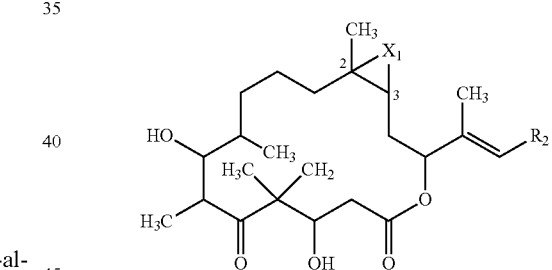

(VII)

wherein:

$X_1$ is —O— or —$NR_a$—; wherein $R_a$ is hydrogen or alkyl$_{(C \leq 8)}$, cycloalkyl$_{(C \leq 8)}$, -alkanediyl$_{(C \leq 6)}$-cycloalkyl$_{(C \leq 8)}$, or a substituted version of either of these groups;

$R_2$ is heteroaryl$_{(C \leq 12)}$, -heteroarenediyl$_{(C \leq 8)}$-$R_d$, or a substituted version of either of these groups; wherein:

$R_d$ is alkyl$_{(C \leq 12)}$, aryl$_{(C \leq 12)}$, or a substituted version of either of these groups;

provided that $R_2$ is not 2-methyl-thiazolyl, 2-hydroxymethyl-thiazolyl, N-2-methyl-3-methylthiopyrazolyl, or 2-methylthio-thiazolyl;

or a pharmaceutically acceptable salt thereof.

In some embodiments, atoms 2 and 3 are joined by a single bond. In other embodiments, atoms 2 and 3 are joined by a double bond. In some embodiments, $R_1$ is alkyl$_{(C \leq 8)}$ or substituted alkyl$_{(C \leq 8)}$. In some embodiments, $R_1$ is alkyl$_{(C \leq 8)}$, for example, $R_1$ is methyl. In some embodiments, $R_3$ is alkyl$_{(C \leq 8)}$ or substituted alkyl$_{(C \leq 8)}$. In some embodiments, $R_3$ is alkyl$_{(C \leq 8)}$, for example, $R_3$ is methyl. In some embodiments, $R_4$ is alkyl$_{(C \leq 8)}$ or substituted alkyl$_{(C \leq 8)}$. In some embodiments, $R_4$ is alkyl$_{(C \leq 8)}$, for example, $R_4$ is methyl. In some embodiments, $R_5$ is alkyl$_{(C \leq 8)}$ or substituted alkyl$_{(C \leq 8)}$. In some embodiments, $R_5$ is alkyl$_{(C \leq 8)}$, for example, $R_5$ is methyl. In some embodiments, $R_6$ is alkyl$_{(C \leq 8)}$ or substituted alkyl$_{(C \leq 8)}$. In some embodiments, $R_6$ is alkyl$_{(C \leq 8)}$, for example, $R_6$ is methyl. In some embodiments, $R_7$ is alkyl$_{(C \leq 8)}$ or substituted alkyl$_{(C \leq 8)}$. In some embodiments, $R_7$ is alkyl$_{(C \leq 8)}$, for example, $R_7$ is methyl.

In some embodiments, $Y_1$ is hydroxy. In some embodiments, $Y_2$ is hydroxy. In some embodiments, $X_3$ is O. In some embodiments, $X_4$ is O. In some embodiments, $X_2$ is O. In other embodiments, $X_2$ is $NR_b$, wherein $R_b$ is hydrogen, alkyl$_{(C \leq 8)}$, or substituted alkyl$_{(C \leq 8)}$. In some embodiments, $R_b$ is hydrogen.

In some embodiments, $X_1$ is O. In other embodiments, $X_1$ is $NR_a$, wherein: $R_a$ is hydrogen or alkyl$_{(C \leq 8)}$, cycloalkyl$_{(C \leq 8)}$, -alkanediyl$_{(C \leq 6)}$-cycloalkyl$_{(C \leq 8)}$, or a substituted version of either of these groups. In some embodiments, $R_a$ is hydrogen. In other embodiments, $R_a$ is alkyl$_{(C \leq 8)}$ or substituted alkyl$_{(C \leq 8)}$. In some embodiments, $R_a$ is alkyl$_{(C \leq 8)}$, for example, $R_a$ is methyl or ethyl. In other embodiments, $R_a$ is substituted alkyl$_{(C \leq 8)}$, for example, $R_a$ is 2-hydroxyethyl, 2-aminoethyl, or 2-azidoethyl. In other embodiments, $R_a$ is -alkanediyl$_{(C \leq 6)}$-cycloalkyl$_{(C \leq 8)}$ or substituted-alkanediyl$_{(C \leq 6)}$-cycloalkyl$_{(C \leq 8)}$. In some embodiments, $R_a$ is -alkanediyl$_{(C \leq 6)}$-cycloalkyl$_{(C \leq 8)}$, for example, $R_a$ is cyclopropylmethyl. In some embodiments, $R_2$ is 2-methylthiazolyl, 2-(2-hydroxyethyl)thiazolyl, pyridinyl, benzothiazolyl, 2-(aminomethyl)-thiazolyl, 2-(2-aminoethyl)thiazolyl, 2-methylthiothiazolyl, or (3-methylthio)-pyrazolyl. In some embodiments, $R_2$ is -heteroarenediyl$_{(C \leq 8)}$-$R_d$, or a substituted version thereof; wherein: $R_d$ is alkyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, or a substituted version of either of these groups In some embodiments, $R_d$ is alkyl$_{(C \leq 12)}$, aryl$_{(C \leq 12)}$, or a substituted version of either of these groups. In some embodiments, the heteroarenediyl$_{(C \leq 8)}$ of $R_2$ is pyrazolyl, 3-trifluoromethylpyrazolyl, or 3-methylthiopyrazolyl. In some embodiments, $R_d$ is alkyl$_{(C \leq 12)}$ or substituted alkyl$_{(C \leq 12)}$. In some embodiments, $R_d$ is substituted alkyl$_{(C \leq 12)}$, for example, $R_d$ is 2-aminoethyl. In some embodiments, $R_d$ is a substituted alkyl$_{(C \leq 12)}$ with a protected amine group, for example, the protected amine group is a tert-butyloxycarbonyl protected amine group or a 2-(trimethylsilyl)ethyl carbonate protected amine group. In some embodiments, $R_d$ is —CH$_2$CH$_2$NHBoc or —CH$_2$CH$_2$NHTeoc. In other embodiments, $R_d$ is aryl$_{(C \leq 12)}$ or substituted aryl$_{(C \leq 12)}$. In some embodiments, $R_d$ is substituted aryl$_{(C \leq 12)}$, for example, $R_d$ is 2-aminophenyl, 4-aminophenyl, 4-amino-3-fluorophenyl, 4-amino-3-trifluoromethylphenyl, 4-amino-2-fluorophenyl, or 4-amino-2-trifluoromethylphenyl.

In some embodiments, the compound is further defined as:

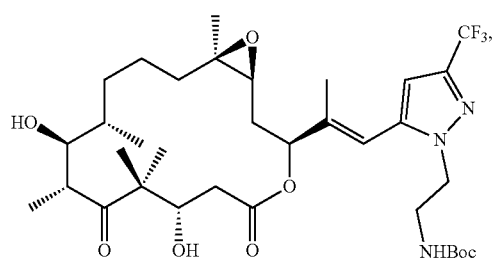

-continued

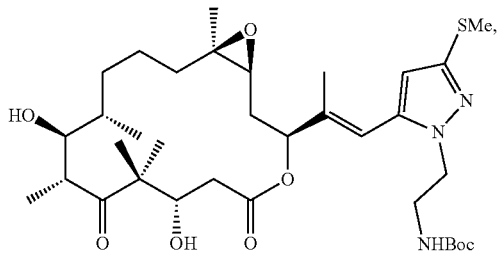

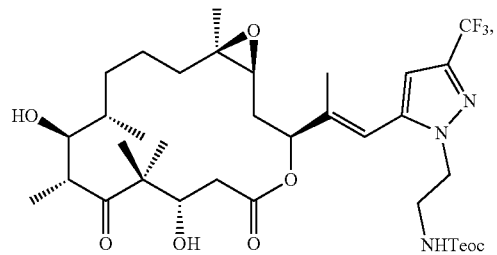

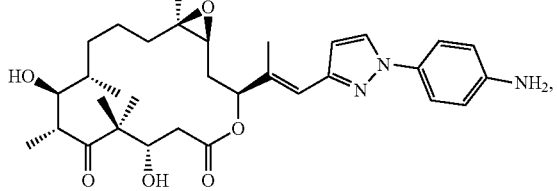

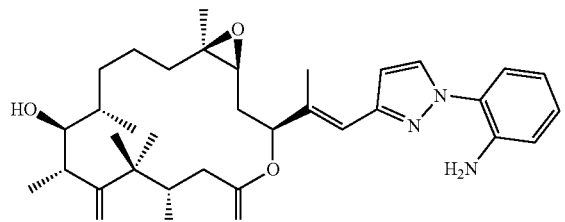

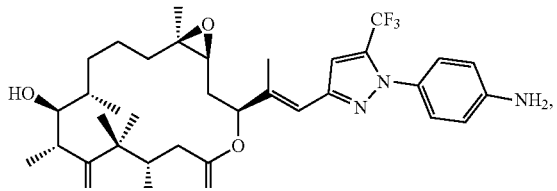

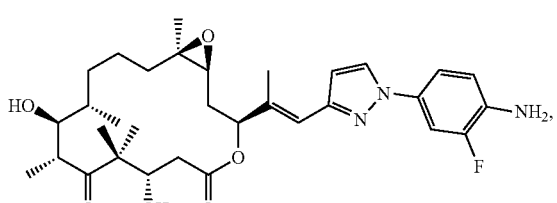

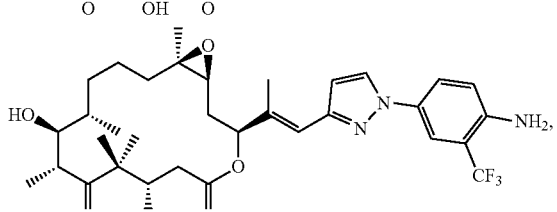

-continued
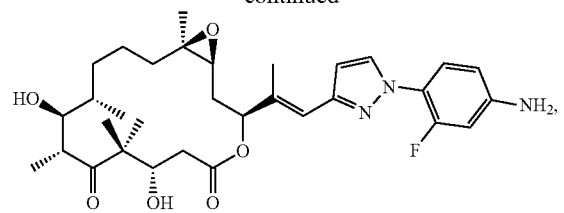
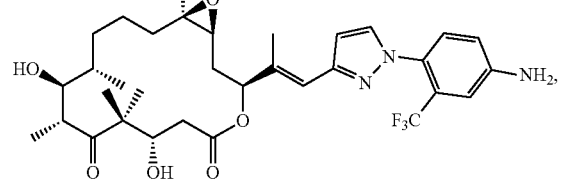
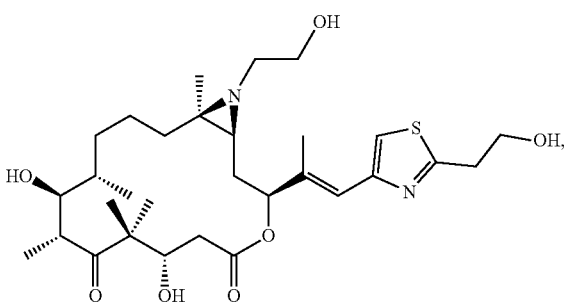
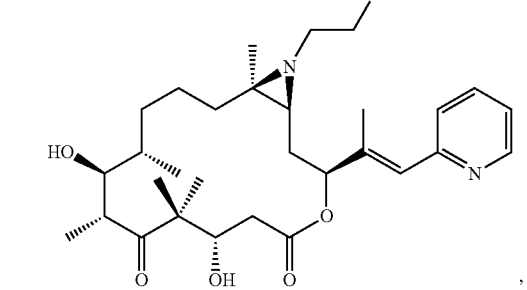
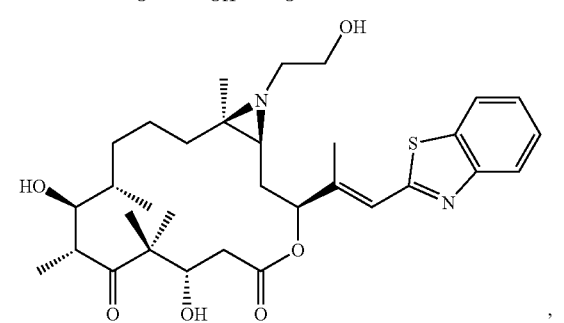
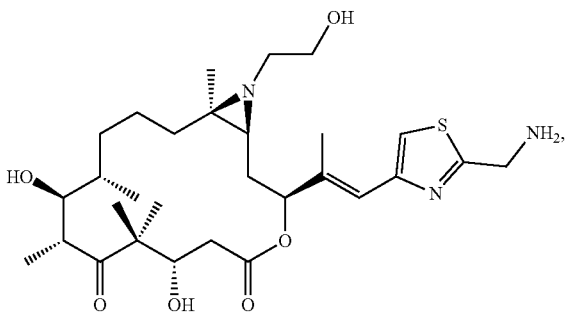
-continued
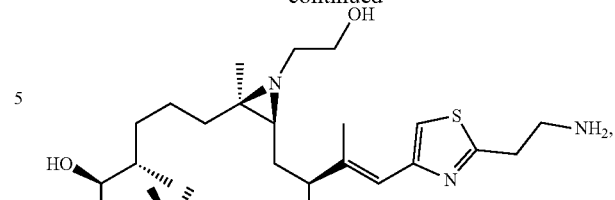
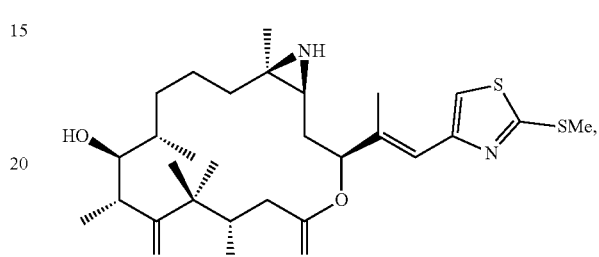
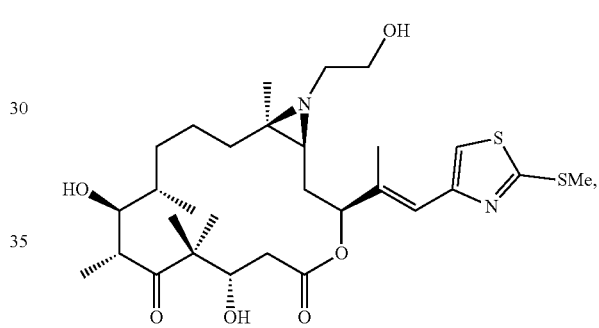
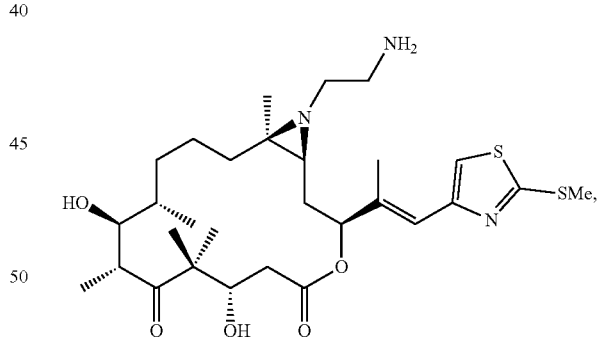
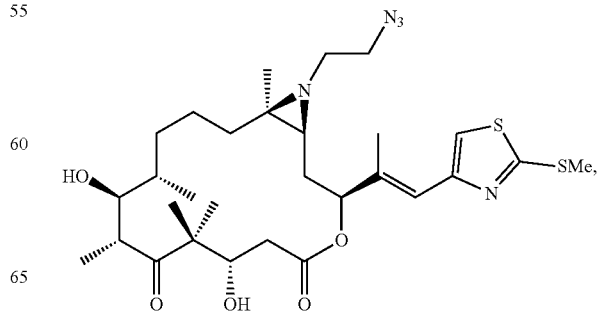

-continued

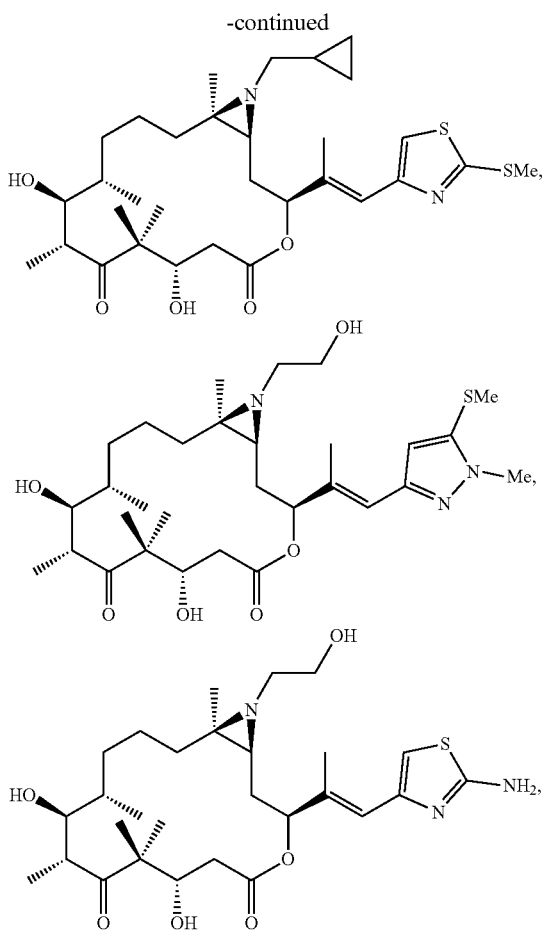

or a pharmaceutically acceptable salt thereof.

In still yet another aspect, the present disclosure provides pharmaceutical compositions comprising:
(a) a compound of the present disclosure; and
(b) a pharmaceutically acceptable carrier.

In some embodiments, the pharmaceutical compositions are formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularly, intravitreally, liposomally, locally, mucosally, parenterally, rectally, subconjunctivally, subcutaneously, sublingually, topically, transbuccally, transdermally, vaginally, in cremes, in lipid compositions, via a catheter, via a lavage, via continuous infusion, via infusion, via inhalation, via injection, via local delivery, or via localized perfusion. In some embodiments, the pharmaceutical compositions are formulated as a unit dose.

In still yet another aspect, the present disclosure provides methods of treating a disease or disorder in a patient comprising administering to the patient in need thereof a therapeutically effective amount of a compound or composition described herein. In some embodiments, the disease or disorder is cancer. In some embodiments, the cancer is a carcinoma, sarcoma, lymphoma, leukemia, melanoma, mesothelioma, multiple myeloma, or seminoma. In some embodiments, the cancer is of the bladder, blood, bone, brain, breast, central nervous system, cervix, colon, endometrium, esophagus, gall bladder, gastrointestinal tract, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In some embodiments, the cancer is breast cancer or ovarian cancer. In some embodiments, the breast cancer is ductal carcinoma. In other embodiments, the ovarian cancer is ovarian adenocarcinoma. In some embodiments, the methods further comprise a second cancer therapy. In some embodiments, the second cancer therapy is surgery, a second chemotherapeutic agent, a radiotherapy, or an immunotherapy. In some embodiments, the patient is a mammal, for example, a human. In some embodiments, the method comprises administering the compound once. In other embodiments, the method comprises administering the compound two or more times.

In yet another aspect, the present disclosure provides antibody drug conjugates comprising:
(a) an antibody; and
(b) a compound of the present disclosure.

In some embodiments, the antibody and the compound are connected through a linker. In some embodiments, the antibody comprises two or more compounds conjugated to the antibody. In some embodiments, the linker is an enzymatically degradable linker.

In still yet another aspect, the present disclosure provides methods of preparing a compound of the formula:

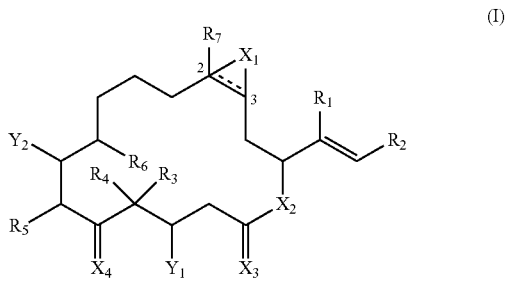

(I)

wherein:
$X_1$ is absent, —O— or —$NR_a$—; wherein
  $R_a$ is hydrogen, a monovalent amine protecting group, or alkyl$_{(C \leq 8)}$, cycloalkyl$_{(C \leq 8)}$, -alkanediyl$_{(C \leq 6)}$-cycloalkyl$_{(C \leq 8)}$, or a substituted version of either of these groups;
provided that when $X_1$ is absent, that the atoms to which it is attached are a part of a double bond; and provided that when the atoms to which it is attached are a part of a double bond, then $X_1$ is absent;
$X_2$, $X_3$, and $X_4$ are each independently —O— or —$NR_b$—; wherein
  $R_b$ is hydrogen, a monovalent amine protecting group, or alkyl$_{(C \leq 8)}$, cycloalkyl$_{(C \leq 8)}$, -alkanediyl$_{(C \leq 6)}$-cycloalkyl$_{(C \leq 8)}$, aralkyl$_{(C \leq 8)}$, or a substituted version of either of these groups;
$Y_1$ and $Y_2$ are each independently amino, hydroxy, or alkoxy$_{(C \leq 8)}$, aralkoxy$_{(C \leq 8)}$, acyloxy$_{(C \leq 8)}$, alkylamino$_{(C \leq 8)}$, dialkylamino$_{(C \leq 8)}$, amido$_{(C \leq 8)}$, or a substituted version of any of these groups, or —$OR_c$, wherein:
  $R_c$ is a hydroxy protecting group;
$R_1$, $R_3$, $R_4$, $R_5$, $R_6$ and $R_7$ are each independently hydrogen or alkyl$_{(C \leq 12)}$, cycloalkyl$_{(C \leq 12)}$, alkenyl$_{(C \leq 12)}$, alkynyl$_{(C \leq 12)}$, aryl$_{(C \leq 12)}$, or a substituted version of any of these groups; and $R_2$ is heteroaryl$_{(C \leq 12)}$, -heteroarenediyl$_{(C \leq 8)}$-$R_d$, or a substituted version of either of these groups; wherein:
$R_d$ is alkyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, or a substituted version of either of these groups;

comprising reacting a compound of the formula:

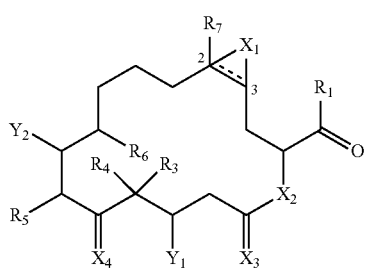

(VIII)

wherein: $X_1$, $X_2$, $X_3$, $X_4$, $Y_1$, $Y_2$, $R_1$, $R_3$, $R_4$, $R_5$, $R_6$, and $R_7$ are as defined above; with a compound of the formula:

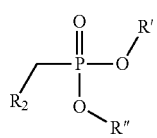

(IX)

wherein:
$R_2$ is as defined above; and
R' and R'' are each independently alkyl$_{(C \leq 8)}$, cycloalkyl$_{(C \leq 8)}$, aryl$_{(C \leq 8)}$, aralkyl$_{(C \leq 8)}$, or a substituted version of any of these groups;

in the presence of a base.

In some embodiments, the base is a strong base. In some embodiments, the base is an organolithium$_{(C \leq 12)}$ reagent, for example, the base is n-butyllithium. In other embodiments, the base is a metal silylamide$_{(C \leq 24)}$. In some embodiments, the base is a metal hexaalkylsilylamide$_{(C6-24)}$, for example, the base is sodium bis(trimethylsilyl)amide. In some embodiments, the methods comprise adding a ratio of the base to the compound of formula IX from about 1:1 to about 1.5:1. In some embodiments, the ratio is about 1.2:1 to about 1.3:1. In some embodiments, the methods further comprise reacting the compounds under the conditions comprising a temperature from about −100° C. to about −50° C. In some embodiments, the methods further comprise allowing the reaction to warm to a temperature from about −30° C. to 30° C. In some embodiments, the methods further comprise reacting the compound for a time period from about 30 minutes to about 8 hours.

In still yet another aspect, the present disclosure provides methods of preparing a compound of the formula:

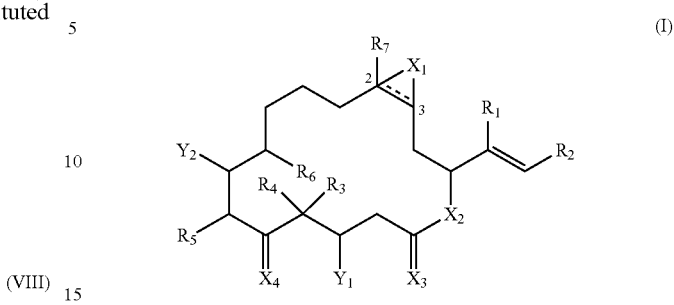

(I)

wherein:
$X_1$ is absent, —O— or —NR$_a$—; wherein
$R_a$ is hydrogen, a monovalent amine protecting group, or alkyl$_{(C \leq 8)}$, cycloalkyl$_{(C \leq 8)}$, -alkanediyl$_{(C \leq 6)}$-cycloalkyl$_{(C \leq 8)}$, or a substituted version of either of these groups;

provided that when $X_1$ is absent, that the atoms to which it is attached are a part of a double bond; and provided that when the atoms to which it is attached are a part of a double bond, then $X_1$ is absent;

$X_2$, $X_3$, and $X_4$ are each independently —O— or —NR$_b$—; wherein
$R_b$ is hydrogen, a monovalent amine protecting group, or alkyl$_{(C \leq 8)}$, cycloalkyl$_{(C \leq 8)}$, -alkanediyl$_{(C \leq 6)}$-cycloalkyl$_{(C \leq 8)}$, aralkyl$_{(C \leq 8)}$, or a substituted version of either of these groups;

$Y_1$ and $Y_2$ are each independently amino, hydroxy, or alkoxy$_{(C \leq 8)}$, aralkoxy$_{(C \leq 8)}$, acyloxy$_{(C \leq 8)}$, alkylamino$_{(C \leq 8)}$, dialkylamino$_{(C \leq 8)}$, amido$_{(C \leq 8)}$, or a substituted version of any of these groups, or —OR$_c$, wherein:
$R_c$ is a hydroxy protecting group;

$R_1$, $R_3$, $R_4$, $R_5$, $R_6$ and $R_7$ are each independently hydrogen or alkyl$_{(C \leq 12)}$, cycloalkyl$_{(C \leq 12)}$, alkenyl$_{(C \leq 12)}$, alkynyl$_{(C \leq 12)}$, aryl$_{(C \leq 12)}$, or a substituted version of any of these groups; and $R_2$ is heteroaryl$_{(C \leq 12)}$, -heteroarenediyl$_{(C \leq 8)}$-$R_d$, or a substituted version of either of these groups; wherein:
$R_d$ is alkyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, or a substituted version of either of these groups;

comprising reacting a compound of the formula:

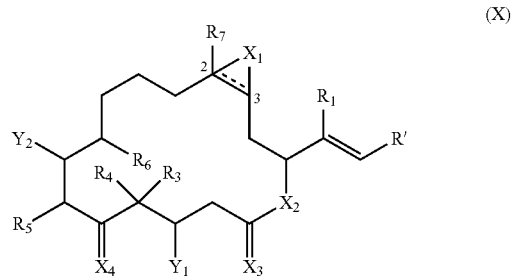

(X)

wherein:
$X_1$, $X_2$, $X_3$, $X_4$, $Y_1$, $Y_2$, $R_1$, $R_3$, $R_4$, $R_5$, $R_6$, and $R_7$ are as defined above; and R' is halo;
with a compound of the formula:

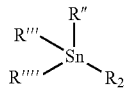
(XI)

wherein:
R$_2$ is as defined above; and
R", R''', and R"" are each independently alkyl$_{(C\leq12)}$ or substituted alkyl$_{(C\leq12)}$; in the presence of a transition metal catalyst.

In some embodiments, transition metal catalyst comprises a palladium complex. In some embodiments, the palladium complex is tris(dibenzylideneacetone)-bispalladium. In some embodiments, the transition metal catalyst further comprises a triarylpnictogen compound$_{(C\leq24)}$. In some embodiments, the transition metal catalyst comprises triarylarsenic compound. In some embodiments, the transition metal catalyst comprises triphenylarsine. In some embodiments, the transition metal catalyst further comprises a copper salt. In some embodiments, the copper salt is a copper(I) salt. In some embodiments, the copper salt is CuI.

In some embodiments, the methods comprise adding a ratio of the compound of formula X to the compound of formula XII from about 1:1 to about 1:5. In some embodiments, the ratio is about 1:2.5. In some embodiments, the methods comprise adding a ratio of the components of the transition metal catalyst from about 1:1:1 to about 1:10:20 for the palladium complex to the triarylpnictogen$_{(C\leq24)}$ to the copper salt. In some embodiments, the ratio is about 1:2:4. In some embodiments, the ratio of the palladium complex to the compound of formula X is about 0.01:1 to about 0.5:1. In some embodiments, the ratio is from about 0.05:1 to about 0.2:1. In some embodiments, the ratio is about 0.1:1.

In still another aspect, the present disclosure provides methods of preparing a compound of the formula:

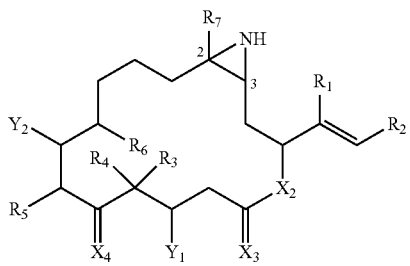
(XIII)

wherein:
X$_2$, X$_3$, and X$_4$ are each independently —O— or —NR$_b$—; wherein
R$_b$ is hydrogen, a monovalent amine protecting group, or alkyl$_{(C\leq8)}$, cycloalkyl$_{(C\leq8)}$, -alkanediyl$_{(C\leq6)}$-cycloalkyl$_{(C\leq8)}$, aralkyl$_{(C\leq8)}$, or a substituted version of either of these groups;
Y$_1$ and Y$_2$ are each independently amino, hydroxy, or alkoxy$_{(C\leq8)}$, aralkoxy$_{(C\leq8)}$, acyloxy$_{(C\leq8)}$, alkylamino$_{(C\leq8)}$, dialkylamino$_{(C\leq8)}$, amido$_{(C\leq8)}$, or a substituted version of any of these groups, or —OR$_c$, wherein:

R$_c$ is a hydroxy protecting group;
R$_1$, R$_3$, R$_4$, R$_5$, R$_6$ and R$_7$ are each independently hydrogen or alkyl$_{(C\leq12)}$, cycloalkyl$_{(C\leq12)}$, alkenyl$_{(C\leq12)}$, alkynyl$_{(C\leq12)}$, aryl$_{(C\leq12)}$, or a substituted version of any of these groups; and
R$_2$ is heteroaryl$_{(C\leq12)}$, -heteroarenediyl$_{(C\leq8)}$-R$_d$, or a substituted version of either of these groups; wherein:
R$_d$ is alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, or a substituted version of either of these groups;
comprising reacting a compound of the formula:

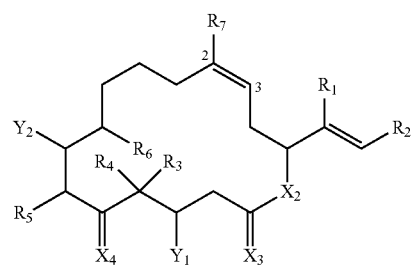
(XIV)

wherein:
X$_1$, X$_2$, X$_3$, X$_4$, Y$_1$, Y$_2$, R$_1$, R$_2$, R$_3$, R$_4$, R$_5$, R$_6$, and R$_7$ are as defined above;
with O-(2,4-dinitrophenyl)hydroxylamine in the presence of a Rh catalyst.

In some embodiments, the Rh catalyst is a Rh(II) catalyst. In some embodiments, the Rh catalyst is bis[rhodium(α,α,α',α',-tetramethyl-1,3-benzenedipropionic acid)]. In some embodiments, the Rh catalyst is present at a mole percentage from about 0.25% to about 5%. In some embodiments, the mole percentage is about 2%. In some embodiments, the method comprises adding a ratio of the compound of formula XIV to the O-(2,4-dinitrophenyl)hydroxylamine from about 1:1 to about 1:5. In some embodiments, the ratio is about 1:1.5.

It is contemplated that any method or composition described herein can be implemented with respect to any other method or composition described herein. For example, a compound synthesized by one method may be used in the preparation of a final compound according to a different method.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE FIGURES

The following drawings form part of the present specification and are included to further demonstrate certain aspects of the present invention. The invention may be better understood by reference to one or more of these drawings in combination with the detailed description.

FIGS. 6A-6G show the in vitro testing results of compound 8 (FIG. 6A), compound 9 (FIG. 6B), compound 10 (FIG. 6C), compound 11 (FIG. 6D), compound 12 (FIG. 6E), compound 13 (FIG. 6F), or compound 14 (FIG. 6G).

DESCRIPTION OF ILLUSTRATIVE EMBODIMENTS

Figure 1:
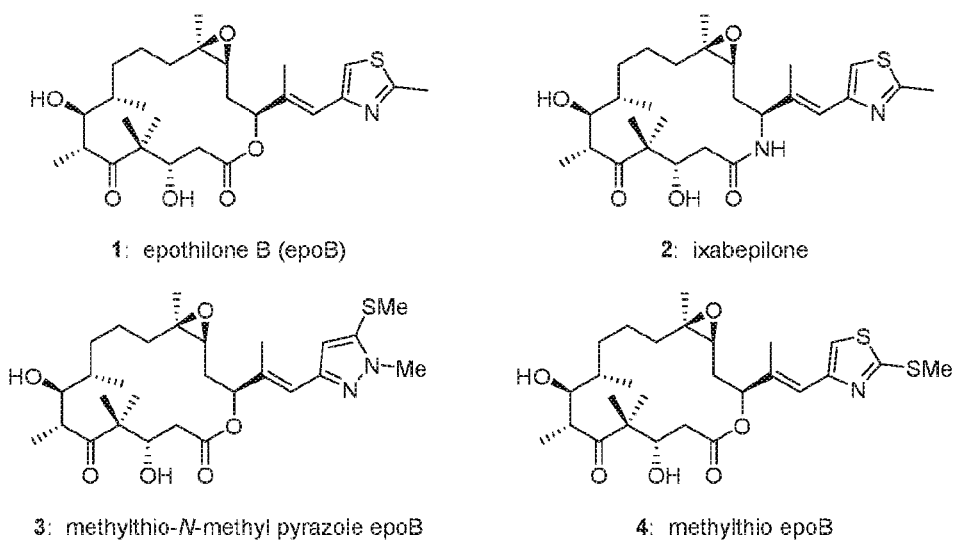
FIG. 1 shows selected natural and designed epothilones (1-4).

The present disclosure relates to new analogs of epothilone including 12,13-aziridine epothilone analogs which contains a handle capable of conjugating to a cell targeting moiety. The cell targeting moieties attached to the epothilone analogs allow for the targeting of the epothilone analogs to particular cells and thus focusing the cytotoxic activity to specific cells.

Also, the present disclosure provides methods of preparing the analogs of epothilone such as 12,13-aziridine epothilone analogs. In some embodiments, the methods of preparing the aziridine analogs show improved reactivity and decrease the total number of synthetic steps. Additionally, also provided are methods of connecting the heteroaryl group to the extracyclic double bond.

I. COMPOUNDS AND FORMULATIONS THEREOF

A. Compounds

The compounds provided by the present disclosure are shown, for example, above in the summary of the invention section and in the examples and claims below. They may be made using the methods outlined in the Examples section. The epothilone analogs described herein can be synthesized according to the methods described, for example, in the Examples section below. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

The epothilone analogs described herein may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers.

In some embodiments, a single diastereomer is obtained. The chiral centers of the compounds of the present disclosure can have the S or the R configuration.

Chemical formulas used to represent the epothilone analogs described herein will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

The epothilone analogs described herein may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the epothilone analogs described herein are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

The epothilone analogs described herein may also exist in prodrug form. Since prodrugs are known to enhance numerous desirable qualities of pharmaceuticals (e.g., solubility, bioavailability, manufacturing, etc.), the compounds employed in some methods of the disclosure may, if desired, be delivered in prodrug form. Thus, the invention contemplates prodrugs of compounds of the present invention as well as methods of delivering prodrugs. Prodrugs of the epothilone analogs described herein may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

Those skilled in the art of organic chemistry will appreciate that many organic compounds can form complexes with solvents in which they are reacted or from which they are precipitated or crystallized. These complexes are known as "solvates." For example, a complex with water is known as a "hydrate." Solvates of the epothilone analogs described herein are within the scope of the invention. It will also be appreciated by those skilled in organic chemistry that many organic compounds can exist in more than one crystalline form. For example, crystalline form may vary from solvate to solvate. Thus, all crystalline forms of the epothilone analogs described herein are within the scope of the present invention.

B. Formulations

In some embodiments of the present disclosure, the compounds are included a pharmaceutical formulation. Materials for use in the preparation of microspheres and/or microcapsules are, e.g., biodegradable/bioerodible polymers such as polygalactin, poly-(isobutyl cyanoacrylate), poly(2-hydroxyethyl-L-glutamine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly(glycolic acid) or poly(ortho esters) or combinations thereof).

Formulations for oral use include tablets containing the active ingredient(s) (e.g., the epothilone analogs described herein) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and anti-adhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material, such as, e.g., glyceryl monostearate or glyceryl distearate may be employed.

II. CANCER AND OTHER HYPERPROLIFERATIVE DISEASES

While hyperproliferative diseases can be associated with any disease which causes a cell to begin to reproduce uncontrollably, the prototypical example is cancer. One of the key elements of cancer is that the cell's normal apoptotic cycle is interrupted and thus agents that interrupt the growth of the cells are important as therapeutic agents for treating these diseases. In this disclosure, the epothilone analogs described herein may be used to lead to decreased cell counts and as such can potentially be used to treat a variety of types of cancer lines. In some aspects, it is anticipated that the epothilone analogs described herein may be used to treat virtually any malignancy.

Cancer cells that may be treated with the compounds of the present disclosure include but are not limited to cells from the bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; Leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; Mullerian mixed tumor; nephroblastoma; hepatoblastoma; carcinosarcoma; mesenchymoma, malignant; Brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In certain aspects, the tumor may comprise an osteosarcoma, angiosarcoma, rhabdosarcoma, leiomyosarcoma, Ewing sarcoma, glioblastoma, neuroblastoma, or leukemia.

III. CELL TARGETING MOIETIES

In some aspects, the present disclosure provides compounds conjugated directly or through linkers to a cell targeting moiety. In some embodiments, the conjugation of the compound to a cell targeting moiety increases the efficacy of the compound in treating a disease or disorder. Cell targeting moieties according to the embodiments may be, for example, an antibody, a growth factor, a hormone, a peptide, an aptamer, a small molecule such as a hormone, an imaging agent, or cofactor, or a cytokine. For instance, a cell targeting moiety according the embodiments may bind to a liver cancer cell such as a Hep3B cell. It has been demonstrated that the gp240 antigen is expressed in a variety of melanomas but not in normal tissues. Thus, in some embodiments, the compounds of the present disclosure may be used in conjugates with an antibody for a specific antigen that is expressed by a cancer cell but not in normal tissues.

In certain additional embodiments, it is envisioned that cancer cell targeting moieties bind to multiple types of cancer cells. For example, the 8H9 monoclonal antibody and the single chain antibodies derived therefrom bind to a glycoprotein that is expressed on breast cancers, sarcomas and neuroblastomas (Onda et al., 2004). Another example is the cell targeting agents described in U.S. Patent Publication No. 2004/005647 and in Winthrop et al. (2003) that bind to MUC-1, an antigen that is expressed on a variety cancer types. Thus, it will be understood that in certain embodiments, cell targeting constructs according the embodiments may be targeted against a plurality of cancer or tumor types.

Additionally, certain cell surface molecules are highly expressed in tumor cells, including hormone receptors such as human chorionic gonadotropin receptor and gonadotropin releasing hormone receptor (Nechushtan et al., 1997). Therefore, the corresponding hormones may be used as the cell-specific targeting moieties in cancer therapy. Additionally, the cell targeting moiety that may be used include a cofactor, a sugar, a drug molecule, an imaging agent, or a fluorescent dye. Many cancerous cells are known to over express folate receptors and thus folic acid or other folate derivatives may be used as conjugates to trigger cell-specific interaction between the conjugates of the present disclosure and a cell (Campbell, et al., 1991; Weitman, et al., 1992).

Since a large number of cell surface receptors have been identified in hematopoietic cells of various lineages, ligands or antibodies specific for these receptors may be used as cell-specific targeting moieties. IL-2 may also be used as a cell-specific targeting moiety in a chimeric protein to target IL-2R+ cells. Alternatively, other molecules such as B7-1, B7-2 and CD40 may be used to specifically target activated T cells (The Leucocyte Antigen Facts Book, 1993, Barclay et al. (eds.), Academic Press). Furthermore, B cells express CD19, CD40 and IL-4 receptor and may be targeted by moieties that bind these receptors, such as CD40 ligand, IL-4, IL-5, IL-6 and CD28. The elimination of immune cells such as T cells and B cells is particularly useful in the treatment of lymphoid tumors.

Other cytokines that may be used to target specific cell subsets include the interleukins (IL-1 through IL-15), granulocyte-colony stimulating factor, macrophage-colony stimulating factor, granulocyte-macrophage colony stimulating factor, leukemia inhibitory factor, tumor necrosis factor, transforming growth factor, epidermal growth factor, insulin-like growth factors, and/or fibroblast growth factor (Thompson (ed.), 1994, The Cytokine Handbook, Academic Press, San Diego). In some aspects, the targeting polypeptide is a cytokine that binds to the Fn14 receptor, such as TWEAK (see, e.g., Winkles, 2008; Zhou et al., 2011 and Burkly et al., 2007, incorporated herein by reference).

A skilled artisan recognizes that there are a variety of known cytokines, including hematopoietins (four-helix bundles) (such as EPO (erythropoietin), IL-2 (T-cell growth factor), IL-3 (multicolony CSF), IL-4 (BCGF-1, BSF-1), IL-5 (BCGF-2), IL-6 IL-4 (IFN-β2, BSF-2, BCDF), IL-7, IL-8, IL-9, IL-11, IL-13 (P600), G-CSF, IL-15 (T-cell growth factor), GM-CSF (granulocyte macrophage colony stimulating factor), OSM (OM, oncostatin M), and LIF (leukemia inhibitory factor)); interferons (such as IFN-γ, IFN-α, and IFN-β); immunoglobin superfamily (such as B7.1 (CD80), and B7.2 (B70, CD86)); TNF family (such as TNF-α (cachectin), TNF-β (lymphotoxin, LT, LT-α), LT-β, CD40 ligand (CD40L), Fas ligand (FasL), CD27 ligand (CD27L), CD30 ligand (CD30L), and 4-1BBL)); and those unassigned to a particular family (such as TGF-β, IL 1α, IL-1β, IL-1 RA, IL-10 (cytokine synthesis inhibitor F), IL-12 (NK cell stimulatory factor), MIF, IL-16, IL-17 (mCTLA-8), and/or IL-18 (IGIF, interferon-γ inducing factor)). Furthermore, the Fc portion of the heavy chain of an antibody may be used to target Fc receptor-expressing cells such as the use of the Fc portion of an IgE antibody to target mast cells and basophils.

Furthermore, in some aspects, the cell-targeting moiety may be a peptide sequence or a cyclic peptide. Examples, cell- and tissue-targeting peptides that may be used according to the embodiments are provided, for instance, in U.S. Pat. Nos. 6,232,287; 6,528,481; 7,452,964; 7,671,010; 7,781,565; 8,507,445; and 8,450,278, each of which is incorporated herein by reference.

Thus, in some embodiments, cell targeting moieties are antibodies or avimers. Antibodies and avimers can be generated against virtually any cell surface marker thus, providing a method for targeted to delivery of GrB to virtually any cell population of interest. Methods for generating antibodies that may be used as cell targeting moieties are detailed below. Methods for generating avimers that bind to a given cell surface marker are detailed in U.S. Patent Publications Nos. 2006/0234299 and 2006/0223114, each incorporated herein by reference.

Additionally, it is contemplated that the compounds described herein may be conjugated to a nanoparticle or other nanomaterial. Some non-limiting examples of nanoparticles include metal nanoparticles such as gold or silver nanoparticles or polymeric nanoparticles such as poly-L-lactic acid or poly(ethylene) glycol polymers. Nanoparticles and nanomaterials which may be conjugated to the instant compounds include those described in U.S. Patent Publications Nos. 2006/0034925, 2006/0115537, 2007/0148095, 2012/0141550, 2013/0138032, and 2014/0024610 and PCT Publication No. 2008/121949, 2011/053435, and 2014/087413, each incorporated herein by reference.

IV. THERAPIES

A. Pharmaceutical Formulations and Routes of Administration

Where clinical applications are contemplated, it will be necessary to prepare pharmaceutical compositions in a form appropriate for the intended application. In some embodiments, such formulation with the compounds of the present disclosure is contemplated. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. Such routes include oral, nasal, buccal, rectal, vaginal or topical route. Alternatively, administration may be by orthotopic, intradermal, subcutaneous, intramuscular, intratumoral, intraperitoneal, or intravenous injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the epothilone analogs described herein may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present disclosure may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

B. Methods of Treatment

In particular, the compositions that may be used in treating microbial infections and cancer in a subject (e.g., a human subject) are disclosed herein. The compositions described above are preferably administered to a mammal (e.g., rodent, human, non-human primates, canine, bovine, ovine, equine, feline, etc.) in an effective amount, that is, an amount capable of producing a desirable result in a treated subject (e.g., causing apoptosis of cancerous cells or killing bacterial cells). Toxicity and therapeutic efficacy of the compositions utilized in methods of the invention can be determined by standard pharmaceutical procedures. As is well known in the medical and veterinary arts, dosage for any one animal depends on many factors, including the subject's size, body surface area, body weight, age, the particular composition to be administered, time and route of administration, general health, the clinical symptoms of the infection or cancer and other drugs being administered concurrently. A composition as described herein is typically administered at a dosage that inhibits the growth or proliferation of a bacterial cell, inhibits the growth of a biofilm, or induces death of cancerous cells (e.g., induces apoptosis of a cancer cell), as assayed by identifying a reduction in hematological parameters (complete blood count—CBC), or cancer cell growth or proliferation. In some embodiments, amounts of the epothilone analogs used to inhibit bacterial growth or induce apoptosis of the cancer cells is calculated to be from about 0.01 mg to about 10,000 mg/day. In some embodiments, the amount is from about 1 mg to about 1,000 mg/day. In some embodiments, these dosings may be reduced or increased based upon the biological factors of a particular patient such as increased or decreased metabolic breakdown of the drug or decreased uptake by the digestive tract if administered orally. Additionally, the epothilone analogs may be more efficacious and thus a smaller dose is required to achieve a similar effect. Such a dose is typically administered once a day for a few weeks or until sufficient reducing in cancer cells has been achieved.

The therapeutic methods of the invention (which include prophylactic treatment) in general include administration of a therapeutically effective amount of the compositions described herein to a subject in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, marker (as defined herein), family history, and the like).

In one embodiment, the invention provides a method of monitoring treatment progress. The method includes the step of determining a level of changes in hematological parameters and/or cancer stem cell (CSC) analysis with cell surface proteins as diagnostic markers (which can include, for example, but are not limited to CD34, CD38, CD90, and CD117) or diagnostic measurement (e.g., screen, assay) in a subject suffering from or susceptible to a disorder or symptoms thereof associated with cancer (e.g., leukemia) in which the subject has been administered a therapeutic amount of a composition as described herein. The level of marker determined in the method can be compared to known levels of marker in either healthy normal controls or in other afflicted patients to establish the subject's disease status. In preferred embodiments, a second level of marker in the subject is determined at a time point later than the determination of the first level, and the two levels are compared to monitor the course of disease or the efficacy of the therapy. In certain preferred embodiments, a pre-treatment level of marker in the subject is determined prior to beginning treatment according to the methods described herein; this pre-treatment level of marker can then be compared to the level of marker in the subject after the treatment commences, to determine the efficacy of the treatment.

C. Combination Therapies

It is envisioned that the epothilone analogs described herein may be used in combination therapies with one or more cancer therapies or a compound which mitigates one or more of the side effects experienced by the patient. It is common in the field of cancer therapy to combine therapeutic modalities. The following is a general discussion of therapies that may be used in conjunction with the therapies of the present disclosure.

To treat cancers using the methods and compositions of the present disclosure, one would generally contact a tumor cell or subject with a compound and at least one other therapy. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the compound and the other includes the other agent.

Alternatively, the epothilone analogs described herein may precede or follow the other treatment by intervals ranging from minutes to weeks. One would generally ensure that a significant period of time did not expire between the time of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 1-2 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the compound or the other therapy will be desired. Various combinations may be employed, where a compound of the present disclosure is "A," and the other therapy is "B," as exemplified below:

| A/B/A | B/A/B | B/B/A | A/A/B | B/A/A | A/B/B |
|-------|-------|-------|-------|-------|-------|
| B/B/B/A | B/B/A/B | A/A/B/B | A/B/A/B | A/B/B/A | B/B/A/A |
| B/A/B/A | B/A/A/B | B/B/B/A | A/A/A/B | B/A/A/A | A/B/A/A |
| A/A/B/A | A/B/B/A | B/A/B/B | B/B/A/B | | |

Other combinations are also contemplated. The following is a general discussion of cancer therapies that may be used combination with the compounds of the present disclosure.

1. Chemotherapy

The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin γ1 and calicheamicin ω1; dynemicin, including dynemicin A; uncialamycin and derivatives thereof; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, or zorubicin; antimetabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and docetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, paclitaxel, docetaxel, gemcitabien, navelbine, farnesyl-protein tansferase inhibitors, transplatinum, 5-fluorouracil, vincristin, vinblastin and methotrexate and pharmaceutically acceptable salts, acids or derivatives of any of the above.

2. Radiotherapy

Radiotherapy, also called radiation therapy, is the treatment of cancer and other diseases with ionizing radiation. Ionizing radiation deposits energy that injures or destroys cells in the area being treated by damaging their genetic material, making it impossible for these cells to continue to grow. Although radiation damages both cancer cells and normal cells, the latter are able to repair themselves and function properly.

Radiation therapy used according to the present invention may include, but is not limited to, the use of γ-rays, X-rays, and/or the directed delivery of radioisotopes to tumor cells. Other forms of DNA damaging factors are also contemplated such as microwaves and UV-irradiation. It is most likely that all of these factors induce a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Radiotherapy may comprise the use of radiolabeled antibodies to deliver doses of radiation directly to the cancer site (radioimmunotherapy). Antibodies are highly specific proteins that are made by the body in response to the presence of antigens (substances recognized as foreign by the immune system). Some tumor cells contain specific antigens that trigger the production of tumor-specific antibodies. Large quantities of these antibodies can be made in the laboratory and attached to radioactive substances (a process known as radiolabeling). Once injected into the body, the antibodies actively seek out the cancer cells, which are destroyed by the cell-killing (cytotoxic) action of the radiation. This approach can minimize the risk of radiation damage to healthy cells.

Conformal radiotherapy uses the same radiotherapy machine, a linear accelerator, as the normal radiotherapy treatment but metal blocks are placed in the path of the x-ray beam to alter its shape to match that of the cancer. This ensures that a higher radiation dose is given to the tumor. Healthy surrounding cells and nearby structures receive a lower dose of radiation, so the possibility of side effects is reduced. A device called a multi-leaf collimator has been developed and may be used as an alternative to the metal blocks. The multi-leaf collimator consists of a number of metal sheets which are fixed to the linear accelerator. Each layer can be adjusted so that the radiotherapy beams can be shaped to the treatment area without the need for metal blocks. Precise positioning of the radiotherapy machine is very important for conformal radiotherapy treatment and a special scanning machine may be used to check the position of internal organs at the beginning of each treatment.

High-resolution intensity modulated radiotherapy also uses a multi-leaf collimator. During this treatment the layers of the multi-leaf collimator are moved while the treatment is being given. This method is likely to achieve even more precise shaping of the treatment beams and allows the dose of radiotherapy to be constant over the whole treatment area.

Although research studies have shown that conformal radiotherapy and intensity modulated radiotherapy may reduce the side effects of radiotherapy treatment, it is possible that shaping the treatment area so precisely could stop microscopic cancer cells just outside the treatment area being destroyed. This means that the risk of the cancer coming back in the future may be higher with these specialized radiotherapy techniques.

Scientists also are looking for ways to increase the effectiveness of radiation therapy. Two types of investigational drugs are being studied for their effect on cells undergoing radiation. Radiosensitizers make the tumor cells more likely to be damaged, and radioprotectors protect normal tissues from the effects of radiation. Hyperthermia, the use of heat, is also being studied for its effectiveness in sensitizing tissue to radiation.

3. Immunotherapy

In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-12, GM-CSF, γ-IFN, chemokines such as MIP-1, MCP-1, IL-8 and growth factors such as FLT3 ligand. Combining immune stimulating molecules, either as proteins or using gene delivery in combination with a tumor suppressor has been shown to enhance anti-tumor effects (Ju et al., 2000). Moreover, antibodies against any of these compounds may be used to target the anti-cancer agents discussed herein.

Examples of immunotherapies currently under investigation or in use are immune adjuvants e.g., *Mycobacterium bovis, Plasmodium falciparum*, dinitrochlorobenzene and aromatic compounds (U.S. Pat. Nos. 5,801,005 and 5,739,169; Hui and Hashimoto, 1998; Christodoulides et al., 1998), cytokine therapy, e.g., interferons α, β, and γ; IL-1, GM-CSF and TNF (Bukowski et al., 1998; Davidson et al., 1998; Hellstrand et al., 1998) gene therapy, e.g., TNF, IL-1, IL-2, p53 (Qin et al., 1998; Austin-Ward and Villaseca, 1998; U.S. Pat. Nos. 5,830,880 and 5,846,945) and monoclonal antibodies, e.g., anti-ganglioside GM2, anti-HER-2, anti-p185 (Pietras et al., 1998; Hanibuchi et al., 1998; U.S. Pat. No. 5,824,311). It is contemplated that one or more anti-cancer therapies may be employed with the gene silencing therapies described herein.

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton et al., 1992; Mitchell et al., 1990; Mitchell et al., 1993).

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989).

4. Surgery

Approximately 60% of persons with cancer will undergo surgery of some type, which includes preventative, diagnostic or staging, curative, and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

In some particular embodiments, after removal of the tumor, an adjuvant treatment with a compound of the present disclosure is believe to be particularly efficacious in reducing the reoccurrence of the tumor. Additionally, the compounds of the present disclosure can also be used in a neoadjuvant setting.

5. Other Agents

It is contemplated that other agents may be used with the present invention. These additional agents include immunomodulatory agents, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon alpha, beta, and gamma; IL-2 and other cytokines; F42K and other cytokine analogs; or MIP-1, MIP-1β, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents may be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as gene therapy.

Another form of therapy for use in conjunction with chemotherapy, radiation therapy or biological therapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

It also should be pointed out that any of the foregoing therapies may prove useful by themselves in treating cancer.

V. SYNTHETIC METHODS

In some aspects, the compounds of this invention can be synthesized using the methods of organic chemistry as described in this application. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

A. Process Scale-Up

The synthetic methods described herein can be further modified and optimized for preparative, pilot- or large-scale production, either batch of continuous, using the principles and techniques of process chemistry as applied by a person skilled in the art. Such principles and techniques are taught, for example, in *Practical Process Research & Development* (2000), which is incorporated by reference herein. The synthetic method described herein may be used to produce preparative scale amounts of the epothilone analogs described herein.

B. Chemical Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; "hydrazine" means —NHNH$_2$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "hydroxysulfonyl" means —SO$_3$H, "sulfonyl" means —S(O)$_2$—; and "sulfinyl" means —S(O)—.

In the context of chemical formulas, the symbol "-" means a single bond, "=" means a double bond, and "≡" means triple bond. The symbol "----" represents an optional bond, which if present is either single or double. The symbol "⹀" represents a single bond or a double bond. Thus, for example, the formula includes

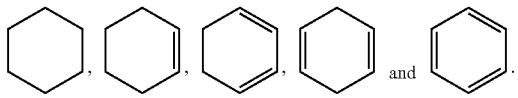

And it is understood that no one such ring atom forms part of more than one double bond. Furthermore, it is noted that the covalent bond symbol "-", when connecting one or two stereogenic atoms, does not indicate any preferred stereochemistry. Instead, it covers all stereoisomers as well as mixtures thereof. The symbol "⌇⌇⌇" when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◂" means a single bond where the group attached to the thick end of the wedge is "out of the page." The symbol "⌇⌇⌇" means a single bond where the group attached to the thick end of the wedge is "into the page". The symbol "⋯⋯" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

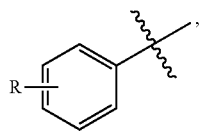

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

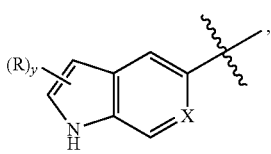

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms. (Cn-n') defines both the minimum (n) and maximum number (n') of carbon atoms in the group. Similarly, "alkyl$_{(C2-10)}$" designates those alkyl groups having from 2 to 10 carbon atoms.

The term "saturated" as used herein means the compound or group so modified has no carbon-carbon double and no carbon-carbon triple bonds, except as noted below. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl).

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, and —CH$_2$CH$_2$CH$_2$—, are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the compound H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —SCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen atoms has been substituted with a halo group and no other atoms aside from carbon, hydrogen and halogen are present. The group, —CH$_2$Cl is a non-limiting example of a haloalkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups.

The term "cycloalkyl" when used without the "substituted" modifier refers to a monovalent saturated aliphatic group with a carbon atom as the point of attachment, said carbon atom forms part of one or more non-aromatic ring structures, a cyclo or cyclic structure, no carbon-carbon double or triple bonds, and no atoms other than carbon and hydrogen. Non-limiting examples of cycloalkyl groups include: —CH(CH$_2$)$_2$ (cyclopropyl), cyclobutyl, cyclopentyl, or cyclohexyl. The term "cycloalkanediyl" when used without the "substituted" modifier refers to a divalent saturated aliphatic group with one or two carbon atom as the point(s) of attachment, said carbon atom(s) forms part of one or more non-aromatic ring structures, a cyclo or cyclic structure, no carbon-carbon double or triple bonds, and no atoms other than carbon and hydrogen.

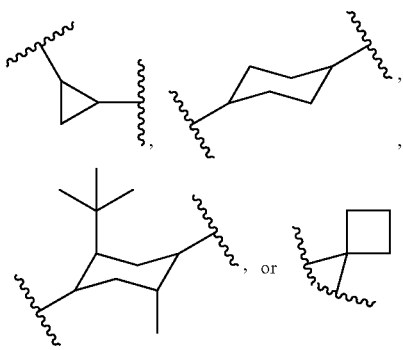

or are non-limiting examples of cycloalkanediyl groups. A "cycloalkane" refers to the compound H—R, wherein R is cycloalkyl as this term is defined above. When any of these terms is used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —SCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted cycloalkyl groups: —C(OH)(CH$_2$)$_2$,

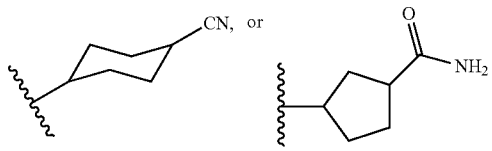

The term "alkenyl" when used without the "substituted" modifier refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, and —CH=CHCH$_2$—, are non-limiting examples of alkenediyl groups. It is noted that while the alkenediyl group is aliphatic, once connected at both ends, this group is not precluded from forming part of an aromatic structure. The terms "alkene" and refer to a compound having the formula H—R, wherein R is alkenyl as this term is defined above. A "terminal alkene" refers to an alkene having just one carbon-carbon double bond, wherein that bond forms a vinyl group at one end of the molecule. When any of these terms are used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —SCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH or —S(O)$_2$NH$_2$. The groups, —CH=CHF, —CH=CHCl and —CH=CHBr, are non-limiting examples of substituted alkenyl groups.

The term "alkynyl" when used without the "substituted" modifier refers to a monovalent unsaturated aliphatic group with a carbon atom as the point of attachment, a linear or branched, acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH$_3$, and —CH$_2$C≡CCH$_3$, are non-limiting examples of alkynyl groups. An "alkyne" refers to the compound H—R, wherein R is alkynyl. When any of these terms are used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —SCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C₆H₄CH₂CH₃ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

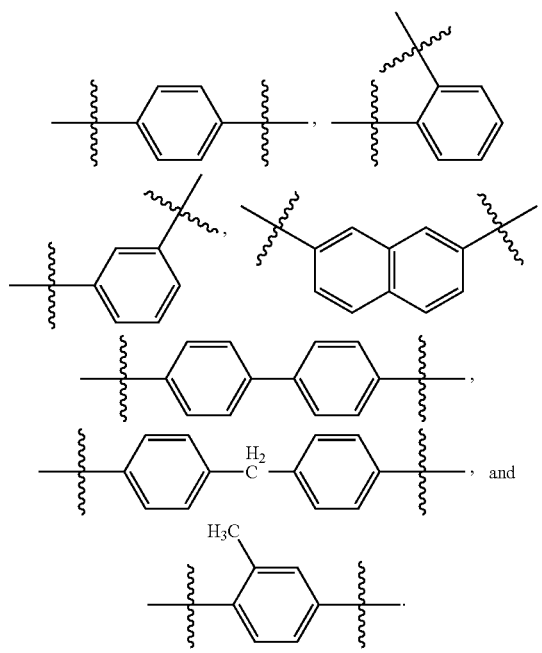

An "arene" refers to the compound H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH₂, —NO₂, —N₃, —CO₂H, —CO₂CH₃, —CN, —SH, —OCH₃, —SCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH₂, —NO₂, —N₃, —CO₂H, —CO₂CH₃, —CN, —SH, —OCH₃, —SCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl, isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. As the term is used herein, the term heteroaryl includes pyrimidine base and base analogs. The term "N-heteroaryl" refers to a heteroaryl group with a nitrogen atom as the point of attachment. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl, aryl, aralkyl, and/or heteroaralkyl groups (carbon number limitation permitting) attached to the aromatic ring or aromatic ring system. Non-limiting examples of heteroarenediyl groups include:

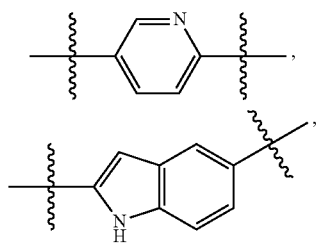

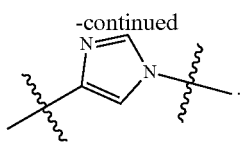

A "heteroarene" refers to the compound H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —SCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "heteroaralkyl" when used without the "substituted" modifier refers to the monovalent group -alkanediyl-heteroaryl, in which the terms alkanediyl and heteroaryl are each used in a manner consistent with the definitions provided above. Non-limiting examples of heteroaralkyls are: N-pyrazolylmethyl or quinolylmethyl. When the term heteroaralkyl is used with the "substituted" modifier one or more hydrogen atom from the alkanediyl and/or the heteroaryl group has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —SCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. Non-limiting examples of substituted aralkyls are: (3-nitropyrimidinyl)-methyl, and 4-chloro-2-quinolyl-eth-1-yl.

The term "acyl" when used without the "substituted" modifier refers to the group —C(O)R, in which R is a hydrogen, alkyl, cycloalkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. An "anhydride" is a group of the formula ROR', wherein R and R' are acyl groups as defined above. When any of these terms are used with the "substituted" modifier one or more hydrogen atom (including a hydrogen atom directly attached the carbonyl or thiocarbonyl group, if any) has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —SCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can each independently be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "cycloalkylamino", "alkenylamino", "cycloalkenylamino", "alkynylamino", "arylamino", "aralkylamino", "heteroarylamino", "heterocycloalkylamino" and "alkylsulfonylamino" when used without the "substituted" modifier, refers to groups, defined as —NHR, in which R is alkoxy, cycloalkyl, alkenyl, cycloalkenyl, alkynyl, aryl, aralkyl, heteroaryl, heterocycloalkyl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl-NH—, or -alkanediyl-NH-alkanediyl-. When any of these terms is used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —SCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —NHC(O)OCH$_3$ and —NHC(O)NHCH$_3$ are non-limiting examples of substituted amido groups.

The term "alkoxy" when used without the "substituted" modifier refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), and —OC(CH$_3$)$_3$ (tert-butoxy). The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkoxydiyl" refers to the divalent group —O-alkanediyl-, —O-alkanediyl-O—, or -alkanediyl-O-alkanediyl-. The terms "alkylthio" and "acylthio" when used without the "substituted" modifier refers to the group —SR, in which R is an alkyl and acyl, respectively. The term "alkylthiodiyl" refers to the divalent group —S-alkanediyl-, —S-alkanediyl-S—, or -alkanediyl-S-alkanediyl-. The term "alcohol" corresponds to an alkane, as defined above, wherein at least one of the hydrogen atoms has been replaced with a hydroxy group. The term "ether" corresponds to an alkane or cycloalkane, as defined above, wherein at least one of the hydrogen atoms has been replaced with an alkoxy or cycloalkoxy group. When any of these terms is used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —SCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkylsilyl" when used without the "substituted" modifier refers to the groups —SiR$_3$, respectively, in which each R is an alkyl, as that term is defined above. The terms "alkenylsilyl", "alkynylsilyl", "arylsilyl", "aralkylsilyl", "heteroarylsilyl", and "heterocycloalkylsilyl" are defined in an analogous manner. When any of these terms is used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —SCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The terms "phosphine" and "phosphane" are used synonymously herein. When used without the "substituted" modifier these terms refer to a compound of the formula PR$_3$, wherein each R is independently hydrogen, alkyl, cycloalkyl, alkenyl, aryl, or aralkyl, as those terms are defined above. Non-limiting examples include PMe$_3$, PPh$_3$, and PCy$_3$ (tricyclohexylphosphine). The terms "trialkylphosphine" and "trialkylphosphane" are also synonymous. Such groups are a subset of phosphine, wherein each R is an alkyl group. The term "diphosphine" when used without the "substituted" modifier refers to a compound of the formula R$_2$—P-L-P—R$_2$, wherein each R is independently hydrogen, alkyl, cycloalkyl, alkenyl, aryl, or aralkyl, and wherein L is alkanediyl, cycloalkanediyl, alkenediyl, or arenediyl. When any of these terms is used with the "substituted" modifier one or more hydrogen atom attached to a carbon atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —SCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH or —S(O)$_2$NH$_2$.

As indicated above in some aspects the cell-targeting moiety is an antibody. As used herein, the term "antibody" is intended to include immunoglobulins and fragments thereof which are specifically reactive to the designated protein or peptide, or fragments thereof. Suitable antibodies include, but are not limited to, human antibodies, primatized antibodies, de-immunized antibodies, chimeric antibodies, bi-specific antibodies, humanized antibodies, conjugated antibodies (i.e., antibodies conjugated or fused to other proteins, radiolabels, cytotoxins), Small Modular Immuno-Pharmaceuticals ("SMIPs™"), single chain antibodies, cameloid antibodies, antibody-like molecules (e.g., anticalins), and antibody fragments. As used herein, the term "antibodies" also includes intact monoclonal antibodies, polyclonal antibodies, single domain antibodies (e.g., shark single domain antibodies (e.g., IgNAR or fragments thereof)), multispecific antibodies (e.g., bi-specific antibodies) formed from at least two intact antibodies, and antibody fragments so long as they exhibit the desired biological activity. Antibody polypeptides for use herein may be of any type (e.g., IgG, IgM, IgA, IgD and IgE). Generally, IgG and/or IgM are preferred because they are the most common antibodies in the physiological situation and because they are most easily made in a laboratory setting. As used herein the term antibody also encompasses an antibody fragment such as a portion of an intact antibody, such as, for example, the antigen-binding or variable region of an antibody. Examples of antibody fragments include Fab, Fab', F(ab')$_2$, Fc and Fv fragments; triabodies; tetrabodies; linear antibodies; single-chain antibody molecules; and multi specific antibodies formed from antibody fragments. The term "antibody fragment" also includes any synthetic or genetically engineered protein that acts like an antibody by binding to a specific antigen to form a complex. For example, antibody fragments include isolated fragments, "Fv" fragments, consisting of the variable regions of the heavy and light chains, recombinant single chain polypeptide molecules in which light and heavy chain variable regions are connected by a peptide linker ("ScFv proteins"), and minimal recognition units consisting of the amino acid residues that mimic the hypervariable region. An oxygen linked antibody is an antibody which has a chemical function group such that the linkage between the antibody and the linker or compound is joined via an oxygen atom. Similarly, a nitrogen linked antibody is an antibody which has a chemical function group such that the linkage between the antibody and the linker or compound is joined via an nitrogen atom.

A "base" in the context of this application is a compound which has a lone pair of electron that can accept a proton. Non-limiting examples of a base can include triethylamine, a metal hydroxide, a metal alkoxide, a metal hydride, or a metal alkane. An alkyllithium or organolithium is a compound of the formula alkyl$_{(C\leq 12)}$-Li. A nitrogenous base is an alkylamine, dialkylamino, trialkylamine, nitrogen containing heterocycloalkane or heteroarene wherein the base can accept a proton to form a positively charged species. For example, but not limited to, a nitrogenous base could be 4,4-dimethylpyridine, pyridine, 1,8-diazabicyclo[5.4.0]undec-7-ene, diisopropylethylamine, or triethylamine. A metal alkoxide is an alkoxy group wherein the oxygen atom, which was the point of connectivity, has an extra electron and thus a negative charge which is charged balanced by the metal ion. For example, a metal alkoxide could be a sodium tert-butoxide or potassium methoxide. As used herein, the term "strong base" indicates a base which has a pK$_a$ of greater than 20.

A "metal" in the context of this application is a transition metal or a metal of groups I or II. It may also be an element of Group 13 such as, but not limited to, boron and aluminum.

A "linker" in the context of this application is divalent chemical group which may be used to join one or more molecules to the compound of the instant disclosure. Linkers may also be an amino acid chain wherein the carboxy and amino terminus serve as the points of attachment for the linker. In some embodiments, the linker contains a reactive functional group, such as a carboxyl, an amide, a amine, a hydroxy, a mercapto, an aldehyde, or a ketone on each end that be used to join one or more molecules to the compounds of the instant disclosure. In some non-limiting examples, —CH$_2$CH$_2$CH$_2$CH$_2$—, —C(O)CH$_2$CH$_2$CH$_2$—, —OCH$_2$CH$_2$NH—, —NHCH$_2$CH$_2$NH—, and —(OCH$_2$CH$_2$)$_n$—, wherein n is between 1-1000, are linkers.

An "amine protecting group" is well understood in the art. An amine protecting group is a group which prevents the reactivity of the amine group during a reaction which modifies some other portion of the molecule and can be easily removed to generate the desired amine. Amine protecting groups can be found at least in Greene and Wuts, 1999, which is incorporated herein by reference. Some non-limiting examples of amino protecting groups include formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxycarbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Additionally, the "amine protecting group" can be a divalent protecting group such that both hydrogen atoms on a primary amine are replaced with a single protecting group. In such a situation the amine protecting group can be phthalimide (phth) or a substituted derivative thereof wherein the term "substituted" is as defined above. In some embodiments, the halogenated phthalimide derivative may be tetrachlorophthalimide (TCphth). When used herein, a "protected amino group", is a group of the formula $PG_{MA}NH-$ or $PG_{DA}N-$ wherein $PG_{MA}$ is a monovalent amine protecting group, which may also be described as a "monvalently protected amino group" and $PG_{DA}$ is a divalent amine protecting group as described above, which may also be described as a "divalently protected amino group".

A "hydroxyl protecting group" is well understood in the art. A hydroxyl protecting group is a group which prevents the reactivity of the hydroxyl group during a reaction which modifies some other portion of the molecule and can be easily removed to generate the desired hydroxyl. Hydroxyl protecting groups can be found at least in Greene and Wuts, 1999, which is incorporated herein by reference. Some non-limiting examples of hydroxyl protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. When used herein, a protected hydroxy group is a group of the formula $PG_HO-$ wherein $PG_H$ is a hydroxyl protecting group as described above.

A "thiol protecting group" is well understood in the art. A thiol protecting group is a group which prevents the reactivity of the mercapto group during a reaction which modifies some other portion of the molecule and can be easily removed to generate the desired mercapto group. Thiol protecting groups can be found at least in Greene and Wuts, 1999, which is incorporated herein by reference. Some non-limiting examples of thiol protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. When used herein, a protected thiol group is a group of the formula $PG_TS-$ wherein $PG_T$ is a thiol protecting group as described above.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Synthesis of Epothilone and Analogs

Synthesis.

Figure 2:
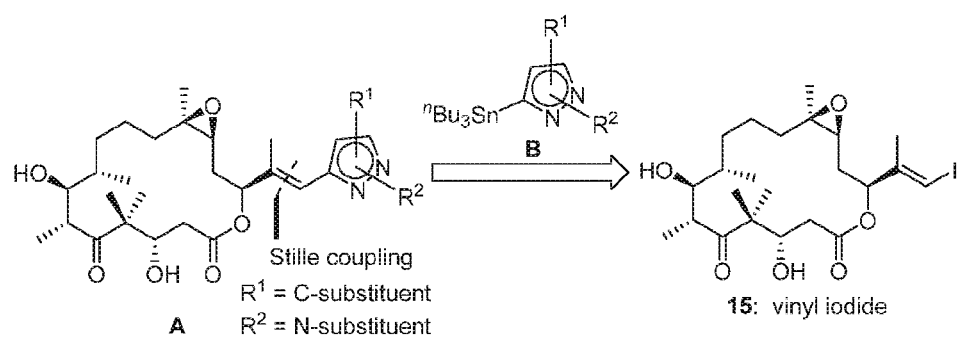
FIG. 2 shows the general strategy for the synthesis of epothilone B analogues (A) from vinyl iodide and pyrazole stannanes (B).

The retrosynthetic analysis for the introduction of the amino groups is shown in FIG. 2. Scheme 1 summarizes the synthesis of Teoc-protected and Boc-protected aminoethyl pyrazole analogues 5 and 6 from the readily available building blocks 3-(methylthio)-1H-pyrazole (16a) (Schank et al., 1994) and commercially available 3-(trifluoromethyl)-1H-pyrazole (16b). Thus, alkylation of 16a with N-boc bromide 17a (prepared from the corresponding commercially available bromoamine by the standard method) (Shoji et al., 2007) under basic conditions (NaH) led to pyrazole derivative 18a (74% yield) which was regioselectively stannylated through lithiation ("BuLi) followed by addition of "BuSnCl (38% yield). Palladium-catalyzed coupling of the latter with vinyl iodide 15 (Nicolaou et al., 1900; Nicolaou et al., 2000 and Pratt, 2008) (Pd$_2$(dba)$_3$, AsPh$_3$, CuI) furnished epothilone analogue 5 in 74% yield. Similar processing of trifluoromethyl pyrazole 16b employing N-boc protected bromide 17a and vinyl iodide 15 (Nicolaou et al., 1900; Nicolaou et al., 2000 and Pratt, 2008) afforded epothilone analogue 6 [65% yield for the last step (19b+15→6)] via intermediates 18b (67% yield) and 19b (42% yield).

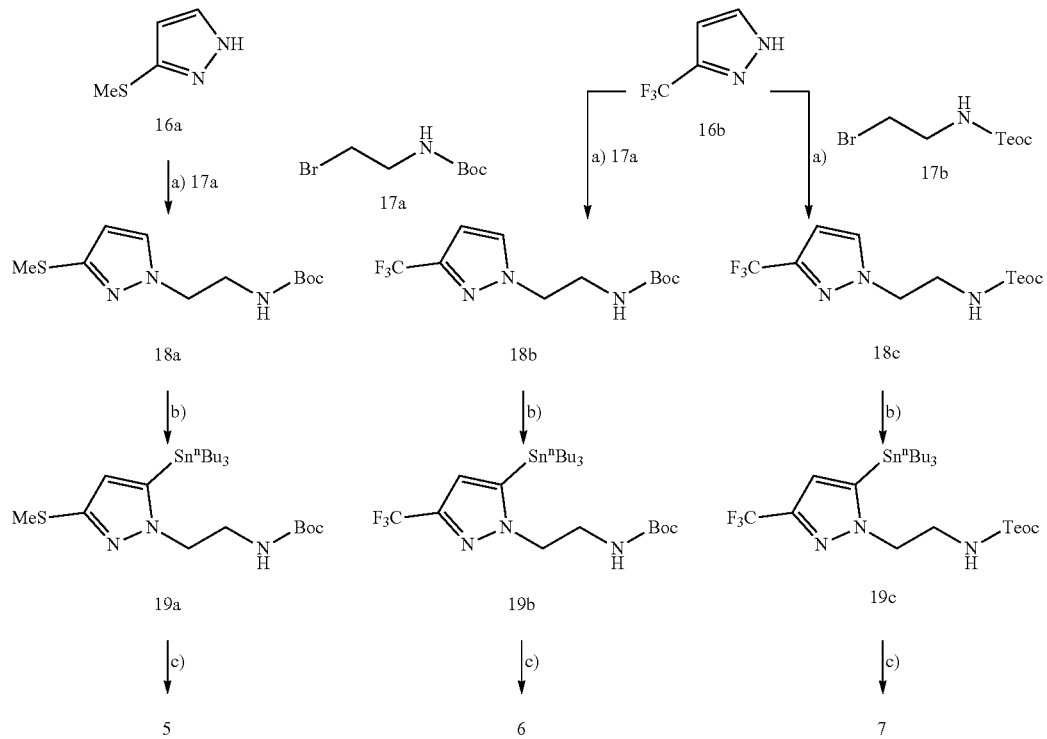

Scheme 1.

Synthesis of analogues 5-7. Reagents and conditions: a) NaH, 3-(methylthio)-1H-pyrazole (16a) or 3-(trifluoromethyl)-1H-pyrazole (16b) (1.2 equiv), 17a or 17b (1.0 equiv), THF, 0 → 60° C., 12 h (74% for 18a, 67% for 18b, 96% for 18c); b) "BuLi (3.0 equiv), "Bu$_3$SnCl (1.1 equiv), THF, -78° C., 30 min (38% for 19a, 42% for 19b, 54% for 19c); c) Pd$_2$(dba)$_3$ (0.1 equiv), AsPh$_3$ (0.2 equiv), CuI (0.4 equiv), 15 (1.0 equiv), DMF, 25° C. (74% for 5, 65% for 6, 77% for 7). Abbreviations: dba = dibenzylideneacetone.

Analogue 7 was prepared from commercially available trifluoromethyl pyrazole 16b and N-Teoc protected bromide 17b (WO 2012/003498A1) in a similar manner [42% yield for the last step (19c+15→7)] via intermediates 18c (96% yield) and 19c (54% yield). It is noteworthy that 17a-b, 18a-c, 19a-c, and especially 5, 6, and 7 exhibit signal splitting in their $^1$H and $^{13}$C NMR spectra, apparently due to hindered rotation around their bulky protecting groups (Boc and Teoc, respectively).

Figure 3:
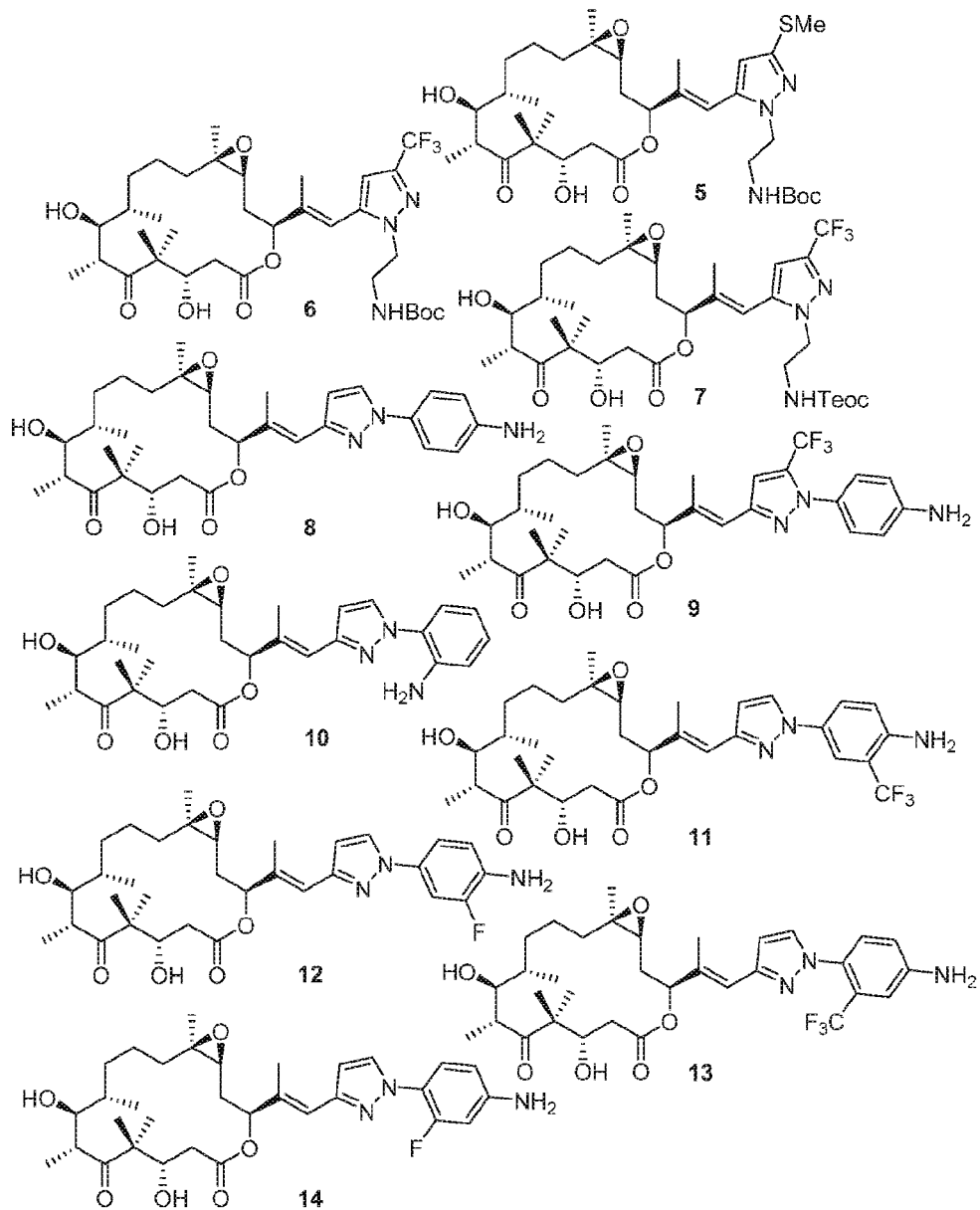
FIG. 3 shows the designed and synthesized epothilone B analogues 5-14.
Figure 4:
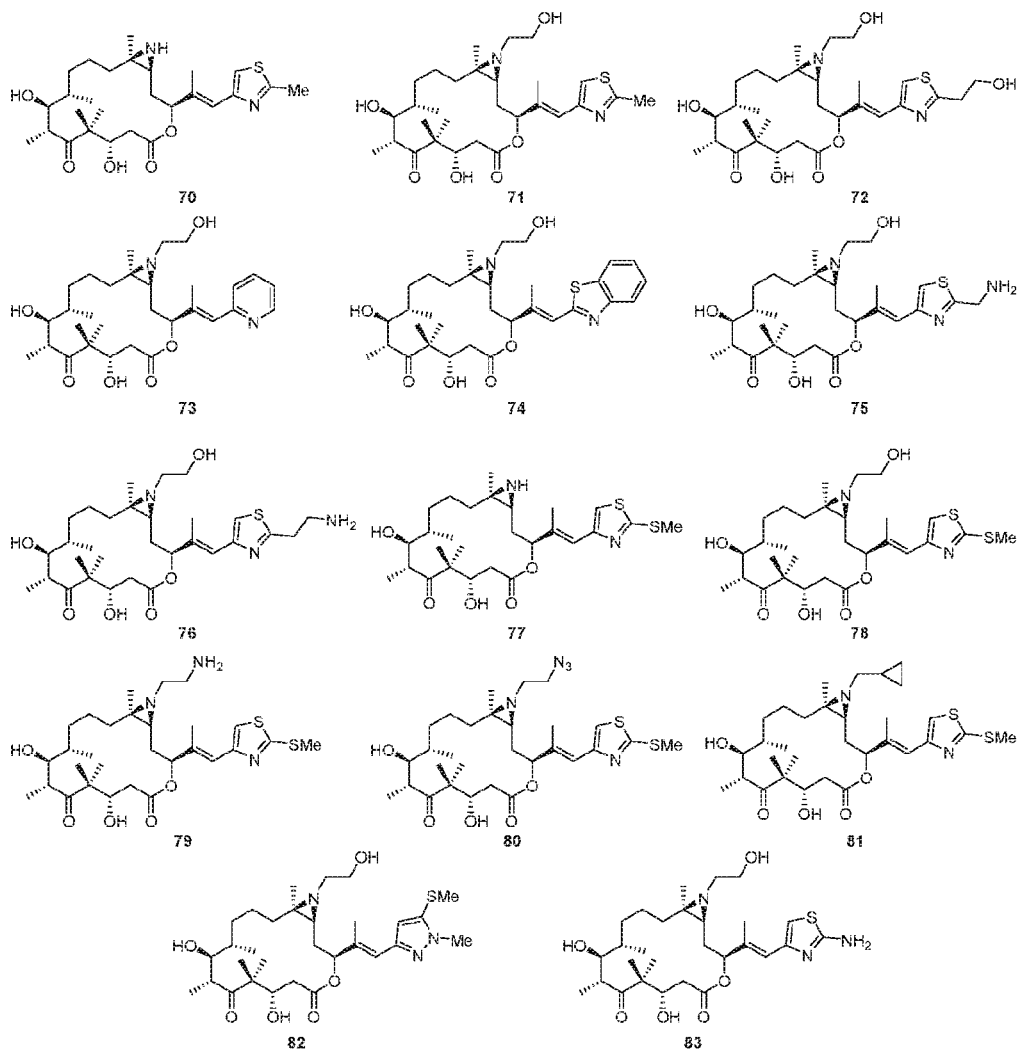
FIG. 4 shows the structures of synthesized 12,13-aziridine epothilone B analogues (70-83).
Figure 5:
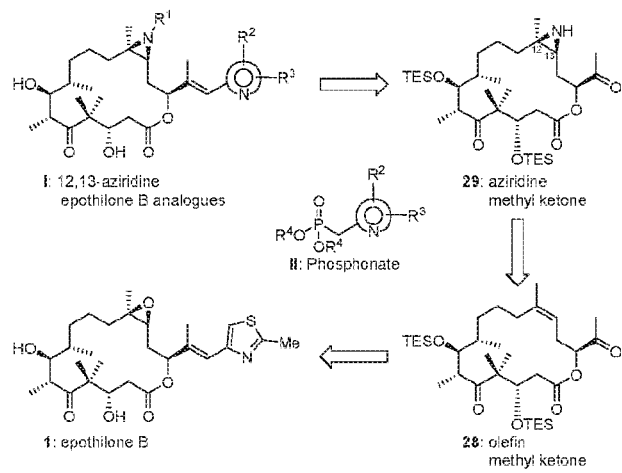
FIG. 5 shows 12,13-aziridine epothilone analogues (I) and general strategy for their synthesis from epothilone B (1) via key intermediates 28, 29 and II.
Figure 7A:
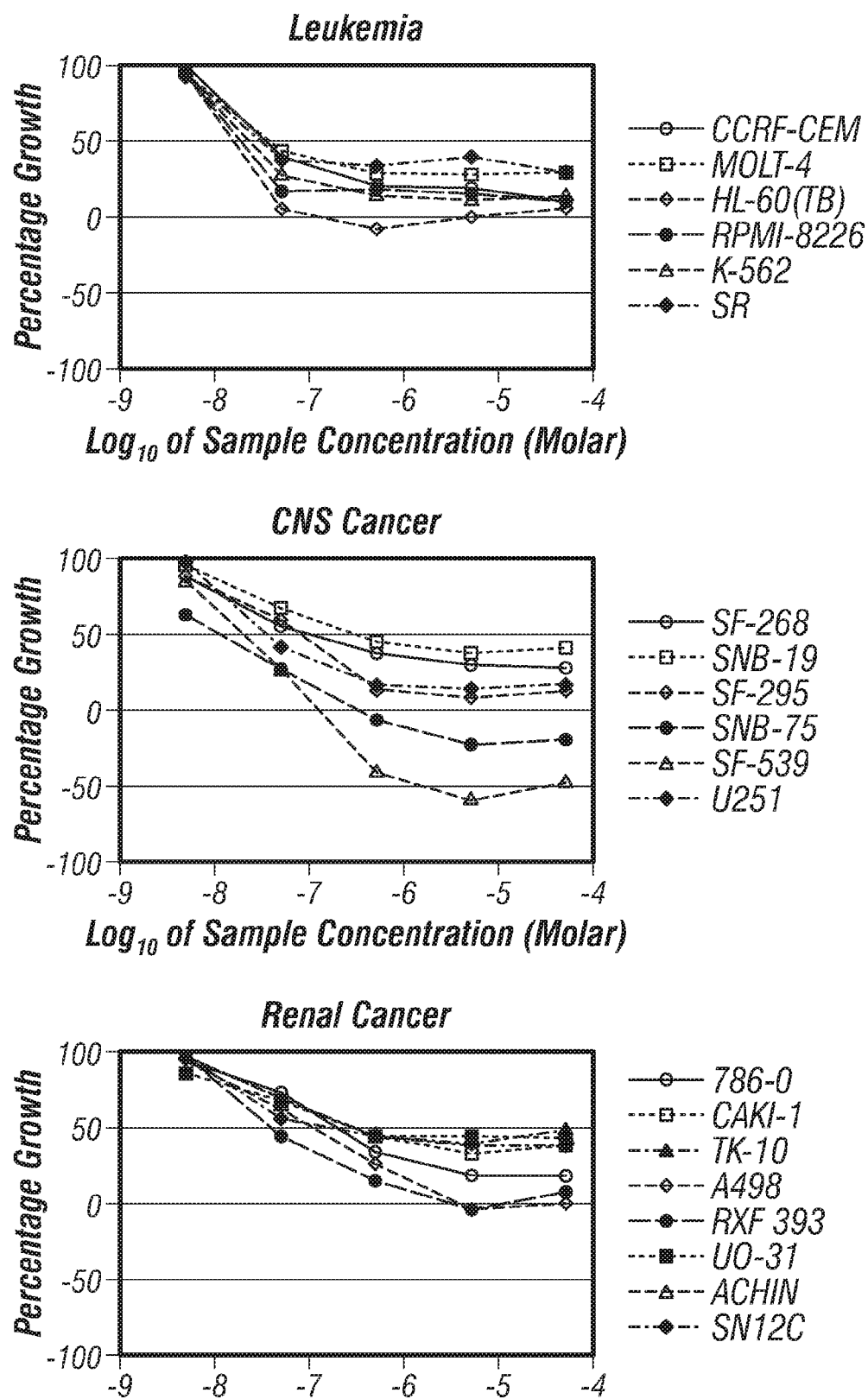
FIGS. 7A-7G show dose response curves of compound 8 (FIG. 7A), compound 9 (FIG. 7B), compound 10 (FIG. 7C), compound 11 (FIG. 7D), compound 12 (FIG. 7E), compound 13 (FIG. 7F), or compound 14 (FIG. 7G).
Figure 7A:
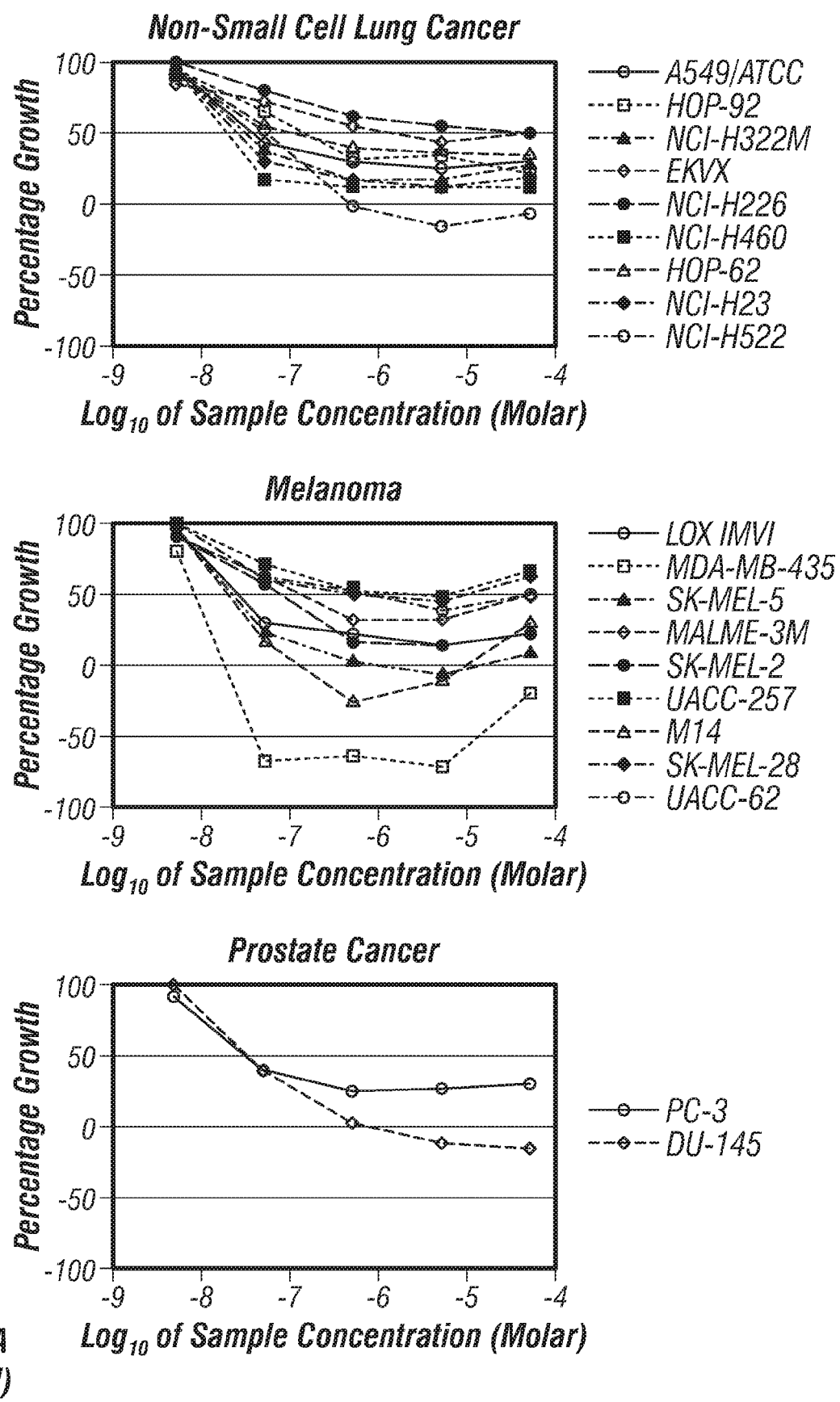
Figure 7A:
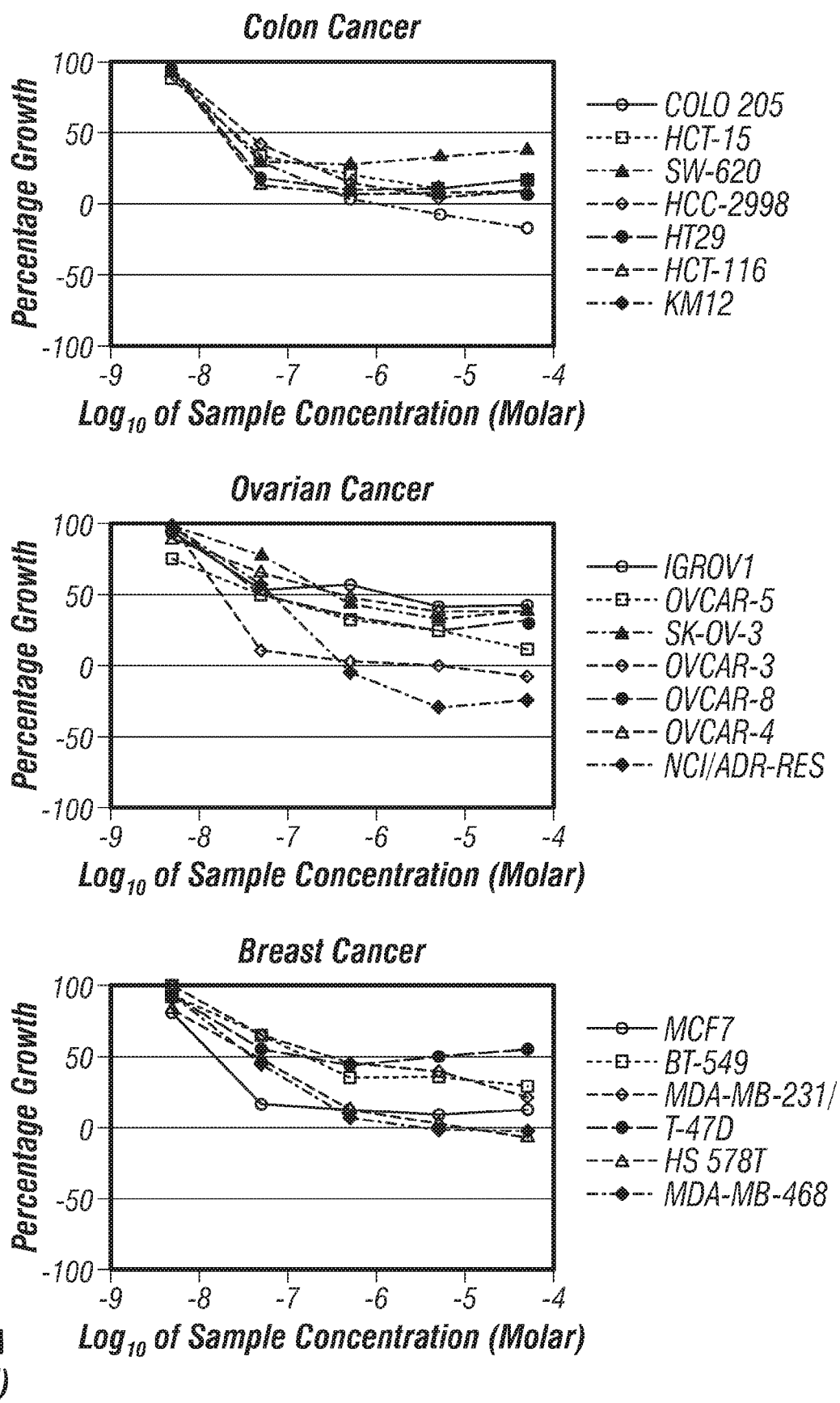
Figure 7B:
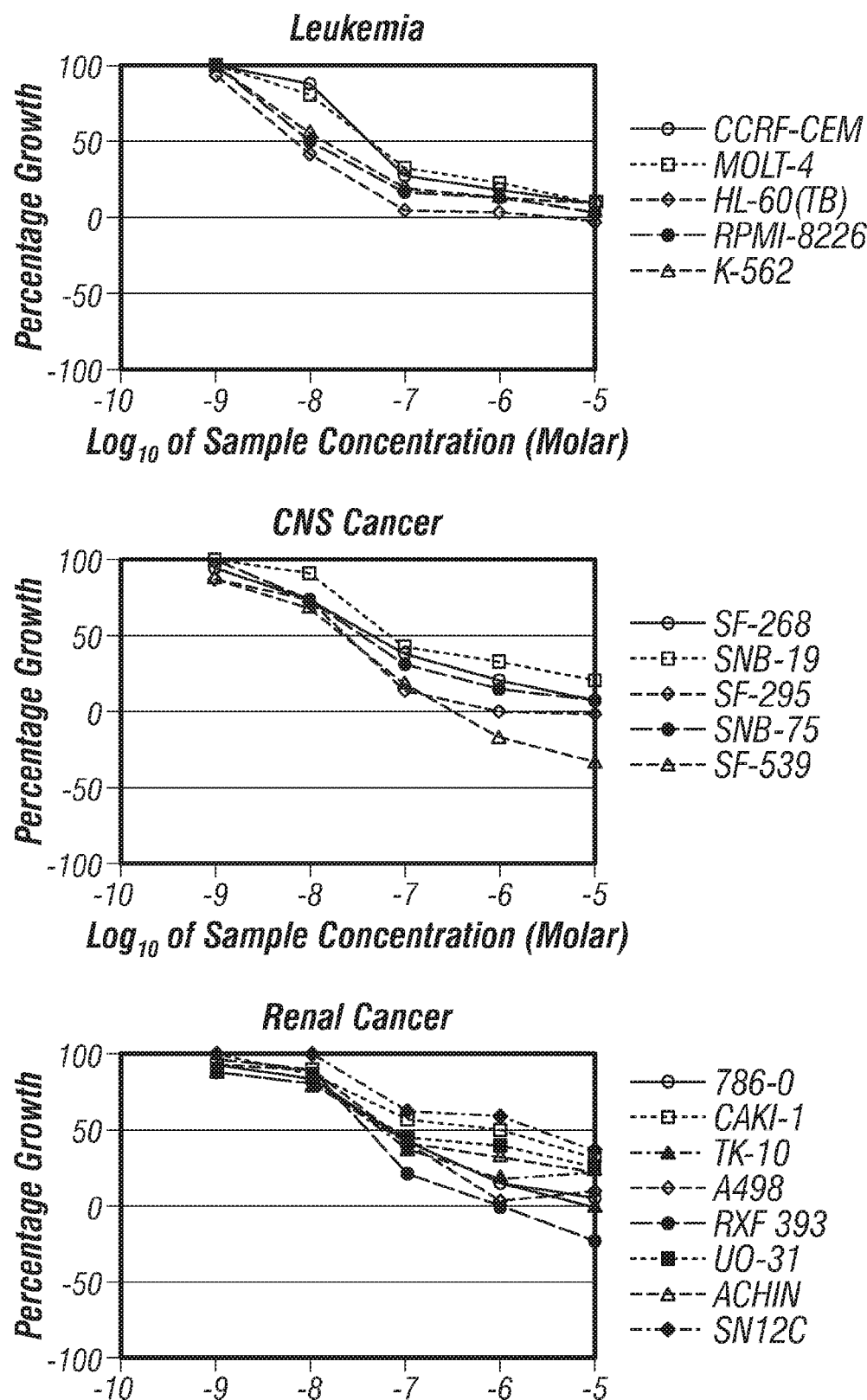
Figure 7B:
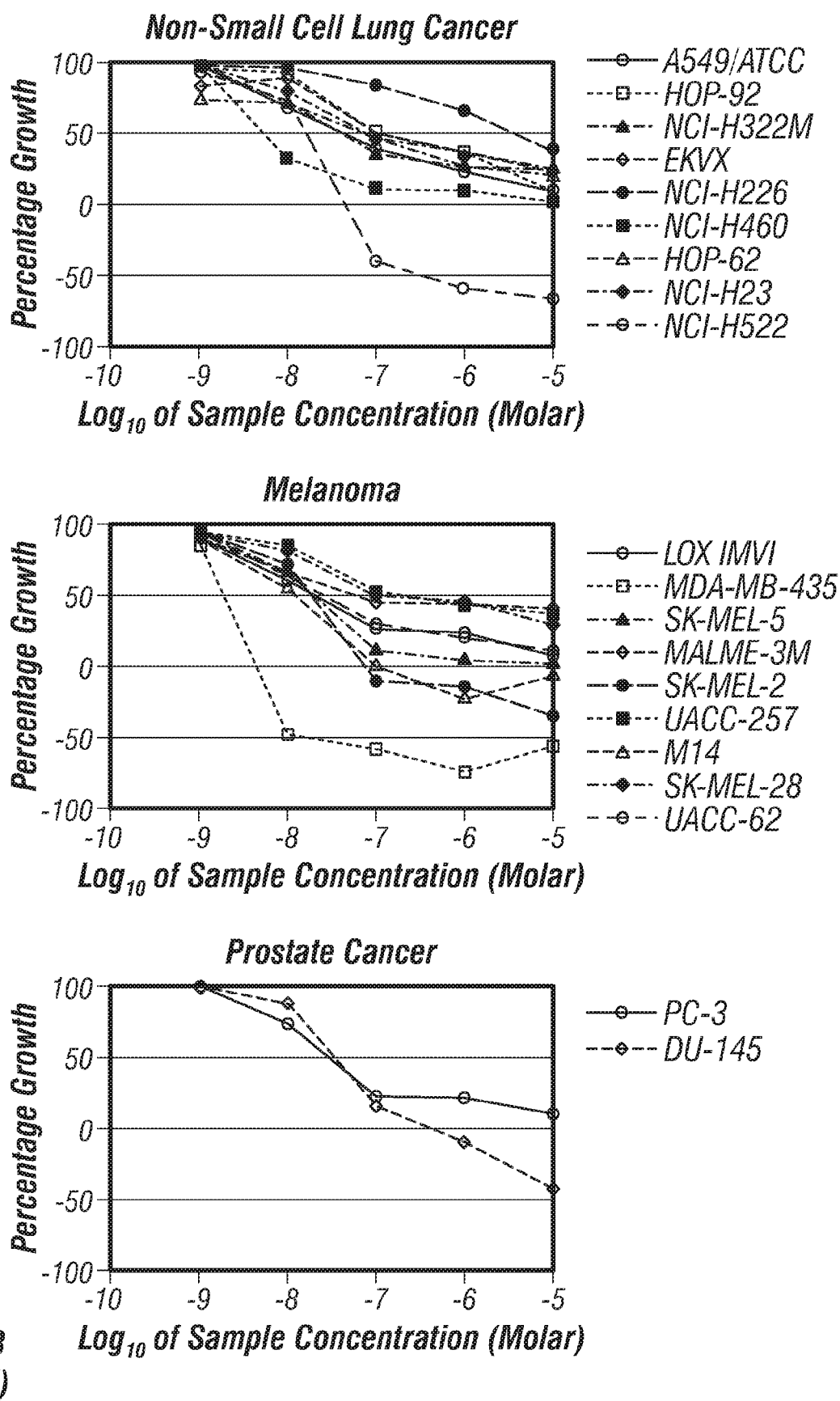
Figure 7B:
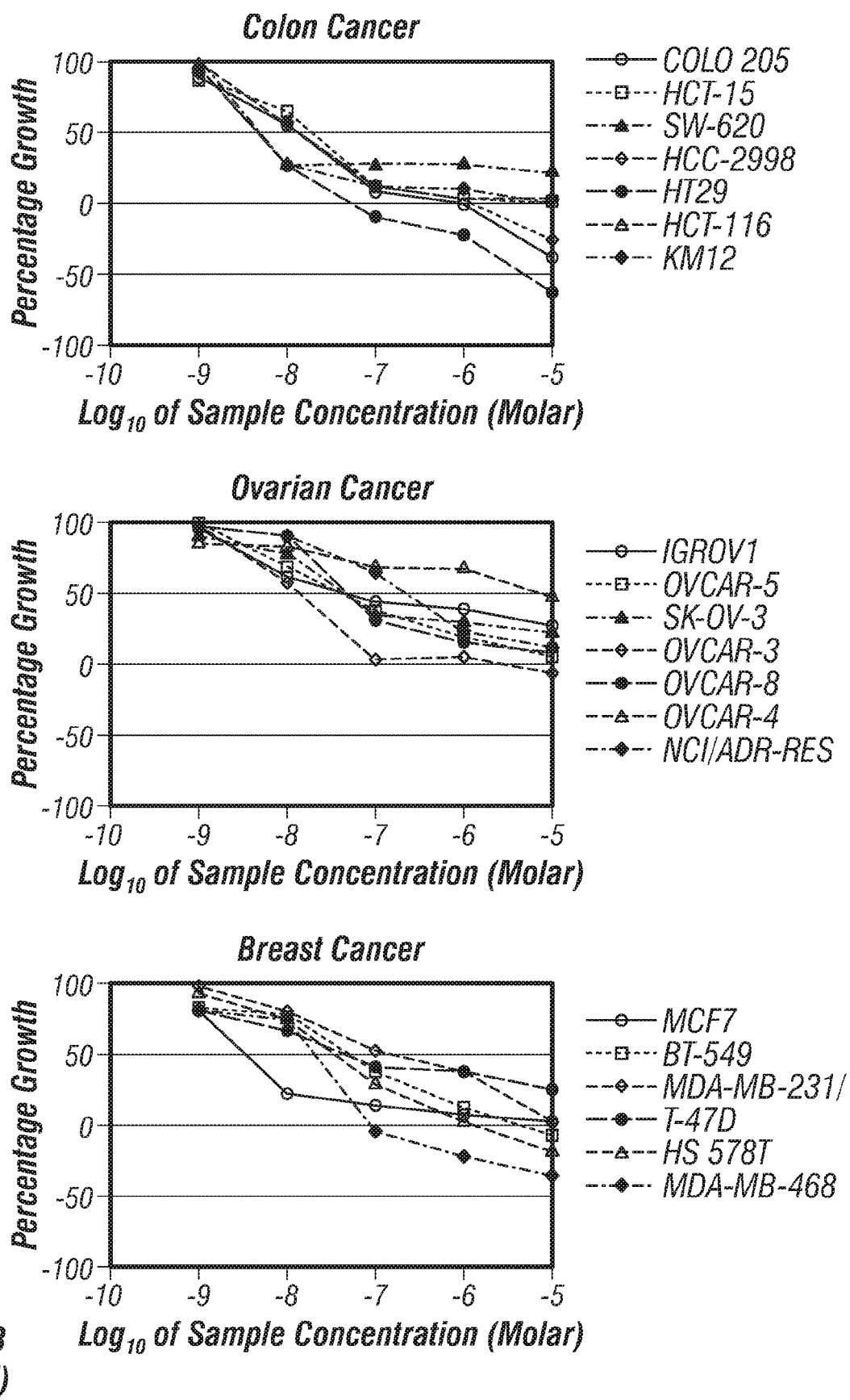
Figure 7C:
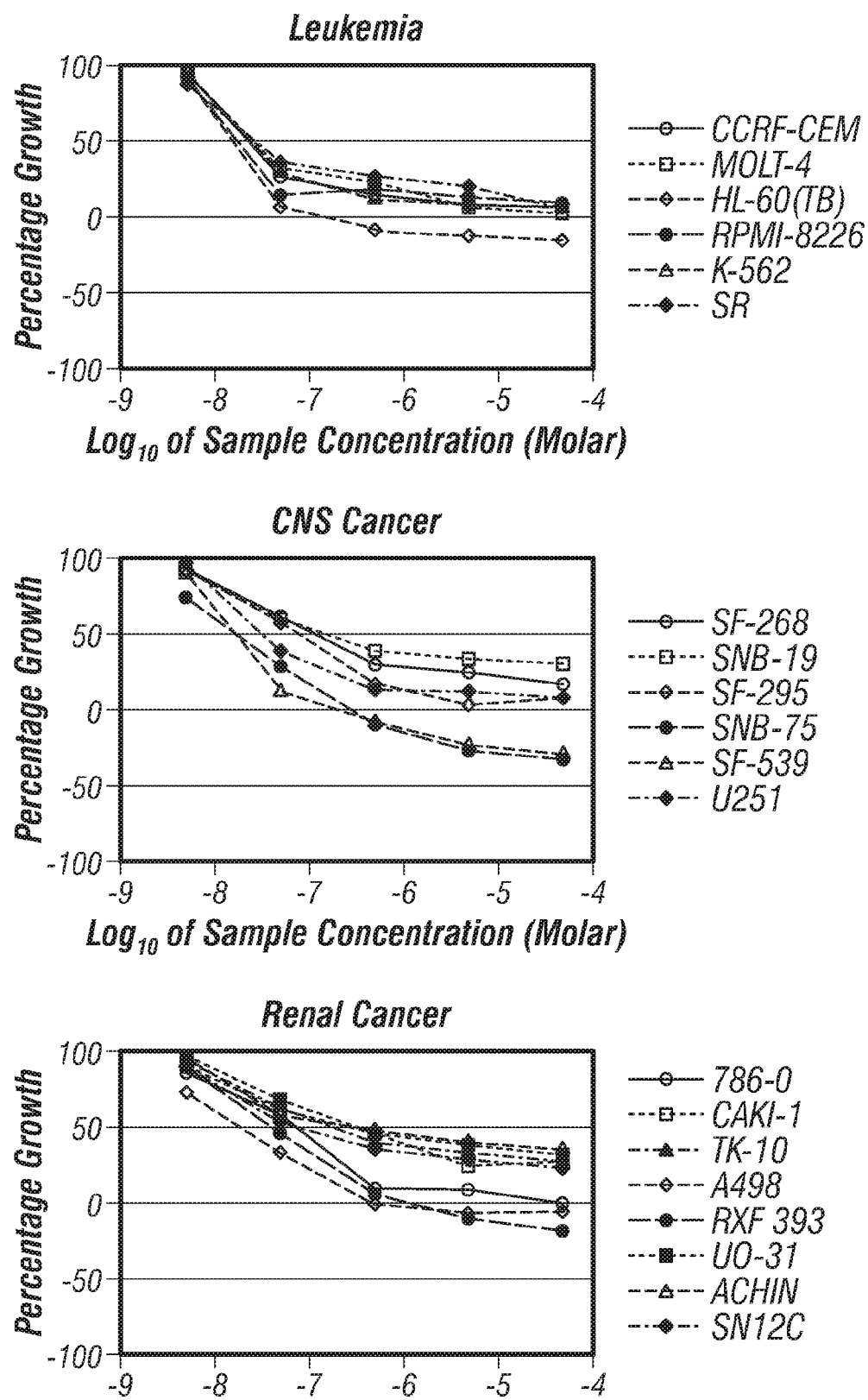
Figure 7C:
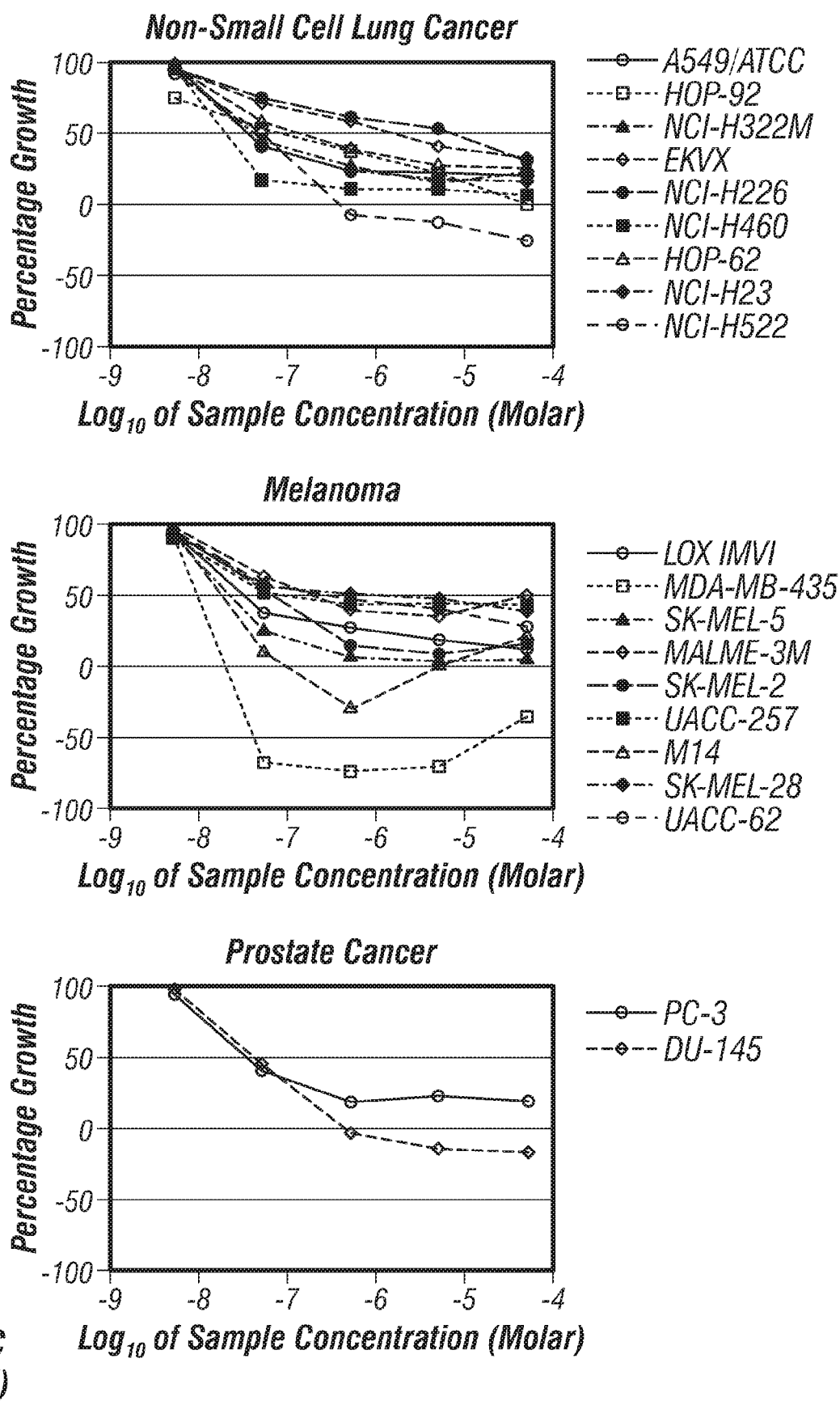
Figure 7C:
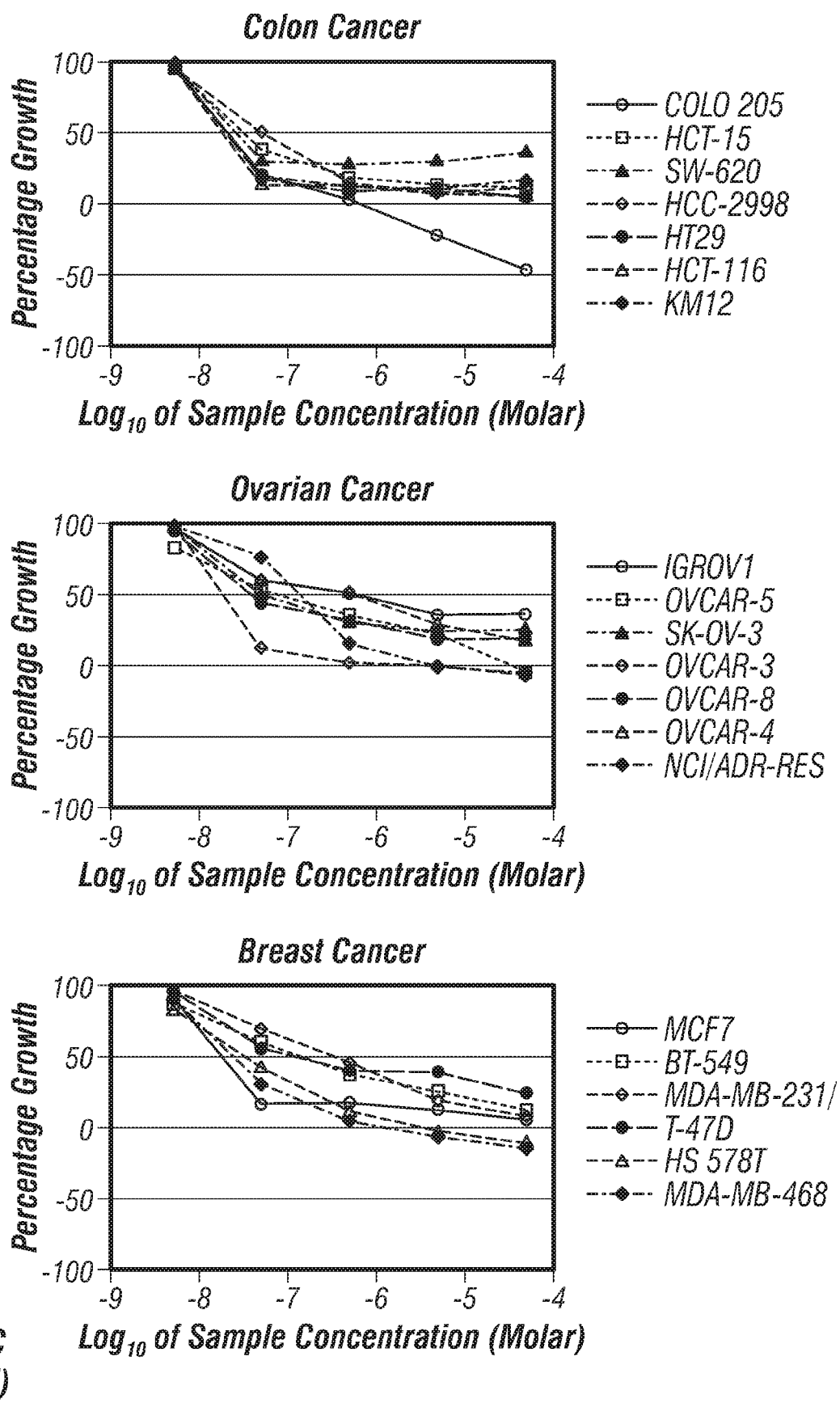
Figure 7D:
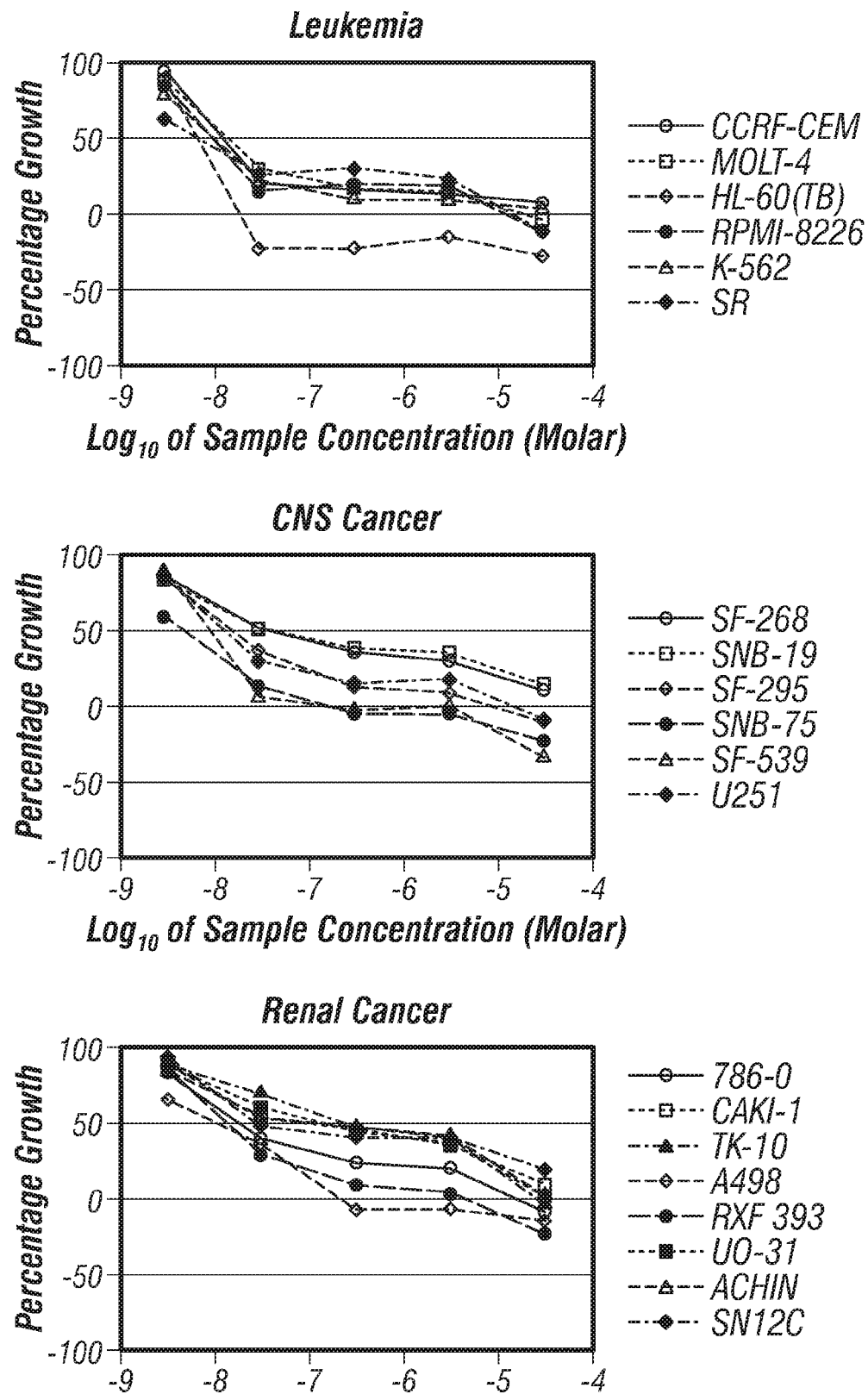
Figure 7D:
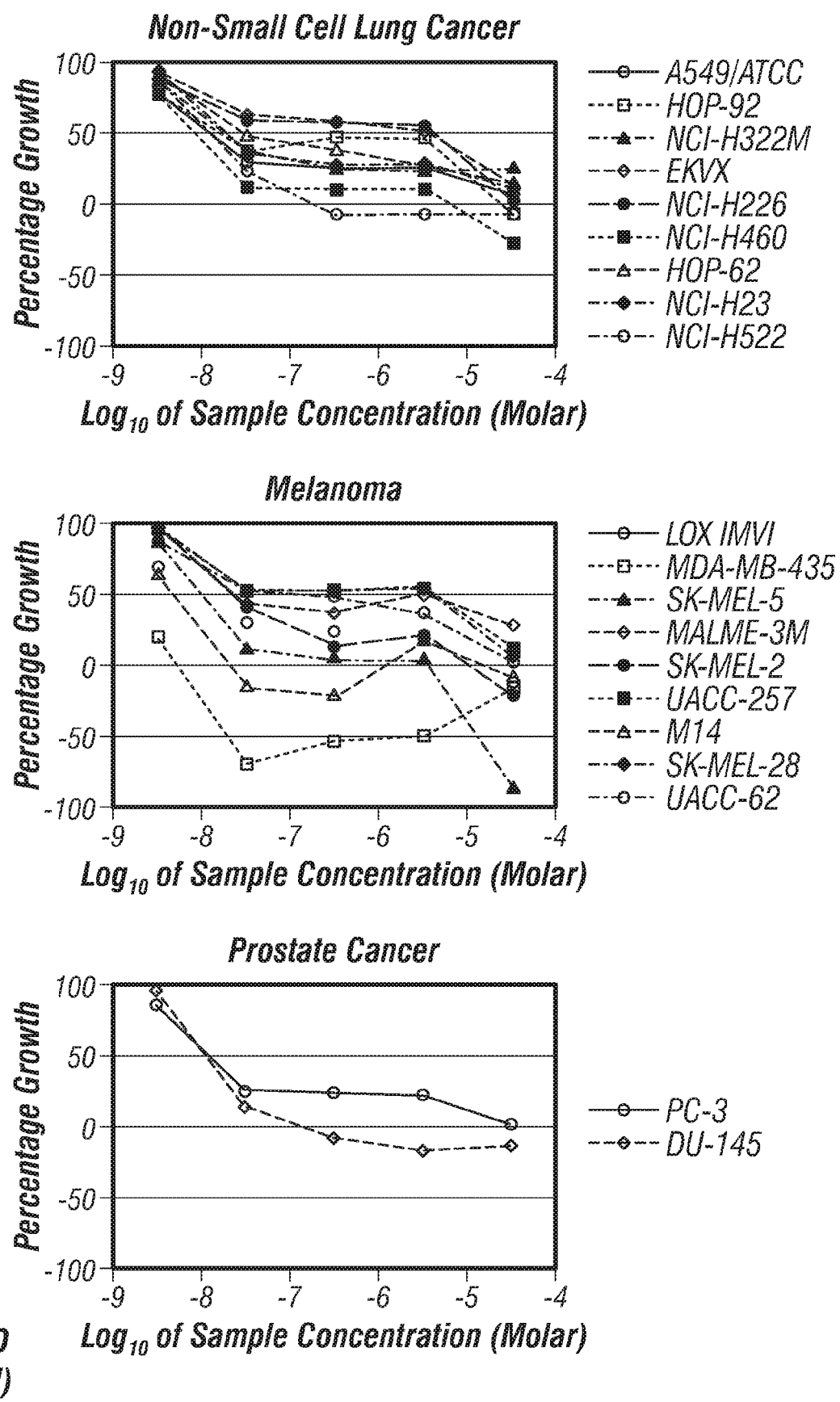
Figure 7D:
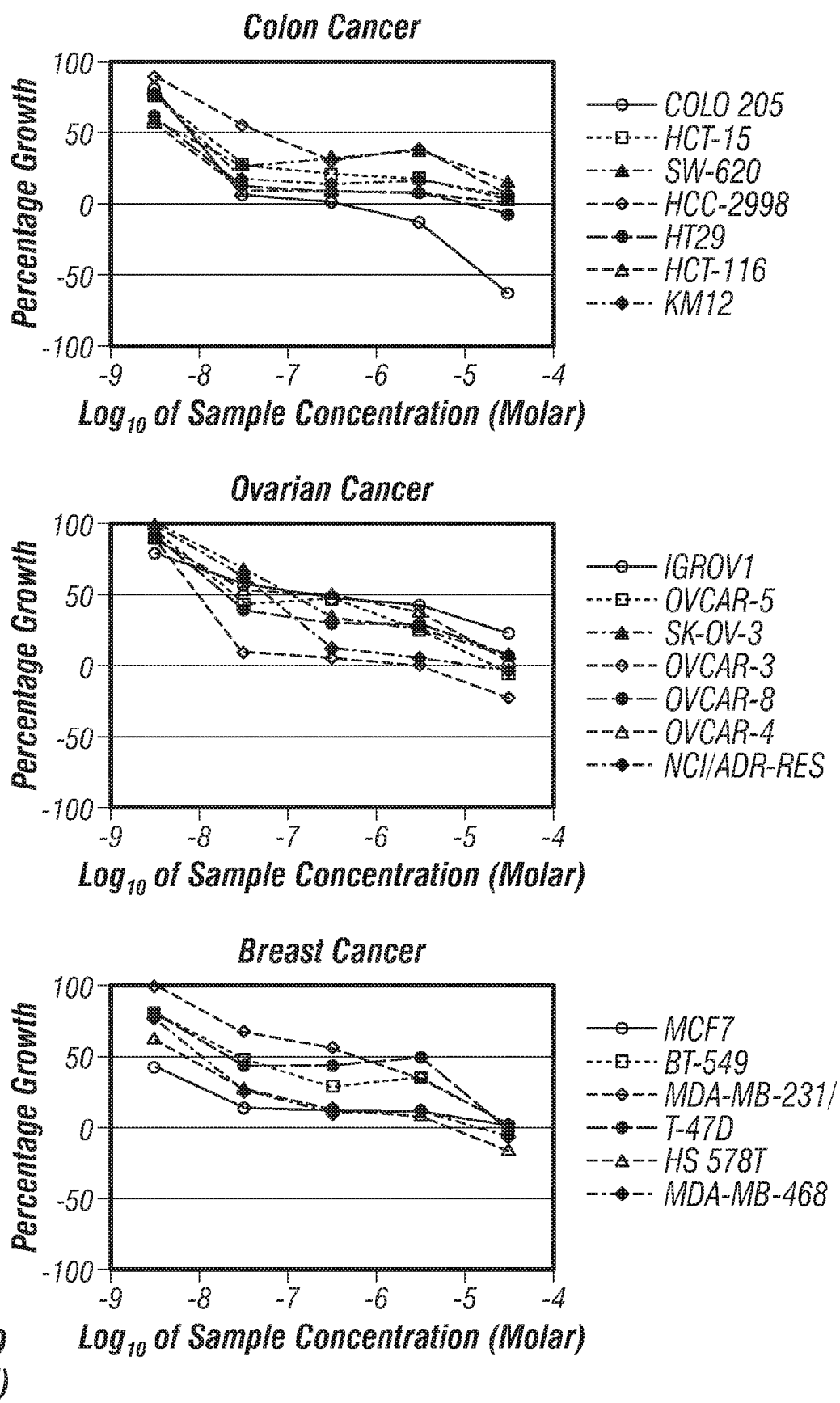
Figure 7E:
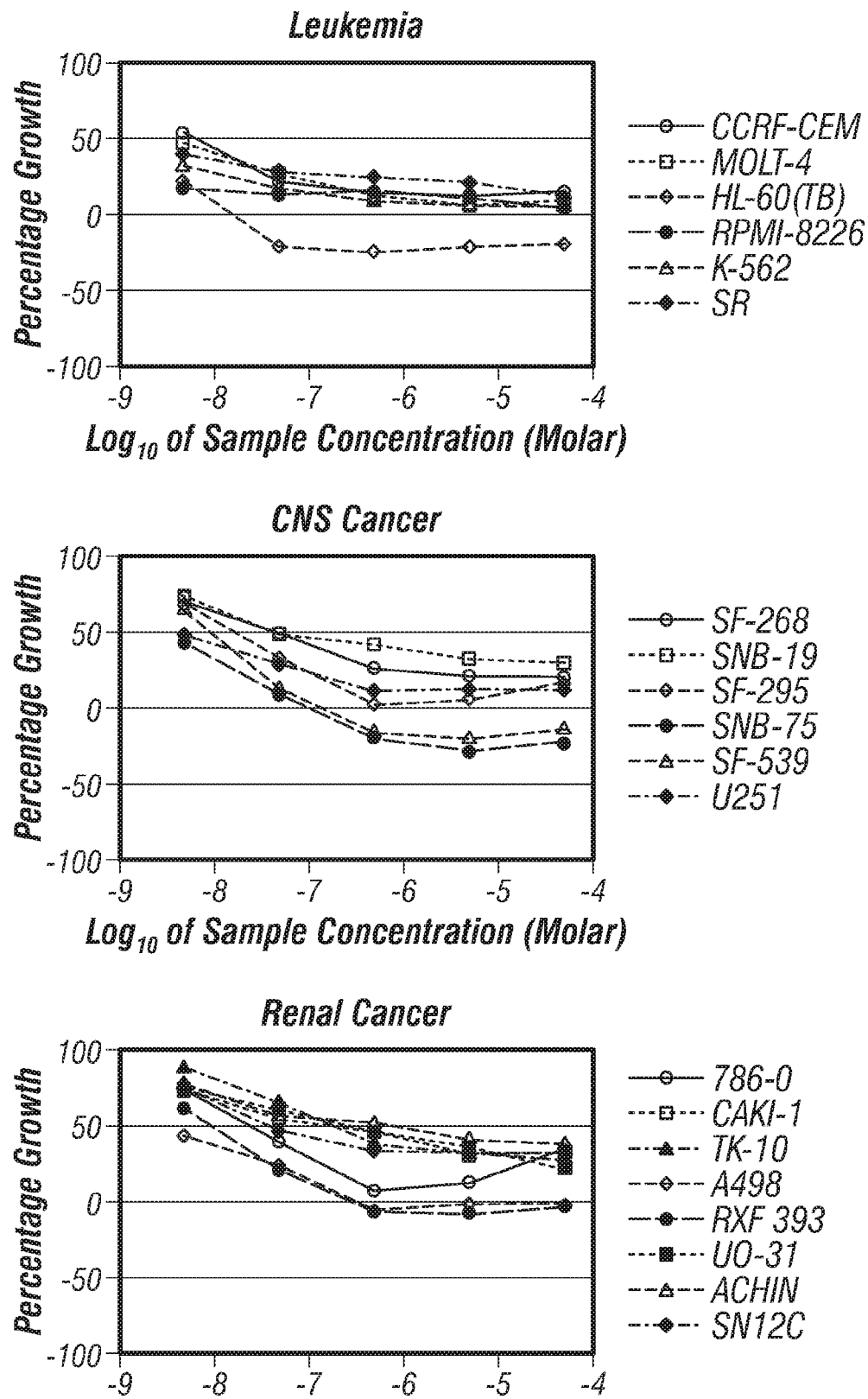
Figure 7E:
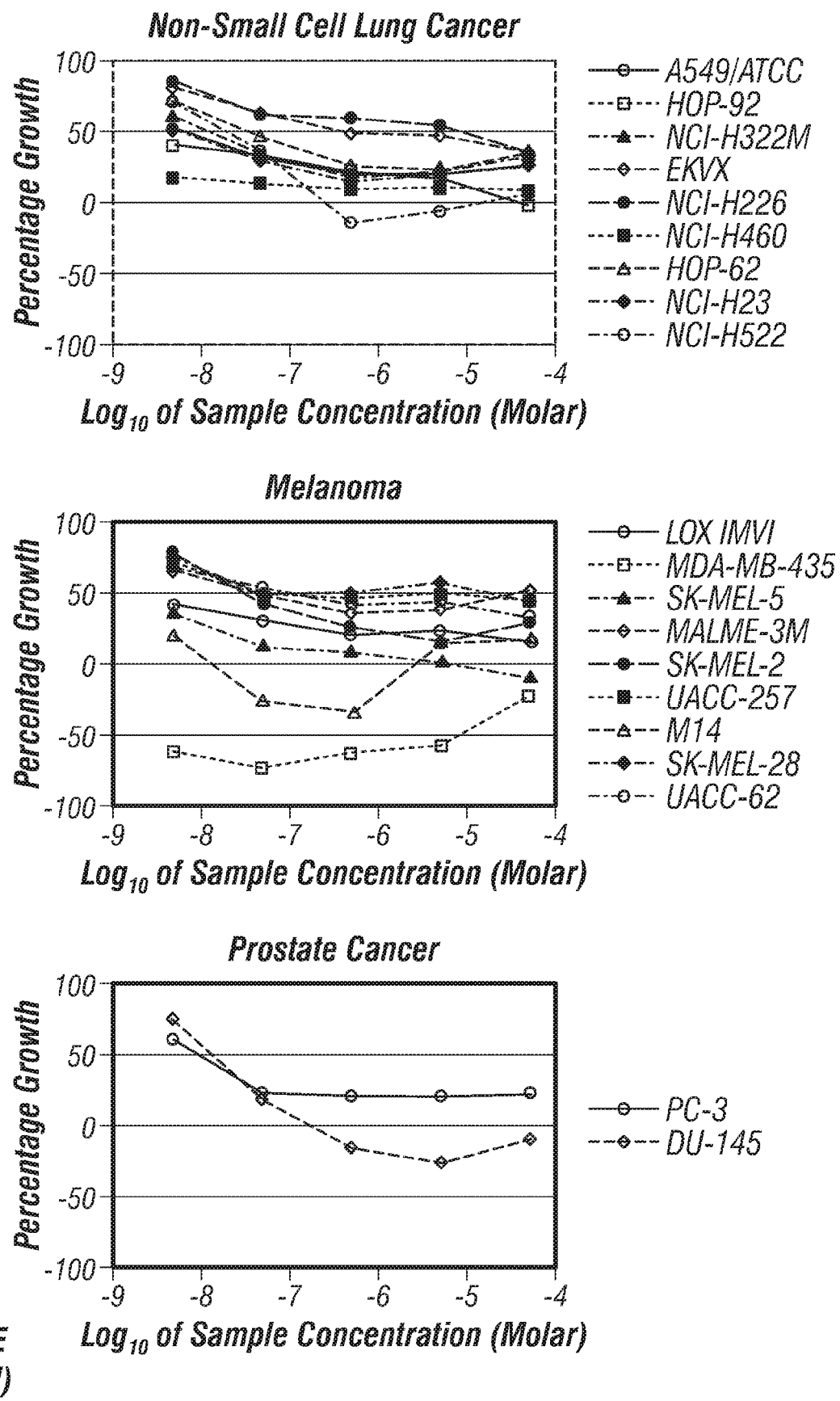
Figure 7E:
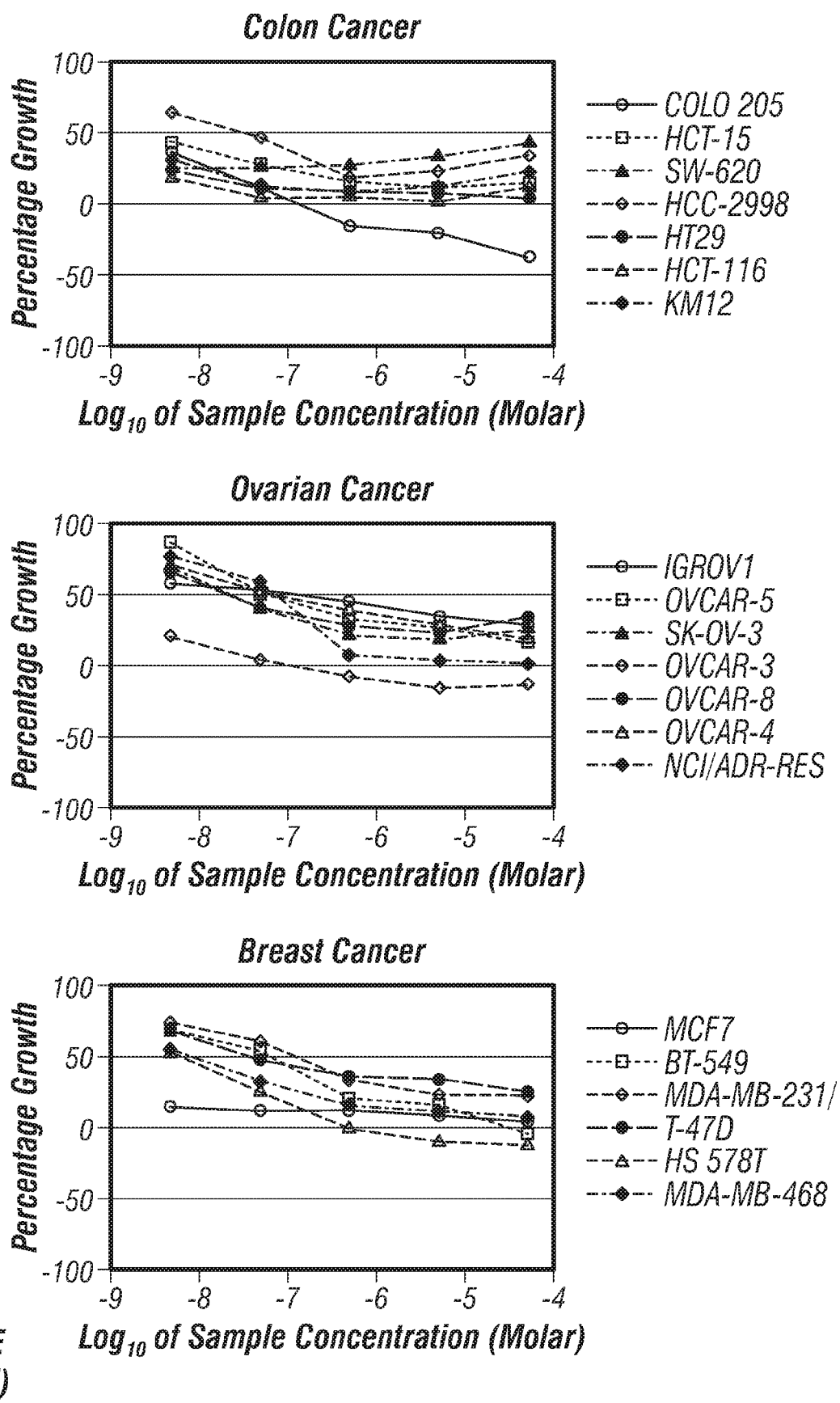
Figure 7F:
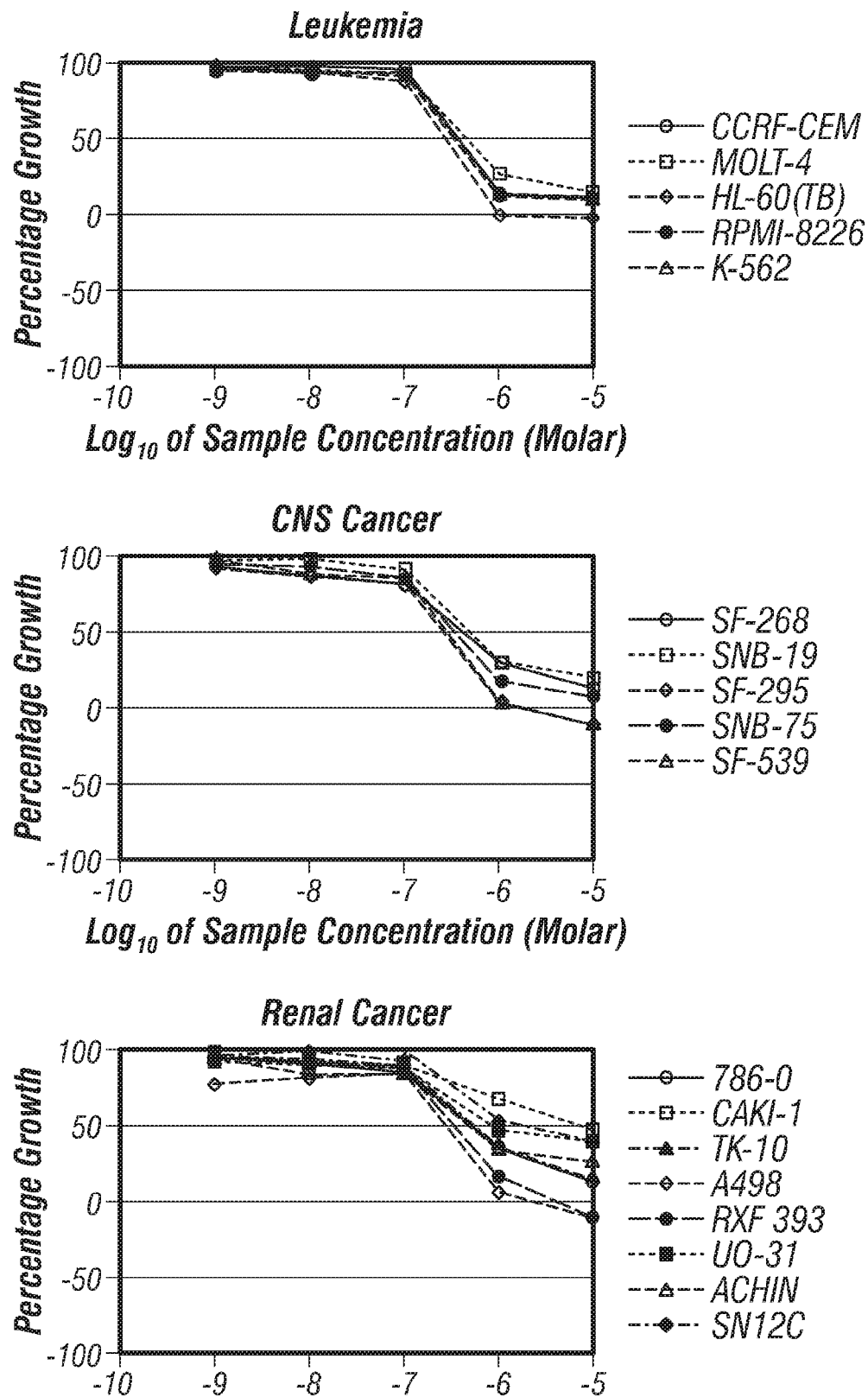
Figure 7F:
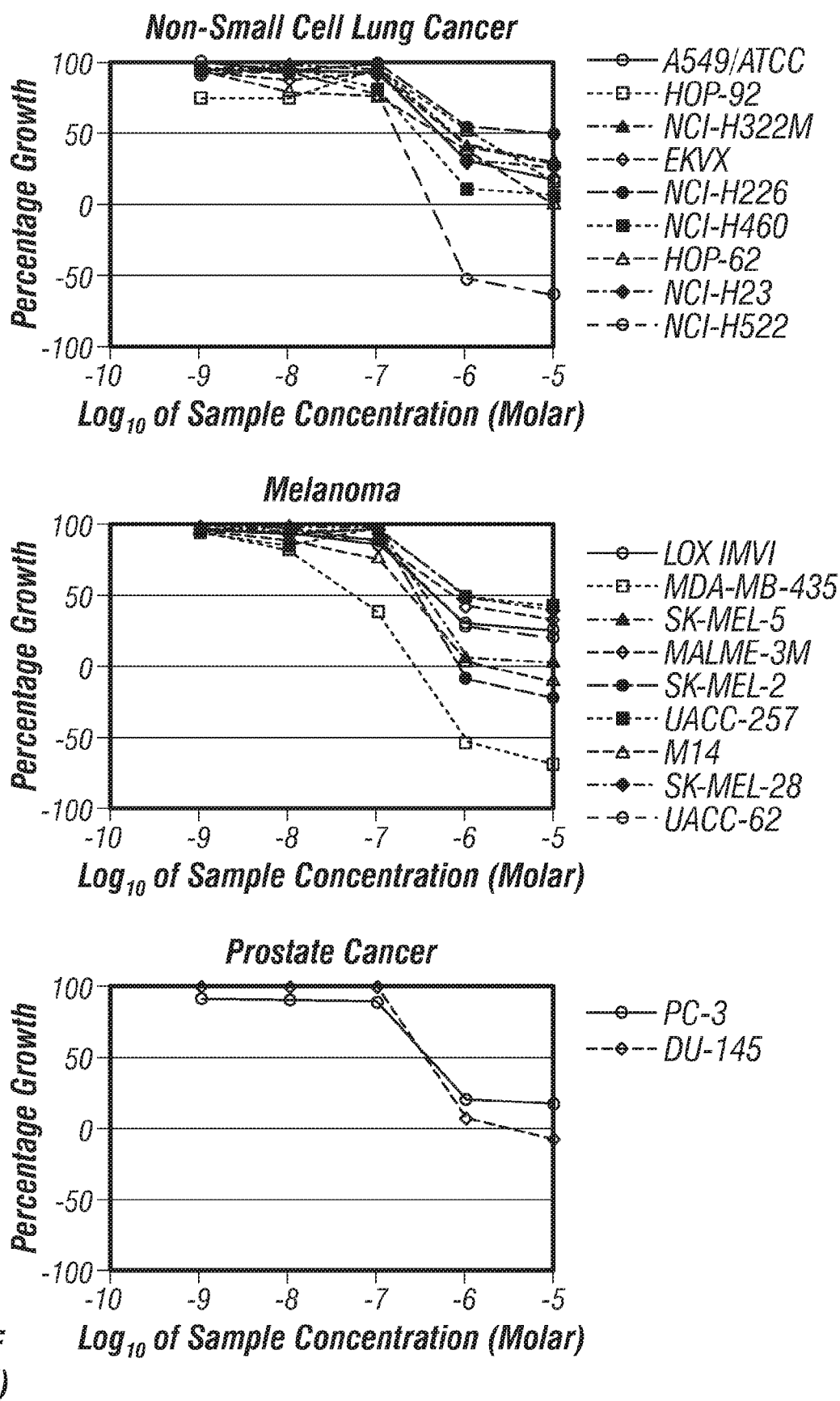
Figure 7F:
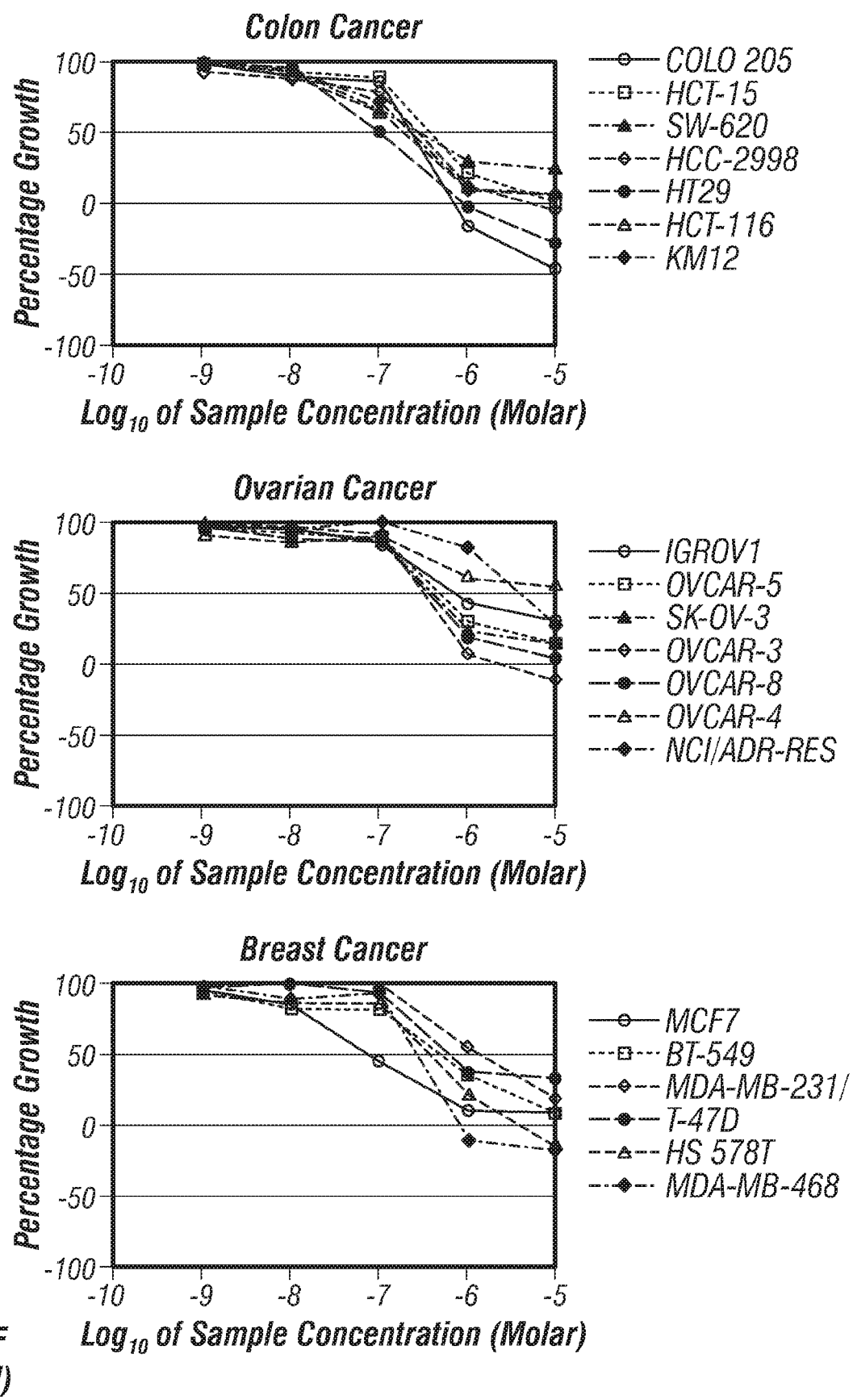
Figure 7G:
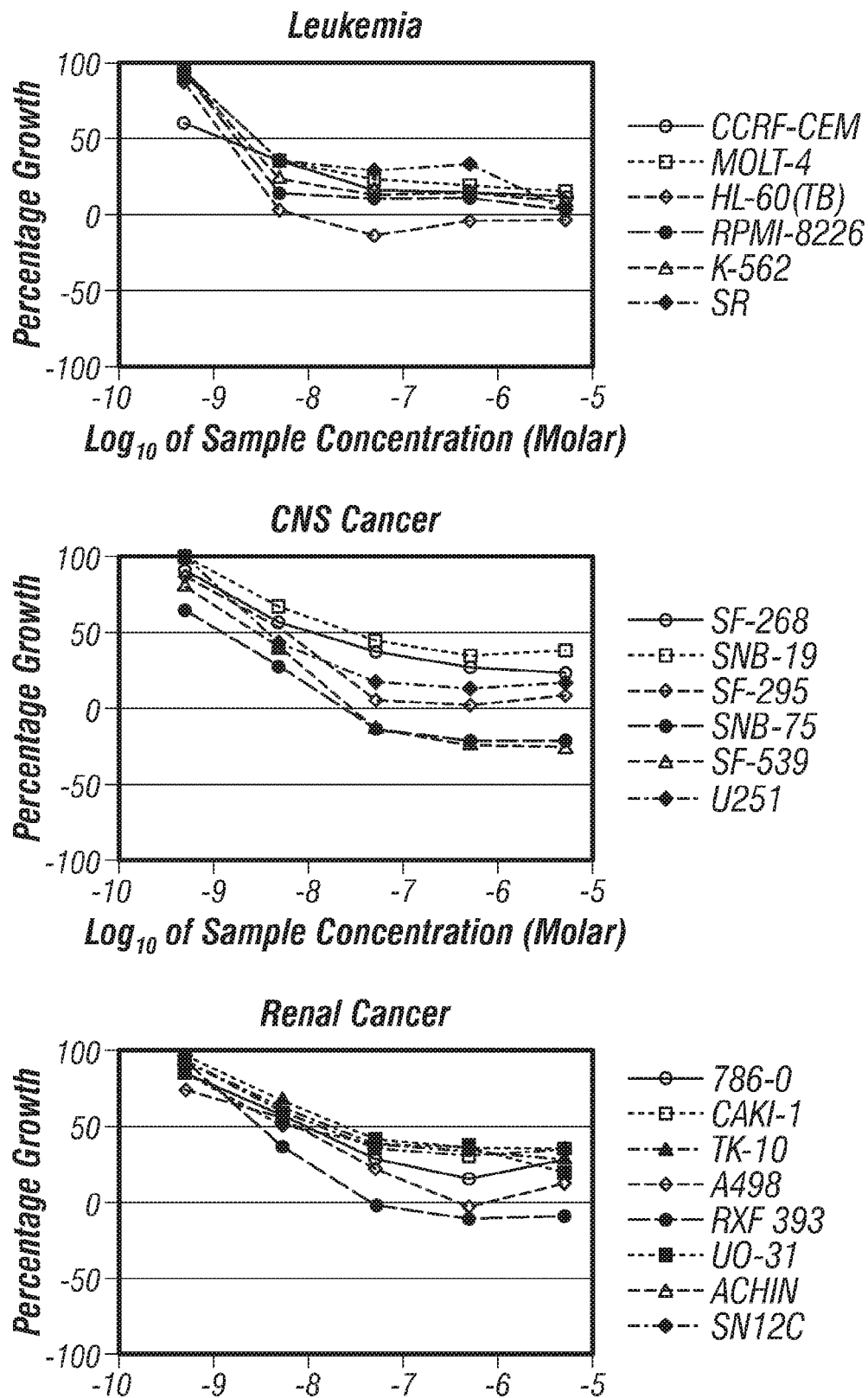
Figure 7G:
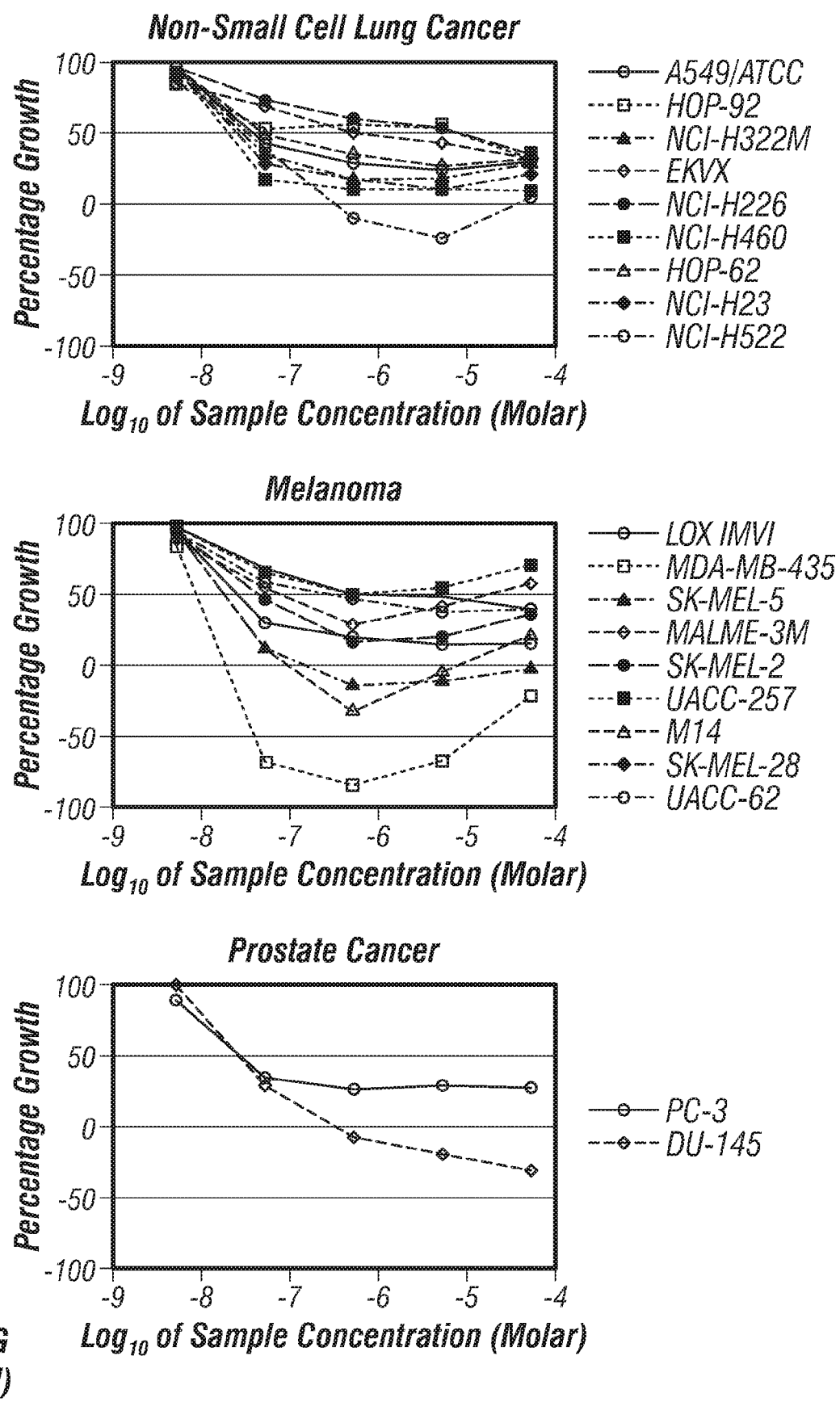
Figure 7G:
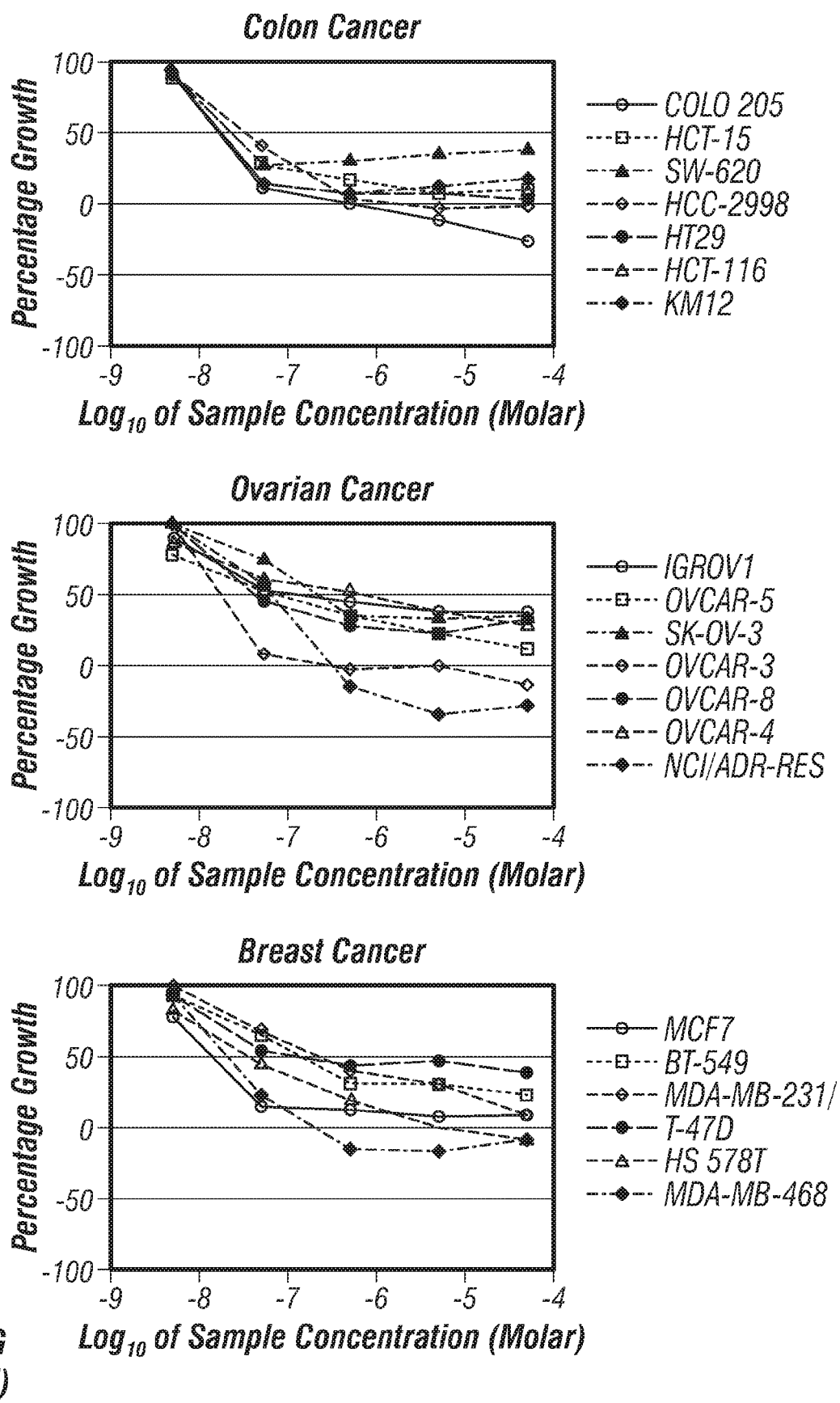

Several attempts to remove the Boc (Brønsted and Lewis acids) or Teoc (fluoride) groups from analogues 5-7 under various conditions in order to obtain the free amino epothilones were met with failure. TLC and LCMS analysis of reaction mixtures demonstrated liberation of the free amine, which decomposed rapidly. Concluding that the strongly basic and nucleophilic nature of the so placed primary amino group was responsible for the lability of these transiently detected compounds, aniline-type analogues were designed and synthesized (i.e. 8-14, FIG. 3). The inventors reasoned that the less basic character of this moiety would abrogate its destructive effect on the molecule, which may be exerted intramolecularly or intermolecularly, and yet be reactive enough to form amide bonds for conjugation purposes. In addition, anilines are quite tolerant to the intended Stille coupling conditions such that a final deprotection step would not be necessary (Izgu and Hoye, 2012.)

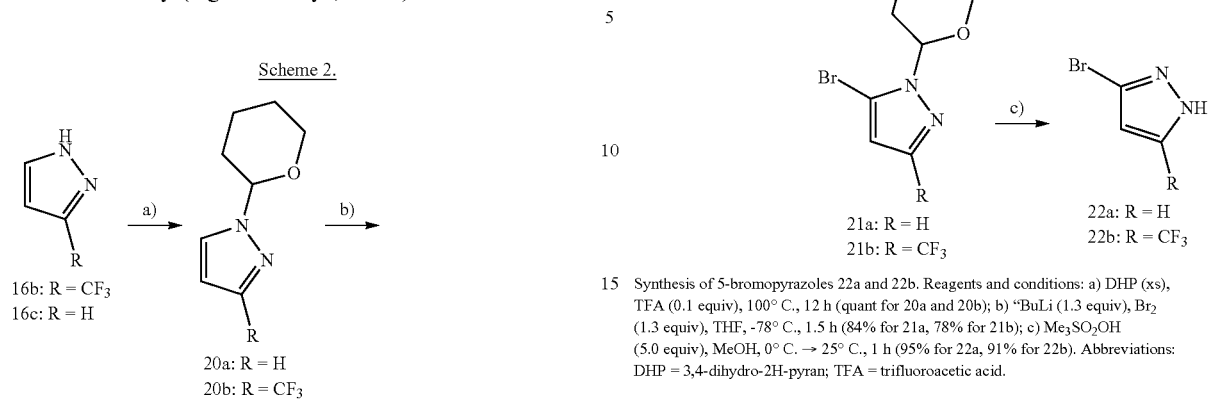

Synthesis of 5-bromopyrazoles 22a and 22b. Reagents and conditions: a) DHP (xs), TFA (0.1 equiv), 100° C., 12 h (quant for 20a and 20b); b) "BuLi (1.3 equiv), Br$_2$ (1.3 equiv), THF, -78° C., 1.5 h (84% for 21a, 78% for 21b); c) Me$_3$SO$_2$OH (5.0 equiv), MeOH, 0° C. → 25° C., 1 h (95% for 22a, 91% for 22b). Abbreviations: DHP = 3,4-dihydro-2H-pyran; TFA = trifluoroacetic acid.

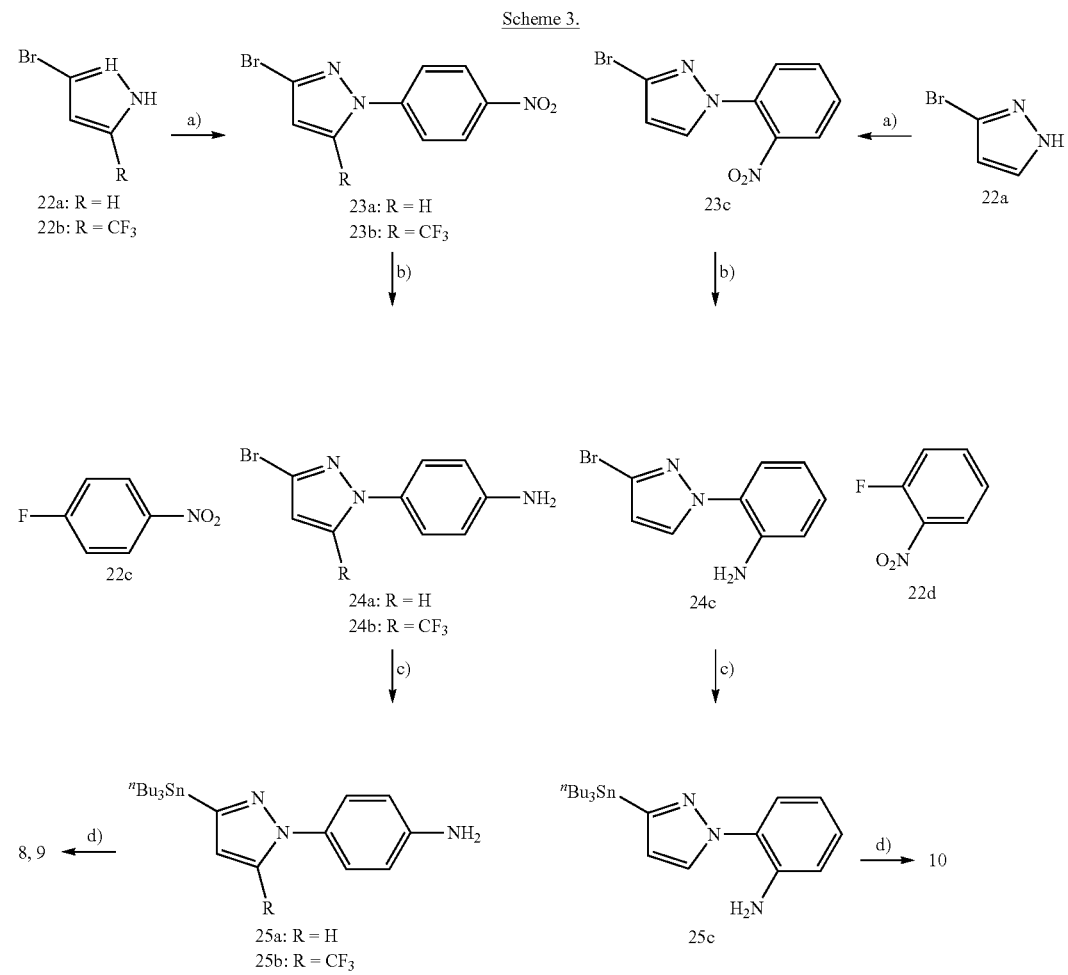

Synthesis of analogues 8-10. Reagents and conditions: (a) Method 1. NaH (1.5 equiv), 22c or 22d (1.1 equiv), THF, 0 → 25° C. (79% for 23a, 74% for 23c). Method 2. K$_2$CO$_3$ (1.2 equiv), 22c (1.01 equiv), DMF, 25 → 80° C., 12 h [20% for 23b (60% for undesired N regioisomer)]. (b) SnCl$_2$ (3.0 equiv), conc HCl, $^i$PrOH, 70° C. (75% for 24a, 76% for 24b, 70% for 24c); (c) "Bu$_3$SnSn"Bu$_3$ (3.0 equiv), Pd(PPh$_3$)$_4$ (0.1 equiv), PhMe, 110° C., 12 h (80% for 25a, 66% for 25b, 78% for 25c); (d) Pd$_2$(dba)$_3$ (0.1 equiv), AsPh$_3$ (0.2 equiv), CuI (0.4 equiv), 15 (1.0 equiv), DMF, 25° C. (84% for 8, 84% for 9, 75% for 10).

Scheme 2 depicts the synthesis of bromopyrazoles 22a and 22b from commercially available pyrazoles 16b and 16c, respectively. Thus, protection of 16b or 16c with 3,4-dihydro-2H-pyran in the presence of TFA led to tetrahydropyran derivatives 20a or 20b in quantitative yield. These intermediates were regioselectively brominated via their lithioderivatives ("BuLi; $Br_2$) to afford bromopyrazoles 21a (84% yield) and 21b (78% yield). Acid ($MeSO_2OH$)-mediated deprotection of the latter led smoothly to the desired pyrazole building blocks 22a (95% yield) and 22b (91% yield), respectively.

Scheme 3 summarizes the synthesis of epothilone analogues 8-10 from bromopyrazoles 22a and 22b. Reaction of 22a or 22b with commercially available 1-fluoro-4-nitrobenzene (22c) in the presence of NaH resulted in the formation of N-aryl bromopyrazole derivatives 23a (79% yield) or 23b (20% yield) through nucleophilic aromatic substitution. Reduction of the nitro group within 23a and 23b to the corresponding anilines was best realized with $SnCl_2$ in the presence of HCl (24a, 75% yield; 24b, 76% yield) (Xing and Ogata, 1982 and Bellamy and Ou, 1984). Subsequent palladium-catalyzed [$Pd(PPh_3)_4$] stannylation of the latter using "$Bu_3SnSn$"$Bu_3$ furnished stannanes 25a (80% yield) and 25b (66% yield), respectively. A similar sequence of reactions starting from bromopyrazole 22a and commercially available 1-fluoro-4-nitrobenzene (22d) led to the required amino stannane 25c in similar yields as shown in Scheme 3. Palladium-catalyzed couplings [$Pd_2(dba)_3$, $AsPh_3$, CuI] of stannanes 25a, 25b, and 25c with vinyl iodide 15 provided targeted epothilone analogues 8 (84% yield), 9 (84% yield) and 10 (75% yield), respectively, as shown in Scheme 3.

Epothilone analogues 11-14 were synthesized from bromopyrazole 22a and commercially available nitroaryl fluorides 22e-22h, respectively, employing analogous reactions to those described above for epothilones 8-10 (Scheme 3) and in similar yields, as shown in Scheme 4.

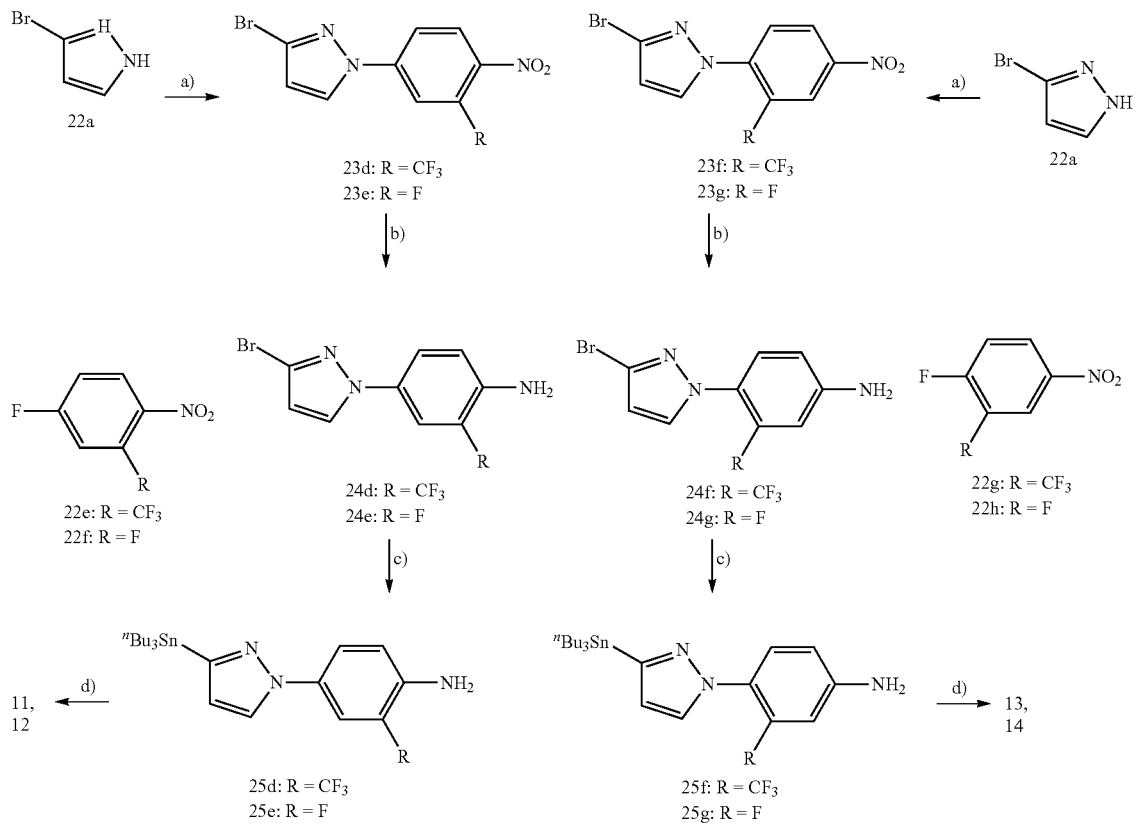

Scheme 4.

Synthesis of analogues 11-14. Reagents and conditions: (a) Method 1. NaH (1.5 equiv), 22e or 22g (1.1 equiv), THF, 0 → 25° C. (80% for 23d, 68% for 23f). Method 2. $K_2CO_3$ (1.2 equiv), 22f or 22h (1.01 equiv), DMF, 25 → 80° C., 12 h (58% for 23e 89% for 23g); e) $SnCl_2$ (3.0 equiv), conc HCl, $^i$PrOH, 70° C. (63% for 24d, 72% for 24e, 57% for 24f, 85% for 24g); f) "$Bu_3SnSn$"$Bu_3$ (3.0 equiv), Pd(PPh$_3$)$_4$ (0.1 equiv), PhMe, 110° C., 12 h (55% for 25d, 70% for 25e, 52% for 25f, 69% for 25g);
g) Pd$_2$(dba)$_3$ (0.1 equiv), AsPh$_3$ (0.2 equiv), CuI (0.4 equiv), 15 (1.0 equiv), DMF, 25° C. (68% for 11, 63% for 12, 60% for 13, 91% for 14).

In some aspects, the epothilone compound is transformed into an aziridine analog. Using the Kürti-Falck aziridination reaction, the epoxide of epothilone B is transformed into an aziridine analog as shown in Scheme 5. First, the epothilone B was subjected to oxidatative cleavage of the extracyclic double bond to obtain a methyl ketone. After protection of the hydroxyl groups, the epoxide was reduced to the corresponding double bond. The double bond was then subjected to the Kürti-Falck aziridination reaction conditions to obtain the corresponding aziridine.

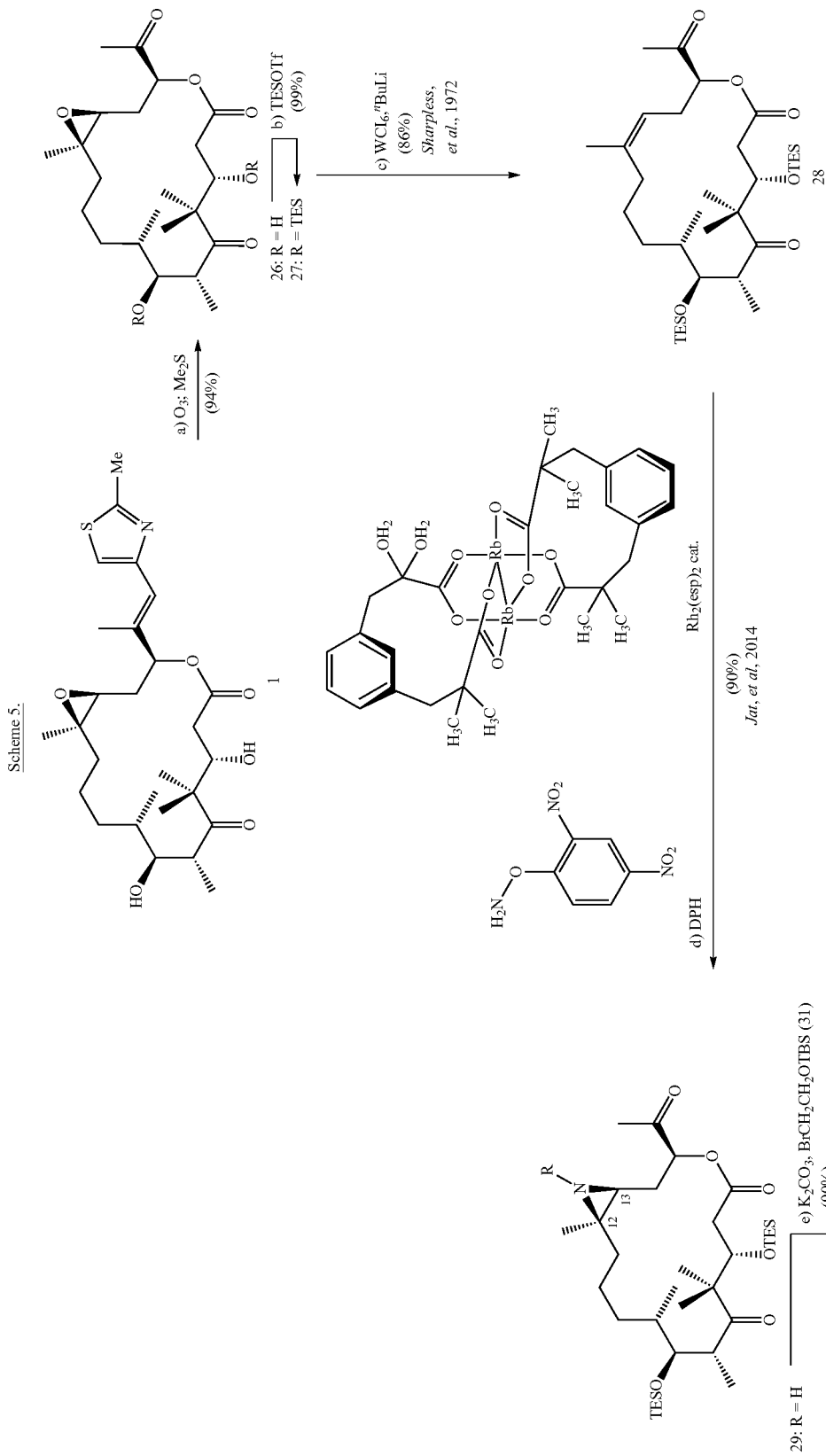

Synthesis of 12, 13-aziridine epothilone B methyl ketones 29 and 30 from epothilone B (1). Reagents and conditions: (a) O₃; Me₂S, CH₂Cl₂, -78° C., 5 min, 94%; (b) TESOTf (3.0 equiv.), 2,6-lutidine (4.0 equiv.), CH₂Cl₂, -78° C., 15 min, 99% (c) WCl₆ (2.0 equiv.), ⁿBuLi (4.0 equiv.), THF, -78 → 25° C., 40 min; 27, -20 → 0° C., 2 h, 86%; (d) Rh₂(esp)₂ (2 mol %), DPH (1.5 equiv.), CF₃CH₂OH, 25° C., 30 min, 90%; (e) 31 (5.0 equiv.), K₂CO₃ (4.0 equiv.), DMF, 65° C., 12 h, 90%. Abbreviations: DMF = dimethylformamide; DPH = O-(2,4-dinitrophenyl)hydroxylamine; TBS = tert-butyldimethylsilyl; TES = triethylsilyl; TFA = trifluoroacetic acid. THF = tetrahydrofuran.

In order to modify the methyl ketone analog (29), phosphonate coupling partners were prepared as outlined in Scheme 6 and Scheme 7.
Scheme 6.
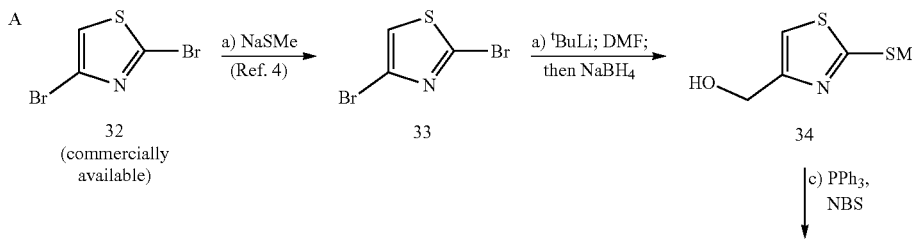
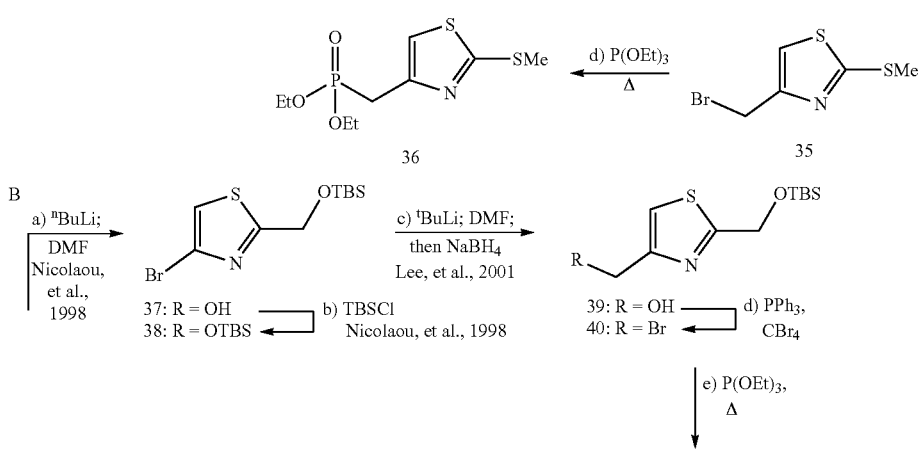
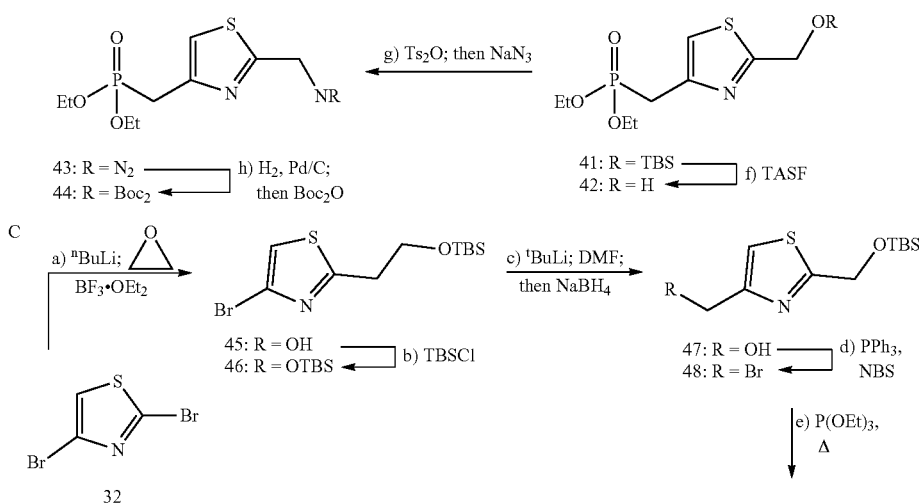
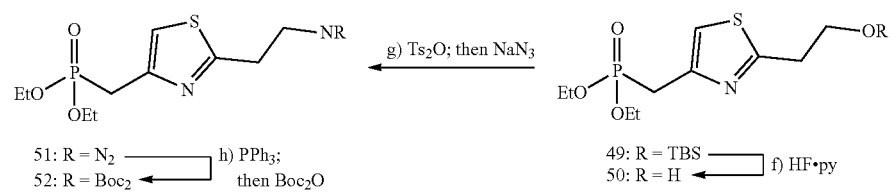

-continued

Synthesis of phosphonates 36 (A), 41 (B), 44 (B), and 52 (C). Reagents and conditions. A: a) NaSMe (3.0 equiv.), EtOH, 25° C., 3 h, 95%; b) $^t$BuLi (1.2 equiv.); DMF (2.0 equiv.), Et$_2$O, -78° C., 20 min; then NaBH$_4$ (1.9 equiv.), MeOH, 25° C., 15 min, 75% overall; c) PPh$_3$ (1.05 equiv.), NBS (1.0 equiv.), THF, -78° C., 5 min, 78%; d) P(OEt)$_3$, 120° C., 2 h, 92%. B: a) $^n$BuLi (1.2 equiv.); DMF (2.0 equiv.), Et$_2$O, -78° C., 20 min; then NaBH$_4$ (1.9 equiv.), MeOH, 25° C., 15 min, 66% overall; b) TBSCl (1.3 equiv.), imidazole (2.0 equiv.), CH$_2$Cl$_2$, 25° C., 12 h, 96%; c) $^t$BuLi (1.2 equiv.); DMF (2.0 equiv.), Et$_2$O, -78° C., 20 min; then NaBH$_4$ (1.9 equiv.), MeOH, 25° C., 15 min, 78% overall; d) CBr$_4$ (1.7 equiv.), PPh$_3$ (1.7 equiv.), 2,6-lutidine (0.4 equiv.), MeCN, 0 → 25° C., 45 min, 93%; e) P(OEt)$_3$, 160° C., 3 h, 80%; f) TASF (2.5 equiv.), H$_2$O (10 equiv.), DMF, 0 → 25° C., 12 h, 79%; g) Ts$_2$O (1.5 equiv.), NEt$_3$ (2.0 equiv.), DMAP (0.1 equiv.), -20° C., 30 min; then NaN$_3$ (3.0 equiv.), DMF, -20° C., 15 min, 80% overall; h) 5% Pd/C (10% w/w), H$_2$ (1 atm), EtOAc, 25° C., 12 h; then Boc$_2$O (4.0 equiv.), THF, 25° C., 4 h, 91% overall. C: a) $^n$BuLi (1.0 equiv.); oxirane (1.0 equiv.), BF$_3$•OEt$_2$ (1.0 equiv.), Et$_2$O, -78° C., 40 min, 57%; b) TBSCl (1.2 equiv.), imidazole (1.5 equiv.), DMF, 25° C., 1 h, 99%; c) $^t$BuLi (1.2 equiv.); DMF (2.0 equiv.), Et$_2$O, -78° C., 5 min; then NaBH$_4$ (1.9 equiv.), MeOH 25° C., 15 min, 82% overall; d) PPh$_3$ (1.05 equiv.), NBS (1.0 equiv.), CH$_2$Cl$_2$, -78° C., 25 min, 97%; e) P(OEt)$_3$, 160° C., 2 h, 99%; f) HF•py (5.0 equiv.), THF, 0° C., 5 h, 99%; g) Ts$_2$O (1.5 equiv), NEt$_3$ (2.0 equiv), DMAP (0.1 equiv), CH$_2$Cl$_2$, 0° C., 40 min; then NaN$_3$ (3.0 equiv), DMF, 65° C., 2 h, 78% overall; j) PPh$_3$ (3.0 equiv.), THF/H$_2$O (9:1), 60° C., 2 h; then Boc$_2$O (3.0 equiv.), NEt$_3$ (3.0 equiv.), DMAP (0.2 equiv.), MeCN, 25° C., 4 h, 95% overall. Abbreviations: Boc = tert-butyloxycarbonyl; DMAP = 4-dimethylaminopyridine; NBS = N-bromosuccinimide; TASF = tris(dimethylamino)sulfonium difluorotrimethylsilicate; Ts = 4-toluenesulfonyl.

Scheme 8.

A

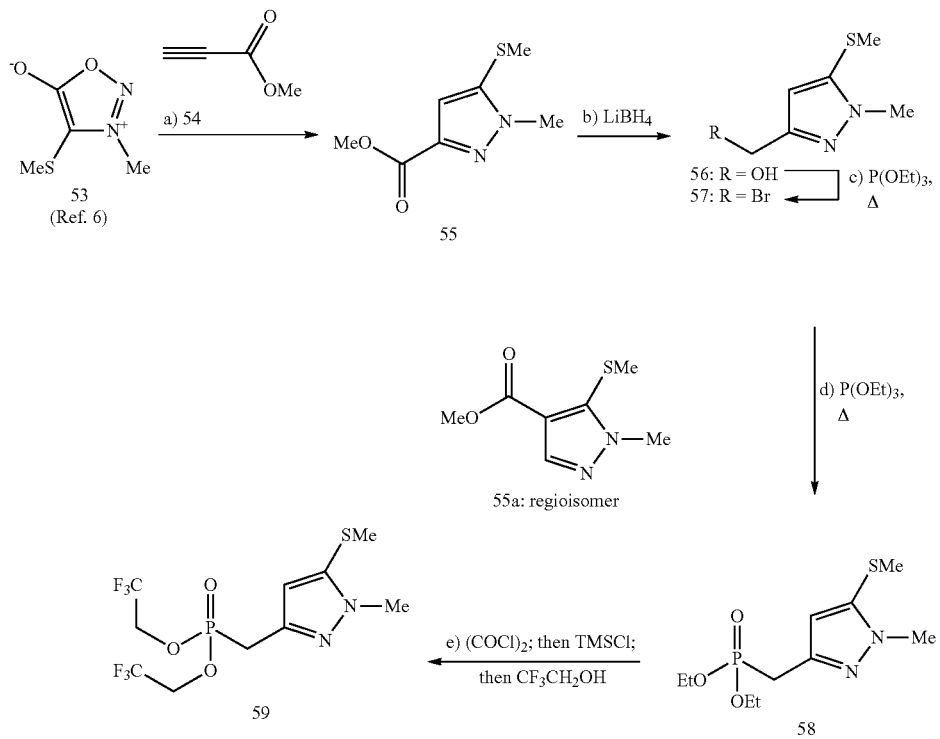

B

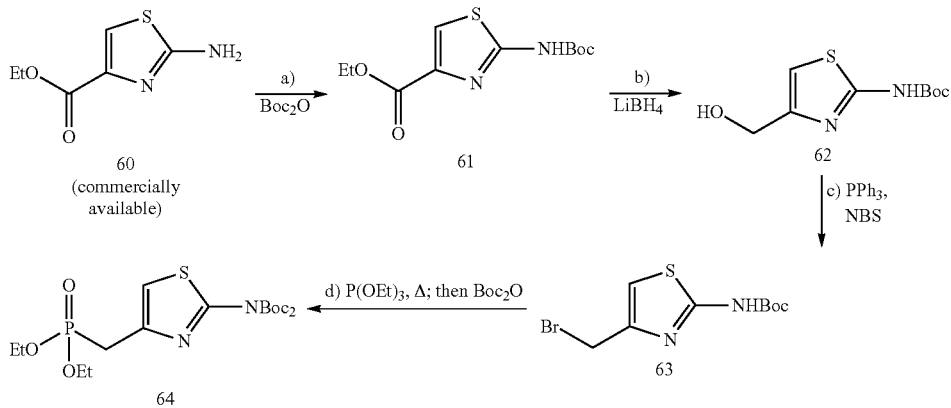

C

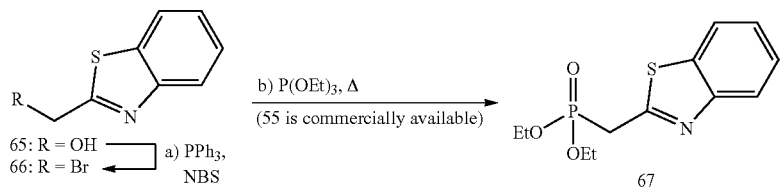

D

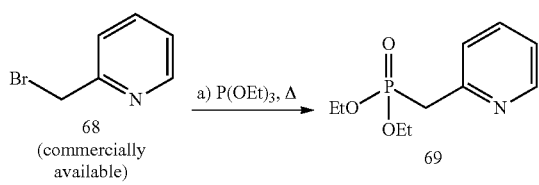

Synthesis of phosphonates 58 (A), 59 (A), 64 (B), 67 (C), and 69 (D), Reagents and conditions A: a) 50 (2.0 equiv.), xylenes, 130° C., 12 h, 68%; b) LiBH₄ (10 equiv.), Et₂O, 0 → 25° C., 3 h, 82%; (c) PPh₃ (1.05 equiv.), NBS (1.0 equiv.), CH₂Cl₂, -78° C., 10 min, 85%; (d) P(OEt)₃, 120° C., 2h, 99%; (e) TMSCl (5.0 equiv.), CH₂Cl₂, 72 h; then (COCl)₂ (2.5 equiv.), DMF (cat.), CH₂Cl₂, 0° C., 4 h; then CF₃CH₂OH (4.0 equiv.), NEt₃ (6.0 equiv.), DMAP (0.02 equiv.), CH₂Cl₂, 25° C., 12 h, 86% overall. B: a) Boc₂O (1.2 equiv.), NEt₃ (2.0 equiv.), DMAP (0.1 equiv.), THF, 60° C., 3 h, 88%; b) LiBH₄ (3.0 equiv.), Et₂O, 0 → 25° C., 4 h, 94%; c) PPh₃ (1.05 equiv.), NBS (1.0 equiv.), CH₂Cl₂, -78° C., 15 min, 78%; d) P(OEt)₃, 120° C., 3 h, 87%. C: a) PPh₃ (1.05 equiv.), NBS (1.0 equiv.), CH₂Cl₂, -78° C., 10 min, 57%; b) P(OEt)₃, 120° C., 2 h 85%. D: a) P(OEt)₃, 120° C., 2 h, 60%. Abbreviations: TMS = trimethylsilyl.

The phosphonates were then coupled with the methyl ketone epothilone analog (30) as shown in Scheme 9 and Scheme 10. These compounds were then subjected to deprotection to afford the corresponding epothiolone analogs. In some cases, the epothilone analogs were further reacted to modify the aziridine group to introduce new functional groups such as the conversion of 78 to 80.

Scheme 9.

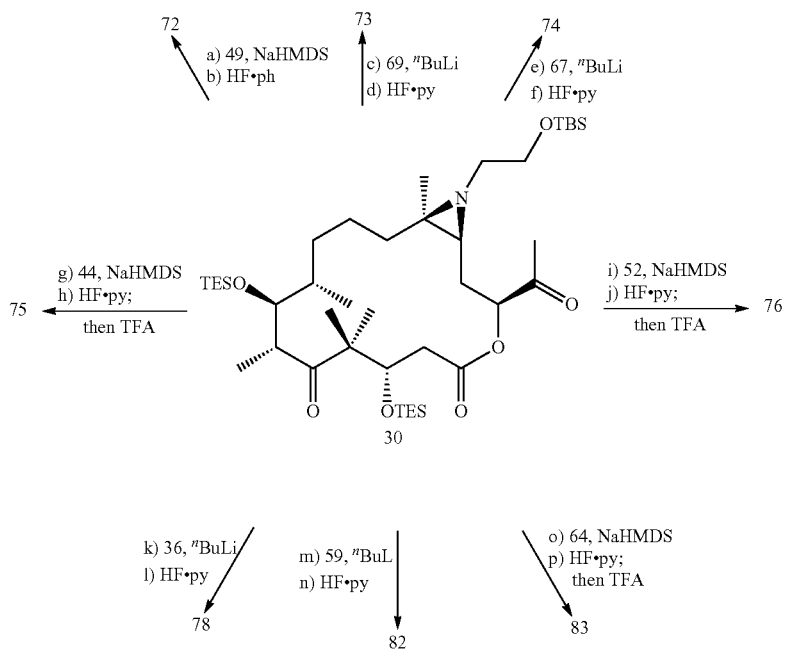

-continued

Synthesis of 12,13-aziridine epothilone B analogues 3-7, 9, 13, and 14 from tertiary aziridine 30. Reagents and conditions. a) 49 (12 equiv.), NaHMDS (9.7 equiv.); 30 (1.0 equiv.), THF, -78 → 0° C., 2.5 h, 50%. b) HF•py (165 equiv.), THF, 0 → 25° C., 4 h, 90%. c) 69 (28 equiv.), $^n$BuLi (22 equiv.); 30 (1.0 equiv.), THF, -78 → 25° C., 2 h, 94%. d) HF•py (170 equiv.), THF, 0 → 25° C., 5 h, 93%. e) 67 (13 equiv.), $^n$BuLi (10 equiv.); 30 (1.0 equiv.), THF, -78 → 10° C., 1.5 h, 65%. f) HF•py (150 equiv.), THF, 0 → 25° C., 9 h, 81%. g) 44 (8.3 equiv.), NaHMDS (6.8 equiv.); 30 (1.0 equiv.), THF, -78° C., 2.5 h, 68%. h) HF•py (265 equiv.), THF, 0 → 25° C., 5 h; then TFA (224 equiv.), CH$_2$Cl$_2$, 0° C., 2.5 h, 48% overall. i) 52 (12 equiv.), NaHMDS (9.7 equiv.); 30 (1.0 equiv.), THF, -78 → 0° C., 2.5 h, 45%. j) HF•py (178 equiv.), THF, 0 → 25° C., 5 h; then TFA (100 equiv.), CH$_2$Cl$_2$, 0 → 25° C., 3 h, 71% overall. k) 36 (15 equiv.), $^n$BuLi (12 equiv.); 30 (1.0 equiv.), THF, -78 → 0° C., 3 h, 60%. l) HF•py (120 equiv.), THF, 0 → 25° C., 1 h, 79%. m) 59 (16 equiv.), $^n$BuLi (13 equiv.); 30 (1.0 equiv.), THF, -78 → 25° C., 3 h, 70% (E:Z = 1:1). n) HF•py (428 equiv.), THF, 0 → 25° C., 5 h, 82%. o) 64 (14 equiv.), NaHMDS (14 equiv.); 30 (1.0 equiv.), THF, -78 → 0° C., 4 h, 69%. p) HF•py (215 equiv.), THF, 0 → 25° C., 5 h; then TFA (144 equiv.), CH$_2$Cl$_2$, 0 → 25° C., 6 h, 80% overall. Abbreviations: HMDS = hexamethyldisilazone.

Scheme 10.

A

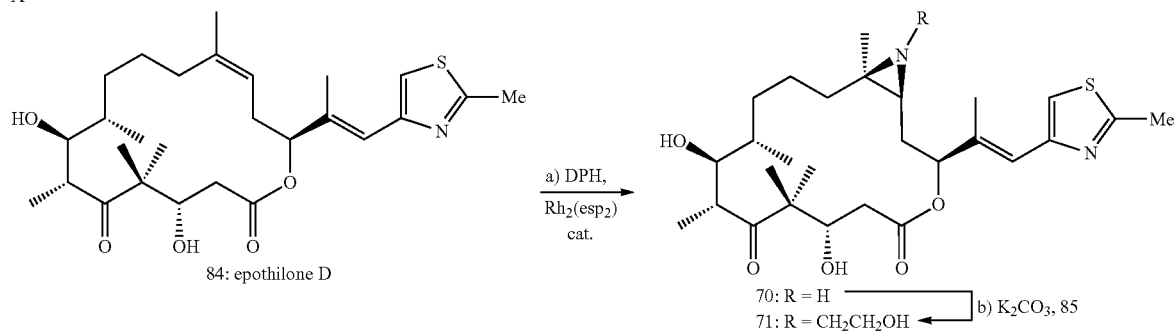

85: BrCH$_2$CH$_2$OH

B

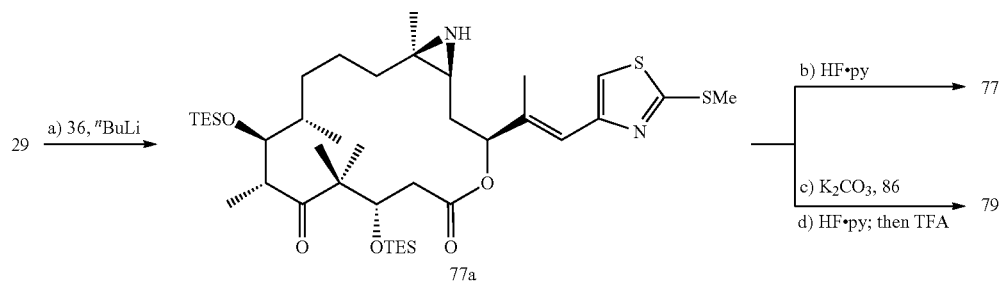

86: BrCH$_2$CH$_2$NHBoc

C

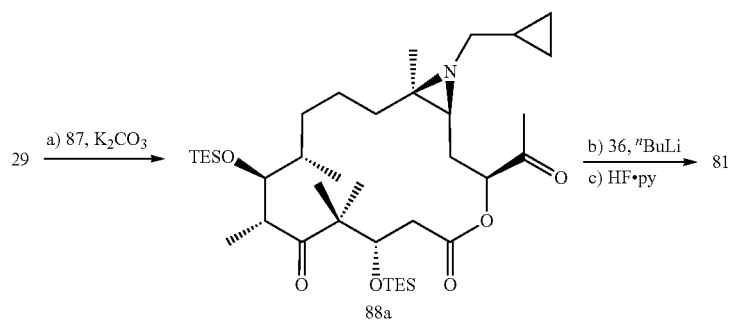

-continued

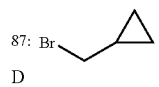
87: D

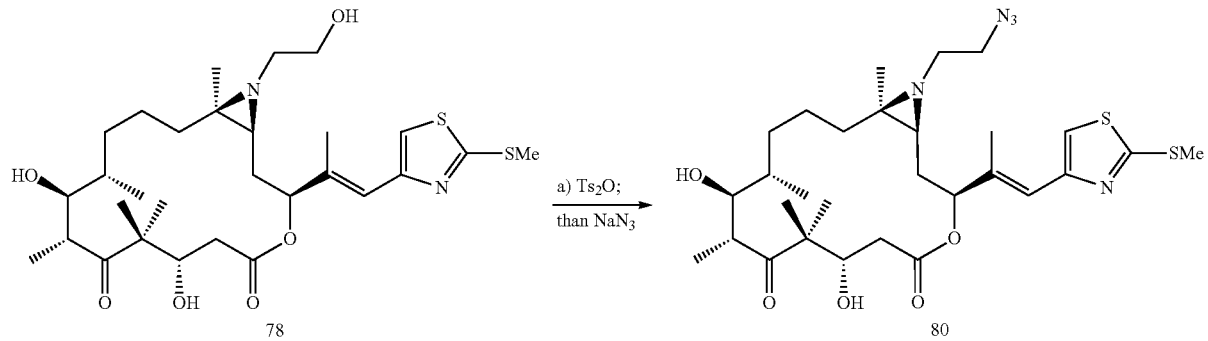

Synthesis of 12,13-aziridine epothilone B analogues 1 and 2 from epothilone D (50) (A), analogues 8 and 10 from methyl ketone 19 (B), analogue 12 from methyl ketone 19 (C), and analogue 11 from analogue 9 (D). Reagents and conditions. A: a) Rh$_2$(esp)$_2$ (5 mol %), DPH (1.1 equiv.), CF$_3$CH$_2$OH, 25° C., 4 h, 70%; b) 61 (6.0 equiv.), K$_2$CO$_3$ (6.0 equiv.), DMF, 70° C., 15 h, 93% B: a) 26 (9.6 equiv.), $^n$BuLi (7.7 equiv.); 19 (1.0 equiv.), THF, -78 → 25° C., 1.5 H, 59%. b) HF·py (220 equiv.), THF, 0 → 25° C., 1 h, 93%. c) 62 (6.0 equiv.), K$_2$CO$_3$ (5.0 equiv.), DMF, 75° C., 12 h, 32%. d) HF·py (500 equiv.), THF, 0° C., 1 h; then TFA (90 equiv.), CH$_2$Cl$_2$, 0 → 25° C., 1 h; 65% overall. C: a) 63 (6.0 equiv.), K$_2$CO$_3$ (5.0 equiv.), DMF, 75° C., 16 h, 92%. b) a) 26 (13 equiv.), $^n$BuLi (10 equiv.); 19a (1.0 equiv.), THF, -78 → 10° C., 1.5 h, 65%. c) HF·py (175 equiv.), THF, 0 → 25° C., 3.5 h, 92%. D: a) Ts$_2$O (5.0 equiv), NEt$_3$ (4.0 equiv), DMAP (0.7 equiv), CH$_2$Cl$_2$, 0 → 25° C., 45 min; then NaN$_3$ (4.0 equiv), DMF, 25° C., 17 h, 40% overall.

Additional Aziridine Compounds

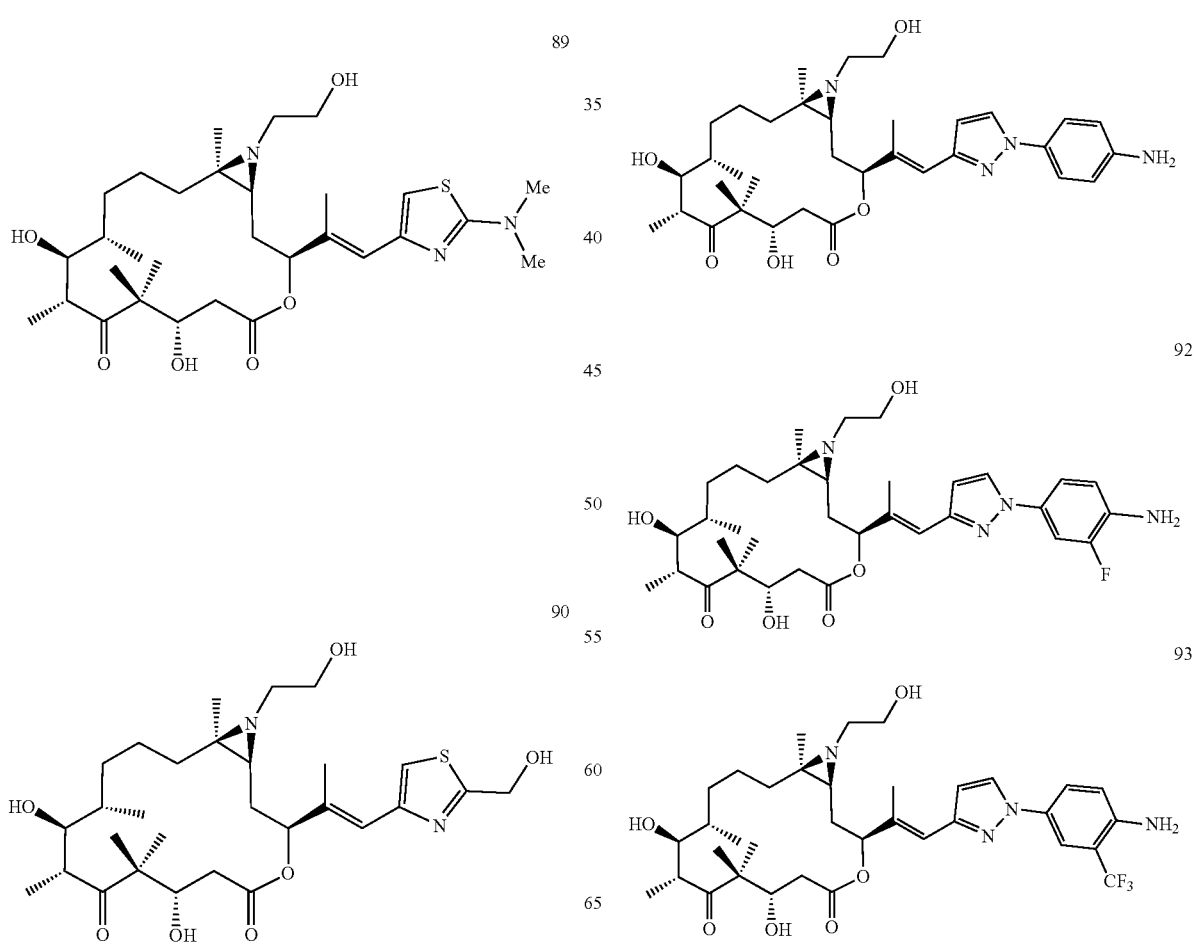

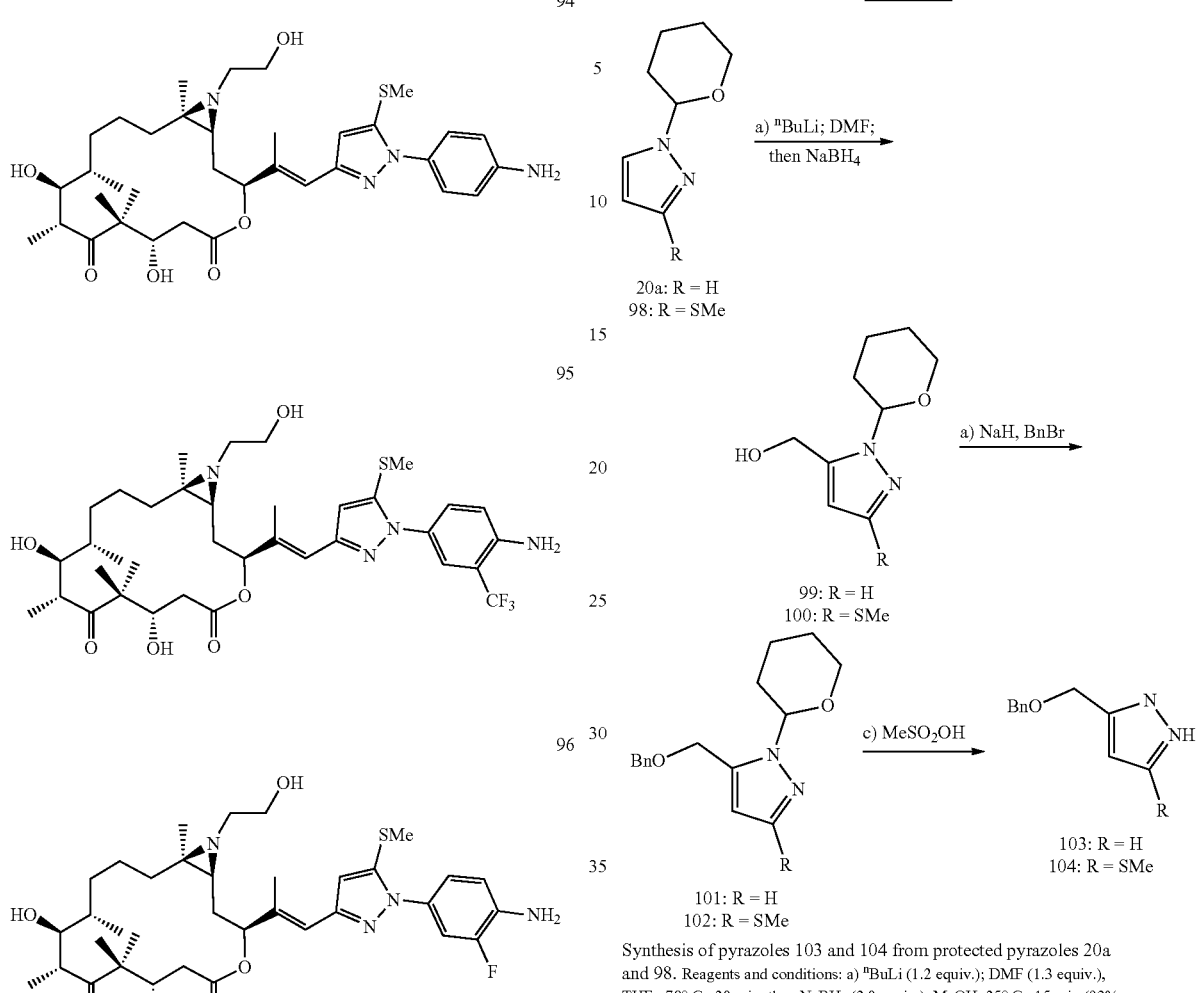
Scheme 11.
Synthesis of pyrazoles 103 and 104 from protected pyrazoles 20a and 98. Reagents and conditions: a) ⁿBuLi (1.2 equiv.); DMF (1.3 equiv.), THF, -78° C., 20 min; then NaBH₄ (2.0 equiv.), MeOH, 25° C., 15 min (93% overall for 99, 90% overall for 100); b) NaH (1.5 equiv.), BnBr (1.2 equiv.), DMF, 0 → 25° C., 1 h (94% for 101, 92% for 102); c) MeSO₂OH (5.0 equiv.), MeOH, 25° C., 30 min (99% for 103, 99% for 104).
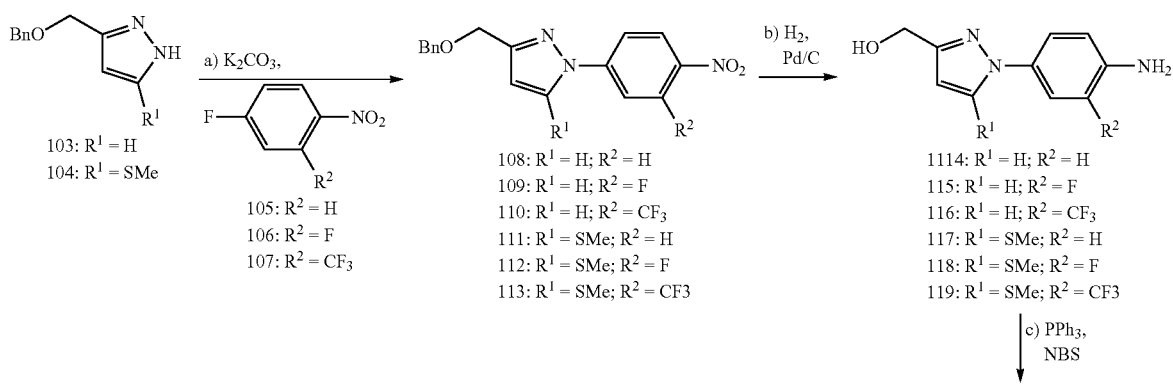
Scheme 12.

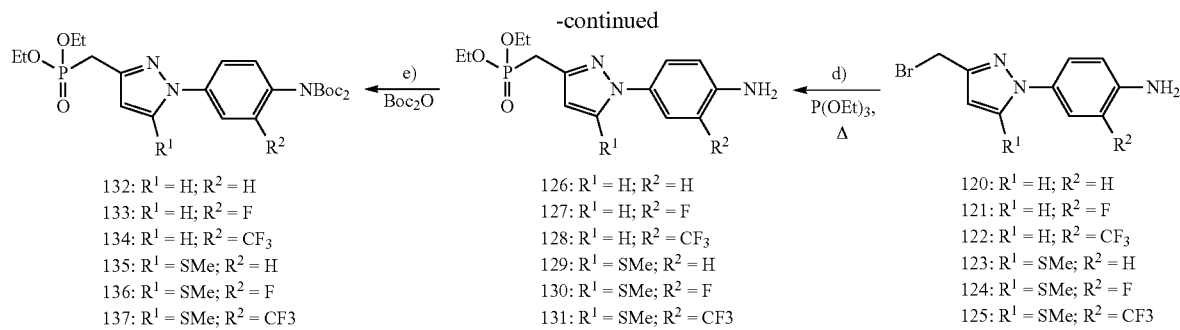

132: R¹ = H; R² = H
133: R¹ = H; R² = F
134: R¹ = H; R² = CF₃
135: R¹ = SMe; R² = H
136: R¹ = SMe; R² = F
137: R¹ = SMe; R² = CF3

126: R¹ = H; R² = H
127: R¹ = H; R² = F
128: R¹ = H; R² = CF₃
129: R¹ = SMe; R² = H
130: R¹ = SMe; R² = F
131: R¹ = SMe; R² = CF3

120: R¹ = H; R² = H
121: R¹ = H; R² = F
122: R¹ = H; R² = CF₃
123: R¹ = SMe; R² = H
124: R¹ = SMe; R² = F
125: R¹ = SMe; R² = CF3

Synthesis of phosphonates 132-137. Reagents and conditions: a) K₂CO₃ (1.5 equiv.), 105 or 106 or 107 (1.1 equiv.), DMF, 0 → 25° C., 3 h (72% for 108, 65% for 109, 68% for 110, 78% for 111, 82% for 112, 89% for 113); b) Pd/C (30% w/w), H₂ (1 atm), AcOH, 25° C., 12 h (95% for 114, 92% for 115, 97% for 116, 88% for 117, 83% for 118, 85% for 119); c) PPh₃ (1.05 equiv.), NBS (1.0 equiv.), CH₂Cl₂, -78° C., 20 min (64% for 120, 68% for 121, 73% for 122, 78% for 123, 83% for 124, 60% for 125); d) P(OEt)₃, 160° C., 3 h (90% for 126, 85% for 127, 88% for 128, 82% for 129, 80% for 130, 75% for 131); e) Boc₂O (3.0 equiv.), NEt₃ (3.0 equiv.), DMAP (0.2 equiv.), THF, 60° C., 4 h (87% for 132, 73% for 133, 70% for 134, 77% for 135, 82% for 136, 76% for 137).

Scheme 13.

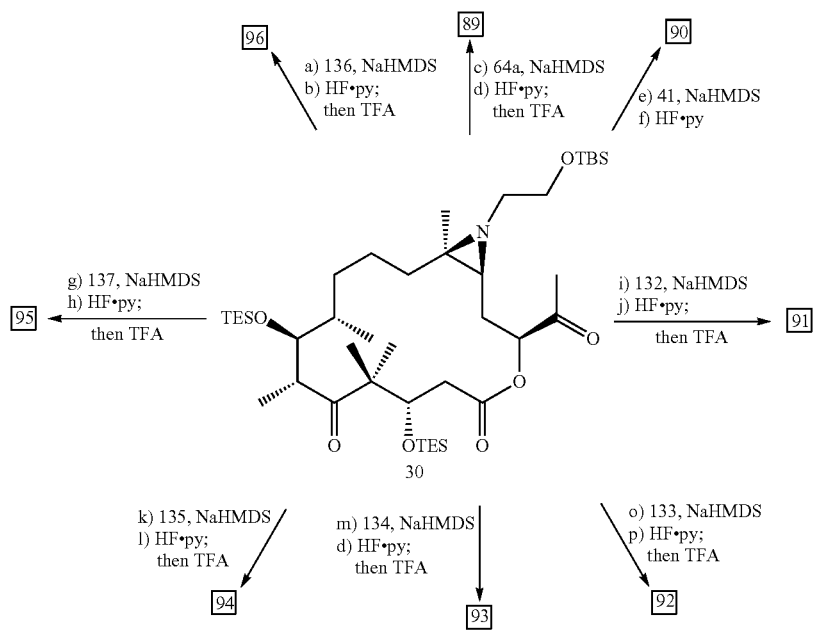

Synthesis of 12,13-aziridine epothilone B analogues 89-96 from tertiary aziridine 30. Reagents and conditions. a) 136 (12 equiv.), NaHMDS (9.7 equiv.); 20 (1.0 equiv.), THF, -78 → 0° C., 2.5 h, 50%. b) HF•py (165 equiv.), THF, 0 → 25° C., 4 h, then TFA (100 equiv.), CH₂Cl₂, 0 → 25° C., 3 h, 71% overall; c) 64a (28 equiv.), NaHMDS (22 equiv.); 20 (1.0 equiv.), THF, -78 → 25° C., 2 h, 94%; d) HF•py (170 equiv.), THF, 0 → 25° C., 5 h; then TFA (100 equiv.), CH₂Cl₂, 0 → 25° C., 3 h, 68% overall; e) 41 (13 equiv.), NaHMDS (10 equiv.); 20 (1.0 equiv.), THF, -78 → 10° C., 1.5 h, 65%; f) HF•py (150 equiv.), THF, 0 → 25° C., 9 h, 80%; g) 137 (8.3 equiv.), NaHMDS (6.8 equiv.); 20 (1.0 equiv.), THF, -78° C., 2.5 h, 68%; h) HF•py (265 equiv.), THF, 0 → 25° C., 5 h; then TFA (224 equiv.), CH₂Cl₂, 0° C., 2.5 h, 48% overall; i) 132 (12 equiv.), NaHMDS (9.7 equiv.); 20 (1.0 equiv.), THF, -78 → 0° C., 2.5 h, 45%. j) HF•py (178 equiv.), THF, 0 → 25° C., 5 h; then TFA (100 equiv.), CH₂Cl₂, 0 → 25° C., 3 h, 71% overall; k) 135 (15 equiv.), NaHMDS (12 equiv.); 20 (1.0 equiv.), THF, -78 → 0° C., 3 h, 60%; l) HF•py (120 equiv.), THF, 0 → 25° C., 1 h; then TFA (224 equiv.), CH₂Cl₂, 0° C., 2.5 h, 79% overall; m) 134 (16 equiv.), NaHMDS (13 equiv.); 20 (1.0 equiv.), THF, -78 → 25° C., 3 h, 70%. n) HF•py (428 equiv.), THF, 0 → 25° C., 5 h; then TFA (250 equiv.), CH₂Cl₂, 0° C., 2.5 h, 82% overall; o) 133 (14 equiv.), NaHMDS (14 equiv.); 20 (1.0 equiv.), THF, -78 → 0° C., 4 h, 69%. p) HF•py (215 equiv.), THF, 0 → 25° C., 5 h; then TFA (144 equiv.), CH₂Cl₂, 0° C., 6 h, 80% overall. Abbreviations: HMDS = hexamethyldisilazane.

Example 2—General Methods and Materials

All reactions were carried out under an argon atmosphere with dry solvents under anhydrous conditions, unless otherwise noted. Dry acetonitrile (MeCN), dimethylformamide (DMF), methylene chloride (DCM), tetrahydrofuran (THF), dichloromethane, diethyl ether and toluene were obtained by passing commercially available pre-dried, oxygen-free formulations through activated alumina columns. Yields refer to chromatographically and spectroscopically ($^1$H NMR) homogeneous materials, unless otherwise stated. Reagents were purchased at the highest commercial quality and used without further purification, unless otherwise stated. Reactions were monitored by thin-layer chromatography (TLC) carried out on S-2 0.25 mm E. Merck silica gel plates (60F-254) using UV light as visualizing agent and an ethanolic solution of phosphomolybdic acid, an aqueous solution of cerium sulfate, or a basic aqueous solution of potassium permanganate as developing agents. E. Merck silica gel (60, particle size 0.040-0.063 mm) was used for flash column chromatography. NMR spectra were recorded on a Bruker DRX-600 instrument and calibrated using residual undeuterated solvent (CDCl$_3$: $\delta_H$=7.26 ppm, $\delta_C$=77.16 ppm; C$_6$D$_6$: $\delta_H$=7.16 ppm, $\delta_C$=128.06 ppm) as an internal reference. The following abbreviations were used to designate multiplicities: s=singlet, d=doublet, t=triplet, q=quartet, m=multiplet, qd=quartet of doublets, dd=doublet of doublets, ddd=doublet of doublet of doublets, dq=doublet of quartets, br=broad. Infrared (IR) spectra were recorded on a Perkin-Elmer 100 FT-IR spectrometer. High-resolution mass spectra (HRMS) were recorded on an Agilent ESI-TOF (time of flight) mass spectrometer using MALDI (matrix-assisted laser desorption ionization) or ESI (electrospray ionization). Optical rotations were recorded on a POLARTRONIC M100 polarimeter at 589 nm, and are reported in units of 10$^{-1}$ (deg cm$^2$ g$^{-1}$). Purity was assessed by analytical HPLC using a Shimadzu LC-10AT with a Luna C18 column (50 mm×4.6 mm, 5 µm) with 5% water in acetonitrile (isocratic). The purity of all final compounds was ≥95% (UV detection, λ=254 nm).

Example 3—Compound Characterization

General Methods for the Synthesis of 18a-18c

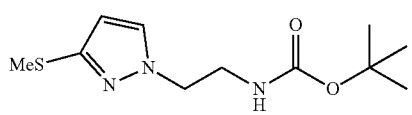

Tert-Butyl (2-(3-(methylthio)-1H-pyrazol-1-yl)ethyl) carbamate 18a

To a stirred solution of 3-(methylthio)-1H-pyrazole 16a (1.0 g, 8.8 mmol, 1.2 equiv) in THF (88 mL) at 0° C. was added NaH (60% in mineral oil, 352 mg, 8.8 mmol, 1.2 equiv) in small portions. After 15 min, a solution of tert-butyl (2-bromoethyl)carbamate 17a (1.64 g, 7.3 mmol, 1.0 equiv) in THF (14.6 mL) was added dropwise, and after the reaction mixture warmed to room temperature, it was set to reflux for 12 h. Upon cooling back down to 25° C., the reaction mixture was quenched with a saturated aqueous solution of ammonium chloride (25 mL), and the phases were separated. The aqueous layer was extracted with methylene chloride (3×15 mL), and the combined organic layers were dried with anhydrous magnesium sulfate and concentrated in vacuo. The obtained residue was purified by flash column chromatography (silica gel, 30% ethyl acetate in methylene chloride) to afford pure 18a (1.39 g, 5.4 mmol, 74%) as a white amorphous solid. 18a: $R_f$=0.62 (silica gel, 50% ethyl acetate in methylene chloride); FT-IR (neat) $v_{max}$ 3347, 3114, 2977, 2928, 1694, 1501, 1452, 1391, 1365, 1270, 1248, 1164, 1083, 1048, 984, 964, 923, 857, 750, 667 cm$^{-1}$; $^1$H NMR (600 MHz, CDCl$_3$) δ=7.32 (d, J=2.1 Hz, 1H), 6.16 (d, J=2.1 Hz, 1H), 4.92 (br s, 1H), 4.16 (m, 2H), 3.52 (m, 2H), 2.47 (s, 3H), 1.41 (s, 9H) ppm; $^{13}$C NMR (151 MHz, CDCl$_3$) δ=155.8, 147.4, 131.4, 105.8, 79.6, 51.6, 40.7, 28.3, 16.4 ppm; HRMS (ESI) calcd for C$_{11}$H$_{19}$N$_3$O$_2$S [M+H]$^+$ 258.1271, found 258.1272.

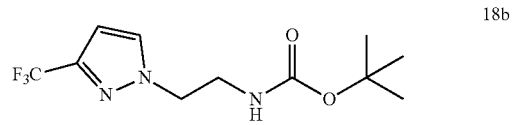 [SMILES: CC(C)(C)OC(=O)NCCn1ccc(C(F)(F)F)n1]

Tert-Butyl (2-(3-(trifluoromethyl)-1H-pyrazol-1-yl) ethyl)carbamate 18b

Prepared from tert-butyl (2-bromoethyl)carbamate 17a (695 mg, 3.1 mmol, 1.0 equiv) and 3-(trifluoromethyl)-1H-pyrazole 16b (500 mg, 3.7 mmol, 1.2 equiv) according to the general procedure described above for the preparation of 18a to give 18b (1.39 g, 5.4 mmol, 67%) as a white amorphous solid. 18b: $R_f$=0.47 (silica gel, 50% ethyl acetate in hexanes); FT-IR (neat) $v_{max}$ 3344, 2981, 2933, 1693, 1512, 1493, 1455, 1385, 1367, 1341, 1321, 1240, 1163, 1124, 1053, 1008, 988, 967, 930, 911, 856, 768, 738, 703 cm$^{-1}$; $^1$H NMR (600 MHz, CDCl$_3$) δ=7.43 (br s, 1H), 6.49 (br s, 1H), 4.91 (br s, 1H), 4.28 (m, 2H), 3.55 (m, 2H), 1.40 (s, 9H) ppm; $^{13}$C NMR (151 MHz, CDCl$_3$) δ=155.9, 142.4 (q, J=38.2 Hz), 138.8, 118.5 (q, J=268.5 Hz), 104.3, 79.8, 52.1, 40.5, 28.2 ppm; HRMS (ESI) calcd for C$_{11}$H$_6$F$_3$N$_3$O$_2$ [M+H]$^+$ 280.1267, found 280.1267.

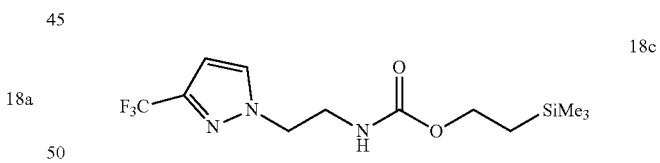

2-(Trimethylsilyl)ethyl (2-(3-(trifluoromethyl)-1H-pyrazol-1-yl)ethyl)carbamate 18c Prepared from 2-(trimethylsilyl)ethyl (2-(3-(trifluoromethyl)-1H-pyrazol-1-yl)ethyl)carbamate 17b (335 mg, 1.3 mmol, 1.0 equiv) and 3-(trifluoromethyl)-1H-pyrazole 16b (200 mg, 1.5 mmol, 1.2 equiv) according to the general procedure described above for the preparation of 18a to yield 18c (402 mg, 1.44 mmol, 96%) as a colorless oil. 18c: $R_f$=0.30 (silica gel, 40% ethyl acetate in hexanes); FT-IR (neat) $v_{max}$ 3337, 2978, 2939, 1687, 1501, 1474, 1457, 1388, 1358, 1333, 1311, 1262, 1180, 1120, 1045, 1013, 988, 964, 960, 940, 915, 874, 772, 710 cm$^{-1}$; $^1$H NMR (600 MHz, CDCl$_3$) δ=7.53 (br s, 1H), 6.62 (br s, 1H), 5.10 (br s, 1H), 4.34 (m, 2H), 4.13 (m, 2H), 3.69 (m, 2H), 0.95 (m, 2H), 0.02

(s, 9H) ppm; $^{13}$C NMR (151 MHz, CDCl$_3$) δ=156.8, 139.1, 132.1 (q, J=39.0 Hz), 117.5 (q, J=269.2 Hz), 107.8, 63.4, 50.6, 40.6, 17.8, −1.4 ppm; HRMS (ESI) calcd for C$_{12}$H$_{20}$F$_3$N$_3$O$_2$Si [M+H]$^+$ 324.1350, found 324.1355.

General Method for the Synthesis of 19a-19c

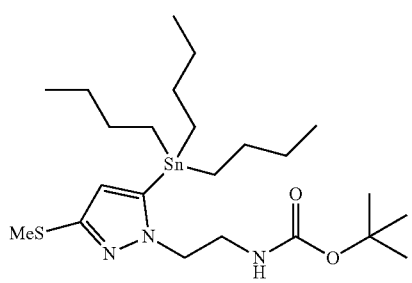

19a

Tert-Butyl (2-(3-(methylthio)-5-(tributylstannyl)-1H-pyrazol-1-yl)ethyl)carbamate 19a n-Butyllithium (2.5 M hexanes, 6.1 mL, 15.3 mmol, 3.0 equiv) was added dropwise to a stirred solution of 18a (1.31 g, 5.1 mmol, 1.0 equiv) in THF (51 mL) at −78° C. After stirring for 10 min, tributyltin chloride (1.5 mL, 5.6 mmol, 1.1 equiv) was added dropwise, and stirring was continued at −78° C. for an additional 30 min. The reaction mixture was then quenched with a saturated aqueous solution of ammonium chloride (20 mL) and allowed to warm to 25° C. The two phases were separated, the aqueous layer was extracted with ethyl acetate (3×15 mL), and the combined organic layers were dried with anhydrous magnesium sulfate and concentrated in vacuo. The oily residue was purified by flash column chromatography (silica gel, 40% ethyl acetate in hexanes) to provide 19a (1.06 g, 1.9 mmol, 38%) as a colorless oil. 19a: R$_f$=0.37 (silica gel, 40% ethyl acetate in hexanes); FT-IR (neat) ν$_{max}$ 3361, 2956, 2925, 2871, 2853, 1713, 1503, 1456, 1391, 1376, 1364, 1300, 1265, 1247, 1168, 1118, 1071, 1047, 1026, 983, 960, 864, 775, 758, 670 cm$^{-1}$; $^1$H NMR (600 MHz, CDCl$_3$) δ=6.16 (s, 1H), 5.17 (br s, 1H), 4.07 (m, 2H), 3.60 (m, 2H), 2.49 (s, 3H), 1.56-1.46 (m, 6H), 1.42 (s, 9H), 1.35-1.29 (m, 6H), 1.16-1.05 (m, 6H), 0.87 (t, J=7.4 Hz, 9H) ppm; $^{13}$C NMR (151 MHz, CDCl$_3$) δ=155.8, 147.0, 144.9, 114.3, 79.3, 53.4, 40.9, 28.9, 28.4, 27.1, 16.4, 13.6, 10.4 ppm; HRMS (ESI) calcd for C$_{23}$H$_{45}$N$_3$O$_2$SSn [M+H]$^+$ 548.2327, found 548.2331.

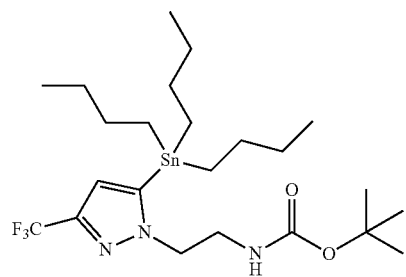

19b

Tert-Butyl (2-(5-(tributylstannyl)-3-(trifluoromethyl)-1H-pyrazol-1-yl)ethyl)carbamate 19b Prepared from carbamate 18b (1.67 g, 6.0 mmol, 1.0 equiv) according to the general procedure described above for the preparation of 19a to provide 19b (1.43 g, 2.5 mmol, 42%) as a colorless oil. 19b: R$_f$=0.42 (silica gel, 20% ethyl acetate in hexanes); FT-IR (neat) ν$_{max}$ 3354, 2958, 2928, 2873, 2855, 1714, 1504, 1456, 1392, 1365, 1356, 1268, 1249, 1210, 1160, 1125, 1073, 1040, 999, 974, 962, 865, 804, 779, 758, 746, 736, 722, 692, 669 cm$^{-1}$; $^1$H NMR (600 MHz, CDCl$_3$) δ=6.49 (s, 1H), 4.97 (br s, 1H), 4.16 (m, 2H), 3.65 (m, 2H), 1.57-1.46 (m, 6H), 1.43 (s, 9H), 1.36-1.30 (m, 6H), 1.21-1.10 (m, 6H), 0.88 (t, J=7.3 Hz, 9H) ppm; $^{13}$C NMR (151 MHz, CDCl$_3$) δ=155.7, 145.5, 142.5 (q, J=37.2 Hz), 119.1 (q, J=268.9 Hz), 112.8, 79.6, 53.9, 40.6, 28.8, 28.3, 27.1, 13.6, 10.5 ppm; HRMS (ESI) calcd for C$_{23}$H$_{42}$F$_3$N$_3$O$_2$Sn [M+H]$^+$ 570.2324, found 570.2324.

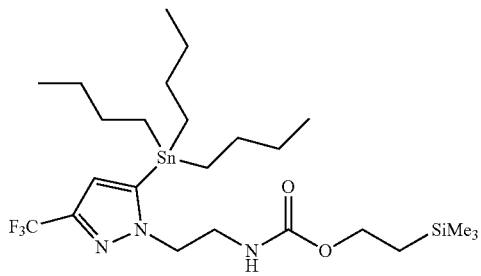

19c 2-(Trimethylsilyl)ethyl(2-(5-(tributylstannyl)-3-(trifluoromethyl)-1H-pyrazol-1-yl)ethyl)carbamate 19c Prepared from carbamate 18c (110 mg, 0.31 mmol, 1.0 equiv) according to the general procedure described above for the preparation of 19a to provide 19c (102 mg, 0.17 mmol, 54%) as a colorless oil. 19c: R$_f$=0.62 (silica gel, 20% ethyl acetate in hexanes); FT-IR (neat) ν$_{max}$ 3330, 2956, 2928, 2873, 2855, 1720, 1516, 1464, 1416, 1377, 1356, 1250, 1211, 1162, 1128, 1063, 1042, 975, 946, 860, 838, 805, 774, 748, 694, 665 cm$^{-1}$; $^1$H NMR (600 MHz, CDCl$_3$) δ=6.49 (s, 1H), 5.11 (br s, 1H), 4.16-4.11 (m, 2H), 3.73-3.69 (m, 2H), 1.54-1.48 (m, 6H), 1.38-1.29 (m, 6H), 1.22-1.06 (m, 6H), 0.99-0.94 (m, 2H), 0.88 (t, J=7.3 Hz, 9H), 0.03 (s, 9H) ppm; $^{13}$C NMR (151 MHz, CDCl$_3$) δ=156.7, 145.6, 122.7 (q, J=39.0 Hz), 112.8 (q, J=269.2 Hz), 99.6, 63.3, 53.7, 40.8, 28.9, 27.2, 17.7, 13.6, 10.5, −1.5 ppm; HRMS (ESI) calcd for C$_{24}$H$_{46}$F$_3$N$_3$O$_2$SiSn [M+H]$^+$ 614.2406, found 614.2401.

General Method for the Synthesis of 21a and 21b

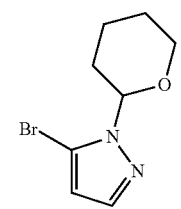

21a

5-Bromo-1-(tetrahydro-2H-pyran-2-yl)-1H-pyrazole 21a n-Butyllithium (2.5 M hexanes, 32.1 mL, 80.3 mmol, 1.3 equiv) was added dropwise to a stirred solution of 20a (9.4 g, 61.8 mmol, 1.0 equiv) in THF (172 mL) at −78° C. After stirring for 15 min, bromine (4.1 mL, 80.3 mmol. 1.3 equiv) was carefully added dropwise to the reaction mixture. The rate of addition was slow enough so as to allow complete decolorization of bromine prior to the next drop. After being allowed to warm to −30° C. over 1.5 h, the reaction mixture was quenched with a saturated solution of sodium bicarbonate (50 mL), and allowed to warm to 25° C. The two phases were separated, the aqueous layer was extracted with ethyl acetate (3×25 mL), and the combined organic layers were dried with anhydrous magnesium sulfate and concentrated in vacuo. Purification of the crude material by flash column chromatography (silica gel, 10% ethyl acetate in hexanes) afforded 21a (12.0 g, 51.9 mmol, 84%) as a white amorphous solid. 21a: $R_f$=0.29 (silica gel, 10% ethyl acetate in hexanes); FT-IR (neat) $v_{max}$ 3120, 2944, 2857, 1499, 1440, 1391, 1342, 1310, 1245, 1204, 1180, 1085, 1041, 977, 953, 911, 877, 822, 755 cm$^{-1}$; $^1$H NMR (600 MHz, CDCl$_3$) δ=7.57 (d, J=1.8 Hz, 1H), 6.33 (d, J=1.8 Hz, 1H), 5.45 (dd, J=10.0, 2.6 Hz, 1H), 4.09-4.04 (m, 1H), 3.72-3.66 (m, 1H), 2.50-2.41 (m, 1H), 2.15-2.10 (m, 1H), 1.96-1.90 (m, 1H), 1.76-1.67 (m, 2H), 1.63-1.57 (m, 1H) ppm; $^{13}$C NMR (151 MHz, CDCl$_3$) δ=141.0, 113.5, 109.3, 84.7, 68.1, 29.5, 25.0, 22.8 ppm; HRMS (ESI) calcd for C$_8$H$_{11}$BrN$_2$O [M+H]$^+$ 231.0127, found 231.0129.

5-Bromo-1-(tetrahydro-2H-pyran-2-yl)-3-(trifluoromethyl)-1H-pyrazole 21b

Prepared from pyrazole 20b (2.50 g, 11.4 mmol, 1.0 equiv) according to the general procedure described above for the preparation of 21a to yield brominated pyrazole 21b (2.66 g, 8.9 mmol, 78%) as a white amorphous solid. 21b: $R_f$=0.67 (silica gel, 20% ethyl acetate in hexanes); FT-IR (neat) $v_{max}$ 3151, 2968, 2949, 2926, 2869, 1468, 1447, 1421, 1386, 1353, 1319, 1287, 1223, 1204, 1171, 1120, 1080, 1060, 1043, 997, 969, 940, 911, 880, 847, 823, 794, 742, 719, 649 cm$^{-1}$; $^1$H NMR (600 MHz, CDCl$_3$) δ=6.61 (s, 1H), 5.51 (dd, J=9.6, 2.8 Hz, 1H), 4.08-4.03 (m, 1H), 3.73-3.66 (m, 1H), 2.50-2.40 (m, 1H), 2.18-2.11 (m, 1H), 1.98-1.91 (m, 1H), 1.77-1.59 (m, 3H) ppm; $^{13}$C NMR (151 MHz, CDCl$_3$) δ=143.1 (q, J=39.1 Hz), 117.5 (q, J=270.0 Hz), 114.8, 107.7 (q, J=2.1 Hz), 85.4, 68.0, 29.1, 24.8, 22.3 ppm; HRMS (ESI) calcd for C$_9$H$_{10}$BrF$_3$N$_2$O [M+Na]$^+$ 320.9821, found 320.9817.

General Method for the Synthesis of 22a and 22b

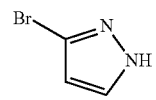

5-Bromo-1H-pyrazole 22a

To a stirred solution of 21a (6.24 g, 27.0 mmol, 1.0 equiv) in methanol (450 mL) was added methanesulfonic acid (8.8 mL, 135 mmol, 5.0 equiv) at 25° C. and the reaction mixture was stirred for 1 h. The resulting reaction mixture was neutralized by the addition of solid sodium bicarbonate (22 g, 0.262 mol, 20 equiv), filtered, and concentrated in vacuo. Purification of the residue by flash column chromatography (silica gel, 20% ethyl acetate in hexanes) provided 22a (3.77 g, 25.7 mmol, 95%) as a white solid. 22a: $R_f$=0.20 (silica gel, 20% ethyl acetate in hexanes); FT-IR (neat) $v_{max}$ 3143, 3034, 2966, 2904, 2858, 2774, 2628, 1544, 1475, 1388, 1342, 1241, 1182, 1082, 1047, 996, 957, 919, 870, 815, 755, 655, 607 cm$^{-1}$; $^1$H NMR (600 MHz, CDCl$_3$) δ=12.20 (br s, 1H), 7.59 (d, J=2.4 Hz, 1H), 6.37 (d, J=2.4 Hz, 1H) ppm; $^{13}$C NMR (151 MHz, CDCl$_3$) δ=131.1, 125.7, 108.0 ppm; HRMS (ESI) calcd for C$_3$H$_3$BrN$_2$ [M+H]$^+$ 146.9552 found 146.9556.

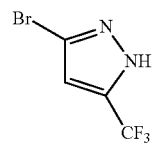

5-Bromo-3-(trifluoromethyl)-1H-pyrazole 22b

Prepared from pyrazole 21b (2.22 g, 3.34 mmol, 1.0 equiv) according to the general procedure described above for the preparation of 22a to yield deprotected pyrazole 22b (1.46 g, 3.0 mmol, 91%) as a white amorphous solid. 22b: $R_f$=0.63 (silica gel, 20% ethyl acetate in hexanes); FT-IR (neat) $v_{max}$ 3119, 3016, 2970, 2934, 2898, 2818, 2771, 1542, 1494, 1456, 1377, 1362, 1319, 1301, 1283, 1232, 1175, 1137, 1071, 1032, 990, 982, 844, 803, 746, 723, 621 cm$^{-1}$; $^1$H NMR (600 MHz, CDCl$_3$) δ=12.12 (br s, 1H), 6.63 (s, 1H) ppm; $^{13}$C NMR (151 MHz, CDCl$_3$) δ=141.97 (q, J=37.6 Hz), 117.2, 116.9 (q, J=269.0 Hz), 107.3 (q, J=2.3 Hz) ppm; HRMS (ESI) calcd for C$_4$H$_2$BrF$_3$N$_2$[M−H]$^-$ 212.9281 found 212.9289.

General Method for the Synthesis of 23a, 23c, 23d, 23f

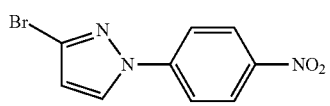

3-Bromo-1-(4-nitrophenyl)-1H-pyrazole 23a

Sodium hydride (60% w/w in mineral oil, 41 mg, 1.02 mmol, 1.5 equiv) was carefully added in portions to a stirred solution of 22a (100 mg, 0.68 mmol, 1.0 equiv) in THF (6.8 mL) at 0° C. After 20 min, 1-fluoro-4-nitrobenzene 22c (0.08 mL, 0.75 mmol, 1.1 equiv) was added dropwise, and the reaction mixture was set to reflux at 60° C. Upon consumption of the starting material as indicated by TLC, the reaction mixture was cooled to 25° C., quenched with a saturated solution of aqueous ammonium chloride (1.2 mL), and the two phases were separated. The aqueous layer was extracted with ethyl acetate (3×5 mL), and the combined organic layers were dried with anhydrous magnesium sulfate and concentrated in vacuo. The crude residue obtained was purified by flash column chromatography (silica gel, 20% ethyl acetate in hexanes) to afford N-arylpyrazole 23a (144 mg, 0.54 mmol, 79%) as a white solid. 23a: $R_f$=0.30 (silica gel, 20% ethyl acetate in hexanes); FT-IR (neat) $v_{max}$ 3144, 1595, 1516, 1407, 1359, 1335, 1200, 1176, 1112, 1042, 955, 937, 852, 749, 732, 684 cm$^{-1}$; $^1$H NMR (600 MHz, CDCl$_3$) δ=8.33 (d, J=9.2 Hz, 2H), 7.93 (d, J=2.6 Hz, 1H), 7.84 (d, J=9.2 Hz, 2H), 6.58 (d, J=2.6 Hz, 1H) ppm; $^{13}$C NMR (151 MHz, CDCl$_3$) δ=145.9, 143.7, 130.7, 129.0, 125.6, 118.6, 112.6 ppm; HRMS (ESI) calcd for C$_9$H$_6$BrN$_3$O$_2$[M+H]$^+$ 267.9716 found 267.9711.

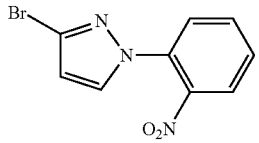

3-Bromo-1-(2-nitrophenyl)-1H-pyrazole 23c

Prepared from pyrazole 22a (100 mg, 0.68 mmol, 1.0 equiv) according to the general procedure described above for the preparation of 23a to yield N-arylpyrazole 23c (134 mg, 0.50 mmol, 74%) as a white amorphous solid. 23c: $R_f$=0.15 (silica gel, 20% ethyl acetate in hexanes); FT-IR (neat) $v_{max}$ 3216, 2877, 1682, 1608, 1532, 1513, 1466, 1416, 1364, 1303, 1185, 1104, 1045, 955, 941, 852, 777, 746, 705 cm$^{-1}$; $^1$H NMR (600 MHz, CDCl$_3$) δ=7.92 (dd, J=8.1 1.4 Hz, 1H), 7.69 (ddd, J=8.0, 7.5, 1.5 Hz, 1H), 7.59 (dd, J=8.0, 1.4 Hz, 1H), 7.59 (d, J=2.5 Hz, 1H), 7.55 (ddd, J=8.1, 7.5, 1.4 Hz, 1H), 6.51 (d, J=2.5 Hz, 1H) ppm; $^{13}$C NMR (151 MHz, CDCl$_3$) δ=133.5, 133.1, 132.4, 129.5, 129.3, 127.1, 125.4, 111.4 ppm; HRMS (ESI) calcd for C$_9$H$_6$BrN$_3$O$_2$[M+H]$^+$ 267.9716 found 267.9704.

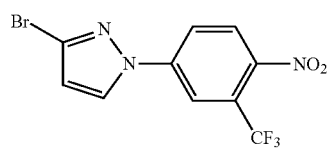

3-Bromo-1-(4-nitro-3-(trifluoromethyl)phenyl)-1H-pyrazole 23d

Prepared from pyrazole 22a (300 mg, 2.04 mmol, 1.0 equiv) according to the general procedure described above for the preparation of 23a to yield N-arylpyrazole 23d (548 mg, 1.63 mmol, 80%) as a white amorphous solid. 23d: $R_f$=0.41 (silica gel, 25% ethyl acetate in hexanes); FT-IR (neat) $v_{max}$ 3135, 3094, 2925, 2869, 1596, 1538, 1514, 1458, 1433, 1397, 1345, 1296, 1274, 1238, 1176, 1143, 1072, 1042, 952, 904, 885, 859, 841, 756, 723, 660, 613 cm$^{-1}$; $^1$H NMR (600 MHz, CDCl$_3$) δ=8.17 (d, J=2.2 Hz, 1H), 8.07 (d, J=8.9 Hz, 1H), 7.98 (dd, J=8.9, 2.2 Hz, 1H), 7.94 (d, J=2.6 Hz, 1H), 6.61 (d, J=2.6 Hz, 1H) ppm; $^{13}$C NMR (151 MHz, CDCl$_3$) δ=145.5, 142.0, 131.4, 129.0, 127.5, 125.8 (q, J=34.7 Hz), 121.3, 118.9 (q, J=274.0 Hz), 117.7 (q, J=5.8 Hz), 113.2 ppm; HRMS (ESI) calcd for C$_{10}$H$_5$BrF$_3$N$_3$O$_2$ [M+H]$^+$ 335.9590 found 335.9581.

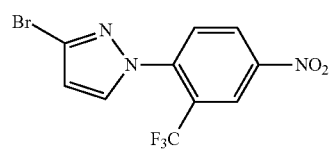

3-Bromo-1-(4-nitro-2-(trifluoromethyl)phenyl)-1H-pyrazole 23f

Prepared from pyrazole 22a (450 mg, 3.06 mmol, 1.0 equiv) according to the general procedure described above for the preparation of 23a to yield N-arylpyrazole 23f (699 mg, 2.08 mmol, 68%) as a white amorphous solid. 23f: $R_f$=0.53 (silica gel, 25% ethyl acetate in hexanes); FT-IR (neat) $v_{max}$ 3129, 3094, 2924, 2855, 1624, 1594, 1536, 1511, 1442, 1407, 1346, 1313, 1287, 1173, 1139, 1116, 1075, 1048, 1031, 954, 942, 916, 886, 848, 790, 752, 735, 720, 668, 653, 625 cm$^{-1}$; $^1$H NMR (600 MHz, CDCl$_3$) δ=8.69 (d, J=2.4 Hz, 1H), 8.51 (dd, J=8.8, 2.4 Hz, 1H), 7.87 (d, J=8.8 Hz, 1H), 7.71 (d, J=2.3 Hz, 1H), 6.57 (d, J=2.6 Hz, 1H) ppm; $^{13}$C NMR (151 MHz, CDCl$_3$) δ=146.9, 142.6, 133.9 (q, J=3.3 Hz), 130.5, 130.1, 127.9, 125.4 (q, J=33.4 Hz), 123.5 (q, J=5.5 Hz), 119.2 (q, J=274.3 Hz), 111.9 ppm; HRMS (ESI) calcd for C$_{10}$H$_5$BrF$_3$N$_3$O$_2$ [M+H]$^+$ 335.9590 found 335.9583.

General Method for the Synthesis of 23b, 23e, 23g

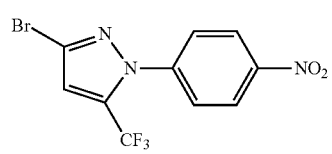

3-Bromo-1-(4-nitrophenyl)-5-(trifluoromethyl)-1H-pyrazole 23b

To a stirred suspension of 22b (5.0 g, 23.3 mmol, 1.0 equiv) and anhydrous potassium carbonate (3.9 g, 27.9 mmol, 1.2 equiv) in DMF (116 mL), 1-fluoro-4-nitrobenzene (2.5 mL, 23.5 mmol, 1.01 equiv) was added at 25° C., and the reaction mixture was heated to 80° C. for 12 h. After cooling to 25° C., the reaction mixture was quenched with a saturated aqueous solution of ammonium chloride (20 mL), and the two phases were separated. The aqueous layer was extracted with ethyl acetate (3×15 mL), and the combined organic layers were backwashed with water (2×15 mL) and brine (15 mL), dried with anhydrous magnesium sulfate, and concentrated in vacuo. Flash column chromatography (silica gel, 8% to 20% ethyl acetate in hexanes) with a slow gradient to separate the undesired regioisomer afforded 23b (1.57 g, 4.66 mmol, 20%) as a white amorphous solid. 23b: $R_f$=0.61 (silica gel, 20% ethyl acetate in hexanes); FT-IR (neat) $v_{max}$ 3149, 2923, 2853, 1598, 1527, 1502, 1454, 1347, 1288, 1216, 1180, 1141, 1112, 1076, 986, 963, 854, 812, 757, 689 cm$^{-1}$; $^1$H NMR (600 MHz, CDCl$_3$) δ=8.37 (d, J=9.0 Hz, 2H), 7.71 (d, J=9.0 Hz, 2H), 6.93 (s, 1H) ppm; $^{13}$C NMR (151 MHz, CDCl$_3$) δ=148.1, 143.1, 134.3 (q, J=40.4 Hz), 128.6, 125.9, 124.9, 116.1 (q, J=270.0 Hz), 113.3 (q, J=2.6 Hz) ppm; HRMS (ESI) calcd for C$_{10}$H$_5$BrF$_3$N$_3$O$_2$ [M+H]$^+$ 335.9590 found 335.9588.

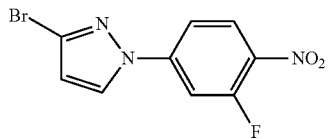

3-Bromo-1-(3-fluoro-4-nitrophenyl)-1H-pyrazole 23e

Prepared from pyrazole 22a (120 mg, 0.82 mmol, 1.0 equiv) according to the general procedure described above for the preparation of 23b to yield N-arylpyrazole 23e (141 mg, 0.49 mmol, 58%) as a white amorphous solid. 23e: $R_f$=0.29 (silica gel, 20% ethyl acetate in hexanes); FT-IR (neat) $v_{max}$ 3124, 3087, 2923, 2873, 1618, 1597, 1532, 1512, 1489, 1443, 1410, 1350, 1308, 1279, 1255, 1218, 1173, 1110, 1055, 1041, 969, 954, 881, 831, 751, 700, 656, 629 cm$^{-1}$; $^1$H NMR (600 MHz, CDCl$_3$) δ=7.98 (dd, J=9.0, 5.3 Hz, 1 Hz), 7.57 (d, J=2.3 Hz, 1H), 7.35 (dd, J=8.4, 2.4 Hz, 1H), 7.22 (dt, J=6.7, 2.5 Hz, 1H), 6.53 (d, J=2.3 Hz, 1H) ppm; $^{13}$C NMR (151 MHz, CDCl$_3$) δ=163.5 (d, J=258.9 Hz), 140.4 (d, J=2.9 Hz), 135.1 (d, J=11.1 Hz), 132.5, 130.2, 127.9 (d, J=9.9 Hz), 116.0 (d, J=23.1 Hz), 114.6 (d, J=25.9 Hz), 111.9 ppm; HRMS (ESI) calcd for C$_9$H$_5$BrFN$_3$O$_2$[M+H]$^+$ 285.9622 found 285.9627.

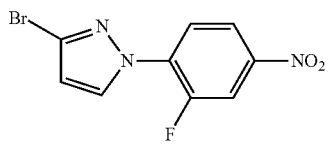

3-Bromo-1-(2-fluoro-4-nitrophenyl)-1H-pyrazole 23g

Prepared from pyrazole 22a (120 mg, 0.82 mmol, 1.0 equiv) according to the general procedure described above for the preparation of 23b to yield N-arylpyrazole 23g (215 mg, 0.75 mmol, 89%) as a white amorphous solid. 23g: $R_f$=0.63 (silica gel, 20% ethyl acetate in hexanes); FT-IR (neat) $v_{max}$ 3175, 3136, 3090, 2945, 1609, 1512, 1406, 1340, 1228, 1133, 1030, 953, 915, 893, 836, 810, 768, 739 cm$^{-1}$; $^1$H NMR (600 MHz, CDCl$_3$) δ=8.28-8.25 (m, 1H), 8.20-8.17 (m, 2H), 8.10 (t, J=2.6 Hz, 1H), 6.61 (d, J=2.6 Hz, 1H) ppm; $^{13}$C NMR (151 MHz, CDCl$_3$) δ=150.7 (d, J=252.9 Hz), 145.8 (d, J=7.7 Hz), 133.3 (14.6 Hz), 132.5 (d, J=8.5 Hz), 130.8 (d, J=1.3 Hz), 123.8, 120.8 (d, J=3.3 Hz), 113.4 (d, J=26.1 Hz), 112.5 (d, J=2.5 Hz) ppm; HRMS (ESI) calcd for C$_9$H$_5$BrFN$_3$O$_2$[M+H]$^+$ 285.9622 found 285.9636.

General Method for the Synthesis of 24a-24g

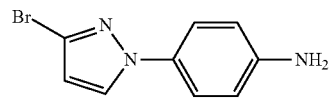

4-(3-Bromo-1H-pyrazol-1-yl)aniline 24a

A solution of concentrated hydrochloric acid in isopropanol (15:100 HCl/$^i$PrOH, 0.74 mL) was carefully added to a flask containing tin dichloride (364 mg, 1.9 mmol, 3.0 equiv) and 23a (171 mg, 0.64 mmol, 1.0 equiv) at 0° C. with stirring. The reaction mixture was then heated to 70° C. until the starting material was consumed as judged by TLC. Following neutralization with a saturated aqueous solution of sodium bicarbonate (15 mL), the two phases were separated, the aqueous layer was extracted with ethyl acetate (3×4 mL), and the combined organic layers were dried with anhydrous magnesium sulfate and concentrated in vacuo. Purification by flash column chromatography (silica gel, 40% ethyl acetate in hexanes) afforded 24a (114 mg, 0.48 mmol, 75%) as a pale yellow amorphous solid. 24a: $R_f$=0.47 (silica gel, 50% ethyl acetate in hexanes); FT-IR (neat) $v_{max}$ 3420, 3353, 3223, 3143, 2923, 1624, 1521, 1416, 1366, 1286, 1176, 1127, 1044, 957, 942, 827, 751 cm$^{-1}$; $^1$H NMR (600 MHz, CDCl$_3$) δ=7.65 (d, J=2.4 Hz, 1H), 7.38 (d, J=8.9 Hz, 2H), 6.71 (d, J=8.9 Hz, 2H), 6.41 (d, J=2.4 Hz, 1H), 3.76 (br s, 2H) ppm; $^{13}$C NMR (151 MHz, CDCl$_3$) δ=145.8, 131.9, 128.8, 127.1, 121.2, 115.5, 109.9 ppm; HRMS (ESI) calcd for C$_9$H$_8$BrN$_3$ [M+H]$^+$ 237.9974 found 237.9983.

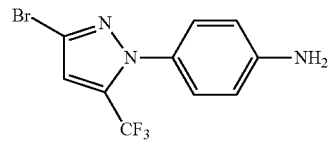

4-(3-Bromo-4-(trifluoromethyl)-1H-pyrazol-1-yl)aniline 24b

Prepared from pyrazole 23b (342 mg, 1.02 mmol, 1.0 equiv) according to the general procedure described above for the preparation of 24a to yield N-arylpyrazole 24b (238 mg, 0.78 mmol, 76%) as a pale yellow amorphous solid. 24b: $R_f$=0.61 (silica gel, 20% ethyl acetate in hexanes); FT-IR (neat) $v_{max}$ 3149, 2923, 2853, 1598, 1527, 1502, 1454, 1347, 1288, 1216, 1180, 1141, 1112, 1076, 986, 963, 854, 812, 757, 689 cm$^{-1}$; $^1$H NMR (600 MHz, CDCl$_3$) δ=8.37 (d, J=9.0 Hz, 2H), 7.71 (d, J=9.0 Hz, 2H), 6.93 (s, 1H) ppm; $^{13}$C NMR (151 MHz, CDCl$_3$) δ=148.1, 143.1, 134.3 (q, J=40.4 Hz), 128.6, 125.9, 124.9, 116.1 (q, J=270.0

Hz), 113.3 (q, J=2.6 Hz) ppm; HRMS (ESI) calcd for $C_{10}H_5BrF_3N_3O_2$ [M+H]$^+$ 335.9590 found 335.9588.

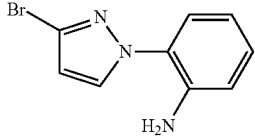

2-(3-Bromo-1H-pyrazol-1-yl)aniline 24c

Prepared from pyrazole 23c (121 mg, 0.45 mmol, 1.0 equiv) according to the general procedure described above for the preparation of 24a to yield N-arylpyrazole 24c (75 mg, 0.32 mmol, 70%) as an orange amorphous solid. 24c: $R_f$=0.51 (silica gel, 20% ethyl acetate in hexanes); FT-IR (neat) $v_{max}$ 3452, 3359, 3143, 1619, 1511, 1462, 1420, 1363, 1339, 1282, 1180, 1159, 1044, 957, 942, 749, 673 cm$^{-1}$; $^1$H NMR (600 MHz, CDCl$_3$) δ=7.59 (d, J=2.4 Hz, 1H), 7.19-7.12 (m, 2H), 6.84-6.76 (m, 2H), 6.46 (d, J=2.4 Hz, 1H), 4.55 (br s, 2H) ppm; $^{13}$C NMR (151 MHz, CDCl$_3$) δ=141.2, 132.1, 129.2, 127.3, 126.2, 124.3, 118.3, 117.5, 109.7 ppm; HRMS (ESI) calcd for $C_9H_8BrN_3$ [M+H]$^+$ 237.9974 found 237.9963.

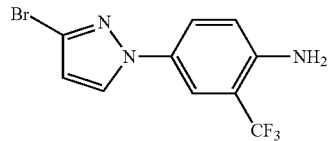

4-(3-Bromo-1H-pyrazol-1-yl)-2-(trifluoromethyl)aniline 24d

Prepared from pyrazole 23d (227 mg, 0.68 mmol, 1.0 equiv) according to the general procedure described above for the preparation of 24a to yield N-arylpyrazole 24d (132 mg, 0.43 mmol, 63%) as a pale yellow amorphous solid. 24d: $R_f$=0.36 (silica gel, 25% ethyl acetate in hexanes); FT-IR (neat) $v_{max}$ 3504, 3408, 3245, 3148, 2924, 1637, 1590, 1516, 1465, 1454, 1414, 1370, 1347, 1313, 1297, 1263, 1232, 1172, 1142, 1107, 1075, 1043, 961, 951, 898, 859, 822, 750, 686, 646, 614 cm$^{-1}$; $^1$H NMR (600 MHz, CDCl$_3$) δ=7.67 (m, 2H), 7.55 (dd, J=8.7, 2.1 Hz, 1H), 6.79 (d, J=8.7 Hz, 1H), 6.45 (d, J=2.3 Hz, 1H), 4.27 (br s, 2H) ppm; $^{13}$C NMR (151 MHz, CDCl$_3$) δ=143.6, 130.9, 128.8, 127.8, 124.6, 121.7 (q, J=272.6 Hz), 118.3 (q, J=5.5 Hz), 118.1, 113.8 (q, J=31.0 Hz), 110.4 ppm; HRMS (ESI) calcd for $C_{10}H_7BrF_3N_3$ [M+H]$^+$ 305.9848 found 305.9850.

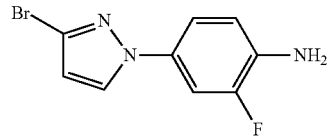

4-(3-Bromo-1H-pyrazol-1-yl)-2-fluoroaniline 24e

Prepared from pyrazole 23e (380 mg, 1.3 mmol, 1.0 equiv) according to the general procedure described above for the preparation of 24a to yield N-arylpyrazole 24e (240 mg, 0.94 mmol, 72%) as a light brown oil. 24e: $R_f$=0.29 (silica gel, 20% ethyl acetate in hexanes); FT-IR (neat) $v_{max}$ 3451, 3357, 3219, 3144, 2923, 2852, 1601, 1515, 1499, 1441, 1421, 1364, 1344, 1294, 1274, 1205, 1165, 1141, 1040, 971, 954, 875, 860, 812, 784, 756, 681, 625 cm$^{-1}$; $^1$H NMR (600 MHz, CDCl$_3$) δ=7.60 (d, J=2.5 Hz, 1H), 6.94-6.91 (m, 2H), 6.83-6.80 (m, 1H), 6.48 (d, J=2.5 Hz, 1H), 4.21 (br s, 2H) ppm; $^{13}$C NMR (151 MHz, CDCl$_3$) δ=154.6 (d, J=237.7 Hz), 137.3 (d, J=2.4 Hz), 132.0, 127.8, 125.9 (d, J=9.1 Hz), 118.2 (d, J=8.0 Hz), 115.9 (d, J=22.0 Hz), 111.0 (d, J=25.3 Hz), 110.1 ppm; HRMS (ESI) calcd for $C_9H_7BrFN_3$ [M+H]$^+$ 255.9880 found 255.9870.

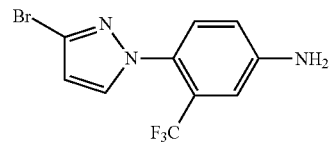

4-(3-Bromo-1H-pyrazol-1-yl)-3-(trifluoromethyl)aniline 24f

Prepared from pyrazole 23f (340 mg, 1.0 mmol, 1.0 equiv) according to the general procedure described above for the preparation of 24a to yield N-arylpyrazole 24f (179 mg, 0.59 mmol, 57%) as a pale orange amorphous solid. 24f: $R_f$=0.19 (silica gel, 25% ethyl acetate in hexanes); FT-IR (neat) $v_{max}$ 3478, 3349, 3230, 3147, 3030, 1632, 1527, 1457, 1424, 1367, 1336, 1269, 1169, 1128, 1078, 1046, 1032, 958, 944, 905, 872, 830, 758, 681, 647 cm$^{-1}$; $^1$H NMR (600 MHz, CDCl$_3$) δ=7.45 (d, J=1.6 Hz, 1H), 7.24 (s, 1H), 6.97 (d, J=2.5 Hz, 1H), 6.82 (dd, J=8.5, 2.5 Hz, 1H), 6.41 (d, J=2.4 Hz, 1H), 4.06 (br s, 2H) ppm; $^{13}$C NMR (151 MHz, CDCl$_3$) δ=147.5, 134.3 (q, J=1.8 Hz), 130.8, 128.4, 127.4, 127.2 (q, J=31.3 Hz), 120.2 (q, J=273.6 Hz), 117.6, 112.2 (q, J=5.2 Hz), 109.4 ppm; HRMS (ESI) calcd for $C_{10}H_7BrF_3N_3$ [M+H]$^+$ 305.9848 found 305.9854.

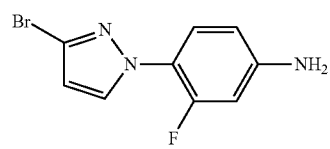

4-(3-Bromo-1H-pyrazol-1-yl)-3-fluoroaniline 24g

Prepared from pyrazole 23g (420 mg, 1.47 mmol, 1.0 equiv) according to the general procedure described above for the preparation of 24a to yield N-arylpyrazole 24g (320 mg, 1.25 mmol, 85%) as a white amorphous solid. 24g: $R_f$=0.24 (silica gel, 33% ethyl acetate in hexanes); FT-IR (neat) $v_{max}$ 3468, 3354, 3227, 3146, 2924, 1633, 1590, 1527, 1461, 1423, 1370, 1327, 1256, 1171, 1134, 1038, 955, 937, 840, 813, 754 cm$^{-1}$; $^1$H NMR (600 MHz, CDCl$_3$) δ=7.67 (t, J=2.4 Hz, 1H), 7.50-7.47 (m, 1H), 6.46 (m, 2H), 6.43 (d, J=2.4 Hz, 1H), 3.90 (br s, 2H) ppm; $^{13}$C NMR (151 MHz, CDCl$_3$) δ=154.0 (d, J=247.6 Hz), 147.4 (d, J=10.8 Hz), 132.9 (d, J=7.3 Hz), 127.3, 126.2 (d, J=1.8 Hz), 119.2 (d, J=11.0 Hz), 111.1 (d, J=2.8 Hz), 109.8, 102.4 (d, J=23.5 Hz) ppm; HRMS (ESI) calcd for C$_9$H$_7$BrFN$_3$ [M+H]$^+$ 255.9980 found 255.9980.

General Method for the Synthesis of 25a-25g

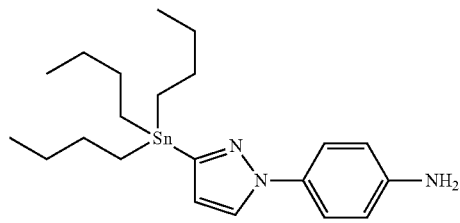

4-(3-(Tributylstannyl)-1H-pyrazol-1-yl)aniline 25a

To a sealed tube containing 24a (120 mg, 0.50 mmol, 1.0 equiv) and tetrakis(triphenylphosphine)palladium (58 mg, 0.05 mmol, 0.1 equiv) in carefully degassed (freeze-pump-thaw technique) toluene (5 mL) was added hexabutylditin (0.76 mL, 1.5 mmol, 3.0 equiv) with stirring. The reaction mixture was heated to 110° C. and stirred for 12 h. The reaction mixture was cooled to 25° C., then filtered through celite and concentrated in vacuo. Flash column chromatography (silica gel, 5% to 25% ethyl acetate in hexanes) provided stannane 25a (180 mg, 0.40 mmol, 80%) as a light brown oil. 25a: R$_f$=0.24 (silica gel, 25% ethyl acetate in hexanes); FT-IR (neat) ν$_{max}$ 3463, 3343, 2955, 2923, 2870, 2852, 1625, 1520, 1479, 1463, 1417, 1376, 1342, 1283, 1216, 1170, 1125, 1072, 1030, 956, 874, 865, 827, 751, 692, 669, 625 cm$^{-1}$; $^1$H NMR (600 MHz, CDCl$_3$) δ=7.83 (d, J=1.9 Hz, 1H), 7.46 (d, J=8.6 Hz, 2H), 6.72 (d, J=8.6 Hz, 2H), 6.46 (d, J=1.9 Hz, 1H), 1.62-1.55 (m, 6H), 1.38-1.32 (m, 6H), 1.17-1.05 (m, 6H), 0.89 (t, J=7.4 Hz, 9H) ppm; $^{13}$C NMR (151 MHz, CDCl$_3$) δ=153.4, 144.9, 133.0, 126.6, 121.3, 115.6, 115.2, 29.3, 27.4, 13.9, 10.1 ppm; HRMS (ESI) calcd for C$_{21}$H$_{35}$N$_3$Sn [M+H]$^+$ 450.1929 found 450.1926.

for the preparation of 25a to yield stannane 25b (192 mg, 0.36 mmol, 66%) as a light brown oil. 25b: R$_f$=0.29 (silica gel, 20% ethyl acetate in hexanes); FT-IR (neat) ν$_{max}$ 3474, 3379, 3219, 2957, 2924, 2872, 2853, 1627, 1519, 1463, 1417, 1376, 1350, 1278, 1195, 1164, 1130, 1097, 1066, 1016, 986, 960, 875, 830, 746, 696, 668, 645 cm$^{-1}$; $^1$H NMR (600 MHz, CDCl$_3$) δ=7.23 (d, J=8.4 Hz, 2H), 6.75 (m, 3H), 1.60-1.55 (m, 6H), 1.39-1.30 (m, 6H), 1.18-1.06 (m, 6H), 0.88 (t, J=7.4 Hz, 9H) ppm; $^{13}$C NMR (151 MHz, CDCl$_3$) δ=152.8, 132.4 (q, J=38.4 Hz), 131.1, 127.1, 125.3, 118.3 (q, J=269.0 Hz), 116.4, 115.3, 29.2, 27.4, 13.8, 10.2 ppm; HRMS (ESI) calcd for C$_{22}$H$_{34}$F$_3$N$_3$Sn [M+H]$^+$ 518.1803 found 518.1815.

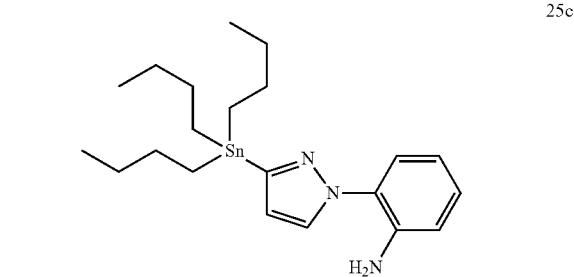 [SMILES: CCC[CH2][Sn]([CH2]CCC)([CH2]CCC)[c]1ccn(-c2ccccc2N)n1]

2-(3-(Tributylstannyl)-1H-pyrazol-1-yl)aniline 25c

Prepared from pyrazole 24c (182 mg, 0.76 mmol, 1.0 equiv) according to the general procedure described above for the preparation of 25a to yield stannane 25c (276 mg, 0.60 mmol, 78%) as a pale orange oil. 25c: R$_f$=0.36 (silica gel, 10% ethyl acetate in hexanes); FT-IR (neat) ν$_{max}$ 3463, 3337, 2956, 2925, 2870, 2852, 1617, 1589, 1509, 1462, 1376, 1340, 1293, 1159, 1072, 1019, 959, 875, 744, 695, 671 cm$^{-1}$; $^1$H NMR (600 MHz, C$_6$D$_6$) δ=7.42 (d, J=2.3 Hz, 1H), 6.95-6.91 (m, 2H), 6.54 (ddd, J=7.9, 7.3, 1.4 Hz, 1H), 6.48 (d, J=2.3 Hz, 1H), 6.40 (ddd, J=7.9, 1.4, 0.3 Hz, 1H), 4.75 (br s, 2H), 1.74-1.68 (m, 6H), 1.44-1.37 (m, 6H), 1.22-1.19 (m, 6H), 0.91 (t, J=7.3 Hz, 9H) ppm; $^{13}$C NMR (151 MHz, CDCl$_3$) δ=132.8, 131.2, 128.9, 128.5, 128.4, 126.0, 123.4, 119.5, 104.3, 29.9, 27.0, 14.3, 13.8 ppm; HRMS (ESI) calcd for C$_{21}$H$_{35}$N$_3$Sn [M+H]$^+$ 450.1929 found 450.1926.

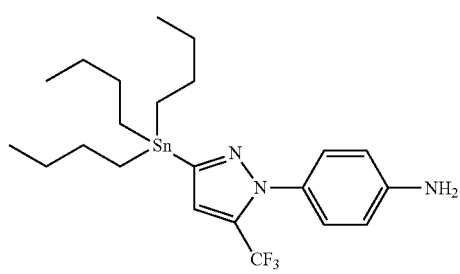

4-(3-(Tributylstannyl)-5-(trifluoromethyl)-1H-pyrazol-1-yl)aniline 25b

Prepared from pyrazole 24b (177 mg, 0.58 mmol, 1.0 equiv) according to the general procedure described above

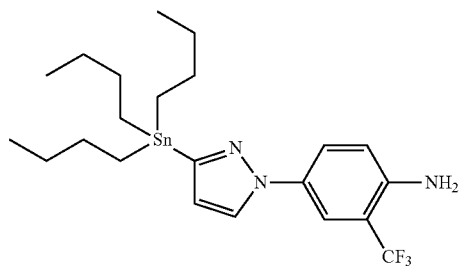

4-(3-(Tributylstannyl)-1H-pyrazol-1-yl)-2-(trifluoromethyl)aniline 25d

Prepared from pyrazole 24d (450 mg, 1.47 mmol, 1.0 equiv) according to the general procedure described above for the preparation of 25a to yield stannane 25d (415 mg, 0.80 mmol, 55%) as a light brown oil. 25d: $R_f$=0.36 (silica gel, 25% ethyl acetate in hexanes); FT-IR (neat) $v_{max}$ 3509, 3402, 2957, 2925, 2872, 2853, 1638, 1517, 1464, 1418, 1356, 1299, 1260, 1212, 1142, 1113, 1032, 962, 901, 877, 825, 751, 686 cm$^{-1}$; $^1$H NMR (600 MHz, CDCl$_3$) δ=7.85 (d, J=2.3 Hz, 1H), 7.75 (d, J=2.6 Hz, 1H), 7.61 (dd, J=8.7, 2.6 Hz, 1H), 6.80 (d, J=8.7 Hz, 1H), 6.48 (d, J=2.3 Hz, 1H), 4.19 (br s, 2H), 1.65-1.56 (m, 6H), 1.39-1.31 (m, 6H), 1.13-1.09 (m, 6H), 0.88 (t, J=7.3 Hz, 9H) ppm; $^{13}$C NMR (151 MHz, CDCl$_3$) δ=154.3, 142.8 (q, J=1.7 Hz), 132.1, 126.5, 124.7, 121.9 (q, J=270.9 Hz), 118.3 (q, J=5.5 Hz), 118.0, 115.7, 113.9 (q, J=30.9 Hz), 29.2, 27.4, 13.9, 10.1 ppm; HRMS (ESI) calcd for C$_{22}$H$_{34}$F$_3$N$_3$Sn [M+H]$^+$ 518.1803 found 518.1781.

for the preparation of 25a to yield stannane 25f (520 mg, 1.0 mmol, 52%) as a light brown oil. 25f: $R_f$=0.29 (silica gel, 25% ethyl acetate in hexanes); FT-IR (neat) $v_{max}$ 3322, 3208, 2957, 2924, 2872, 2853, 1633, 1523, 1457, 1376, 1349, 1334, 1267, 1219, 1173, 1131, 1073, 1046, 1019, 958, 905, 873, 829, 758, 647 cm$^{-1}$; $^1$H NMR (600 MHz, CDCl$_3$) δ=7.62 (dm, J=2.3 Hz, 1H), 7.23 (d, J=8.5 Hz, 1H), 6.96 (d, J=2.7 Hz, 1H), 6.81 (dd, J=8.5, 2.7 Hz, 1H), 6.45 (d, J=2.3 Hz, 1H), 4.01 (br s, 2H), 1.59-1.53 (m, 6H), 1.36-1.29 (m, 6H), 1.11-1.08 (m, 6H), 0.86 (t, J=7.3 Hz, 9H) ppm; $^{13}$C NMR (151 MHz, CDCl$_3$) δ=153.2, 146.9, 131.8, 130.6, 127.1 (q, J=31.0 Hz), 120.4 (q, J=274.0 Hz), 117.7, 114.4, 112.4 (q, J=5.2 Hz), 29.2, 27.4, 13.8, 10.1 ppm; HRMS (ESI) calcd for C$_{22}$H$_{34}$F$_3$N$_3$Sn [M+H]$^+$ 518.1803 found 518.1801.

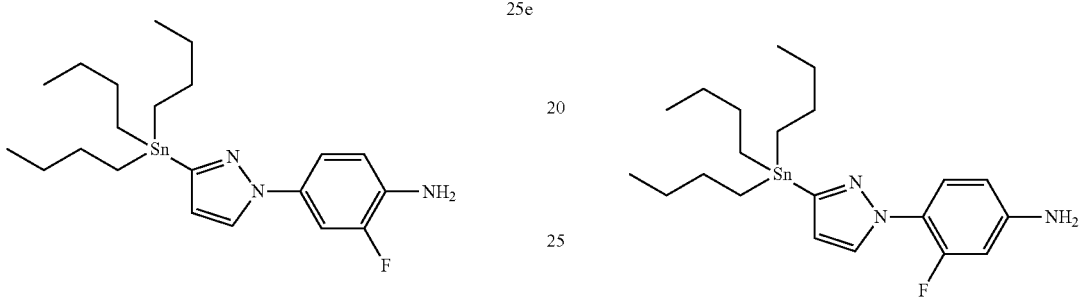

2-Fluoro-4-(3-(tributylstannyl)-1H-pyrazol-1-yl)aniline 25e

Prepared from pyrazole 24e (1.13 g, 4.4 mmol, 1.0 equiv) according to the general procedure described above for the preparation of 25a to yield stannane 25e (1.44 g, 3.10 mmol, 70%) as a light brown oil. 25e: $R_f$=0.32 (silica gel, 10% ethyl acetate in hexanes); FT-IR (neat) $v_{max}$ 3453, 3334, 2956, 2926, 2852, 1600, 1518, 1486, 1463, 1376, 1346, 1293, 1271, 1197, 1139, 1073, 1030, 971, 875, 808, 756, 693 cm$^{-1}$; $^1$H NMR (600 MHz, C$_6$D$_6$) δ=7.22 (d, J=2.3 Hz, 1H), 6.67 (dd, J=9.2, 2.9 Hz, 1H), 6.60 (ddd, J=8.8, 2.9, 0.9 Hz, 1H), 6.41 (d, J=2.3 Hz, 1H), 6.11 (dd, J=8.8, 5.2 Hz, 1H), 4.64 (br s, 2H), 1.72-1.66 (m, 6H), 1.44-1.36 (m, 6H), 1.21-1.17 (m, 6H), 0.91 (t, J=7.4 Hz, 9H) ppm; $^{13}$C NMR (151 MHz, C$_6$D$_6$) δ=154.5 (d, J=235.4 Hz), 153.7, 137.6 (d, J=2.3 Hz), 134.1 (d, J=19.7 Hz), 129.5, 117.9 (d, J=8.1 Hz), 114.8, 114.2 (d, J=21.9 Hz), 110.2 (d, J=25.3 Hz), 29.6, 27.7, 14.0, 10.4 ppm; HRMS (ESI) calcd for C$_{21}$H$_{34}$FN$_3$Sn [M+H]$^+$ 468.1835 found 468.1816.

3-Fluoro-4-(3-(tributylstannyl)-1H-pyrazol-1-yl)aniline 25g

Prepared from pyrazole 24g (591 mg, 2.3 mmol, 1.0 equiv) according to the general procedure described above for the preparation of 25a to yield stannane 25g (735 mg, 1.59 mmol, 69%) as a pale orange oil. 25g: $R_f$=0.19 (silica gel, 20% ethyl acetate in hexanes); FT-IR (neat) $v_{max}$ 3362, 3210, 2956, 2925, 2853, 1635, 1589, 1525, 1462, 1325, 1295, 1247, 1170, 1130, 1073, 1020, 964, 838, 811, 755, 693, 666, 624 cm$^{-1}$; $^1$H NMR (600 MHz, C$_6$D$_6$) δ=7.90 (dd, J=5.3, 2.3 Hz, 1H), 7.79 (t, J=8.6 Hz, 1H), 6.58 (d, J=2.3 Hz, 1H), 5.91-5.86 (m, 2H), 2.57 (br s, 2H), 1.77-1.71 (m, 6H), 1.46-1.39 (m, 6H), 1.26-1.23 (m, 6H), 0.92 (t, J=7.4 Hz, 9H) ppm; $^{13}$C NMR (151 MHz, CDCl$_3$) δ=154.0 (d, J=246.8 Hz), 153.1, 146.5 (d, J=9.2 Hz), 130.3 (d, J=6.0 Hz), 126.2 (d, J=1.6 Hz), 114.9, 111.2 (d, J=2.8 Hz), 102.6 (d, J=23.7 Hz), 29.2, 27.4, 13.9, 10.1 ppm; HRMS (ESI) calcd for C$_{21}$H$_{34}$FN$_3$Sn [M+H]$^+$ 468.1835 found 468.1815.

General Method for the Synthesis of Epothilones 5-14

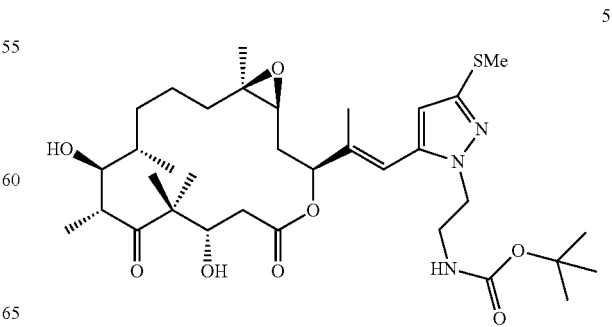

4-(3-(Tributylstannyl)-1H-pyrazol-1-yl)-3-(trifluoromethyl)aniline 25f

Prepared from pyrazole 24f (600 mg, 1.96 mmol, 1.0 equiv) according to the general procedure described above Epothilone 5:

A solution of vinyl iodide 15 (20 mg, 0.037 mmol, 1.0 equiv) and stannane 19a (49 mg, 0.09 mmol, 2.5 equiv) in degassed DMF (0.42 mL) was added to a stirring suspension of tris(dibenzylideneacetone)bispalladium (3.6 mg, 0.004 mmol, 0.1 equiv), copper iodide (3.0 mg, 0.016 mmol, 0.4 equiv), and triphenylarsine (2.4 mg, 0.008 mmol, 0.2 equiv) in degassed DMF (0.12 mL) at 25° C. Following consumption of the starting material as indicated by TLC (15 to 30 min), the reaction mixture was diluted with ethyl acetate (1 mL) and filtered through celite. The filtrate was then washed with $H_2O$ (2×2 mL) and brine (3 mL). Then the organic layer was dried with anhydrous magnesium sulfate and concentrated in vacuo to afford an oily residue which was purified by flash column chromatography (silica gel, 5% to 50% ethyl acetate in hexanes) and subsequent preparative TLC (silica gel, 50% ethyl acetate in hexanes) to provide 5 (19 mg, 0.029 mmol, 77%) as a white amorphous solid. 5: $R_f$=0.44 (silica gel, 70% ethyl acetate in hexanes); $[\alpha]_D^{25}$=+21.1 (c=1.0 in $CHCl_3$); FT-IR (neat) $v_{max}$ 3394, 2974, 2932, 1686, 1519, 1452, 1367, 1250, 1167, 1056, 1007, 973, 910, 857, 777, 730, 669 cm$^{-1}$; $^1$H NMR (600 MHz, $CDCl_3$, rotamer peaks found in square brackets) δ=[6.39, 6.33] (br s, 1H), 6.10 (br s, 1 H), 5.43 (d, J=8.5 Hz, 1H), [4.86, 4.71] (m, 1H), 4.23 (dd, J=10.1, 2.3 Hz, 1H), 4.21-4.13 (m, 2H), 4.10-3.98 (m, 1H), 3.84-3.64 (m, 2H), 3.57-3.43 (m, 2H), 3.26-3.17 (m, 2H), 2.79-2.77 (m, 1H), 2.56-2.51 (m, 1H), 2.49 (s, 3H), 2.29-1.88 (m, 4H), 1.83 (s, 3H), 1.77-1.70 (m, 2H), 1.59-1.45 (m, 2H), 1.39 (s, 3H), 1.35 (s, 3H), 1.31-1.28 (m, 5H), 1.24 (s, 3H), 1.15 (d, J=6.9 Hz, 3H), 1.05-0.97 (m, 6H) ppm; $^{13}$C NMR (151 MHz, $CDCl_3$, rotamer peaks found in square brackets) δ=220.4, 170.2, 156.4, [146.6, 146.3], [140.6, 140.4], 117.0, 113.9, [106.5, 105.9], [80.5, 79.9], 78.5, 76.6, [71.8, 71.2], [62.1, 61.7], [54.6, 54.0], [49.2, 48.2], [42.3, 42.0], [39.8, 39.6], 36.2, [33.3, 32.7], 32.0, [31.1, 30.7], 29.7, [28.3, 28.0], [22.8, 22.7], [22.5, 22.4], [22.0, 21.8], 19.5, 17.5, [16.7, 16.5], 16.0, 15.1, 14.1, [13.2, 13.0] ppm; HRMS (ESI) calcd for $C_{34}H_{55}N_3O_8S$ [M+H]$^+$ 666.3782 found 666.3787; Purity: ≥95% (UV detection, λ=254 nm).

6

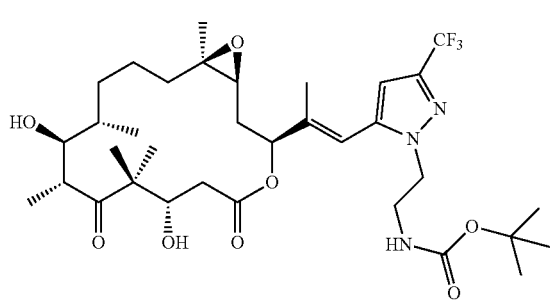

Epothilone 6:

Prepared from vinyl iodide 15 (20 mg, 0.037 mmol, 1.0 equiv) and stannane 19b (51 mg, 0.09 mmol, 2.5 equiv) according to the general procedure described above for the preparation of 5 to yield 6 (16.5 mg, 0.024 mmol, 65%) as a white amorphous solid. 6: $R_f$=0.30 (silica gel, 50% ethyl acetate in hexanes); $[\alpha]_D^{25}$=+11.0 (c=1.0 in $CHCl_3$); FT-IR (neat) $v_{max}$ 3384, 2967, 2932, 1684, 1482, 1392, 1367, 1251, 1232, 1167, 1129, 1059, 1007, 975, 942, 916, 857, 759, 735 cm$^{-1}$; $^1$H NMR (600 MHz, $CDCl_3$, rotamer peaks found in square brackets) δ=[6.44, 6.38] (br s, 1H), 6.43 (s, 1H), 5.44 (dd, J=9.4, 1.8 Hz, 1H), 4.84-4.77 (m, 1H), [4.53, 4.31-4.08] (m, 4H), 3.26-3.20 (m, 1H), 2.80-2.77 (m, 1H), 2.57-2.50 (m, 1H), 2.30-2.01 (m, 3H), 1.96-1.89 (m, 1H), [1.85, 1.83] (s, 3H), 1.80-1.70 (m, 3H), 1.67-1.42 (br m, 6H), 1.39 (s, 3H), 1.36-1.32 (m, 5H), 1.29 (s, 3H), 1.25 (s, 3H), 1.16 (d, J=6.8 Hz, 3H), 1.06-0.98 (m, 6H) ppm; $^{13}$C NMR (151 MHz, $CDCl_3$, rotamer peaks found in square brackets) δ=220.3, 170.2, 156.4, [142.1, 141.9], 140.4 (q, J=29.5 Hz), 118.2 (q, J=268.5 Hz), 116.2, [104.5, 104.2], [80.8, 80.2], 78.3, 76.4, 73.5, [71.8, 71.1], [62.1, 61.8], [54.5, 54.1], [49.9, 49.0], [42.1, 42.0], [39.6, 39.5], 36.3, 33.3, 32.7, [32.0, 31.9], 31.1, 30.7, 29.7, [28.3, 27.9], [22.8, 22.7], [22.4, 22.0], [17.3, 16.7], 16.1, 15.1, [13.2, 13.1] ppm; HRMS (ESI) calcd for $C_{34}H_{52}F_3N_3O_8$[M+H]$^+$ 688.3779 found 666.3782; Purity: ≥95% (UV detection, λ=254 nm).

7

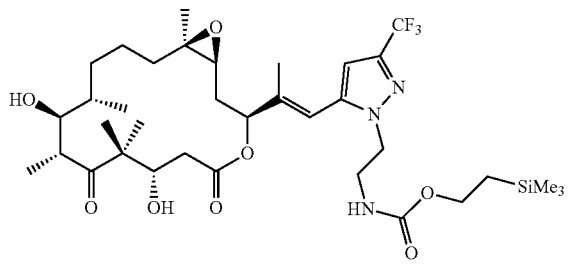

Epothilone 7:

Prepared from vinyl iodide 15 (20 mg, 0.037 mmol, 1.0 equiv) and stannane 19c (55 mg, 0.09 mmol, 2.5 equiv) according to the general procedure described above for the preparation of 5 to yield 7 (20 mg, 0.027 mmol, 74%) as a colorless oil. 7: $R_f$=0.35 (silica gel, 50% ethyl acetate in hexanes); $[\alpha]_D^{25}$=+26.3 (c=1.0 in $CHCl_3$); FT-IR (neat) $v_{max}$ 3381, 2967, 2930, 1680, 1475, 1422, 1367, 1243, 1232, 1169, 1135, 1050, 1015, 987, 942, 912, 857, 760, 730 cm$^{-1}$; $^1$H NMR (600 MHz, $CDCl_3$, rotamer peaks found in square brackets) δ=[6.47, 6.41] (br s, 1H), [6.44, 6.38] (br s, 1H), 5.43 (d, J=7.1 Hz, 1H), [4.99, 4.91] (br s, 1H), 4.28-4.15 (m, 4H), 4.12-3.78 (m, 2H), 3.70-3.52 (m, 2H), 3.35-3.19 (m, 1H), 2.78 (m, 1H), 2.70-2.41 (m, 2H), 2.34-1.91 (m 4H), [1.88, 1.84] (s, 3H), 1.80-1.63 (m, 4H), 1.61-1.39 (m, 6H), 1.37 (s, 3H), 1.35-1.32 (m, 2H), 1.30 (s, 3H), 1.25-1.06 (m, 3H), 1.01-0.91 (m, 6H), [0.02, 0.00] (s, 9H) ppm; $^{13}$C NMR (151 MHz, $CDCl_3$, rotamer peaks found in square brackets) δ=220.3, 170.1, 157.3, [142.1, 141.9], 140.4 (q, J=29.1 Hz), 118.6 (q, J=269.2 Hz), 116.2, 112.7, [104.5, 104.1], 78.4, 76.3, [73.9, 73.1], [71.9, 71.3], [64.1, 63.7], [62.3, 62.2], [61.9, 61.6], [53.8, 54.5], [49.8, 49.0], [42.3, 41.8], [40.2, 39.5], [36.5. 36.1], [32.5, 31.9], [31.0, 30.8], 29.7, 27.8, 26.9, [22.5, 22.4], 22.1, [17.8, 17.6], 17.5, [16.8, 16.7], 15.4, [13.6, 13.2], [−1.5, −1.7] ppm; HRMS (ESI) calcd for $C_{34}H_{52}F_3N_3O_8$[M+H]$^+$ 732.3867 found 732.3838; Purity: ≥95% (UV detection, λ=254 nm).

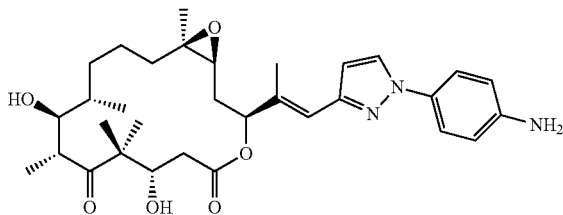

8

Epothilone 8:

Prepared from vinyl iodide 15 (10 mg, 0.019 mmol, 1.0 equiv) and stannane 25a (22 mg, 0.048 mmol, 2.5 equiv) according to the general procedure described above for the preparation of 5 to yield 8 (9 mg, 0.016 mmol, 84%) as a white foam. 8: $R_f$=0.29 (silica gel, 70% ethyl acetate in hexanes); $[\alpha]_D^{25}$=+17.0 (c=0.2 in CHCl$_3$); FT-IR (neat) $v_{max}$ 3361, 2925, 2853, 1733, 1687, 1523, 1464, 1378, 1262, 1146, 1060, 978, 881, 834, 758 cm$^{-1}$; $^1$H NMR (600 MHz, CDCl$_3$) δ=7.74 (d, J=2.4 Hz, 1H), 7.43 (d, J=8.8 Hz, 2H), 6.73 (d, J=8.8 Hz, 2H), 6.60, (s, 1H), 6.46 (d, J=2.4 Hz, 1H), 5.46 (dd, J=7.3, 2.9 Hz, 1H), 4.20 (dd, J=10.2, 3.1 Hz, 1H), 3.79 (t, J=4.3 Hz, 1H), 3.33-3.28 (m, 1H), 2.82 (dd, J=7.3, 4.9 Hz, 1H), 2.54 (dd, J=14.2, 10.2 Hz, 1H), 2.38 (dd, J=14.2, 3.1 Hz, 1H), 2.11 (d, J=1.0 Hz, 3H), 2.09-2.06 (m, 1H), 1.98-1.91 (m, 1H), 1.74-1.66 (m, 2H), 1.64-1.36 (m, 6H), 1.35 (s, 3H), 1.28 (s, 3H), 1.15 (d, J=6.8 Hz, 3H), 1.07 (s, 3H), 0.99 (d, J=7.0 Hz, 3H) ppm; $^{13}$C NMR (151 MHz, CDCl$_3$) δ=220.8, 170.6, 149.5, 145.3, 136.4, 132.1, 127.4, 120.9, 118.3, 115.4, 107.4, 74.2, 73.2, 61.6, 61.3, 52.8, 43.0, 39.1, 36.5, 32.1, 31.9, 29.7, 23.0, 22.9, 22.7, 21.4, 17.3, 16.0, 14.3, 13.9 ppm; HRMS (ESI) calcd for C$_{32}$H$_{45}$N$_3$O$_6$ [M+H]$^+$ 568.3381 found 568.3368; Purity: ≥95% (UV detection, λ=254 nm).

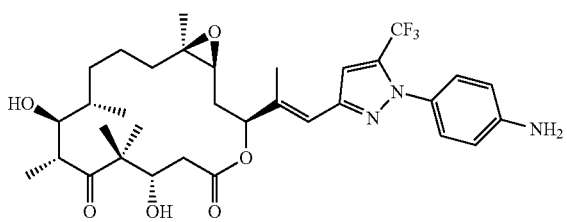

9

Epothilone 9:

Prepared from vinyl iodide 15 (10 mg, 0.019 mmol, 1.0 equiv) and stannane 25b (22 mg, 0.048 mmol, 2.5 equiv) according to the general procedure described above for the preparation of 5 to yield 9 (9 mg, 0.016 mmol, 84%) as a white foam. 9: $R_f$=0.34 (silica gel, 70% ethyl acetate in hexanes); $[\alpha]_D^{25}$=+22.4 (c=1.0 in CHCl$_3$); FT-IR (neat) $v_{max}$ 3340, 2925, 2843, 1732, 1690, 1527, 1445, 1378, 1250, 1137, 1040, 962, 880, 825, 758 cm$^{-1}$; $^1$H NMR (600 MHz, CDCl$_3$) δ=7.21 (d, J=8.5 Hz, 2H), 6.78 (s, 1H), 6.71 (d, J=8.5 Hz, 2H), 6.55 (s, 1H), 5.46 (dd, J=6.5, 3.4 Hz, 1H), 4.14 (dd, J=9.7, 3.2 Hz, 1H), 3.88 (br s, 2H), 3.79 (m, 2H), 3.28 (qd, J=6.8, 6.8 Hz, 1H), 2.81 (t, J=6.2 Hz, 1H), 2.54 (dd, J=14.3, 10.2 Hz, 1H), 2.49 (br s, 1H), 2.41 (dd, J=14.3, 3.2 Hz, 1H), 2.08 (s, 3H), 2.07-2.04 (m, 2H), 1.98-1.93 (m, 1H), 1.71-1.67 (m, 2H), 1.53-1.37 (m, 6H), 1.33 (s, 3H), 1.28 (s, 3H), 1.16 (d, J=6.9 Hz, 3H), 1.08 (s, 3H), 0.99 (d, J=6.9 Hz, 3H) ppm; $^{13}$C NMR (151 MHz, CDCl$_3$) δ=220.6, 170.5, 148.2, 147.4, 137.8, 132.8 (q, J=38.9 Hz), 129.8, 126.9, 117.4, 117.0 (q, J=269.3 Hz), 114.7, 108.3, 76.5, 74.6, 73.5, 61.2, 61.1, 52.6, 43.4, 38.9, 36.5, 31.9, 31.7, 30.7, 22.9, 22.8, 20.9, 20.8, 17.2, 15.7, 14.1 ppm; HRMS (ESI) calcd for C$_{39}$H$_{58}$F$_3$N$_3$O$_6$[M+H]$^+$ 636.3255 found 636.3164; Purity: ≥95% (UV detection, λ=254 nm).

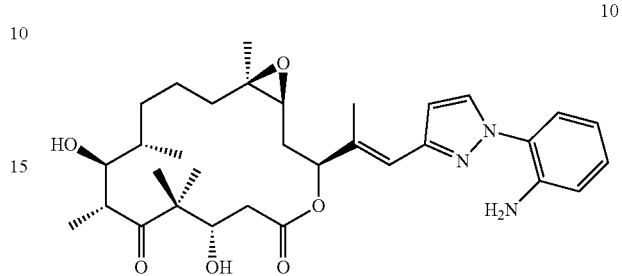

10

Epothilone 10:

Prepared from vinyl iodide 15 (15 mg, 0.028 mmol, 1.0 equiv) and stannane 25c (36 mg, 0.07 mmol, 2.5 equiv) according to the general procedure described above for the preparation of 5 to yield 10 (12 mg, 0.021 mmol, 75%) as a white foam. 10: $R_f$=0.32 (silica gel, 50% ethyl acetate in hexanes); $[\alpha]_D^{25}$=−43.3 (c=0.2 in CHCl$_3$); FT-IR (neat) $v_{max}$ 3456, 3351, 2958, 2926, 2856, 1732, 1687, 1619, 1514, 1462, 1380, 1288, 1251, 1147, 1053, 1009, 978, 953, 911, 886, 751, 673 cm$^{-1}$; $^1$H NMR (600 MHz, CDCl$_3$) δ=7.69 (d, J=2.4 Hz, 1H), 7.18-7.14 (m, 2H), 6.83 (dd, J=8.0, 1.2 Hz, 1H), 6.77 (dt, J=7.6, 1.2 Hz, 1H), 6.59 (s, 1H), 6.49 (d, 2.4 Hz, 1H), 5.48 (dd, J=6.8, 3.6 Hz, 1H), 4.11 (dd, J=10.0, 3.5 Hz, 1H), 3.85 (br s, 1H), 3.79 (t, J=4.3 Hz, 1H), 3.29 (qd, J=6.9, 6.9 Hz, 1H), 2.82 (dd, J=6.8, 5.6 Hz, 1H), 2.55 (dd, J=14.4, 9.9 Hz, 1H), 2.42 (dd, J=14.4, 3.3 Hz, 1H), 2.10 (d, J=1.1 Hz, 3H), 1.99-1.94 (m, 1H), 1.71-1.58 (m, 6H), 1.47-1.38 (m, 5H), 1.34 (s, 3H), 1.28 (s, 3H), 1.16 (d, J=6.9 Hz, 3H), 1.08 (s, 3H), 1.00 (d, J=7.0 Hz, 3H) ppm; $^{13}$C NMR (151 MHz, CDCl$_3$) δ=220.9, 170.8, 149.9, 136.3, 130.7, 128.7, 126.4, 124.1, 118.7, 118.4, 117.5, 107.3, 74.8, 73.8, 61.4, 61.3, 52.6, 43.7, 39.1, 36.7, 32.0, 31.9, 30.9, 29.9, 28.0, 27.0, 21.2, 21.0, 17.4, 15.9, 14.3, 13.8 ppm; HRMS (ESI) calcd for C$_{32}$H$_{45}$N$_3$O$_6$ [M+H]$^+$ 568.3381 found 568.3369; Purity: ≥95% (UV detection, λ=254 nm).

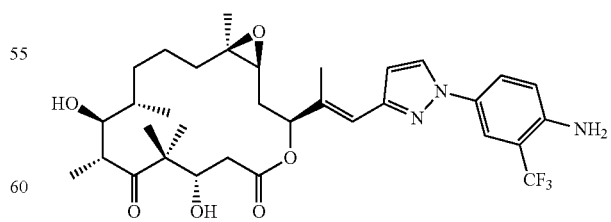

11

Epothilone 11:

Prepared from vinyl iodide 15 (20 mg, 0.037 mmol, 1.0 equiv) and stannane 25d (48 mg, 0.09 mmol, 2.5 equiv) according to the general procedure described above for the preparation of 5 to yield 11 (16 mg, 0.025 mmol, 68%) as a white foam. 11: $R_f$=0.49 (silica gel, 70% ethyl acetate in hexanes); $[\alpha]_D^{25}$=−43.3 (c=3.0 in CHCl$_3$); FT-IR (neat) $v_{max}$ 3491, 3389, 3259, 2963, 2929, 2878, 1731, 1688, 1641, 1587, 1521, 1453, 1381, 1333, 1315, 1300, 1263, 1143, 1111, 1062, 1049, 1008, 977, 911, 859, 825, 757, 734, 686 cm$^{-1}$; $^1$H NMR (600 MHz, CDCl$_3$) δ=7.77 (d, J=2.5 Hz, 1H), 7.71 (d, J=2.5 Hz, 1H), 7.56 (dd, J=8.8, 2.5 Hz, 1H), 6.81 (d, J=8.8 Hz, 1H), 6.59 (s, 1H), 6.48 (d, J=2.5 Hz, 1H), 5.45 (dd, J=7.4, 3.1 Hz, 1H), 4.19 (dd, J=10.2, 3.2 Hz, 1H), 3.78 (t, J=4.3 Hz, 1H), 3.34-3.29 (m, 1H), 2.82 (dd, J=7.3, 5.0 Hz, 1H), 2.54 (dd, J=14.2, 10.2 Hz, 1H), 2.38 (dd, J=14.2, 3.3 Hz, 1H), 2.10 (d, J=1.1 Hz, 3H), 2.09-2.06 (m, 1H), 1.97-1.91 (m, 1H), 1.74-1.69 (m, 2H), 1.51-1.37 (m, 5H), 1.36 (s, 3H), 1.34-1.32 (m, 1H), 1.28 (s, 3H), 1.16 (d, J=6.9 Hz, 3H), 1.08 (s, 3H), 1.00 (d, J=7.0 Hz, 3H) ppm; $^{13}$C NMR (151 MHz, CDCl$_3$) δ=220.9, 170.7, 150.1, 143.3, 137.2, 131.2, 127.5, 124.4, 121.2 (q, J=272.6 Hz), 118.1, 118.08 (q, J=5.5 Hz), 113.8 (q, J=30.9 Hz), 108.0, 74.4, 73.4, 61.7, 60.6, 52.9, 43.3, 39.2, 36.6, 32.2, 32.1, 30.9, 23.0, 22.8, 21.3, 20.4, 17.3, 16.0, 14.3, 14.0 ppm; HRMS (ESI) calcd for C$_{33}$H$_{44}$F$_3$N$_3$O$_6$[M+H]$^+$ 636.3255 found 636.3242; Purity: ≥95% (UV detection, λ=254 nm).

12

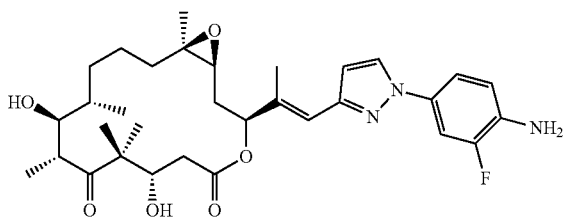

Epothilone 12:

Prepared from vinyl iodide 15 (18 mg, 0.034 mmol, 1.0 equiv) and stannane 25e (39 mg, 0.085 mmol, 2.5 equiv) according to the general procedure described above for the preparation of 5 to yield 12 (12 mg, 0.020 mmol, 63%) as a white foam. 12: $R_f$=0.55 (silica gel, 70% ethyl acetate in hexanes); $[\alpha]_D^{25}$=−10.0 c=0.2 in CHCl$_3$); FT-IR (neat) $v_{max}$ 3456, 3374, 2924, 2853, 1733, 1685, 1632, 1518, 1464, 1380, 1258, 1188, 1145, 1044, 977, 879, 814, 769, 652 cm$^{-1}$; $^1$H NMR (600 MHz, CDCl$_3$) δ=7.70 (s, 1H), 6.95 (dd, J=8.8, 2.5 Hz, 1H), 6.92-6.82 (m, 2H), 6.58 (s, 1H), 6.50 (s, 1H), 5.47 (dd, J=6.5, 3.5 Hz, 1H), 4.12 (dd, J=9.7, 3.2 Hz, 1H), 3.78 (t. J=4.2 Hz, 1H), 3.29 (qd, J=6.9, 6.9 Hz, 1 H), 2.82 (t, J=6.2 Hz, 1H), 2.55 (dd, J=14.4, 9.9 Hz, 1H), 2.41 (dd, J=14.4, 3.3 Hz, 1H), 2.09 (s, 3H), 2.08-2.04 (m, 2H), 2.00-1.94 (m, 1H), 1.73-1.67 (m, 2H), 1.54-1.37 (m, 6H), 1.35 (s, 3H), 1.28 (s, 3H), 1.16 (d, J=6.9 Hz, 3H), 1.07 (s, 3H), 0.99 (d, J=7.0 Hz, 3H) ppm; $^{13}$C NMR (151 MHz, CDCl$_3$) δ=220.8, 170.4, 154.5 (d, J=237.9 Hz), 150.2, 136.9, 136.7, 130.5, 126.3, 118.5, 118.3 (d, J=8.7 Hz), 115.2 (d, J=22.3 Hz), 110.7 (d, J=25.4 Hz), 107.7, 74.8, 73.8, 61.4, 61.3, 52.6, 43.7, 39.1, 36.7, 32.0, 31.8, 30.8, 29.8, 23.1, 23.0, 21.3, 21.0, 17.4, 15.9, 14.3 ppm; HRMS (ESI) calcd for C$_{32}$H$_{44}$FN$_3$O$_6$ [M+H]$^+$ 586.3314 found 586.3313; Purity: ≥95% (UV detection, λ=254 nm).

13

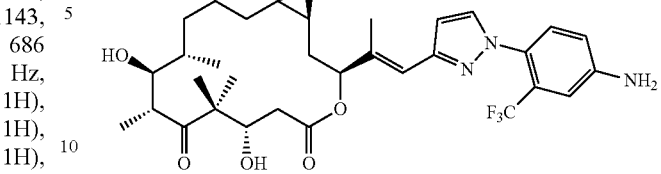

Epothilone 13:

Prepared from vinyl iodide 15 (26 mg, 0.048 mmol, 1.0 equiv) and stannane 25f (63 mg, 0.12 mmol, 2.5 equiv) according to the general procedure described above for the preparation of 5 to yield 13 (18 mg, 0.028 mmol, 60%) as a white foam. 13: $R_f$=0.41 (silica gel, 70% ethyl acetate in hexanes); $[\alpha]_D^{25}$=−54.2 (c=1.0 in CHCl$_3$); FT-IR (neat) $v_{max}$ 3496, 3384, 3265, 2963, 2928, 2882, 1740, 1685, 1642, 1590, 1521, 1438, 1365, 1354, 1322, 1292, 1263, 1136, 1110, 1076, 1048, 1010, 972, 905, 868, 832, 755, 734, 690 cm$^{-1}$; $^1$H NMR (600 MHz, CDCl$_3$) δ=7.54 (m, 1H), 7.25 (m, 1H), 6.99 (d, J=2.6 Hz, 1H), 6.84 (dd, J=8.5, 2.3 Hz, 1H), 6.58 (s, 1H), 6.44 (d, J=2.6 Hz, 1H), 5.46 (dd, J=7.1, 3.0 Hz, 1H), 4.15 (m, 1H), 4.03 (br s, 2H), 3.86 (br s, 1H), 3.78 (dd, J=7.4, 3.8 Hz, 1H), 3.27 (qd, J=6.5, 6.5 Hz, 1H), 2.83 (dd, J=6.9, 5.3 Hz, 1H), 2.53 (dd, J=14.2, 10.0 Hz, 1H), 2.52 (br s, 1H), 2.38 (dd, J=14.2, 3.2 Hz, 1H), 2.14-2.10 (m, 1H), 2.08 (s, 3H), 1.97-1.92 (m, 1H), 1.74-1.68 (m, 2H), 1.51-1.38 (m, 6H), 1.31 (s, 3H), 1.28 (s, 3H), 1.15 (d, J=6.9 Hz, 3H), 1.07 (s, 3H), 1.00 (d, J=6.9 Hz, 3H) ppm; $^{13}$C NMR (151 MHz, CDCl$_3$) δ=220.7, 170.6, 149.7, 147.0, 136.7, 132.7, 130.4, 128.9, 126.8 (q, J=30.4 Hz), 120.2 (q, J=272.9 Hz), 118.4, 117.6, 112.3 (q, J=30.9 Hz), 106.6, 77.5, 74.3, 73.3, 61.5, 61.2, 52.7, 43.2, 39.0, 36.6, 32.1, 32.0, 22.9, 22.7, 21.0, 20.5, 17.1, 15.7, 13.9 ppm; HRMS (ESI) calcd for C$_{33}$H$_{44}$F$_3$N$_3$O$_6$[M+H]$^+$ 636.3255 found 636.3268; Purity: ≥95% (UV detection, λ=254 nm).

14

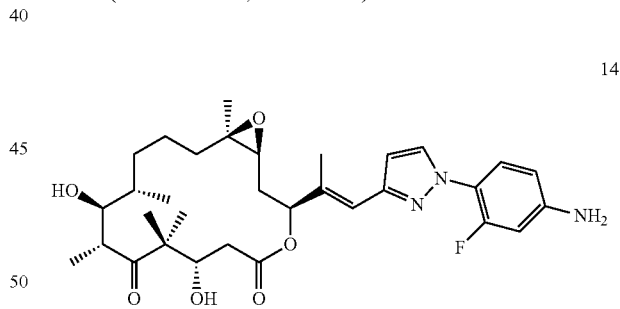

Epothilone 14:

Prepared from vinyl iodide 15 (15 mg, 0.028 mmol, 1.0 equiv) and stannane 25g (33 mg, 0.07 mmol, 2.5 equiv) according to the general procedure described above for the preparation of 5 to yield 14 (15 mg, 0.026 mmol, 91%) as a white foam. 14: $R_f$=0.44 (silica gel, 70% ethyl acetate in hexanes); $[\alpha]_D^{25}$=−65.0 (c=0.2 in CHCl$_3$); FT-IR (neat) $v_{max}$ 3443, 3362, 3237, 2958, 2925, 1730, 1688, 1635, 1590, 1528, 1460, 1382, 1327, 1258, 1171, 1046, 965, 915, 887, 841, 815, 762, 734 cm$^{-1}$; $^1$H NMR (600 MHz, CDCl$_3$) δ=7.78 (t, J=2.3 Hz, 1H), 7.53-7.50 (m, 1H), 6.60 (s, 1H), 6.52-6.47 (m, 3H), 5.46 (dd, J=7.2, 3.1 Hz, 1H), 4.17 (d, J=9.4 Hz, 1H), 3.88 (br s, 2H), 3.79 (t, J=4.2 Hz, 1H), 3.29 (qd, J=6.8, 6.8 Hz, 1H), 2.82 (dd, J=7.0, 5.4 Hz, 1H), 2.58-2.55 (br s, 1H), 2.54 (dd, J=14.1, 10.1 Hz, 1H), 2.39

(dd, J=14.2, 3.2 Hz, 1H), 2.10 (s, 3H), 2.09-2.07 (m, 1H), 1.97-1.92 (m, 1H), 1.74-1.65 (m, 3H), 1.53-1.49 (m, 1H), 1.46-1.38 (m, 4H), 1.35 (s, 3H), 1.28 (s, 3H), 1.16 (d, J=6.9 Hz, 3H), 1.08 (s, 3H), 1.00 (d, J=7.0 Hz, 3H) ppm; $^{13}$C NMR (151 MHz, CDCl$_3$) δ=220.8, 170.7, 154.3 (d, J=247.6 Hz), 149.5, 147.0 (d, J=10.5 Hz), 136.8, 131.4 (d, J=7.7 Hz), 125.9 (d, J=1.4 Hz), 119.7 (d, J=10.4 Hz), 118.5, 111.1 (d, J=2.2 Hz), 107.3, 102.6 (d, J=23.2 Hz), 74.5, 73.5, 61.6, 61.3, 52.9, 43.4, 39.2, 36.7, 32.2, 32.1, 30.9, 23.0, 22.8, 21.3, 20.6, 17.3, 15.9, 14.0 ppm; HRMS (ESI) calcd for C$_{32}$H$_{44}$FN$_3$O$_6$[M+H]+ 586.3287, found 586.3289; Purity: ≥95% (UV detection, λ=254 nm).

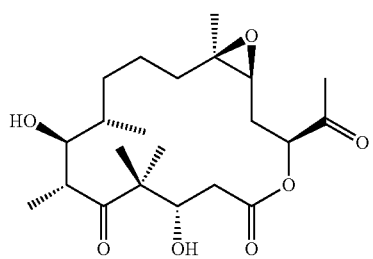

26

Epoxy Methyl Ketone 26:

To a stirred solution of epothilone B (1) (122 mg, 0.240 mmol, 1.0 equiv.) in dichloromethane (5 mL) at −78° C. was bubbled freshly generated ozone. After the color of the solution changed to light blue, the reaction mixture was quenched with methyl disulfide (0.18 mL, 2.45 mmol, 10 equiv.), allowed to warm to 25° C., and stirred for 1 h. The solvent was removed in vacuo, and the obtained residue was purified by flash column chromatography (silica gel, 40→70% ethyl acetate in hexanes) to afford pure epoxy methyl ketone 26 (93.0 mg, 0.225 mmol, 94%) as an amorphous solid. 26: R$_f$=0.26 (silica gel, 60% ethyl acetate in hexanes); [α]$_D^{25}$=+12.7 (c=0.60, CH$_2$Cl$_2$); FT-IR (neat) ν$_{max}$ 3473, 2960, 2937, 2879, 1746, 1723, 1689, 1465, 1423, 1368, 1284, 1250, 1180, 1145, 1076, 1010, 980, 957, 916, 733, 672 cm$^{-1}$; $^1$H NMR (600 MHz, CDCl$_3$) δ=5.31 (dd, J=10.2, 1.8 Hz, 1H), 4.31 (ddd, J=10.8, 4.8, 3.0 Hz, 1H), 4.10 (d, J=4.8 Hz, 1H), 3.70 (ddd, J=3.6, 3.6, 3.6 Hz, 1H), 3.25 (qd, J=6.6, 5.4 Hz, 1H), 2.82 (dd, J=9.0, 3.0 Hz, 1H), 2.57 (br s, 1H), 2.54 (dd, J=14.4, 10.8 Hz, 1H), 2.34 (ddd, J=15.0, 3.0, 1.8 Hz, 1H), 2.28 (s, 3H), 2.27 (dd, J=15.0, 3.0 Hz, 1H), 1.79-1.72 (m, 2H), 1.69-1.63 (m, 1H), 1.49-1.43 (m, 1H), 1.44-1.37 (m, 1H), 1.42 (s, 3H), 1.36-1.25 (m, 2H), 1.29 (s, 3H), 1.20 (d, J=6.6 Hz, 3H), 1.09 (s, 3H), 0.99 (d, J=7.2 Hz, 3H) ppm; $^{13}$C NMR (151 MHz, CDCl$_3$) δ=220.6, 205.0, 170.7, 76.8, 74.5, 71.7, 62.5, 62.2, 53.4, 42.7, 40.0, 37.4, 32.9, 31.3, 29.0, 26.4, 23.3, 22.6, 22.5, 18.0, 17.3, 14.4 ppm; HRMS (ESI) calcd for C$_{22}$H$_{36}$O$_7$Na [M+Na]$^+$ 435.2353, found 435.2351.

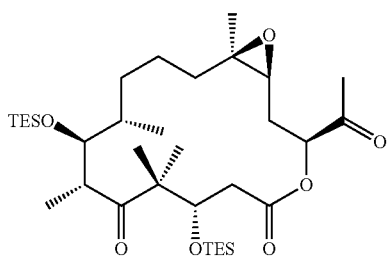

27

Silyl Ether 27:

To a stirred solution of epoxide 26 (150 mg, 0.364 mmol, 1.0 equiv.) in dichloromethane (5 mL) at −78° C. was added 2,6-lutidine (0.126 mL, 1.09 mmol, 3.0 equiv.) followed by triethylsilyl trifluoromethanesulfonate (0.197 mL, 0.873 mmol, 2.4 equiv.). After 5 min, the reaction mixture was quenched with water (10 mL), and allowed to warm to 25° C. The two phases were separated, and the aqueous layer was extracted with dichloromethane (3×5 mL). The combined organic layers were dried with anhydrous sodium sulfate and concentrated in vacuo. The obtained residue was purified by flash column chromatography (silica gel, 5→15% ethyl acetate in hexanes) to afford pure silyl ether 27 (231 mg, 0.360 mmol, 99%) as an amorphous solid. 27: R$_f$=0.37 (silica gel, 20% ethyl acetate in hexanes); [α]$_D^{25}$ −14.0 (c=1.00, CH$_2$Cl$_2$); FT-IR (neat) ν$_{max}$ 2955, 2913, 2877, 1749, 1734, 1696, 1459, 1414, 1381, 1308, 1240, 1196, 1157, 1106, 1080, 1064, 1040, 1010, 985, 916, 859, 836, 783, 737, 676 cm$^{-1}$; $^1$H NMR (600 MHz, CDCl$_3$) δ=5.01 (dd, J=10.2, 1.8 Hz, 1H), 4.04 (dd, J=10.2, 2.4 Hz, 1H), 3.91 (d, J=9.0 Hz, 1H), 3.04 (dq, J=9.6, 6.6 Hz, 1H), 2.94 (dd, J=16.2, 2.4 Hz, 1H), 2.86 (dd, J=10.2, 4.2 Hz, 1H), 2.77 (dd, J=16.2, 4.2 Hz, 1H), 2.37 (dd, J=16.2, 2.4 Hz, 1H), 2.24 (s, 3H), 1.76-1.68 (m, 2H), 1.63-1.58 (m, 1H), 1.55-1.45 (m, 2H), 1.42-1.38 (m, 1H), 1.30 (s, 3H), 1.27-1.23 (m, 1H), 1.25 (s, 3H), 1.17 (s, 3H), 1.10 (d, J=6.6 Hz, 3H), 1.07-1.04 (m, 1H), 1.00 (t, J=7.8 Hz, 9H), 0.99 (d, J=7.2 Hz, 3H), 0.98-0.95 (m, 1H), 0.93 (t, J=7.8 Hz, 9H), 0.67 (q, J=7.8 Hz, 6H), 0.61 (q, J=7.8 Hz, 6H) ppm; $^{13}$C NMR (151 MHz, CDCl$_3$) δ=215.2, 203.4, 171.8, 80.3, 76.5, 76.3, 62.5, 62.2, 53.5, 48.6, 39.4. 36.8, 32.1, 31.1, 30.3, 26.0, 24.9, 24.7, 23.7, 22.6, 19.7, 17.8, 7.3, 7.1, 5.7, 5.4 ppm; HRMS (ESI) calcd for C$_{34}$H$_{64}$O$_7$Si$_2$Na [M+Na]$^+$ 663.4083, found 663.4057.

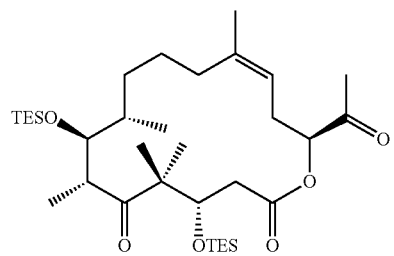

28

Olefin Methyl Ketone 28:

To a stirred suspension of tungsten hexachloride (496 mg, 1.25 mmol, 2.0 equiv.) in tetrahydrofuran (7 mL) at −78° C. was carefully added n-butyllithium (1.6 M hexanes, 1.56 mL, 2.50 mmol, 4.0 equiv.). The reaction mixture was allowed to warm to 25° C., stirred for 40 min, and then cooled to −20° C. A solution of silyl ether 27 (401 mg, 0.626 mmol, 1.0 equiv.) in tetrahydrofuran (4 mL) was then added dropwise, and the reaction mixture was allowed to slowly warm to 0° C. over 2 h. Then the reaction mixture was quenched with a saturated aqueous solution of ammonium chloride (10 mL) and warmed to 25° C. The two phases were separated, the aqueous layer was extracted with ethyl acetate (3×5 mL), and the combined organic layers were dried with anhydrous sodium sulfate and concentrated in vacuo. The obtained residue was purified by flash column chromatography (silica gel, 2.5→30% ethyl acetate in hexanes) to afford pure olefin 28 (335 mg, 0.536 mmol, 86%) as a colorless oil. 28: R$_f$=0.21 (silica gel, 10% diethyl ether in hexanes); $[\alpha]_D^{25}=-18.2$ (c=1.00, CH$_2$Cl$_2$); FT-IR (neat) $\nu_{max}$ 2953, 2912, 2877, 1747, 1731, 1696, 1459, 1414, 1381, 1365, 1307, 1275, 1263, 1240, 1198, 1159, 1110, 1062, 1042, 1018, 984, 859, 835, 783, 744, 674 cm$^{-1}$; $^1$H NMR (600 MHz, CDCl$_3$) δ=5.16 (dd, J=7.8, 7.8 Hz, 1H), 4.84 (dd, J=10.2, 1.8 Hz, 1H), 4.04 (dd, J=10.2, 1.8 Hz, 1H), 3.91 (dd, J=9.0 Hz, 1H), 3.01 (dq, J=9.6, 6.6 Hz, 1H), 2.91 (dd, J=16.2, 1.8 Hz, 1H), 2.76 (dd, J=16.2, 10.8 Hz, 1H), 2.53 (ddd, J=15.0, 10.2, 10.2 Hz, 1H), 2.41 (dd, J=14.4, 10.8 Hz, 1H), 2.24 (dd, J=14.4, 7.2 Hz, 1H), 2.19 (s, 3H), 1.76-1.66 (m, 2H), 1.69 (s, 3H), 1.57-1.49 (m, 2H), 1.22 (s, 3H), 1.14 (s, 3H), 1.10-1.00 (m, 2H), 1.09 (d, J=6.6 Hz, 3H), 0.98 (t, J=7.8 Hz, 9H), 0.97 (d, J=6.6 Hz, 3H), 0.88 (t, J=7.8 Hz, 9H), 0.65 (q, J=7.8 Hz, 6H), 0.55 (q, J=7.8 Hz, 6H) ppm; $^{13}$C NMR (151 MHz, CDCl$_3$) δ=215.2, 204.4, 171.9, 142.4, 117.7, 80.1, 79.8, 76.6, 53.6, 48.2, 39.3, 37.6, 32.3, 31.4, 28.6, 27.5, 26.3, 25.1, 23.7, 23.2, 19.2, 17.7, 7.4, 7.0, 5.8, 5.4 ppm; HRMS (ESI) calcd for C$_{34}$H$_{64}$O$_6$Si$_2$Na [M+Na]$^+$ 647.4134, found 647.4134.

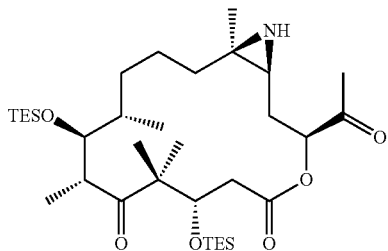

29

Aziridine Methyl Ketone 29:

To a stirred solution of olefin 28 (320 mg, 0.512 mmol, 1.0 equiv.) in trifluoroethanol (3 mL) at 25° C. was added O-(2,4-dinitrophenyl)hydroxylamine (153 mg, 0.768 mmol, 1.5 equiv.) followed by bis[rhodium(α,α,α',α',-tetramethyl-1,3-benzenedipropionic acid)] (7.8 mg, 0.0102 mmol, 0.02 equiv.). The reaction mixture was stirred for 30 min, diluted with dichloromethane (40 mL), and washed with a saturated aqueous solution of sodium bicarbonate (3×15 mL) and brine (20 mL). The combined organic layers were dried with anhydrous sodium sulfate and concentrated in vacuo. The obtained residue was purified by flash column chromatography (silica gel, 2.5→5% methanol in dichloromethane) to afford pure aziridine 29 (290 mg, 0.462 mmol, 90%) as a pale yellow oil. 29: R$_f$=0.29 (silica gel, 5% methanol in ethyl acetate); $[\alpha]_D^{25}=-14.5$ (c=0.64, CH$_2$Cl$_2$); FT-IR (neat) $\nu_{max}$ 2953, 2918, 2877, 1747, 1732, 1696, 1460, 1414, 1382, 1307, 1240, 1199, 1157, 1107, 1067, 1043, 1018, 985, 835, 783, 736, 675 cm$^{-1}$; $^1$H NMR (600 MHz, C$_6$D$_6$) δ=4.90 (dd, J=9.0, 1.8 Hz, 1H), 4.18 (d, J=9.6 Hz, 1H), 4.07 (dd, J=9.0, 3.0 Hz, 1H), 2.88 (dq, J=10.2, 6.6 Hz, 1H), 2.76-2.68 (m, 2H), 1.94 (d, J=16.2 Hz, 1H), 1.83-1.78 (m, 1H), 1.76-1.65 (m, 2H), 1.72 (s, 3H), 1.60-1.53 (m, 1H), 1.51-1.45 (m, 1H), 1.41-1.35 (m, 3H), 1.26-1.19 (m, 1H), 1.19 (d, J=6.6 Hz, 3H), 1.15 (s, 3H), 1.09-1.04 (m, 24H), 0.79-0.71 (m, 12H), 0.67 (s, 3H) ppm; $^{13}$C NMR (151 MHz, C$_6$D$_6$) δ=213.9, 202.3, 171.7, 80.8, 78.2, 76.7, 53.1, 48.3, 42.4, 39.4, 39.3, 36.9, 33.7, 31.43, 31.37, 25.7, 25.4, 25.2, 25.0, 22.8, 20.0, 17.7, 7.5, 7.3, 6.0, 5.8 ppm; HRMS (ESI) calcd for C$_{34}$H$_{66}$NO$_6$Si$_2$ [M+H]$^+$ 640.4423, found 640.4442.

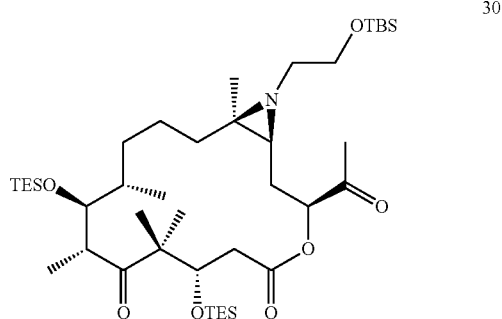

Tertiary Aziridine 30:

To a stirred solution of aziridine 29 (105 mg, 0.164 mmol, 1.0 equiv.) in dimethylformamide (0.8 mL) at 25° C. was added (2-bromoethoxy)-tert-butyldimethylsilane (196 mg, 0.820 mmol, 5.0 equiv.), followed by potassium carbonate (91 mg, 0.656 mmol, 4.0 equiv.). The reaction mixture was heated to 75° C., stirred for 12 h, and then allowed to cool to 25° C. Water (1.5 mL) was added, and the quenched reaction mixture was extracted with ethyl acetate (3×3 mL). The combined organic layers were dried with anhydrous sodium sulfate and concentrated in vacuo. The obtained residue was purified by flash column chromatography (silica gel, 10→40% ethyl acetate in hexanes) to afford pure N-alkylated aziridine 30 (118 mg, 0.148 mmol, 90%) as a pale yellow oil. 30: R$_f$=0.31 (silica gel, 30% ethyl acetate in hexanes); $[\alpha]_D^{25}=-6.9$ (c=0.26, CH$_2$Cl$_2$); FT-IR (neat) $\nu_{max}$ 2953, 2931, 2877, 1748, 1734, 1697, 1462, 1414, 1382, 1361, 1307, 1250, 1196, 1158, 1109, 1079, 1042, 1008, 985, 835, 780, 737, 667 cm$^{-1}$; $^1$H NMR (600 MHz, C$_6$D$_6$) δ=4.94 (dd, J=9.0, 1.8 Hz, 1H), 4.19 (d, J=9.6 Hz, 1H), 4.05 (dd, J=7.8, 4.8 Hz, 1H), 3.84 (ddd, J=9.6, 6.6, 6.6 Hz, 1H), 3.77 (ddd, J=10.2, 5.4, 5.4 Hz, 1H), 2.85 (dq, J=9.6, 6.6 Hz, 1H), 2.75-2.71 (m, 2H), 2.42 (ddd, J=12.6, 6.6, 6.6 Hz, 1H), 2.19 (d, J=16.2 Hz, 1H), 1.86-1.76 (m, 2H), 1.83 (s, 3H), 1.72-1.59 (m, 3H), 1.48-1.36 (m, 2H), 1.25-1.10 (m, 3H), 1.21 (d, J=7.2 Hz, 3H), 1.16 (s, 3H), 1.11-1.06 (m, 18H), 1.04 (m, J=6.6 Hz, 3H), 1.00 (s, 9H), 0.83-0.77 (m, 6H), 0.72 (q, J=7.8 Hz, 6H), 0.68 (s, 3H), 0.10 (s, 6H) ppm; $^{13}$C NMR (151 MHz, C$_6$D$_6$) δ=213.9, 202.5, 171.9, 80.8, 78.1, 76.8, 64.3, 54.6, 53.1, 50.7, 48.3, 42.8, 39.4, 36.9, 35.9, 31.7, 31.6, 26.2 (3C), 25.5, 25.1, 25.0, 23.0, 20.0, 18.5, 17.8, 15.5, 7.4, 7.3, 6.0, 5.8, −5.12, −5.13 ppm; HRMS (ESI) calcd for C$_{42}$H$_{84}$NO$_7$Si$_3$ [M+H]$^+$ 798.5550, found 798.5541.

Methylthio Thiazole 33:

Methylthio thiazole 33 was prepared from commercially available 2,4-dibromothiazole (32) as previously described (Nicolaou, et al., 1998). The physical and spectral data are consistent with those reported (Nicolaou, et al., 1998).

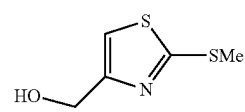

34

Hydroxymethyl Thiazole 34:

To a stirred solution of methylthio thiazole 33 (1.48 g, 7.04 mmol, 1.0 equiv.) in diethyl ether (20 mL) at −78° C. was carefully added tert-butyllithium (1.4 M pentanes, 6.0 mL, 8.40 mmol, 1.2 equiv.). After 5 min, dimethylformamide (1.03 mL, 14.1 mmol, 2.0 equiv.) was added and the stirring was continued for 20 min. Then the reaction mixture was quenched with a saturated aqueous solution of ammonium chloride (10 mL), and allowed to warm to 25° C. The two phases were separated, and the aqueous layer was extracted with ethyl acetate (3×10 mL). The combined organic layers were dried with anhydrous sodium sulfate and concentrated in vacuo. The obtained residue was purified by flash column chromatography (silica gel, 20→50% ethyl acetate in hexanes) to afford pure thiazole 34 (0.850 g, 5.27 mmol, 75%) as a colorless oil. 34: $R_f$=0.26 (silica gel, 50% ethyl acetate in hexanes); FT-IR (neat) $v_{max}$ 3334, 3118, 2924, 2860, 1529, 1407, 1314, 1261, 1213, 1135, 1037, 966, 944, 849, 752, 725 cm$^{-1}$; $^1$H NMR (600 MHz, CDCl$_3$) δ=7.05 (s, 1H), 4.71 (s, 2H), 2.69 (s, 3H) ppm; $^{13}$C NMR (151 MHz, CDCl$_3$) δ=167.5, 156.5, 114.0, 61.2, 17.0 ppm; HRMS (ESI) calcd for C$_5$H$_8$NOS$_2$ [M+H]$^+$ 162.0042, found 162.0048.

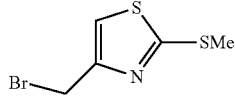

Bromomethyl Thiazole 35:

To a stirred solution of hydroxymethyl thiazole 34 (642 mg, 3.98 mmol, 1.0 equiv.) in dichloromethane (6 mL) at −78° C. was added triphenylphosphine (1.10 g, 4.18 mmol, 1.05 equiv.), followed by N-bromosuccinimide (708 mg, 3.98 mmol, 1.0 equiv.). After 5 min, the reaction mixture was quenched with water (5 mL) and allowed to warm to 25° C. The two phases were separated, and the aqueous layer was extracted with ethyl acetate (3×10 mL). The combined organic layers were dried with anhydrous sodium sulfate and concentrated in vacuo. The obtained residue was purified by flash column chromatography (silica gel, 1→5% ethyl acetate in hexanes) to afford pure bromomethyl thiazole 35 (0.696 g, 3.10 mmol, 78%) as a colorless oil. 35: $R_f$=0.27 (silica gel, 10% diethyl ether in hexanes); FT-IR (neat) $v_{max}$ 3103, 2924, 2850, 1511, 1411, 1314, 1214, 1147, 1108, 1055, 1037, 966, 882, 746, 701, 672 cm$^{-1}$; $^1$H NMR (600 MHz, CDCl$_3$) δ=7.16 (s, 1H), 4.51 (s, 2H), 2.69 (s, 3H) ppm; $^{13}$C NMR (151 MHz, CDCl$_3$) δ=167.7, 152.3, 117.0, 27.1, 16.9 ppm; HRMS (ESI) calcd for C$_5$H$_7$NS$_2$Br [M+H]$^+$ 223.9198, found 223.9201.

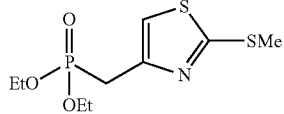

Phosphonate 36:

Triethyl phosphite (5 mL, 29.2 mmol, 6.4 equiv.) was added to a flask containing bromomethyl thiazole 35 (1.02 g, 4.55 mmol, 1.0 equiv.) at 25° C. The stirred reaction mixture was heated to 160° C. for 2 h, and then the excess triethyl phosphite was removed under a steady flow of N$_2$(g). The residue was allowed to cool to 25° C. and purified by flash column chromatography (silica gel, 70→100% ethyl acetate in hexanes) to afford pure phosphonate 36 (1.18 g, 4.19 mmol, 92%) as a colorless oil. 36: $R_f$=0.20 (silica gel, ethyl acetate); FT-IR (neat) $v_{max}$ 3463, 3108, 2982, 2929, 1646, 1515 1478, 1411, 1393, 1368, 1314, 1248, 1163, 1097, 1023, 966, 947, 867, 842, 808, 781, 716, 660 cm$^{-1}$; $^1$H NMR (600 MHz, CDCl$_3$) δ=7.08 (d, J=3.6 Hz, 1H), 4.08 (dq, J=8.4, 7.2 Hz, 4H), 3.32 (d, J=21.0 Hz, 2H), 2.65 (s, 3H), 1.28 (t, J=7.2 Hz, 6H) ppm; $^{13}$C NMR (151 MHz, CDCl$_3$) δ=166.1, 146.8 (d, J=8.1 Hz), 115.6 (d, J=8.0 Hz), 62.4 (d, J=6.5 Hz), 29.5 (d, J=140 Hz), 16.9, 16.5 (d, J=6.0 Hz) ppm; HRMS (ESI) calcd for C$_9$HNO$_3$PS$_2$ [M+H]$^+$ 282.0382, found 282.0378.

Hydroxymethyl Thiazole 37:

Hydroxymethyl thiazole 37 was prepared from commercially available 2,4-dibromothiazole (32) as previously described (Nicolaou, et al., 1998). The physical and spectral data are consistent with those reported (Nicolaou, et al., 1998).

Silyl Ether Thiazole 38:

Silyl Ether Thiazole 38 was Prepared from Hydroxymethyl Thiazole 37 as previously described (Nicolaou, et al., 1998). The physical and spectral data are consistent with those reported (Nicolaou, et al., 1998).

Hydroxymethyl Thiazole 39:

Prepared from silyl ether thiazole 38 (2.42 g, 7.85 mmol, 1.0 equiv.) according to the procedure described above for the preparation of 34 to afford hydroxymethyl thiazole 39 (1.59 g, 6.13 mmol, 78%) as a colorless oil. The physical and spectral data are consistent with those reported (Lee, et al., 2001).

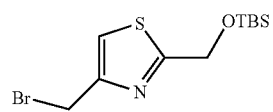

Bromomethyl Thiazole 40:

To a stirred solution of hydroxymethyl thiazole 39 (1.41 g, 5.43 mmol, 1.0 equiv.) in acetonitrile (45 mL) at 25° C. was added triphenylphosphine (2.42 g, 9.23 mmol, 1.7 equiv.), 2,6-lutidine (0.25 mL, 2.17 mmol, 0.4 equiv.), and carbon tetrabromide (3.06 g, 9.23 mmol, 1.7 equiv.) sequentially. The reaction mixture was stirred for 2 h, then quenched with a saturated aqueous solution of sodium bicarbonate (20 mL), and extracted with diethyl ether (3×15 mL). The combined organic layers were dried with anhydrous sodium sulfate and concentrated in vacuo. The obtained residue was purified by flash column chromatography (silica gel, 5→10% ethyl acetate in hexanes) to afford pure bromomethyl thiazole 40 (1.60 g, 4.96 mmol, 91%) as a colorless oil. 40: $R_f$=0.31 (silica gel, 10% ethyl acetate in hexanes); FT-IR (neat) $v_{max}$ 3106, 2954, 2929, 2885, 2857, 1519, 1492, 1471, 1463, 1426, 1390, 1355, 1255, 1197, 1145, 1111, 1006, 964, 939, 836, 778, 706, 684, 662 cm$^{-1}$; $^1$H NMR (600 MHz, CDCl$_3$) δ=7.23 (s, 1H), 4.95 (s, 2H), 4.55 (s, 2H), 0.95 (s, 9H) 0.13 (s, 6H) ppm; $^{13}$C NMR (151 MHz, CDCl$_3$) δ=174.6, 151.9, 117.4, 63.3, 27.4, 25.9, 18.4, −5.3 ppm; HRMS (ESI) calcd for C$_{11}$H$_{20}$BrNOSSi [M+H]$^+$ 322.0291, found 322.0285.

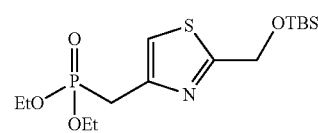

Phosphonate 41:

Triethyl phosphite (2.2 mL, 12.8 mmol, 20 equiv.) was added to a flask containing bromomethyl thiazole 40 (202 mg, 0.63 mmol, 1.0 equiv.) at 25° C. The stirred reaction mixture was heated to 160° C. for 3 h, and then the excess triethyl phosphite was removed under a steady flow of $N_2$(g). The residue was allowed to cool to 25° C. and purified by flash column chromatography (silica gel, 50→100% ethyl acetate in hexanes) to afford pure phosphonate 41 (192 mg, 0.51 mmol, 80%) as a colorless oil. 41: $R_f$=0.28 (silica gel, ethyl acetate); FT-IR (neat) $v_{max}$ 3476, 3107, 2955, 2930, 2903, 2858, 1519, 1472, 1463, 1444, 1392, 1361, 1321, 1253, 1198, 1164, 1099, 1055, 1027, 959, 837, 779, 722, 708, 674, 658 cm$^{-1}$; $^1$H NMR (600 MHz, CDCl$_3$) δ=7.17 (d, J=3.5 Hz, 1H), 4.94 (s, 2H), 4.11-4.06 (m, 4 H), 3.34 (d, J=21.0 Hz, 2H), 1.27 (t, J=7.1 Hz, 6H), 0.95 (s, 9H) 0.12 (s, 6H) ppm; $^{13}$C NMR (151 MHz, CDCl$_3$) δ=173.2, 146.1 (d, J=8.3 Hz) 116.1 (d, J=6.4 Hz), 63.2, 62.4 (d, J=6.6 Hz), 29.0 (d, J=141.0 Hz), 25.9, 18.4, 16.5 (d, J=6.0 Hz), −5.3 ppm; HRMS (ESI) calcd for $C_{15}H_{30}NO_4PSSi$ [M+H]$^+$ 380.1475, found 380.1475.

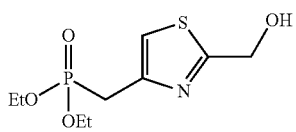

42

Phosphonate 42:

To a stirred solution of phosphonate 41 (56 mg, 0.15 mmol, 1.0 equiv.) in dimethylformamide (1 mL) at 0° C. was added tris(dimethylamino)sulfonium difluorotrimethylsilicate (204 mg, 0.75 mmol, 5.0 equiv.) followed by water (0.03 mL, 1.5 mmol, 10 equiv). The reaction mixture was allowed to slowly warm to 25° C., and stirring was continued for 10 h. Water (3 mL) and ethyl acetate (3 mL) was added, and the two phases were separated. The aqueous layer was extracted with ethyl acetate (3×2 mL), and the combined organic layers were dried with anhydrous sodium sulfate and concentrated in vacuo. The obtained residue was purified by flash column chromatography (5% methanol in dichloromethane) to afford pure phosphonate 42 (31 mg, 0.12 mmol, 79%) as a colorless oil. 42: $R_f$=0.33 (silica gel, 5% methanol in dichloromethane); FT-IR (neat) $v_{max}$ 3319, 2983, 2909, 1520, 1477, 1443, 1393, 1346, 1325, 1231, 1163, 1139, 1097, 1050, 1022, 957, 874, 845, 809, 784, 723, 670 cm$^{-1}$; $^1$H NMR (600 MHz, CDCl$_3$) δ=7.14 (d, J=3.2 Hz, 1H), 4.81 (s, 2H), 4.08-4.04 (m, 4H), 3.32 (d, J=21.0 Hz, 2H), 1.25 (t, J=7.1 Hz, 6H) ppm; $^{13}$C NMR (151 MHz, CDCl$_3$) δ=172.5, 146.0 (d, J=8.2 Hz) 116.4 (d, J=6.8 Hz), 62.5 (d, J=6.6 Hz), 61.9, 28.9 (d, J=141.5 Hz), 16.5 (d, J=6.0 Hz) ppm; HRMS (ESI) calcd for $C_9H_6NO_4PS$ [M+H]$^+$ 266.0610 found 266.0601.

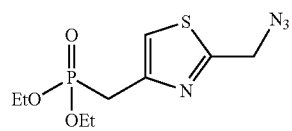

43

Azide 43:

To a stirred solution of phosphonate 42 (687 mg, 2.59 mmol, 1.0 equiv.) in dichloromethane (10.4 mL) at 25° C. was added triethylamine (0.72 mL, 5.18 mmol, 2.0 equiv.) and 4-(dimethylamino)pyridine (32 mg, 0.26 mmol, 0.1 equiv.). After cooling to −20° C., p-tolunesulfonic anhydride (1.27 g, 3.89 mmol, 1.5 equiv.) was added in one portion. Stirring was continued for 30 min, and then the reaction mixture was quenched with water (5 mL) and allowed to warm to 25° C. The two phases were separated, and the aqueous layer was extracted with dichloromethane (3×5 mL). The combined organic layers were dried with anhydrous sodium sulfate and concentrated in vacuo. The crude residue was then resuspended in dimethylformamide (5 mL), and cooled to −20° C. with stirring. Sodium azide (505 mg, 7.77 mmol, 3.0 equiv.) was added, and stirring was continued for an additional 15 min. The reaction mixture was then quenched with water (5 mL), allowed to warm to 25° C., and extracted with ethyl acetate (3×5 mL). The combined organic layers were dried with anhydrous sodium sulfate and concentrated in vacuo. Purification by flash column chromatography (5% methanol in dichloromethane) afforded pure azide 43 (643 mg, 2.22 mmol, 86%) as a colorless oil. 43: $R_f$=0.44 (silica gel, 5% methanol in dichloromethane); FT-IR (neat) $v_{max}$ 3470, 3111, 2983, 2930, 2100, 1517, 1443, 1393, 1327, 1250, 1162, 1098, 1053, 1026, 965, 874, 810, 783, 724 cm$^{-1}$; $^1$H NMR (600 MHz, CDCl$_3$) δ=7.25 (d, J=3.5 Hz, 1H), 4.63 (s, 2H), 4.12-4.07 (m, 4H), 3.37 (d, J=21.0 Hz, 2H), 1.27 (t, J=7.1 Hz, 6H) ppm; $^{13}$C NMR (151 MHz, CDCl$_3$) δ=164.3, 147.4 (d, J=8.1 Hz) 117.6 (d, J=7.5 Hz), 62.4 (d, J=6.6 Hz), 51.4, 29.1 (d, J=141.1 Hz), 16.5 (d, J=6.0 Hz) ppm; HRMS (ESI) calcd for $C_9H_5N_4O_3PS$ [M+H]$^+$ 291.0675, found 291.0675.

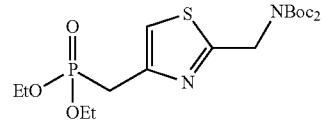

44

Phosphonate 44:

To a stirred solution of azide 43 (200 mg, 0.69 mmol, 1.0 equiv.) in ethyl acetate (4 mL) at 25° C. was added 5% palladium on carbon (50 mg, 25% w/w) and the flask was capped with a hydrogen balloon. Stirring was continued for 12 h. Then the hydrogen balloon was removed, and the reaction mixture was filtered through a pad of celite and concentrated in vacuo. The crude residue was then resuspended in tetrahydrofuran (5 mL) at 25° C., and triethylamine (0.26 mL, 1.80 mmol, 2.6 equiv.), 4-(dimethylamino) pyridine (9 mg, 0.07 mmol, 0.1 equiv.), and di-tert-butyl dicarbonate (332 mg, 1.52 mmol, 2.2 equiv.) were added sequentially with stirring. The reaction mixture was heated to 60° C. for 2.5 h, allowed to cool to 25° C., and then quenched with a saturated aqueous solution of ammonium chloride (3 mL). The two phases were separated, and the aqueous layer was extracted with ethyl acetate (3×5 mL). The combined organic layers were dried with anhydrous sodium sulfate and concentrated in vacuo. Purification by flash column chromatography (50→100% ethyl acetate) afforded pure phosphonate 44 (293 mg, 0.63 mmol, 91%) as a colorless oil. 44: $R_f$=0.27 (silica gel, ethyl acetate); FT-IR (neat) $v_{max}$ 3459, 3109, 2980, 2934, 1793, 1753, 1699, 1519, 1479, 1458, 1422, 1393, 1367, 1341, 1254, 1228, 1129, 1054, 1026, 965, 890, 853, 783 cm$^{-1}$; $^1$H NMR (600 MHz, CDCl$_3$) δ=7.15 (d, J=3.5 Hz, 1H), 5.04 (s, 2H), 4.10-4.05 (m, 4H), 3.34 (d, J=21.0 Hz, 2H), 1.48 (s, 18H) 1.26 (t, J=7.1 Hz, 6H) ppm; $^{13}$C NMR (151 MHz, CDCl$_3$) δ=167.8, 151.9, 146.2 (d, J=7.7 Hz), 116.3 (d, J=7.2 Hz), 83.4, 62.3 (d, J=6.6 Hz), 47.8, 29.0 (d, J=140.9 Hz), 28.1, 16.5 (d, J=6.1 Hz) ppm; HRMS (ESI) calcd for $C_{19}H_{33}N_2O_7PS$ [M+Na]$^+$ 487.1638, found 487.1620.

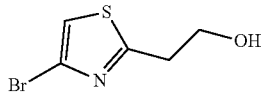

45

Hydroxyethyl Thiazole 45:

To a stirred solution of 2,4-dibromothiazole 32 (10.2 g, 42.0 mmol, 1.0 equiv.) in diethyl ether (250 mL) at −78° C. was carefully added n-butyllithium (2.5 M hexanes, 16.8 mL, 42.0 mmol, 1.0 equiv.). The reaction mixture was stirred for 20 min and then a solution of oxirane (2.5 M tetrahydrofuran, 16.8 mL, 42.0 mmol, 1.0 equiv.) was added, followed by dropwise addition of a solution of boron trifluoride diethyl etherate (5.18 mL, 42.0 mmol, 1.0 equiv.) in diethyl ether (30 mL). After 20 min, the reaction mixture was quenched with a saturated aqueous solution of ammonium chloride (50 mL) and allowed to warm to 25° C. The two phases were separated, and the aqueous layer was extracted with ethyl acetate (3×80 mL). The combined organic layers were dried with anhydrous sodium sulfate and concentrated in vacuo. The obtained residue was purified by flash column chromatography (silica gel, 30→60% ethyl acetate in hexanes) to afford pure thiazole 45 (5.42 g, 26.0 mmol, 62%) as a colorless oil. 45: $R_f$=0.24 (silica gel, 50% ethyl acetate in hexanes); FT-IR (neat) $v_{max}$ 3350, 3122, 2881, 1480, 1421, 1330, 1257, 1210, 1135, 1085, 1052, 938, 887, 857, 832, 733 cm$^{-1}$; $^1$H NMR (600 MHz, CDCl$_3$) δ=7.12 (s, 1H), 4.02 (td, J=6.0, 6.0 Hz, 2H), 3.22 (t, J=6.0 Hz, 2H), 2.67 (t, J=6.0 Hz, 1H) ppm; $^{13}$C NMR (151 MHz, CDCl$_3$) δ=169.7, 124.6, 116.5, 61.3, 36.2 ppm; HRMS (ESI) calcd for $C_5H_7NOSBr$ [M+H]$^+$ 207.9426, found 207.9421.

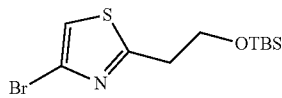

46

Silyl Ether 46:

To a stirred solution of hydroxyethyl thiazole 45 (5.38 g, 25.9 mmol, 1.0 equiv.) in dimethylformamide (25 mL) at 25° C. was added tert-butyldimethylsilyl chloride (4.68 g, 31.0 mmol, 1.2 equiv.) followed by imidazole (2.64 g, 38.9 mmol, 1.5 equiv.). After 1 h, the reaction mixture was diluted with ethyl acetate (100 mL), then washed with water (20 mL) and brine (20 mL). The two phases were separated, and the organic layer was dried with anhydrous sodium sulfate and concentrated in vacuo. The obtained residue was purified by flash column chromatography (silica gel, 2→8% ethyl acetate in hexanes) to afford pure silyl ether 46 (8.25 g, 25.6 mmol, 99%) as a colorless oil. 46: $R_f$=0.24 (silica gel, 5% ethyl acetate in hexanes); FT-IR (neat) $v_{max}$ 3125, 2954, 2928, 2856, 1481, 1471, 1437, 1388, 1361, 1331, 1254, 1147, 1099, 1050, 1006, 939, 914, 884, 831, 810, 776, 728 cm$^{-1}$; $^1$H NMR (600 MHz, CDCl$_3$) δ=7.09 (s, 1H), 3.93 (t, J=6.0 Hz, 2H), 3.19 (t, J=6.0 Hz, 2H), 0.87 (s, 9H), 0.02 (s, 6H) ppm; $^{13}$C NMR (151 MHz, CDCl$_3$) δ=169.6, 124.1, 116.7, 61.9, 37.2, 26.0, 18.4, −5.3 ppm; HRMS (ESI) calcd for $C_{11}H_{21}NOSiSBr$ [M+H]$^+$ 322.0291, found 322.0281.

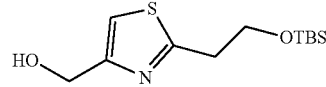

47

Hydroxymethyl Thiazole 47:

To a stirred solution of silyl ether 46 (2.45 g, 7.60 mmol, 1.0 equiv.) in diethyl ether (75 mL) at −78° C. was carefully added t-butyllithium (1.7 M pentanes, 5.40 mL, 9.12 mmol, 1.2 equiv.). After 1 min, dimethylformamide (1.17 mL, 15.2 mmol, 2.0 equiv.) was added dropwise. After 5 min, the reaction mixture was quenched with methanol (30 mL). Then sodium borohydride (1.44 g, 38.0 mmol, 5.0 equiv.) was added and the reaction mixture was allowed to warm to 0° C. After 5 min, the reaction mixture was quenched with water (60 mL) and allowed to warm to 25° C. The two phases were separated, and the aqueous layer was extracted with ethyl acetate (3×40 mL). The combined organic layers were dried with anhydrous sodium sulfate and concentrated in vacuo. The obtained residue was purified by flash column chromatography (silica gel, 30→60% ethyl acetate in hexanes) to afford pure thiazole 47 (1.70 g, 6.23 mmol, 82%) as a colorless oil. 47: $R_f$=0.32 (silica gel, 60% ethyl acetate in hexanes); FT-IR (neat) $v_{max}$ 3301, 2954, 2928, 2857, 1530, 1471, 1387, 1361, 1254, 1156, 1096, 969, 937, 913, 834, 810, 774, 660 cm$^{-1}$; $^1$H NMR (600 MHz, CDCl$_3$) δ=7.05 (s, 1H), 4.73 (d, J=6.0 Hz, 2H), 3.94 (t, J=6.0 Hz, 2H), 3.18 (t, J=6.6 Hz, 2H), 3.09 (t, J=6.0 Hz, 1H), 0.87 (s, 9H), 0.02 (s, 6H) ppm; $^{13}$C NMR (151 MHz, CDCl$_3$) δ=169.0, 155.6, 114.7, 62.2, 60.9, 37.0, 26.0, 18.4, −5.3 ppm; HRMS (ESI) calcd for $C_{12}H_{24}NO_2SiS$ [M+H]$^+$ 296.1111, found 296.1102.

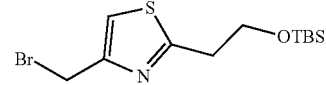

48

Bromomethyl Thiazole 48:

To a stirred solution of hydroxymethyl thiazole 47 (2.45 g, 8.96 mmol, 1.0 equiv.) in dichloromethane (30 mL) at −78° C. was added triphenylphosphine (2.47 g, 9.41 mmol, 1.05 equiv.), followed by N-bromosuccinimide (1.59 g, 8.96 mmol, 1.0 equiv.). After 5 min, the reaction mixture was quenched with water (50 mL) and allowed to warm to 25° C. The two phases were separated, and the aqueous layer was extracted with ethyl acetate (3×20 mL). The combined organic layers were dried with anhydrous sodium sulfate and concentrated in vacuo. The obtained residue was purified by flash column chromatography (silica gel, 2→8% ethyl acetate in hexanes) to afford pure bromomethyl thiazole 48 (2.93 g, 8.71 mmol, 97%) as a colorless oil. 48: $R_f$=0.19 (silica gel, 5% ethyl acetate in hexanes); FT-IR (neat) $v_{max}$ 2954, 2928, 2883, 2856, 1517, 1471, 1424, 1387, 1361, 1333, 1254, 1214, 1161, 1095, 1053, 1006, 977, 937, 915, 834, 810, 775, 731, 679, 659 cm$^{-1}$; $^1$H NMR (600 MHz, CDCl$_3$) δ=7.16 (s, 1H), 4.55 (s, 2H), 3.95 (t, J=6.0 Hz, 2H), 3.19 (t, J=6.0 Hz, 2H), 0.87 (s, 9H), 0.02 (s, 6H) ppm; $^{13}$C NMR (151 MHz, CDCl$_3$) δ=169.2, 151.4, 117.8, 77.4, 62.1, 37.1, 27.4, 26.0, 18.4, −5.3 ppm; HRMS (ESI) calcd for $C_{12}H_{23}NOSiSBr$ [M+H]$^+$ 336.0448, found 336.0441.

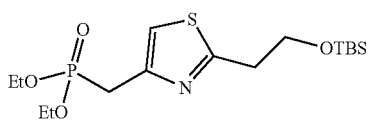

49

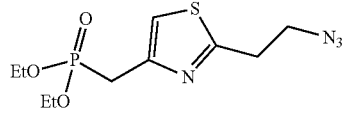

51

Phosphonate 49:

Triethyl phosphite (5.0 mL, 29.2 mmol, 3.5 equiv.) was added to a flask containing bromomethyl thiazole 48 (2.83 g, 8.41 mmol, 1.0 equiv.) at 25° C. The stirred reaction mixture was heated to 160° C. for 2 h, and then the excess triethyl phosphite was removed under a steady flow of $N_2(g)$. The residue was allowed to cool to 25° C. and purified by flash column chromatography (silica gel, 50→100% ethyl acetate in hexanes) to afford pure phosphonate 49 (3.29 g, 8.36 mmol, 99%) as a colorless oil. 49: $R_f$=0.35 (silica gel, ethyl acetate); FT-IR (neat) $v_{max}$ 3468, 2955, 2929, 2857, 1652, 1519, 1472, 1444, 1391, 1361, 1323, 1252, 1162, 1097, 1054, 1026, 964, 917, 836, 811, 777, 723, 662 cm$^{-1}$; $^1$H NMR (600 MHz, CDCl$_3$) δ=7.09 (d, J=3.6 Hz, 1H), 4.08 (dq, J=8.4, 7.2 Hz, 4H), 3.93 (t, J=6.0 Hz, 2H), 3.36 (d, J=21.0 Hz, 2H), 3.17 (t, J=6.0 Hz, 2H), 1.28 (t, J=7.2 Hz, 6H), 0.88 (s, 9H), 0.02 (s, 6H) ppm; $^{13}$C NMR (151 MHz, CDCl$_3$) δ=167.6, 145.7 (d, J=8.0 Hz), 116.2 (d, J=7.1 Hz), 62.4 (d, J=6.5 Hz), 62.3, 37.1, 29.5 (d, J=140.1 Hz), 26.0, 18.4, 16.6 (d, J=6.0 Hz), −5.3 ppm; HRMS (ESI) calcd for $C_{16}H_{32}NO_4SiPSNa$ [M+Na]$^+$ 416.1451, found 416.1441.

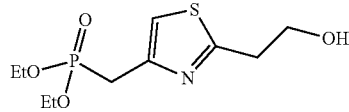

50

Phosphonate 50:

To a stirred solution of phosphonate 49 (2.75 g, 6.99 mmol, 1.0 equiv.) in tetrahydrofuran (20 mL) at 0° C. was added hydrogen fluoride-pyridine complex (70% HF, 0.90 mL, 34.9 mmol). After 1 h, the reaction mixture was quenched with a saturated aqueous solution of sodium bicarbonate (50 mL) and allowed to warm to 25° C. The two phases were separated, and the aqueous layer was extracted with ethyl acetate (3×20 mL). The combined organic layers were dried with anhydrous sodium sulfate and concentrated in vacuo. The obtained residue was purified by flash column chromatography (silica gel, 0→10% methanol in dichloromethane) to afford pure alcohol 50 (1.94 g, 6.95 mmol, 99%) as a colorless oil. 50: $R_f$=0.20 (silica gel, 5% methanol in dichloromethane); FT-IR (neat) $v_{max}$ 3389, 2982, 2909, 1653, 1519, 1477, 1443, 1393, 1368, 1324, 1226, 1162, 1126, 1098, 1048, 1017, 963, 874, 842, 808, 784, 722, 668 cm$^{-1}$; $^1$H NMR (600 MHz, CDCl$_3$) δ=7.07 (d, J=3.6 Hz, 1H), 4.07 (dq, J=7.8, 6.6 Hz, 4H), 3.96 (td, J=6.0, 6.0 Hz, 2H), 3.66 (t, J=6.0 Hz, 1H), 3.33 (d, J=21.0 Hz, 2H), 3.16 (t, J=6.0 Hz, 2H), 1.27 (t, J=7.2 Hz, 6H) ppm; $^{13}$C NMR (151 MHz, CDCl$_3$) δ=168.3, 146.1 (d, J=8.6 Hz), 115.8 (d, J=8.0 Hz), 62.4 (d, J=6.6 Hz), 61.3, 35.7, 29.5 (d, J=140.4 Hz), 16.5 (d, J=6.0 Hz) ppm; HRMS (ESI) calcd for $C_{10}H_{18}NO_4PSNa$ [M+Na]$^+$ 302.0586, found 302.0577.

Azide 51:

To a stirred solution of phosphonate 50 (1.37 g, 4.91 mmol, 1.0 equiv.) in dichloromethane (10 mL) at 25° C. was added triethylamine (2.05 mL, 14.7 mmol, 3.0 equiv.) and 4-(dimethylamino)pyridine (60 mg, 0.49 mmol, 0.1 equiv.). After cooling to −20° C., p-tolunesulfonic anhydride (3.20 g, 9.81 mmol, 2.0 equiv.) was added in one portion. After 30 min, the reaction mixture was quenched with water (10 mL) and warmed to 25° C. The two phases were separated, and the aqueous layer was extracted with dichloromethane (3×10 mL). The combined organic layers were dried with anhydrous sodium sulfate and concentrated in vacuo. The crude residue was then resuspended in dimethylformamide (5 mL) at 25° C., and sodium azide (957 mg, 14.7 mmol, 3.0 equiv.) was added with stirring. The reaction mixture was heated to 65° C. for 2 h, and then allowed to cool to 25° C. The reaction mixture was then quenched with water (20 mL) and extracted with ethyl acetate (3×15 mL). The combined organic layers were dried with anhydrous sodium sulfate and concentrated in vacuo. Purification by flash column chromatography (silica gel, 0→4% methanol in dichloromethane) afforded pure azide 51 (1.16 g, 3.81 mmol, 78%) as a colorless oil. 51: $R_f$=0.38 (silica gel, 5% methanol in dichloromethane); FT-IR (neat) $v_{max}$ 3464, 3111, 2983, 2931, 2098, 1647, 1519, 1477, 1445, 1394, 1323, 1250, 1163, 1124, 1098, 1053, 1025, 965, 873, 846, 828, 783, 725, 663 cm$^{-1}$; $^1$H NMR (600 MHz, CDCl$_3$) δ=7.14 (d, J=3.6 Hz, 1H), 4.09 (dq, J=7.8, 7.2 Hz, 4H), 3.71 (t, J=6.6 Hz, 2H), 3.37 (d, J=21.0 Hz, 2H), 3.23 (t, J=6.6 Hz, 2H), 1.29 (t, J=7.2 Hz, 6H) ppm; $^{13}$C NMR (151 MHz, CDCl$_3$) δ=165.9, 146.7 (d, J=8.1 Hz), 116.5 (d, J=7.2 Hz), 62.4 (d, J=6.0 Hz), 50.7, 33.1, 29.6 (d, J=140.3 Hz), 16.6 (d, J=6.0 Hz) ppm; HRMS (ESI) calcd for $C_{10}H_{17}N_4O_3PSNa$ [M+Na]$^+$ 327.0651, found 327.0661.

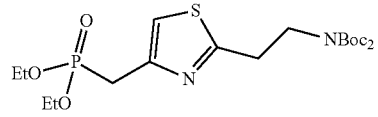

52

Phosphonate 52:

To a stirred solution of azide 51 (1.06 g, 3.48 mmol, 1.0 equiv.) in tetrahydrofuran/water (9:1, 15 mL) at 25° C. was added triphenylphosphine (2.74 g, 10.5 mmol, 3.0 equiv.). The reaction mixture was heated to 65° C. for 1.5 h, and then allowed to cool to 25° C. Then water (6 mL), sodium bicarbonate (0.882 g, 10.5 mmol, 3.0 equiv.), and di-tert-butyl dicarbonate (1.52 g, 6.96 mmol, 2.0 equiv.) were added sequentially, and stirring was continued for 2.5 h. The two phases were separated, and the aqueous layer was extracted with ethyl acetate (3×15 mL). The combined organic layers were dried with anhydrous sodium sulfate and concentrated in vacuo. The obtained residue was purified by flash column chromatography (silica gel, 0→7.5% methanol in dichloromethane) to afford phosphonate 52 (1.65 g, 3.44 mmol, 99%) as a colorless oil. 52: $R_f$=0.37 (silica gel, 5% methanol in dichloromethane); FT-IR (neat) $v_{max}$ 3471, 2980, 2933, 1791, 1748, 1697, 1519, 1478, 1444, 1393, 1367, 1353, 1254, 1220, 1166, 1126, 1054, 1026, 962, 892, 854, 806, 779, 722 cm$^{-1}$; $^1$H NMR (600 MHz, CDCl$_3$) δ=7.10 (d, J=3.6 Hz, 1H), 4.08 (dq, J=7.8, 7.2 Hz, 4H), 3.96-3.94 (m, 2H), 3.35 (d, J=21.0 Hz, 2H), 3.25-3.23 (m, 2H), 1.49 (s, 18H), 1.28 (t, J=7.2 Hz, 6H) ppm; $^{13}$C NMR (151 MHz, CDCl$_3$) δ=166.7, 152.3, 146.5 (d, J=7.8 Hz), 116.1 (d, J=7.2 Hz), 82.8, 62.4 (d, J=6.0 Hz), 46.1, 32.9, 29.5 (d, J=140.0 Hz), 28.2, 16.6 (d, J=6.0 Hz) ppm; HRMS (ESI) calcd for C$_{20}$H$_{35}$N$_2$O$_7$PSNa [M+Na]$^+$ 501.1795, found 501.1803.

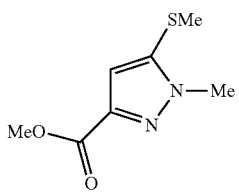

Pyrazole Ester 55:

To a stirred suspension of sydnone 53 (Hammick and Voaden, 1961; Masuda and Okutani, 1974) (3.09 g, 21.1 mmol, 1.0 equiv.) in xylenes (10 mL) at 25° C. was added methyl propiolate (3.55 g, 42.3 mmol, 2.0 equiv.). The reaction mixture was heated to 130° C. for 12 h, then allowed to cool to 25° C. and concentrated in vacuo. The obtained residue was purified by flash column chromatography (silica gel, 5→30% ethyl acetate in hexanes) to afford pure pyrazole ester 55 (2.44 g, 13.1 mmol, 62%) as a colorless oil and its regioisomer 55a (0.943 g, 5.06 mmol, 24%) as a colorless oil. 55: R$_f$=0.26 (silica gel, 40% ethyl acetate in hexanes); FT-IR (neat) ν$_{max}$ 3137, 2996, 2951, 1718, 1503, 1458, 1441, 1397, 1366, 1320, 1290, 1217, 1126, 1076, 1044, 1010, 977, 946, 808, 776, 721 cm$^{-1}$; $^1$H NMR (600 MHz, CDCl$_3$) δ=6.77 (s, 1H), 3.92 (s, 3H), 3.90 (s, 3H), 2.43 (s, 3H) ppm; $^{13}$C NMR (151 MHz, CDCl$_3$) δ=162.6, 142.7, 138.8, 111.2, 52.2, 37.5, 18.6 ppm; HRMS (ESI) calcd for C$_7$H$_{11}$N$_2$O$_2$S [M+H]$^+$ 187.0536, found 187.0531. 55a: R$_f$=0.37 (silica gel, 40% ethyl acetate in hexanes); FT-IR (neat) ν$_{max}$ 2996, 2949, 1713, 1519, 1435, 1405, 1389, 1365, 1314, 1275, 1221, 1169, 1108, 1045, 983, 945, 871, 805, 777, 728 cm$^{-1}$; $^1$H NMR (600 MHz, CDCl$_3$) δ=7.93 (s, 1H), 3.97 (s, 3H), 3.85 (s, 3H), 2.48 (s, 3H) ppm; $^{13}$C NMR (151 MHz, CDCl$_3$) δ=163.0, 141.9, 139.8, 116.4, 51.5, 37.4, 18.8 ppm; HRMS (ESI) calcd for C$_7$H$_{11}$N$_2$O$_2$S [M+H]$^+$ 187.0536, found 187.0529.

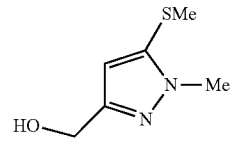

Hydroxymethyl Pyrazole 56:

To a stirred solution of pyrazole ester 55 (2.44 g, 13.1 mmol, 1.0 equiv.) in dichloromethane (36 mL) at −78° C. was added diisobutylaluminum hydride (1.0 M dichloromethane, 40.0 mL, 40.0 mmol, 3.0 equiv.) dropwise. After 10 min, the reaction mixture was quenched with an aqueous solution of HCl (2.0 M, 30 mL), allowed to warm to 25° C., and stirred for an additional 2 h. The two phases were separated, and the aqueous layer was extracted with ethyl acetate (3×20 mL). The combined organic layers were dried with anhydrous sodium sulfate and concentrated in vacuo. The obtained residue was purified by flash column chromatography (silica gel, 50→100% ethyl acetate in hexanes) to afford pure pyrazole 56 (1.70 g, 10.7 mmol, 82%) as a colorless oil. 56: R$_f$=0.22 (silica gel, ethyl acetate); FT-IR (neat) ν$_{max}$ 3327, 2925, 2869, 1508, 1423, 1318, 1379, 1279, 1216, 1147, 1057, 1020, 1001, 976, 771 cm$^{-1}$; $^1$H NMR (600 MHz, CDCl$_3$) δ=6.25 (s, 1H), 4.62 (d, J=6.0 Hz, 2H), 3.83 (s, 3H), 2.40 (s, 3H), 2.27 (t, J=6.0 Hz, 1H) ppm; $^{13}$C NMR (151 MHz, CDCl$_3$) δ=151.7, 137.5, 107.1, 59.2, 36.5, 18.8 ppm; HRMS (ESI) calcd for C$_6$H$_{11}$N$_2$OS [M+H]$^+$ 159.0587, found 159.0581.

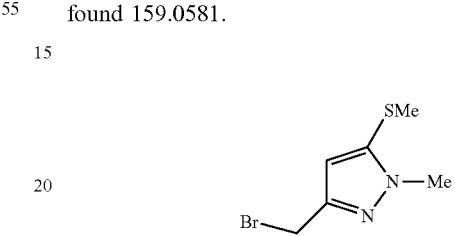

Bromomethyl Pyrazole 57:

To a stirred solution of hydroxymethyl pyrazole 56 (1.70 g, 10.7 mmol, 1.0 equiv.) in dichloromethane (20 mL) at −78° C. was added triphenylphosphine (2.96 g, 11.3 mmol, 1.05 equiv.), followed by N-bromosuccinimide (1.90 g, 10.7 mmol, 1.0 equiv.). After 5 min, the reaction mixture was quenched with water (20 mL) and allowed to warm to 25° C. The two phases were separated, and the aqueous layer was extracted with ethyl acetate (3×15 mL). The combined organic layers were dried with anhydrous sodium sulfate and concentrated in vacuo. The obtained residue was purified by flash column chromatography (silica gel, 5→20% ethyl acetate in hexanes) to afford pure bromomethyl pyrazole 57 (2.03 g, 9.06 mmol, 85%) as a colorless oil. 57: R$_f$=0.30 (silica gel, 20% ethyl acetate in hexanes); FT-IR (neat) ν$_{max}$ 3122, 2924, 1503, 1425, 1317, 1285, 1213, 1159, 1111, 1082, 1043, 1007, 974, 801, 767, 711 cm$^{-1}$; $^1$H NMR (600 MHz, CDCl$_3$) δ=6.30 (s, 1H), 4.43 (s, 2H), 3.84 (s, 3H), 2.41 (s, 3H) ppm; $^{13}$C NMR (151 MHz, CDCl$_3$) δ=148.4, 138.1, 108.4, 36.7, 25.3, 18.7 ppm; HRMS (ESI) calcd for C$_6$H$_{10}$N$_2$SBr [M+H]$^+$ 220.9743, found 220.9749.

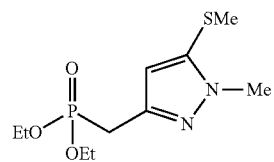

Phosphonate 58:

Triethyl phosphite (4 mL, 23.3 mmol, 2.6 equiv.) was added to a flask containing bromomethyl pyrazole 57 (2.03 g, 9.06 mmol, 1.0 equiv.) at 25° C. The stirred reaction mixture was then heated to 160° C. for 2 h, and then the excess triethyl phosphite was removed under a steady flow of N$_2$(g). The residue was allowed to cool to 25° C. and purified by flash column chromatography (silica gel, 50→90% ethyl acetate in hexanes) to afford pure phosphonate 58 (2.49 g, 8.97 mmol, 99%) as a colorless oil. 58: R$_f$=0.43 (silica gel, acetone); FT-IR (neat) ν$_{max}$ 3471, 2982, 2927, 2905, 1441, 1425, 1392, 1368, 1253, 1163, 1097, 1054, 1025, 963, 848, 815, 757, 727, 696 cm$^{-1}$; $^1$H NMR (600 MHz, CDCl$_3$) δ=6.27 (d, J=1.8 Hz, 1H), 4.08 (dq, J=7.2, 7.2 Hz, 4H), 3.81 (s, 3H), 3.15 (d, J=20.4 Hz, 2H), 2.39 (s, 3H), 1.28 (t, J=7.2 Hz, 6H) ppm; $^{13}$C NMR (151 MHz, CDCl$_3$) δ=142.6 (d, J=7.1 Hz), 137.4 (d, J=2.3 Hz), 108.7 (d, J=3.3 Hz), 62.3 (d, J=6.3 Hz), 36.5, 26.9 (d, J=141.0 Hz), 18.7, 16.6 (d, J=6.0 Hz) ppm; HRMS (ESI) calcd for C$_{10}$H$_{20}$N$_2$O$_3$PS [M+H]$^+$ 279.0927, found 279.0930.

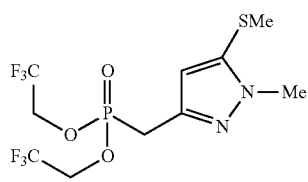

59

Trifluoroethyl Phosphonate 59:

To a flask containing phosphonate 58 (2.49 g, 8.97 mmol, 1.0 equiv.) was added trimethylsilyl chloride (5.75 mL, 45.3 mmol, 5.1 equiv.), and the reaction mixture was stirred at 80° C. for 72 h. The reaction mixture was then allowed to cool to 25° C., and the trimethylsilyl chloride was removed in vacuo. The residue was resuspended in dichloromethane (30 mL), and the solution was cooled to 0° C. with stirring. Then a solution of oxalyl chloride (3.05 g, 24.0 mmol, 2.5 equiv.) in dichloromethane (5 mL) was added dropwise. The reaction mixture was allowed to warm to 25° C. and stirred for 4 h. Then the solvent was removed in vacuo, and the residue was resuspended in dichloromethane (30 mL). The solution was cooled to 0° C. with stirring, and triethyl amine (7.58 mL, 54.4 mmol, 6.0 equiv.), trifluoroethanol (2.72 mL, 36.2 mmol, 4.0 equiv.) and 4-(dimethylamino)pyridine (22.1 mg, 0.181 mmol, 0.02 equiv.) were added sequentially. The reaction mixture was allowed to slowly warm to 25° C. and stirred for 12 h. Then the reaction mixture was diluted with ethyl acetate (100 mL), and washed with water (20 mL) and brine (20 mL). The two phases were separated, and the organic layer was dried with anhydrous sodium sulfate and concentrated in vacuo. The obtained residue was purified by flash column chromatography (silica gel, 20→60% ethyl acetate in hexanes) to afford pure trifluoroethyl phosphonate 59 (3.00 g, 7.77 mmol, 87%) as a colorless oil. 59: R$_f$=0.17 (silica gel, 50% ethyl acetate in hexanes); FT-IR (neat) ν$_{max}$ 2971, 1504, 1422, 1291, 1260, 1168, 1103, 1070, 1007, 963, 879, 845, 780, 704 cm$^{-1}$; $^1$H NMR (600 MHz, CDCl$_3$) δ=6.21 (d, J=1.8 Hz, 1H), 4.42-4.31 (m, 4H), 3.81 (d, J=1.2 Hz, 3H), 3.33 (d, J=21.0 Hz, 2H), 2.39 (s, 3H) ppm; $^{13}$C NMR (151 MHz, CDCl$_3$) δ=140.3 (d, J=8.1 Hz), 138.2 (d, J=2.1 Hz), 122.7 (qd, J=275.9, 8.0 Hz), 108.6 (d, J=5.3 Hz), 62.5 (qd, J=37.7, 6.0 Hz), 36.6, 26.8 (d, J=143.3 Hz), 18.6 ppm; HRMS (ESI) calcd for C$_{10}$H$_{14}$N$_2$O$_3$PS [M+H]$^+$ 387.0361, found 387.0346.

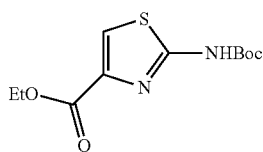

61

Thiazole Carbamate 61:

To a stirred solution of aminothiazole ester 60 (500 mg, 2.90 mmol, 1.0 equiv.) in tetrahydrofuran (9.7 mL) at 25° C. was added triethylamine (0.53 mL, 3.77 mmol, 1.3 equiv.), 4-(dimethylamino)pyridine (35 mg, 0.29 mmol, 0.1 equiv.), and di-tert-butyl-dicarbonate (696 mg, 3.19 mmol, 1.1 equiv.) sequentially. The reaction mixture was heated to 60° C. for 1 h, then allowed to cool to 25° C. and quenched with a saturated aqueous solution of ammonium chloride (5 mL). The two phases were separated, and the aqueous layer was extracted with ethyl acetate (3×5 mL). The combined organic layers were dried with anhydrous sodium sulfate and concentrated in vacuo. Purification by flash column chromatography (25% ethyl acetate in hexanes) afforded pure thiazole carbamate 61 (569 mg, 2.10 mmol, 72%) as a white solid. 61: R$_f$=0.24 (silica gel, 25% ethyl acetate in hexanes); FT-IR (neat) ν$_{max}$ 3168, 3068, 2980, 2935, 1713, 1553, 1478, 1455, 1393, 1368, 1331, 1294, 1235, 1207, 1154, 1098, 1071, 1021, 957, 915, 875, 802, 734, 682 cm$^{-1}$; $^1$H NMR (600 MHz, CDCl$_3$) δ=8.67 (br s, 1H), 7.77 (s, 1H), 4.35 (q, J=7.2 Hz, 2H), 1.52 (s, 9H), 1.36 (t, J=7.2 Hz, 3H) ppm; $^{13}$C NMR (151 MHz, CDCl$_3$) δ=161.5, 159.8, 152.3, 142.1, 121.7, 83.3, 61.4, 28.3, 14.5 ppm; HRMS (ESI) calcd for C$_{11}$H$_{16}$N$_2$O$_4$S [M+Na]$^+$ 295.0723, found 295.0712.

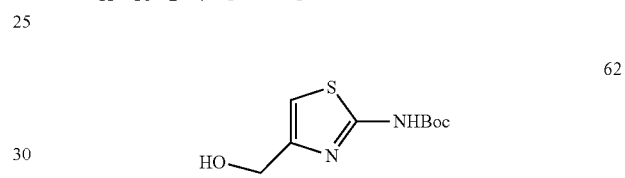

62

Hydroxymethyl Thiazole 62:

To a stirred solution of thiazole carbamate 61 (1.14 g, 4.19 mmol, 1.0 equiv.) in diethyl ether (14 mL) at 25° C. was added lithium borohydride (2.0 M tetrahydrofuran, 10.5 mL, 21.0 mmol, 5.0 equiv.). After 1 h, the reaction mixture was slowly quenched with a saturated aqueous solution of ammonium chloride (10 mL). The two phases were separated, and the aqueous layer was extracted with ethyl acetate (3×8 mL). The combined organic layers were dried with anhydrous sodium sulfate and concentrated in vacuo. Purification by flash column chromatography (70% ethyl acetate in hexanes) afforded pure alcohol 62 (907 mg, 3.94 mmol, 94%) as a colorless oil. 62: R$_f$=0.57 (silica gel, 70% ethyl acetate in hexanes); FT-IR (neat) ν$_{max}$ 3320, 3185, 3064, 2979, 2934, 1718, 1557, 1478, 1455, 1394, 1369, 1330, 1294, 1245, 1157, 1076, 1033, 965, 915, 868, 792, 732, 685 cm$^{-1}$; $^1$H NMR (600 MHz, CDCl$_3$) δ=6.74 (s, 1H), 4.57 (s, 2H), 1.57 (s, 9H) ppm; $^{13}$C NMR (151 MHz, CDCl$_3$) δ=161.6, 152.6, 151.0, 109.2, 83.1, 60.1, 28.3 ppm; HRMS (ESI) calcd for C$_9$H$_{14}$N$_2$O$_3$S [M+Na]$^+$ 253.0617, found 253.0616.

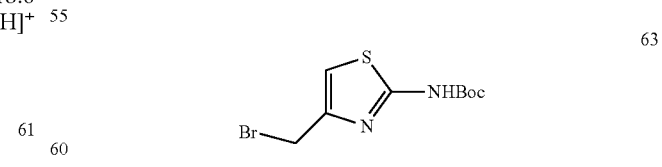

63

Bromomethyl Thiazole 63:

To a stirred solution of hydroxymethyl thiazole 62 (115 mg, 0.50 mmol, 1.0 equiv.) in dichloromethane (5 mL) at −78° C. was added triphenylphosphine (135 mg, 0.51 mmol, 1.05 equiv.), followed by N-bromosuccinimide (89 mg, 0.50 mmol, 1.0 equiv.). After 15 min, the reaction mixture was quenched with water (2.5 mL) and allowed to warm to 25° C. The two phases were separated, and the aqueous layer was extracted with ethyl acetate (3×5 mL). The combined organic layers were dried with anhydrous sodium sulfate and concentrated in vacuo. The obtained residue was purified by flash column chromatography (silica gel, 20% ethyl acetate in hexanes) to afford pure bromomethyl thiazole 63 (104 mg, 0.35 mmol, 71%) as a colorless oil. 63: $R_f$=0.31 (silica gel, 20% ethyl acetate in hexanes); FT-IR (neat) $v_{max}$ 3164, 3056, 2978, 2933, 2803, 1713, 1553, 1478, 1454, 1432, 1393, 1368, 1332, 1289, 1243, 1215, 1151, 1068, 1033, 977, 910, 865, 791, 763, 701, 655 cm$^{-1}$; $^1$H NMR (600 MHz, CDCl$_3$) δ=10.08 (br s, 1H), 6.88 (s, 1H), 4.54 (s, 2H), 1.56 (s, 9H) ppm; $^{13}$C NMR (151 MHz, CDCl$_3$) δ=161.4, 152.6, 146.8, 111.6, 83.2, 28.4, 27.8 ppm; HRMS (ESI) calcd for C$_9$H$_{13}$BrN$_2$O$_2$S [M+H]$^+$ 292.9954, found 292.9950.

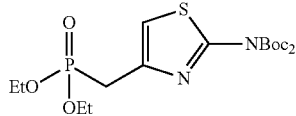

64

Phosphonate 64:

Triethyl phosphite (2.4 mL, 14.2 mmol, 20 equiv.) was added to a flask containing bromomethyl thiazole 63 (208 mg, 0.71 mmol, 1.0 equiv.) at 25° C. The stirred reaction mixture was heated to 160° C. for 3 h, and then the excess triethyl phosphite was removed under a steady flow of N$_2$(g). The residue was allowed to cool to 25° C. and resuspended in tetrahydrofuran (2.4 mL). To the stirred solution was added triethylamine (0.26 mL, 1.85 mmol, 2.6 equiv.), 4-(dimethylamino)pyridine (9 mg, 0.07 mmol, 0.1 equiv.), and di-tert-butyl-dicarbonate (340 mg, 1.56 mmol, 2.2 equiv.) sequentially. The reaction mixture was heated to 60° C. for 3.5 h, allowed to cool to 25° C., and quenched with a saturated aqueous solution of ammonium chloride (10 mL). The two phases were separated, and the aqueous layer was extracted with ethyl acetate (3×5 mL). The combined organic layers were dried with anhydrous sodium sulfate and concentrated in vacuo. Purification by flash column chromatography (65% ethyl acetate in hexanes) afforded pure phosphonate 64 (256 mg, 0.57 mmol, 80%) as a colorless oil. 64: $R_f$=0.28 (silica gel, 65% ethyl acetate in hexanes); FT-IR (neat) $v_{max}$ 3475, 3109, 2981, 2934, 1776, 1725, 1526, 1490, 1458, 1395, 1370, 1345, 1326, 1248, 1156, 1120, 1054, 1027, 966, 948, 846, 802, 777 cm$^{-1}$; $^1$H NMR (600 MHz, CDCl$_3$) δ=7.03 (d, J=3.6 Hz, 1H), 4.10-4.05 (m, 4H), 3.28 (d, J=21.0 Hz, 2H), 1.52 (s, 18H), 1.27 (t, J=7.1 Hz, 6H) ppm; $^{13}$C NMR (151 MHz, CDCl$_3$) δ=158.0, 149.8, 142.8 (d, J=8.3 Hz), 114.5 (d, J=7.7 Hz), 84.7, 62.4 (d, J=6.2 Hz), 29.3 (d, J=140.7 Hz), 27.9, 16.5 (d, J=6.0 Hz) ppm; HRMS (ESI) calcd for C$_{18}$H$_{31}$N$_2$O$_7$PS [M+Na]$^+$ 473.1482, found 473.1471.

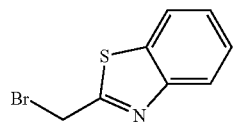

66

Bromomethyl Benzothiazole 66:

To a stirred solution of hydroxymethyl benzothiazole 65 (1.00 g, 6.05 mmol, 1.0 equiv.) in dichloromethane/tetrahydrofuran (1:1, 40 mL) at −78° C. was added triphenylphosphine (1.59 g, 6.05 mmol, 1.0 equiv.), followed by N-bromosuccinimide (1.08 g, 6.05 mmol, 1.0 equiv.). After 5 min, the reaction mixture was quenched with water (20 mL) and allowed to warm to 25° C. The two phases were separated, and the aqueous layer was extracted with ethyl acetate (3×30 mL). The combined organic layers were dried with anhydrous sodium sulfate and concentrated in vacuo. The obtained residue was purified by flash column chromatography (silica gel, 2→8% ethyl acetate in hexanes) to afford pure bromomethyl benzothiazole 66 (0.780 g, 3.42 mmol, 57%) as a white crystalline solid. 66: $R_f$=0.48 (silica gel, 10% ethyl acetate in hexanes); m.p. 45-46° C.; FT-IR (neat) $v_{max}$ 3059, 3028, 1594, 1557, 1505, 1456, 1430, 1313, 1278, 1242, 1190, 1157, 1125, 1090, 1061, 1013, 938, 901, 851, 756, 727, 706 cm$^{-1}$; $^1$H NMR (600 MHz, CDCl$_3$) δ=8.03 (d, J=8.4 Hz, 1H), 7.88 (d, J=7.8 Hz, 1H), 7.51 (ddd, J=7.8, 7.8, 1.2 Hz, 1H), 7.43 (ddd, J=7.8, 7.8, 1.2 Hz, 1H), 4.82 (s, 2H) ppm; $^{13}$C NMR (151 MHz, CDCl$_3$) δ=166.2, 152.8, 136.2, 126.5, 125.9, 123.5, 121.8, 27.1 ppm; HRMS (ESI) calcd for C$_8$H$_7$NS$_2$Br [M+H]$^+$ 227.9477, found 227.9466.

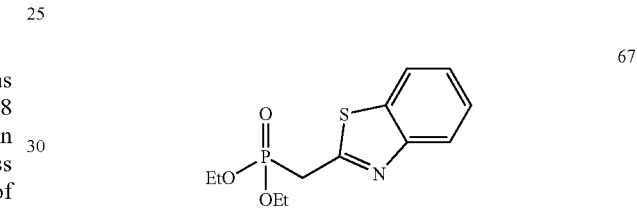

67

Phosphonate 67:

Triethyl phosphite (2.0 mL, 11.7 mmol, 3.4 equiv.) was added to a flask containing bromomethyl benzothiazole 66 (775 mg, 3.40 mmol, 1.0 equiv.) at 25° C. The stirred reaction mixture was heated to 160° C. for 2 h, and then the excess triethyl phosphite was removed under a steady flow of N$_2$(g). The residue was allowed to cool to 25° C. and purified by flash column chromatography (silica gel, 60→90% ethyl acetate in hexanes) to afford pure phosphonate 67 (820 mg, 2.87 mmol, 84%) as a colorless oil. 67: $R_f$=0.32 (silica gel, ethyl acetate); FT-IR (neat) $v_{max}$ 3470, 3060, 2982, 2907, 1639, 1593, 1539, 1511, 1475, 1456, 1436, 1392, 1368, 1313, 1244, 1195, 1162, 1093, 1045, 1015, 963, 891, 842, 761, 731, 708, 677 cm$^{-1}$; $^1$H NMR (600 MHz, CDCl$_3$) δ=7.80 (d, J=7.8 Hz, 1H), 7.86 (d, J=7.8 Hz, 1H), 7.47 (ddd, J=8.4, 7.2, 1.2 Hz, 1H), 7.38 (ddd, J=8.4, 7.2, 1.2 Hz, 1H), 4.19-4.13 (m, 4H), 3.73 (d, J=21.6 Hz, 2H), 1.32 (t, J=7.2 Hz, 6H) ppm; $^{13}$C NMR (151 MHz, CDCl$_3$) δ=161.2 (d, J=9.3 Hz), 153.1 (d, J=2.4 Hz), 136.1, 126.3, 125.3, 123.1, 121.7, 63.0 (d, J=6.6 Hz), 33.3 (d, J=139 Hz), 16.5 (d, J=6.0 Hz) ppm; HRMS (ESI) calcd for C$_{12}$H$_{16}$NO$_3$PSNa [M+Na]$^+$ 308.0481, found 308.0482.

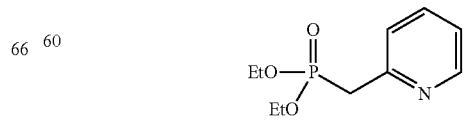

69

Phosphonate 69:

Triethyl phosphite (1.5 mL, 8.75 mmol, 3.7 equiv.) was added to a flask containing bromomethyl pyridine 68 (410 mg, 2.38 mmol, 1.0 equiv.) at 25° C. The stirred reaction mixture was heated to 160° C. for 2.5 h, and then the triethyl phosphite was removed under a steady flow of $N_2$(g). The residue was cooled to 25° C. and purified by flash column chromatography (silica gel, 50→80% ethyl acetate in hexanes) to afford pure phosphonate 69 (355 mg, 2.87 mmol, 65%) as a colorless oil. 69: $R_f$=0.33 (silica gel, ethyl acetate); FT-IR (neat) $v_{max}$ 3467, 2983, 2931, 2908, 1588, 1570, 1474, 1435, 1392, 1368, 1238, 1199, 1162, 1097, 1048, 1018, 957, 839, 809, 748, 704 cm$^{-1}$; $^1$H NMR (600 MHz, CDCl$_3$) δ=8.54 (dd, J=4.8, 1.8 Hz, 1H), 7.64 (ddd, J=7.8, 7.8, 1.8 Hz, 1H), 7.39 (ddd, J=7.8, 2.4, 1.2 Hz, 1H), 7.19-7.16 (m, 1H), 4.08 (dq, J=7.8, 7.2 Hz, 4H), 3.42 (d, J=22.2 Hz, 2H), 1.27 (t, J=7.2 Hz, 6H) ppm; $^{13}$C NMR (151 MHz, CDCl$_3$) δ=152.9 (d, J=8.3 Hz), 149.7 (d, J=2.5 Hz), 136.7 (d, J=2.6 Hz), 124.5 (d, J=5.0 Hz), 122.0 (d, J=3.3 Hz), 62.4 (d, J=6.5 Hz), 36.9 (d, J=134.6 Hz), 16.5 (d, J=6.0 Hz) ppm; HRMS (ESI) calcd for $C_{10}H_{17}NO_3P$ [M+H]$^+$ 230.0941, found 230.0948.

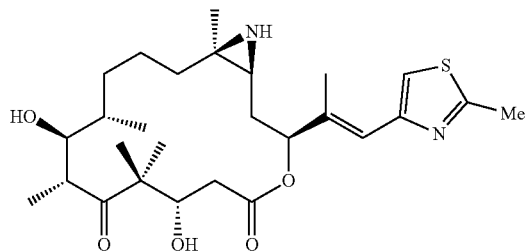

Epothilone 70:

To a stirred solution of epothilone D (84) (50 mg, 0.10 mmol, 1.0 equiv.) in trifluoroethanol (1.1 mL) at 25° C., O-(2,4-dinitrophenyl)hydroxylamine (23 mg, 0.12 mmol, 1.1 equiv.) and Rh$_2$(esp)$_2$ (4 mg, 5 mol %) were added sequentially. After 4 h, the reaction mixture was diluted with ethyl acetate (5 mL) and washed with a saturated aqueous solution of sodium bicarbonate (10 mL). The two phases were separated, and the aqueous layer was extracted with ethyl acetate (3×3 mL). The combined organic layers were dried with anhydrous sodium sulfate and concentrated in vacuo. Flash column chromatography (silica gel, 4→11% methanol in dichloromethane) afforded pure epothilone 70 as a white solid (36 mg, 0.071 mmol, 70% yield). 70: $R_f$=0.24 (silica gel, 7% methanol in dichloromethane); $[α]_D^{25}$=−35.5 (c=0.6 in CHCl$_3$); FT-IR (neat) $v_{max}$ 3294, 2958, 2930, 2876, 1730, 1687, 1598, 1557, 1503, 1452, 1383, 1292, 1256, 1179, 1148, 1042, 1009, 980, 915, 882, 834, 731, 669, 648 cm$^{-1}$; $^1$H NMR (600 MHz, CDCl$_3$) δ=6.98 (s, 1H), 6.63 (s, 1H), 5.54 (dd, J=3.9, 3.9 Hz, 1H), 4.15 (ddd, J=10.5, 3.5, 3.5 Hz, 1H), 3.80 (dd, J=5.3, 4.2 Hz, 1H), 3.35 (dq, J=6.5, 6.5 Hz, 1H), 2.71 (s, 3H), 2.52 (dd, J=12.8, 10.6 Hz, 1H), 2.42 (dd, J=12.9, 3.5 Hz, 1H), 2.07 (s, 3H), 2.06 (s, 1H), 1.96-1.76 (m, 4H), 1.52-1.42 (m, 5H), 1.39 (s, 3H), 1.29-1.25 (m, 3H), 1.24 (s, 3H), 1.13 (d, J=6.9 Hz, 3H), 1.04 (s, 3H), 0.97 (d, J=6.9 Hz, 3H) ppm; $^{13}$C NMR (151 MHz, CDCl$_3$) δ=220.8, 171.1, 165.1, 152.3, 136.7, 119.2, 116.0, 76.4, 75.8, 74.9, 52.6, 44.5, 39.1, 38.5, 35.4, 31.4, 30.4, 29.9, 29.4, 25.5, 22.3, 22.2, 19.5, 19.3, 17.6, 16.3, 14.7 ppm; HRMS (ESI) calcd for $C_{27}H_{42}N_2O_5S$ [M+H]$^+$ 507.2887, found 507.2903.

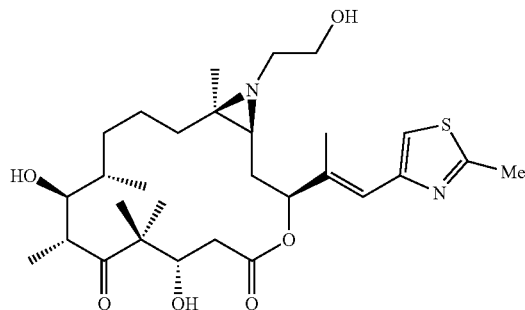

Epothilone 71:

To a stirred suspension of epothilone 70 (15 mg, 0.030 mmol, 1.0 equiv.) in dimethylformamide (0.8 mL) at 25° C. was added K$_2$CO$_3$ (21 mg, 0.156 mmol, 6.0 equiv.) and 2-bromoethanol (10 μL, 0.156 mmol, 6.0 equiv.). The reaction mixture was heated to 70° C. for 15 h, and then allowed to cool to 25° C. The reaction mixture was diluted with ethyl acetate (2.5 mL) and washed with water (2.5 mL). The two phases were separated, and the aqueous layer was extracted with ethyl acetate (3×1 mL). The combined organic layers were backwashed with brine (2 mL), dried with anhydrous magnesium sulfate, and concentrated in vacuo. Flash column chromatography (silica gel, 12% methanol in dichloromethane) afforded pure epothilone 71 as a white solid (15 mg, 0.028 mmol, 93% yield). 71: $R_f$=0.19 (silica gel, 7% methanol in dichloromethane); $[α]_D^{25}$=−42.3 (c=1.0, CHCl$_3$); FT-IR (neat) $v_{max}$ 3369, 2929, 1730, 1685, 1465, 1374, 1263, 1152, 1053, 1009, 980, 882 cm$^{-1}$; $^1$H NMR (600 MHz, CDCl$_3$) δ=6.97 (s, 1H), 6.60 (s, 1H), 5.54 (dd, J=3.9, 3.9 Hz, 1H), 4.00 (dd, J=10.5, 3.5 Hz, 1H), 3.81 (dd, J=5.3, 4.2 Hz, 1H), 3.78-3.70 (m, 2H), 3.28 (dq, J=6.5, 6.5 Hz, 1H), 2.81-2.79 (m, 1H), 2.71 (s, 3H), 2.52 (dd, J=12.8, 10.6 Hz, 1H), 2.43 (dd, J=12.9, 3.5 Hz, 1H), 2.21-2.18 (m, 1H), 2.11 (s, 3H), 2.09-2.00 (m, 2H), 1.75-1.67 (m, 2H), 1.57-1.50 (m, 5H), 1.36 (s, 3H), 1.34-1.25 (m, 3H), 1.24 (s, 3H), 1.15 (d, J=6.9 Hz, 3H), 1.06 (s, 3H), 0.97 (d, J=6.9 Hz, 3H) ppm; $^{13}$C NMR (151 MHz, CDCl$_3$) δ=220.2, 171.4, 165.1, 152.4, 136.0, 119.1, 116.4, 76.6, 75.9, 63.5, 61.8, 52.2, 45.6, 45.1, 39.4, 38.9, 34.3, 30.4, 29.9, 27.7, 25.5, 24.8, 22.4, 19.4, 18.9, 17.8, 16.1, 15.2 ppm; HRMS (ESI) calcd for $C_{29}H_{46}N_2O_6S$ [M+Na]$^+$ 573.2974, found 573.2982.

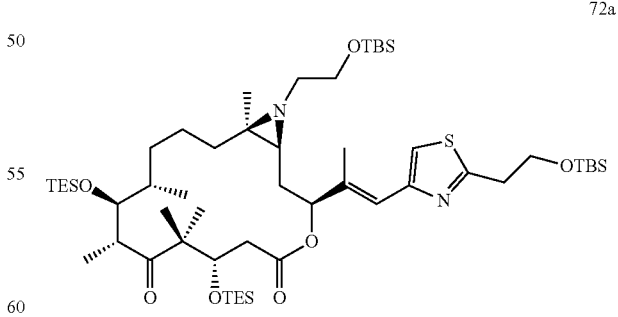

Protected Epothilone 72a:

To a stirred solution of phosphonate 49 (200 mg, 0.508 mmol, 12 equiv.) in tetrahydrofuran (0.8 mL) at −78° C. was carefully added sodium bis(trimethylsilyl)amide (1.0 M tetrahydrofuran, 0.41 mL, 0.41 mmol, 9.7 equiv.). After stirring for 25 min at the same temperature, a solution of tertiary aziridine 30 (33.6 mg, 0.042 mmol, 1.0 equiv.) in tetrahydrofuran (0.5 mL) was added. The reaction mixture was allowed to slowly warm to 0° C., stirred for an additional 2 h, and then quenched with a saturated aqueous solution of ammonium chloride (10 mL). The two phases were separated, and the aqueous layer was extracted with ethyl acetate (3×5 mL). The combined organic layers were dried with anhydrous sodium sulfate and concentrated in vacuo. The obtained residue was purified by flash column chromatography (silica gel, 5→15% ethyl acetate in hexanes) to afford pure protected epothilone 72a (21.8 mg, 0.021 mmol, 50%) as a colorless oil. 72a: $R_f$=0.36 (silica gel, 15% ethyl acetate in hexanes); $[\alpha]_D^{25}$=−2.9 (c=0.63, $CH_2Cl_2$); FT-IR (neat) $v_{max}$ 2954, 2931, 2877, 2858, 1743, 1697, 1502, 1462, 1414, 1381, 1361, 1304, 1252, 1198, 1158, 1103, 1007, 984, 940, 916, 836, 812, 778, 735, 678, 662 cm$^{-1}$; $^1$H NMR (600 MHz, $CDCl_3$) δ=6.78 (s, 1H), 6.60 (s, 1H), 5.48 (dd, J=8.4, 3.0 Hz, 1H), 4.23 (dd, J=8.4, 2.4 Hz, 1H), 4.18 (d, J=9.0 Hz, 1H), 3.86-3.78 (m, 2H), 3.77 (t, J=6.0 Hz, 2H), 3.06-2.99 (m, 1H), 3.02 (t, J=6.0 Hz, 2H), 2.77-2.70 (m, 2H), 2.60 (dd, J=16.2, 3.0 Hz, 1H), 2.45 (ddd, J=12.0, 6.0, 6.0 Hz, 1H), 2.36 (s, 3H), 2.30 (ddd, J=15.0 Hz, 1H), 2.06 (ddd, J=15.6, 9.0, 9.0 Hz, 1H), 1.90-1.81 (m, 2H), 1.76-1.71 (m, 1H), 1.66-1.58 (m, 1H), 1.52-1.48 (m, 2H), 1.28 (dd, J=9.6, 3.0 Hz, 1H), 1.24-1.20 (m, 1H), 1.20 (d, J=6.6 Hz, 3H), 1.18 (s, 3H), 1.16 (s, 3H), 1.13 (d, J=7.2 Hz, 3H), 1.09 (t, J=7.8 Hz, 9H), 1.06 (t, J=7.8 Hz, 9H), 1.00 (s, 9H), 0.94 (s, 9H), 0.86 (s, 3H), 0.85-0.77 (m, 6H), 0.74-0.70 (m, 6H), 0.096 (s, 3H), 0.094 (s, 3H), 0.02 (s, 6H) ppm; $^{13}$C NMR (151 MHz, $CDCl_3$) δ=214.5, 170.7, 166.6, 153.3, 138.3, 121.1, 117.1, 80.1, 79.7, 75.9, 64.3, 62.3, 54.9, 53.4, 50.2, 48.1, 43.3, 40.2, 37.4, 37.2, 36.4, 35.4, 32.4, 26.2, 26.0, 25.5, 23.6, 23.2, 20.2, 18.5, 18.4, 17.6, 15.6, 14.8, 7.43, 7.37, 6.0, 5.8, −5.1, −5.4 ppm; HRMS (ESI) calcd for $C_{54}H_{105}N_2O_7Si_4S$ [M+H]$^+$ 1037.6714, found 1037.6720.

Epothilone 72:

To a stirred solution of protected epothilone 72a (6.9 mg, 0.007 mmol, 1.0 equiv.) in tetrahydrofuran (1.5 mL) at 0° C. was added hydrogen fluoride-pyridine complex (70% HF, 0.03 mL, 1.16 mmol, 165 equiv.). The reaction mixture was allowed to warm to 25° C. and stirred for an additional 4 h. Then the reaction mixture was quenched with a saturated aqueous solution of sodium bicarbonate (10 mL), and the two phases were separated. The aqueous layer was extracted with ethyl acetate (3×10 mL), and the combined organic layers were dried with anhydrous sodium sulfate and concentrated in vacuo. The obtained residue was purified by flash column chromatography (silica gel, 0→30% methanol in ethyl acetate) to afford pure epothilone 72 (3.5 mg, 0.006 mmol, 90%) as a colorless oil. 72: $R_f$=0.35 (silica gel, 30% methanol in ethyl acetate); $[\alpha]_D^{25}$=−20.0 (c=0.35, 10:1 $CH_2Cl_2$/methanol); FT-IR (neat) $v_{max}$ 3362, 2931, 2877, 1726, 1687, 1561, 1505, 1466, 1425, 1383, 1334, 1266, 1148, 1054, 1008, 981, 938, 883, 735, 675 cm$^{-1}$; $^1$H NMR (600 MHz, $CDCl_3$) δ=7.08 (s, 1H), 6.56 (s, 1H), 5.41 (dd, J=6.0, 3.6 Hz, 1H), 4.09 (dd, J=10.2, 2.4 Hz, 1H), 3.97 (t, J=6.0 Hz, 2H), 3.71 (dd, J=4.8, 4.8 Hz, 1H), 3.69-3.62 (m, 2H), 3.29-3.25 (m, 1H), 3.20-3.18 (t, J=6.0 Hz, 2H), 2.66 (ddd, J=12.0, 4.8, 4.8 Hz, 1H), 2.59 (ddd, J=12.0, 4.8, 4.8 Hz, 1H), 2.49 (dd, J=13.8, 10.2 Hz, 1H), 2.37 (dd, J=13.8, 2.4 Hz, 1H), 2.08 (s, 3H), 2.00-1.94 (m, 1H), 1.91 (ddd, J=7.2, 7.2, 7.2 Hz, 1H), 1.68-1.64 (m, 1H), 1.67-1.35 (m, 6H), 1.35 (s, 3H), 1.30-1.22 (m, 1H), 1.26 (s, 3H), 1.17 (s, 3H), 1.13 (d, J=6.6 Hz, 3H), 1.03 (s, 3H), 0.96 (d, J=6.6 Hz, 3H) ppm; $^{13}$C NMR (151 MHz, $CDCl_3$) δ=220.6, 171.4, 168.1, 152.7, 137.2, 119.2, 116.6, 77.9, 75.9, 75.0, 62.4, 61.5, 55.3, 52.7, 48.1, 44.8, 43.4, 39.5, 36.0, 35.5, 34.7, 31.8, 29.5, 21.8, 21.4, 19.9, 17.6, 16.5, 15.9, 14.5 ppm; HRMS (ESI) calcd for $C_{30}H_{48}N_2O_7SNa$ [M+H]$^+$ 603.3074, found 603.3081.

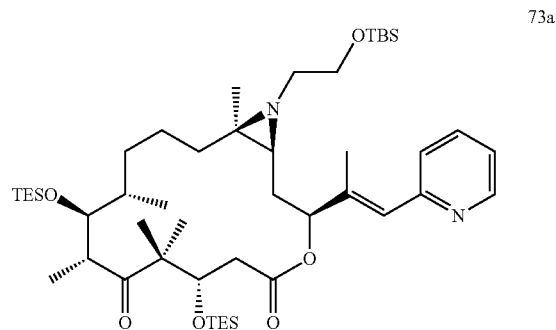

Protected Epothilone 73a:

To a stirred solution of phosphonate 69 (317 mg, 1.38 mmol, 28 equiv.) in tetrahydrofuran (1 mL) at −78° C. was carefully added n-butyllithium (2.5 M hexanes, 0.44 mL, 1.11 mmol, 22 equiv.). After stirring for 30 min at the same temperature, a solution of tertiary aziridine 30 (40.0 mg, 0.050 mmol, 1.0 equiv.) in tetrahydrofuran (0.5 mL) was added. The reaction mixture was allowed to slowly warm to 25° C., stirred for an additional 1.5 h, and then quenched with a saturated aqueous solution of ammonium chloride (10 mL). The two phases were separated, and the aqueous layer was extracted with ethyl acetate (3×5 mL). The combined organic layers were dried with anhydrous sodium sulfate and concentrated in vacuo. The obtained residue was purified by flash column chromatography (silica gel, 10→40% ethyl acetate in hexanes) to afford pure protected epothilone 73a (41 mg, 0.047 mmol, 94%) as a colorless oil. 73a: $R_f$=0.23 (silica gel, 30% ethyl acetate in hexanes); $[\alpha]_D^{25}$=−4.5 (c=1.00, $CH_2Cl_2$); FT-IR (neat) $v_{max}$ 2953, 2935, 2877, 1743, 1696, 1655, 1586, 1561, 1464, 1430, 1381, 1304, 1250, 1198, 1158, 1108, 1069, 1018, 1007, 985, 835, 777, 739, 676 cm$^{-1}$; $^1$H NMR (600 MHz, $C_6D_6$) δ=8.51 (d, J=5.0 Hz, 1H), 7.02 (ddd, J=7.2, 7.2, 1.8 Hz, 1H), 6.89 (d, J=7.8 Hz, 1H), 6.75 (s, 1H), 6.53 (dd, J=7.2, 5.4 Hz, 1H), 5.48 (dd, J=8.4, 3.0 Hz, 1H), 4.22 (dd, J=9.0, 3.0 Hz, 1H), 4.18 (d, J=9.0 Hz, 1H), 3.86-3.78 (m, 2H), 3.04 (dq, J=9.0, 6.6 Hz, 1H), 2.77-2.71 (m, 2H), 2.59 (dd, J=16.2, 3.0 Hz, 1H), 2.48-2.43 (m, 1H), 2.45 (s, 3H), 2.31 (ddd, J=15.0, 3.0, 3.0 Hz, 1H), 2.07 (ddd, J=15.0, 9.0, 9.0 Hz, 1H), 1.90-1.81 (m, 2H), 1.76-1.71 (m, 1H), 1.66-1.59 (m, 1H), 1.52-1.48 (m, 2H), 1.29 (dd, J=9.6, 3.6 Hz, 1H), 1.25-1.21 (m, 1H), 1.20 (d, J=7.2 Hz, 3H), 1.18 (s, 3H), 1.16 (s, 3H), 1.13 (d, J=6.6 Hz, 3H), 1.09 (t, J=7.8 Hz, 9H), 1.06 (t, J=7.8 Hz, 9H), 0.99 (s, 9H), 0.84 (s, 3H), 0.83-0.78 (m, 6H), 0.73-0.69 (m, 6H), 0.09 (s, 3H), 0.08 (s, 3H) ppm; $^{13}$C NMR (151 MHz, $C_6D_6$) δ=214.5, 170.7, 157.0, 149.4, 142.5, 135.6, 126.6, 124.7, 121.0, 80.2, 79.8, 75.9, 64.3, 54.9, 53.4, 50.3, 48.1, 43.3, 40.2, 37.4, 36.4, 35.4, 32.3, 26.2 (3C), 25.4, 23.6, 23.2, 20.2, 18.5, 17.6, 15.6, 14.7, 7.43, 7.37, 6.0, 5.8, −5.1 ppm; HRMS (ESI) calcd for $C_{48}H_{89}N_2O_6Si_3$ [M+H]$^+$ 873.6023, found 873.6044.

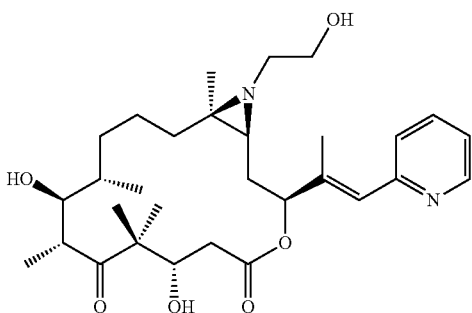

73

Epothilone 73:

To a stirred solution of protected epothilone 73a (39.0 mg, 0.045 mmol, 1.0 equiv.) in tetrahydrofuran (2.0 mL) at 0° C. was added hydrogen fluoride-pyridine complex (70% HF, 0.20 mL, 7.70 mmol, 170 equiv.). The reaction mixture was allowed to warm to 25° C. and stirred for an additional 5 h. Then the reaction mixture was quenched with a saturated aqueous solution of sodium bicarbonate (10 mL), and the two phases were separated. The aqueous layer was extracted with ethyl acetate (3×10 mL), and the combined organic layers were dried with anhydrous sodium sulfate and concentrated in vacuo. The obtained residue was purified by flash column chromatography (silica gel, 5→40% methanol in ethyl acetate) to afford pure epothilone 73 (22 mg, 0.042 mmol, 93%) as a colorless oil. 73: $R_f$=0.40 (silica gel, 30% methanol in ethyl acetate); $[\alpha]_D^{25}$=−34.4 (c=1.00, $CH_2Cl_2$); FT-IR (neat) $v_{max}$ 3340, 2959, 2927, 2875, 1731, 1686, 1589, 1562, 1469, 1434, 1383, 1334, 1261, 1150, 1049, 1010, 982, 885, 800, 771, 745, 704 cm$^{-1}$; $^1$H NMR (600 MHz, $CD_2Cl_2$) δ=8.54 (d, J=4.8 Hz, 1H), 7.70 (ddd, J=7.8, 7.8, 1.8 Hz, 1H), 7.28 (d, J=7.8 Hz, 1H), 7.15 (ddd, J=7.8, 4.8, 1.2 Hz, 1H), 6.60 (s, 1H), 5.40 (dd, J=7.2, 3.0 Hz, 1H), 4.22 (dd, J=11.2, 2.4 Hz, 1H), 3.65 (t, J=4.8 Hz, 1H), 3.62-3.55 (m, 2H), 3.21 (qd, J=6.6, 5.2 Hz, 1H), 2.70-2.66 (m, 1H), 2.62-2.59 (m, 1H), 2.48 (dd, J=13.2, 10.2 Hz, 1H), 2.34 (dd, J=13.8, 2.4 Hz, 1H), 2.08 (s, 3H), 2.01-1.96 (m, 1H), 1.95-1.90 (m, 1H), 1.73-1.67 (m, 1H), 1.54-1.43 (m, 4H), 1.41-1.34 (m, 3H), 1.37 (s, 3H), 1.17 (s, 3H), 1.11 (d, J=6.6 Hz, 3H), 1.03 (s, 3H), 0.95 (d, J=7.2 Hz, 3H) ppm; $^{13}$C NMR (151 MHz, $CD_2Cl_2$) δ=220.8, 171.3, 156.2, 149.4, 141.4, 136.8, 125.0, 124.4, 121.8, 77.7, 74.8, 73.6, 62.2, 60.6, 55.0, 48.9, 44.2, 43.7, 39.8, 35.6, 35.2, 32.2, 30.1, 21.4, 20.8, 19.6, 17.3, 16.5, 15.8, 13.6 ppm; HRMS (ESI) calcd for $C_{30}H_{46}N_2O_6Na$ [M+Na]$^+$ 553.3248, found 553.3255.

74a

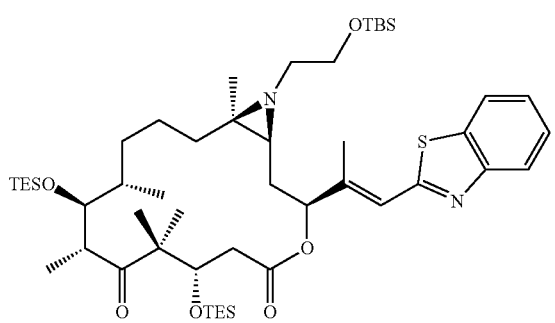

Protected Epothilone 74a:

To a stirred solution of phosphonate 67 (150 mg, 0.533 mmol, 13 equiv.) in tetrahydrofuran (0.5 mL) at −78° C. was carefully added n-butyllithium (2.5 M hexanes, 0.17 mL, 0.425 mmol, 10 equiv.). After stirring for 20 min at the same temperature, a solution of tertiary aziridine 30 (28.7 mg, 0.041 mmol, 1.0 equiv.) in tetrahydrofuran (0.5 mL) was added. The reaction mixture was allowed to slowly warm to 10° C., stirred for an additional 1 h, and then quenched with a saturated aqueous solution of ammonium chloride (10 mL). The two phases were separated, and the aqueous layer was extracted with ethyl acetate (3×5 mL). The combined organic layers were dried with anhydrous sodium sulfate and concentrated in vacuo. The obtained residue was purified by flash column chromatography (silica gel, 5→30% ethyl acetate in hexanes) to afford pure protected epothilone 74a (22 mg, 0.027 mmol, 65%) as a colorless oil. 74a: $R_f$=0.30 (silica gel, 15% ethyl acetate in hexanes); $[\alpha]_D^{25}$=−4.8 (c=1.00, $CH_2Cl_2$); FT-IR (neat) $v_{max}$ 2952, 2876, 1745, 1696, 1643, 1460, 1434, 1414, 1381, 1306, 1283, 1248, 1198, 1157, 1107, 1008, 985, 835 cm$^{-1}$; $^1$H NMR (600 MHz, $CD_2Cl_2$) δ=7.99 (dd, J=8.4, 1.2 Hz, 1H), 7.91 (dd, J=8.4, 1.2 Hz, 1H), 7.48 (ddd, J=7.8, 6.6, 1.2 Hz, 1H), 7.38 (ddd, J=7.8, 6.6, 1.2 Hz, 1H), 6.80 (s, 1H), 5.22 (dd, J=7.8, 3.6 Hz, 1H), 4.15 (dd, J=7.8, 3.6 Hz, 1H), 3.88 (d, J=8.4 Hz, 1H), 3.71-3.65 (m, 2H), 3.05 (dq, J=8.4, 6.6 Hz, 1H), 2.72-2.62 (m, 3H), 2.39 (ddd, J=13.2, 6.6, 6.6 Hz, 1H), 2.29 (s, 3H), 2.16 (ddd, J=15.0, 3.0, 3.0 Hz, 1H), 1.78 (ddd, J=15.0, 9.0, 9.0 Hz, 1H), 1.66-1.58 (m, 4H), 1.48-1.43 (m, 2H), 1.31 (dd, J=10.2, 3.0 Hz, 1H), 1.28-1.24 (m, 1H), 1.19 (s, 3H), 1.16 (s, 3H), 1.12 (s, 3H), 1.09 (d, J=7.2 Hz, 3H), 0.99 (t, J=8.4 Hz, 9H), 0.98 (d, J=6.6 Hz, 3H), 0.94 (t, J=7.8 Hz, 9H), 0.86 (s, 9H), 0.69-0.62 (m, 12H), 0.03 (s, 3H), 0.02 (s, 3H) ppm; $^{13}$C NMR (150 MHz, $CD_2Cl_2$) δ=215.8, 171.2, 164.7, 153.9, 146.9, 135.4, 126.5, 125.3, 123.3, 121.7, 120.5, 80.1, 79.0, 75.8, 64.1, 54.8, 49.9, 48.2, 43.7, 40.6, 37.1, 36.1, 34.9, 32.2, 26.1, 25.3, 24.1, 22.6, 20.0, 18.6, 17.7, 15.52, 15.50, 7.3, 7.1, 5.8, 5.6, −5.23, −5.25 ppm; HRMS (ESI) calcd for $C_{50}H_{89}N_2O_6Si_3S$ [M+H]$^+$ 929.5744, found 929.5768.

74

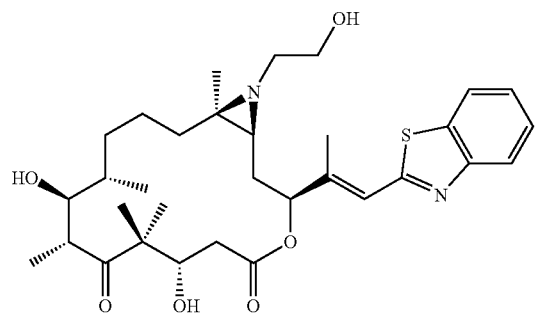

Epothilone 74:

To a stirred solution of protected epothilone 74a (22.0 mg, 0.024 mmol, 1.0 equiv.) in tetrahydrofuran (2.0 mL) at 0° C. was added hydrogen fluoride-pyridine complex (70% HF, 0.10 mL, 3.85 mmol, 150 equiv.). The reaction mixture was allowed to warm to 25° C. and stirred for an additional 9 h. Then the reaction mixture was quenched with a saturated aqueous solution of sodium bicarbonate (10 mL), and the two phases were separated. The aqueous layer was extracted with ethyl acetate (3×10 mL), and the combined organic layers were dried with anhydrous sodium sulfate and concentrated in vacuo. The obtained residue was purified by flash column chromatography (silica gel, 5→20% methanol in ethyl acetate) to afford pure epothilone 74 (11.3 mg, 0.019 mmol, 81%) as a colorless oil. 74: $R_f$=0.39 (silica gel, 20% methanol in ethyl acetate); $[\alpha]_D^{25}$=−15.7 (c=1.13, $CH_2Cl_2$); FT-IR (neat) $v_{max}$ 3366, 2927, 2855, 1735, 1688, 1647, 1467, 1434, 1380, 1261, 1148, 1052, 1010, 980, 937, 876, 761, 730, 709 $cm^{-1}$; $^1H$ NMR (600 MHz, $CD_2Cl_2$) δ=7.99 (dd, J=7.8, 1.2 Hz, 1H), 7.91 (dd, J=7.8, 1.2 Hz, 1H), 7.49 (ddd, J=8.4, 7.2, 1.2 Hz, 1H), 7.39 (ddd, J=8.4, 7.2, 1.2 Hz, 1H), 6.88 (s, 1H), 5.56 (dd, J=3.6, 3.6 Hz, 1H), 4.05 (dd, J=10.2, 2.4 Hz, 1H), 3.75 (dd, J=6.0, 3.6 Hz, 1H), 3.71-3.61 (m, 2H), 3.31 (dq, J=7.2, 7.2 Hz, 1H), 2.70 (ddd, J=13.2, 7.2, 4.2 Hz, 1H), 2.58-2.53 (m, 2H), 2.45 (dd, J=13.8, 1.8 Hz, 1H), 2.32 (s, 3H), 2.06 (ddd, J=15.0, 6.0, 6.0 Hz, 1H), 1.86 (ddd, J=15.6, 7.8, 3.6 Hz, 1H), 1.70-1.64 (m, 1H), 1.60-1.48 (m, 2H), 1.47-1.38 (m, 2H), 1.37 (s, 3H), 1.38-1.28 (m, 2H), 1.27-1.25 (m, 1H), 1.15 (s, 3H), 1.13 (d, J=7.2 Hz, 3H), 1.04 (s, 3H), 0.97 (d, J=7.2 Hz, 3H) ppm; $^{13}C$ NMR (151 MHz, $CD_2Cl_2$) δ=220.5, 171.4, 164.8, 153.8, 144.8, 153.3, 126.6, 125.4, 123.2, 121.8, 119.2, 77.1, 76.4, 75.4, 62.5, 55.5, 52.6, 47.7, 45.2, 43.2, 39.4, 35.3, 34.3, 31.5, 30.1, 29.1, 21.8, 19.5, 17.7, 16.9, 16.5, 14.8 ppm; HRMS (ESI) calcd for $C_{32}H_{47}N_2O_6S$ $[M+H]^+$ 587.3149, found 587.3153.

2.78-2.70 (m, 2H), 2.59 (dd, J=16.2, 3.0 Hz, 1H), 2.47 (ddd, J=12.6, 6.6, 6.6 Hz, 1H), 2.33 (s, 3H), 2.27 (ddd, J=14.4, 3.0, 3.0 Hz, 1H), 2.04 (ddd, J=15.0, 9.0, 9.0 Hz, 1H), 1.90-1.80 (m, 2H), 1.76-1.71 (m, 1H), 1.66-1.59 (m, 1H), 1.52-1.48 (m, 2H), 1.37 (s, 18H), 1.26 (dd, J=15.6, 9.0 Hz, 1H), 1.22-1.17 (m, 1H), 1.20 (d, J=7.2 Hz, 3H), 1.19 (s, 3H), 1.16 (s, 3H), 1.14 (d, J=6.6 Hz, 3H), 1.09 (t, J=7.8 Hz, 9H), 1.06 (t, J=7.8 Hz, 9H), 1.00 (s, 9H), 0.85-0.78 (m, 6H), 0.74-0.70 (m, 6H), 0.101 (s, 3H), 0.097 (s, 3H) ppm; $^{13}C$ NMR (151 MHz, $C_6D_6$) δ=214.4, 170.7, 167.1, 153.4, 152.4, 138.7, 120.7, 117.4, 82.4, 80.2, 79.6, 75.9, 64.3, 54.9, 53.4, 50.2, 48.1, 47.8, 43.3, 40.1, 37.4, 36.4, 35.4, 32.3, 27.9, 26.2, 25.5, 23.6, 23.3, 20.2, 18.5, 17.6, 15.6, 14.7, 7.43, 7.37, 6.0, 5.8, −5.1 ppm; HRMS (ESI) calcd for $C_{57}H_{106}N_3O_{10}Si_3S$ $[M+H]^+$ 1108.6901, found 1108.6892.

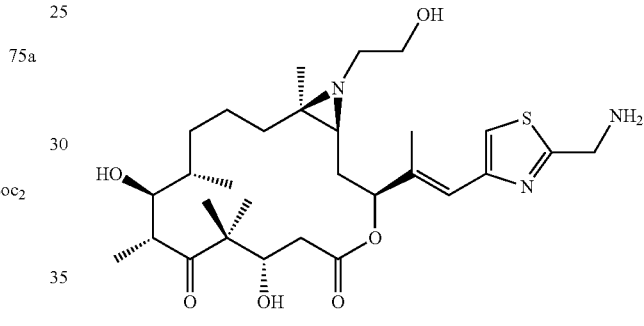

Protected Epothilone 75a:

To a stirred solution of phosphonate 44 (97 mg, 0.209 mmol, 8.3 equiv.) in tetrahydrofuran (0.5 mL) at −78° C. was carefully added sodium bis(trimethylsilyl)amide (1.0 M tetrahydrofuran, 0.17 mL, 0.17 mmol, 6.8 equiv.). After stirring for 35 min at the same temperature, a solution of tertiary aziridine 30 (20 mg, 0.025 mmol, 1.0 equiv.) in tetrahydrofuran (0.4 mL) was added. The reaction mixture was stirred for an additional 2 h at the same temperature, quenched with a saturated aqueous solution of ammonium chloride (10 mL), and allowed to warm to 25° C. The two phases were separated, and the aqueous layer was extracted with ethyl acetate (3×5 mL). The combined organic layers were dried with anhydrous sodium sulfate and concentrated in vacuo. The obtained residue was purified by flash column chromatography (silica gel, 5→20% ethyl acetate in hexanes) to afford pure protected epothilone 75a (18.8 mg, 0.017 mmol, 68%) as a colorless oil. 75a: $R_f$=0.24 (silica gel, 15% ethyl acetate in hexanes); $[\alpha]_D^{25}$=−4.4 (c=0.84, $CH_2Cl_2$); FT-IR (neat) $v_{max}$ 2954, 2933, 2877, 1796, 1742, 1697, 1460, 1418, 1380, 1367, 1343, 1303, 1251, 1230, 1124, 1008, 985, 836 $cm^{-1}$; $^1H$ NMR (600 MHz, $C_6D_6$) δ=6.68 (s, 1H), 6.54 (s, 1H), 5.44 (dd, J=9.0, 3.0 Hz, 1H), 5.08 (s, 2H), 4.23 (dd, J=9.0, 3.0 Hz, 1H), 4.19 (d, J=8.4 Hz, 1H), 3.87-3.79 (m, 2H), 3.04 (dq, J=8.4, 6.6 Hz, 1H), Epothilone 75:

To a stirred solution of protected epothilone 75a (32 mg, 0.029 mmol, 1.0 equiv.) in tetrahydrofuran (2.0 mL) at 0° C. was added hydrogen fluoride-pyridine complex (70% HF, 0.20 mL, 7.70 mmol, 265 equiv.). The reaction mixture was allowed to warm to 25° C. and stirred for an additional 5 h. Then the reaction mixture was quenched with a saturated aqueous solution of sodium bicarbonate (10 mL), and the two phases were separated. The aqueous layer was extracted with ethyl acetate (3×10 mL), and the combined organic layers were dried with anhydrous sodium sulfate and concentrated in vacuo. The crude material was resuspended in dichloromethane (2.0 mL) and cooled to 0° C. Trifluoroacetic acid (0.50 mL, 6.50 mmol, 224 equiv.) was added, the reaction mixture was stirred for 2.5 h, and then allowed to warm to 25° C. The solvent was removed in vacuo, and the resulting residue was redissolved in ethyl acetate (15 mL). A saturated aqueous solution of sodium bicarbonate (5 mL) was added with stirring. After 10 min, the two phases were separated, and the organic layer was dried with anhydrous sodium sulfate and concentrated in vacuo. The obtained residue was purified by flash column chromatography (silica gel, 0→20% methanol in acetone) to afford pure epothilone 75 (10.6 mg, 0.014 mmol, 48%) as a colorless oil. 75: $R_f$=0.18 (silica gel, 10% methanol in acetone); $[\alpha]_D^{25}$=−0.9 (c=0.47, $CH_2Cl_2$); FT-IR (neat) $v_{max}$ 3386, 2922, 2851, 1676, 1557, 1463, 1396, 1261, 1201, 1180, 1132, 1033, 832, 800, 721, 672 $cm^{-1}$; $^1H$ NMR (600 MHz, $CD_2Cl_2$) δ=7.09 (s, 1H), 6.55 (s, 1H), 5.42 (dd, J=5.4 Hz, 1H), 4.10-4.08 (m, 1H), 3.73 (dd, J=4.8, 4.8 Hz, 1H), 3.68-3.60 (m, 2H), 3.30-3.26 (m, 1H), 2.61 (t, J=4.8 Hz, 1H), 2.50 (dd, J=13.8, 10.2 Hz, 1H), 2.38 (dd, J=13.8, 2.4 Hz, 1H), 2.09 (s, 3H), 1.96-1.87 (m, 2H), 1.70-1.65 (m, 1H), 1.56-1.49 (m, 1H), 1.46-1.26 (m, 6H), 1.35 (m, 3H), 1.15 (s, 3H), 1.12 (d, J=7.2 Hz, 3H), 1.03 (s, 3H), 0.96 (d, J=7.2 Hz, 3H) ppm; $^{13}$C NMR (151 MHz, CD$_2$Cl$_2$) δ=220.7, 174.2, 171.3, 152.8, 137.5, 119.4, 116.6, 77.9, 75.4, 74.4, 62.4, 55.2, 53.8, 53.0, 48.4, 44.3, 43.6, 39.6, 35.5, 35.0, 32.1, 29.8, 21.7, 20.7, 20.3, 17.5, 16.4, 15.9, 14.1 ppm; HRMS (ESI) calcd for C$_{29}$H$_{47}$N$_3$O$_6$SNa [M+Na]$^+$ 588.3078, found 588.3087.

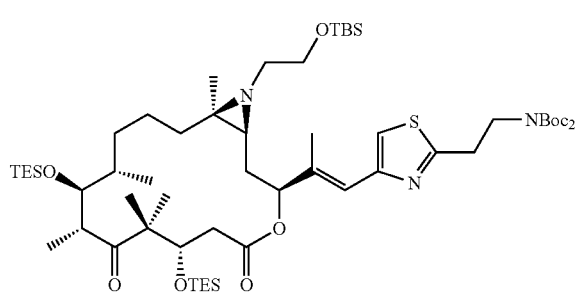

76a

Protected Epothilone 76a:

To a stirred solution of phosphonate 52 (330 mg, 0.690 mmol, 12 equiv.) in tetrahydrofuran (1.0 mL) at −78° C. was carefully added sodium bis(trimethylsilyl)amide (1.0 M tetrahydrofuran, 0.41 mL, 0.41 mmol, 9.7 equiv.). After stirring for 25 min at the same temperature, a solution of tertiary aziridine 30 (45.0 mg, 0.056 mmol, 1.0 equiv.) in tetrahydrofuran (0.5 mL) was added. The reaction mixture was allowed to slowly warm to 0° C., stirred for an additional 2 h, and then quenched with a saturated aqueous solution of ammonium chloride (10 mL). The two phases were separated, and the aqueous layer was extracted with ethyl acetate (3×5 mL). The combined organic layers were dried with anhydrous sodium sulfate and concentrated in vacuo. The obtained residue was purified by flash column chromatography (silica gel, 5→20% ethyl acetate in hexanes) to afford pure protected epothilone 76a (28.2 mg, 0.025 mmol, 45%) as a colorless oil. 76a: R$_f$=0.30 (silica gel, 20% ethyl acetate in hexanes); [α]$_D^{25}$=−4.0 (c=1.00, CH$_2$Cl$_2$); FT-IR (neat) ν$_{max}$ 2954, 2935, 2877, 1794, 1744, 1697, 1500, 1459, 1390, 1367, 1353, 1306, 1278, 1251, 1220, 1158, 1118, 1040, 1008, 984, 858, 835, 779, 738, 668 cm$^{-1}$; $^1$H NMR (600 MHz, CDCl$_3$) δ=6.71 (s, 1H), 6.53 (s, 1H), 5.43 (dd, J=8.4, 3.0 Hz, 1H), 4.20 (dd, J=9.0, 3.0 Hz, 1H), 4.18 (d, J=8.4 Hz, 1H), 4.08 (t, J=7.2 Hz, 2H), 3.86-3.79 (m, 2H), 3.28-3.20 (m, 2H), 3.03 (dq, J=9.0, 7.2 Hz, 1H), 2.78-2.70 (m, 2H), 2.61 (dd, J=16.2, 3.0 Hz, 1H), 2.46 (ddd, J=13.2, 6.6, 6.6 Hz, 1H), 2.34 (s, 3H), 2.29 (ddd, J=15.0, 3.0, 3.0 Hz, 1H), 2.04 (ddd, J=15.6, 9.0, 9.0 Hz, 1H), 1.91-1.81 (m, 2H), 1.75-1.71 (m, 1H), 1.67-1.59 (m, 1H), 1.52-1.48 (m, 2H), 1.39 (s, 18H), 1.26 (dd, J=10.2, 3.6 Hz, 1H), 1.22-1.8 (m, 1H), 1.20 (d, J=7.2 Hz, 3H), 1.19 (s, 3H), 1.16 (s, 3H), 1.13 (d, J=6.6 Hz, 3H), 1.09 (t, J=7.8 Hz, 9H), 1.06 (t, J=7.8 Hz, 9H), 0.99 (s, 9H), 0.87 (s, 3H), 0.85-0.77 (m, 6H), 0.74-0.70 (m, 6H), 0.097 (s, 3H), 0.093 (s, 3H) ppm; $^{13}$C NMR (151 MHz, CDCl$_3$) δ=214.4, 170.7, 165.9, 153.8, 152.6, 138.6, 120.8, 117.0, 81.8, 80.2, 79.6, 75.9, 64.3, 54.9, 53.4, 50.2, 48.1, 46.1, 43.3, 40.1, 37.3, 36.4, 35.4, 32.9, 32.3, 28.0, 26.2, 25.5, 23.6, 23.3, 20.1, 15.5, 17.6, 15.6, 14.8, 7.43, 7.37, 6.0, 5.8, −5.1 ppm; HRMS (ESI) calcd for C$_{58}$H$_{108}$N$_3$O$_{10}$Si$_3$S [M+H]$^+$ 1122.7058, found 1122.7033.

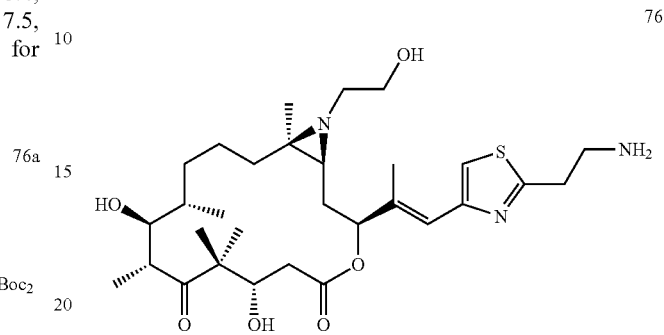

76

Epothilone 76:

To a stirred solution of protected epothilone 76a (14.9 mg, 0.013 mmol, 1.0 equiv.) in tetrahydrofuran (2.0 mL) at 0° C. was added hydrogen fluoride-pyridine complex (70% HF, 0.06 mL, 2.31 mmol, 178 equiv.). The reaction mixture was allowed to warm to 25° C. and stirred for an additional 5 h. Then the reaction mixture was quenched with a saturated aqueous solution of sodium bicarbonate (10 mL), and the two phases were separated. The aqueous layer was extracted with ethyl acetate (3×10 mL), and the combined organic layers were dried with anhydrous sodium sulfate and concentrated in vacuo. The crude material was resuspended in dichloromethane (1.0 mL) and cooled to 0° C. Trifluoroacetic acid (0.10 mL, 1.30 mmol, 100 equiv.) was added, the reaction mixture was stirred for 3 h, and then allowed to warm to 25° C. The solvent was removed in vacuo, and the resulting residue was redissolved in ethyl acetate (15 mL). A saturated aqueous solution of sodium bicarbonate (5 mL) was added with stirring. After 10 min, the two phases were separated, and the organic layer was dried with anhydrous sodium sulfate and concentrated in vacuo. The obtained residue was purified by flash column chromatography (silica gel, 40% methanol in acetone) to afford pure epothilone 76 (5.5 mg, 0.010 mmol, 71%) as a colorless oil. 76: R$_f$=0.39 (silica gel, 40% methanol in acetone); [α]$_D^{25}$=−27.2 (c=0.50, 10:1 CH$_2$Cl$_2$/MeOH); FT-IR (neat) ν$_{max}$ 3360, 2925, 2855, 1727, 1686, 1559, 1505, 1464, 1425, 1382, 1336, 1265, 1147, 1053, 1008, 980, 937, 883, 826, 733, 701, 669 cm$^{-1}$; $^1$H NMR (600 MHz, CDCl$_3$) δ=7.05 (s, 1H), 6.56 (s, 1H), 5.43 (dd, J=4.8, 4.8 Hz, 1H), 4.09 (dd, J=10.2, 2.4 Hz, 1H), 3.73 (t, J=4.8 Hz, 1H), 3.68-3.60 (m, 2H), 3.28 (dq, J=6.6, 6.6 Hz, 1H), 3.09 (s, 4H), 2.61 (t, J=5.4 Hz, 2H), 2.50 (dd, J=13.8, 10.2 Hz, 1H), 2.38 (dd, J=13.8, 2.4 Hz, 1H), 2.10 (s, 3H), 1.96-1.86 (m, 2H), 1.70-1.65 (m, 1H), 1.54-1.24 (m, 9H), 1.35 (s, 3H), 1.26 (s, 2H), 1.15 (s, 3H), 1.12 (d, J=6.6 Hz, 3H), 1.03 (s, 3H), 0.96 (d, J=6.6 Hz, 3H) ppm; $^{13}$C NMR (151 MHz, CDCl$_3$) δ=220.7, 171.3, 168.4, 152.7, 137.5, 119.3, 116.5, 78.0, 75.4, 74.4, 62.4, 55.3, 53.0, 48.3, 44.3, 43.5, 42.0, 39.6, 37.5, 35.5, 35.1, 32.1, 29.8, 21.7, 20.7, 20.3, 17.5, 16.4, 15.9, 14.1 ppm; HRMS (ESI) calcd for C$_{30}$H$_{49}$N$_3$O$_6$SNa [M+Na]$^+$ 602.3234, found 602.3217.

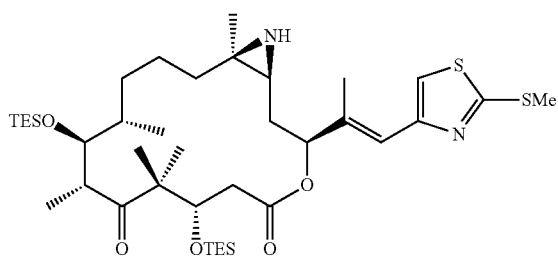

77a

Protected Epothilone 77a:

To a stirred solution of phosphonate 36 (190 mg, 0.675 mmol, 9.6 equiv.) in tetrahydrofuran (1.0 mL) at −78° C. was carefully added n-butyllithium (2.5 M hexanes, 0.22 mL, 0.550 mmol, 7.7 equiv.). After stirring for 30 min at the same temperature, a solution of aziridine methyl ketone 29 (45 mg, 0.070 mmol, 1.0 equiv.) in tetrahydrofuran (0.5 mL) was added. The reaction mixture was allowed to slowly warm to 25° C., stirred for an additional 1 h, and then quenched with a saturated aqueous solution of ammonium chloride (10 mL). The two phases were separated, and the aqueous layer was extracted with ethyl acetate (3×5 mL). The combined organic layers were dried with anhydrous sodium sulfate and concentrated in vacuo. The obtained residue was purified by flash column chromatography (silica gel, 30→100% ethyl acetate in hexanes) to afford pure protected epothilone 77a (32 mg, 0.042 mmol, 59%) as a colorless oil. 77a: $R_f$=0.34 (silica gel, 70% ethyl acetate in hexanes); $[\alpha]_D^{25}$=−13.3 (c=0.36, $CH_2Cl_2$); FT-IR (neat) $v_{max}$ 2953, 2928, 2876, 1742, 1696, 1459, 1416, 1345, 1304, 1240, 1197, 1157, 1068, 1035, 1019, 985, 915, 862, 838, 783, 737, 676 cm$^{-1}$; $^1$H NMR (600 MHz, $C_6D_6$) δ=6.63 (s, 1H), 6.43 (s, 1H), 5.39 (dd, J=8.4, 3.0 Hz, 1H), 4.26 (dd, J=9.0, 3.6 Hz, 1H), 4.15 (d, J=8.4 Hz, 1H), 3.06 (dq, J=8.4, 7.2 Hz, 1H), 2.72 (dd, J=16.2, 8.4 Hz, 1H), 2.60 (dd, J=16.2, 3.6 Hz, 1H), 2.22 (s, 3H), 2.20 (s, 3H), 2.11-2.06 (m, 1H), 1.89-1.84 (m, 2H), 1.79-1.70 (m, 2H), 1.61-1.55 (m, 2H), 1.49-1.36 (m, 2H), 1.24-1.18 (m, 1H), 1.18 (d, J=7.2 Hz, 3H), 1.17 (s, 3H), 1.13 (d, J=7.2 Hz, 3H), 1.08 (t, J=7.8 Hz, 9H), 1.07 (t, J=7.8 Hz, 9H), 1.05 (s, 3H), 0.85 (s, 3H), 0.81-0.77 (m, 6H), 0.75-0.71 (m, 6H) ppm; $^{13}$C NMR (151 MHz, $C_6D_6$) δ=214.4, 170.7, 165.3, 153.6, 138.8, 120.1, 116.4, 80.2, 79.3, 75.9, 53.5, 47.9, 41.7, 40.0, 39.4, 37.2, 35.2, 34.0, 31.9, 25.8, 25.1, 23.3, 23.1, 20.0, 17.5, 15.9, 14.9, 7.4, 7.3, 6.0, 5.8 ppm; HRMS (ESI) calcd for $C_{39}H_{71}N_2O_5Si_2S_2$[M+H]$^+$ 767.4337, found 767.4358.

77

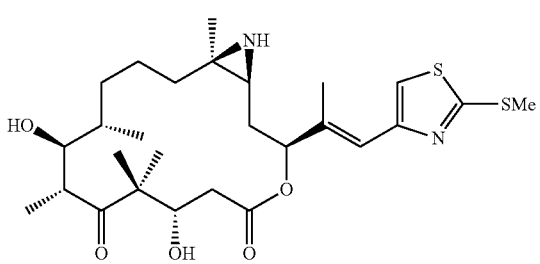

Epothilone 77:

To a stirred solution of protected epothilone 77a (13.0 mg, 0.017 mmol, 1.0 equiv.) in tetrahydrofuran (1.0 mL) at 0° C. was added hydrogen fluoride-pyridine complex (70% HF, 0.10 mL, 3.85 mmol, 220 equiv.). The reaction mixture was allowed to warm to 25° C. and stirred for 1 h. Then the reaction mixture was quenched with a saturated aqueous solution of sodium bicarbonate (10 mL), and the two phases were separated. The aqueous layer was extracted with ethyl acetate (3×10 mL), and the combined organic layers were dried with anhydrous sodium sulfate and concentrated in vacuo. The obtained residue was purified by flash column chromatography (silica gel, 5→15% methanol in ethyl acetate) to afford pure epothilone 77 (8.5 mg, 0.016 mmol, 93%) as a colorless oil. 77: $R_f$=0.29 (silica gel, 15% methanol in ethyl acetate); $[u]_D^{25}$=−28.8 (c=0.85, $CH_2Cl_2$); FT-IR (neat) $v_{max}$ 3292, 2956, 2930, 2875, 1730, 1687, 1456, 1422, 1384, 1334, 1293, 1263, 1174, 1145, 1037, 1009, 980, 881, 735, 668 cm$^{-1}$; $^1$H NMR (600 MHz, $CD_2Cl_2$) δ=7.04 (s, 1H), 6.54 (s, 1H), 5.55 (dd, J=4.2, 4.2 Hz, 1H), 4.08 (ddd, J=14.4, 3.6, 3.6 Hz, 1H), 3.78 (dd, J=6.6, 3.6 Hz, 1H), 3.33 (dq, J=6.6, 6.6 Hz, 1H), 2.71 (s, 3H), 2.54 (dd, J=12.6, 10.8 Hz, 1H), 2.43 (dd, J=12.6, 4.2 Hz, 1H), 2.14 (s, 3H), 2.00 (s, 1H), 1.96 (ddd, J=15.0, 4.2, 4.2 Hz, 1H), 1.85 (dd, J=9.0, 4.8 Hz, 1H), 1.78-1.71 (m, 2H), 1.58-1.49 (m, 2H), 1.45-1.34 (m, 3H), 1.40 (s, 3H), 1.24-1.20 (m, 1H), 1.22 (s, 3H), 1.10 (d, J=7.2 Hz, 3H), 1.01 (s, 3H), 0.95 (d, J=6.6 Hz, 3H) ppm; $^{13}$C NMR (151 MHz, $CD_2Cl_2$) δ=220.6, 171.2, 165.7, 153.5, 137.2, 118.3, 116.3, 76.3, 76.2, 75.6, 60.6, 52.6, 44.9, 38.7, 38.4, 35.2, 31.1, 30.3, 28.8, 25.7, 22.6, 22.4, 18.9, 17.6, 16.9, 16.3, 14.9 ppm; HRMS (ESI) calcd for $C_{27}H_{42}N_2O_5S_2Na$ [M+Na]$^+$ 561.2427, found 561.2409.

78a

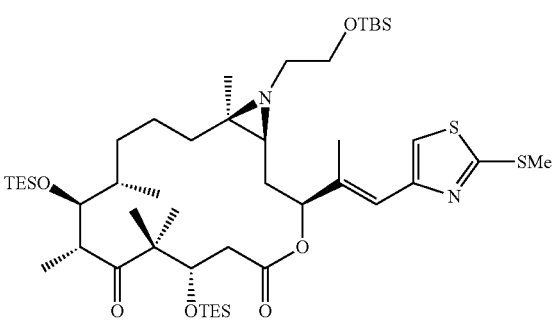

Protected Epothilone 78a:

To a stirred solution of phosphonate 36 (115 mg, 0.409 mmol, 15 equiv.) in tetrahydrofuran (0.5 mL) at −78° C. was carefully added n-butyllithium (1.6 M hexanes, 0.20 mL, 0.327 mmol, 12 equiv.). After stirring for 45 min at the same temperature, a solution of tertiary aziridine 30 (21.6 mg, 0.027 mmol, 1.0 equiv.) in tetrahydrofuran (0.5 mL) was added. The reaction mixture was allowed to slowly warm to 0° C. and stirred for an additional 2 h. Then the reaction mixture was quenched with a saturated aqueous solution of ammonium chloride (10 mL) and allowed to warm to 25° C. The two phases were separated, and the aqueous layer was extracted with ethyl acetate (3×5 mL). The combined organic layers were dried with anhydrous sodium sulfate and concentrated in vacuo. The obtained residue was purified by flash column chromatography (silica gel, 5→15% ethyl acetate in hexanes) to afford pure protected epothilone 78a (15.0 mg, 0.016 mmol, 60%) as a colorless oil. 78a: $R_f$=0.30 (silica gel, 15% ethyl acetate in hexanes); $[\alpha]_D^{25}$=−3.0 (c=1.15, $CH_2Cl_2$); FT-IR (neat) $v_{max}$ 2953, 2931, 2877, 1741, 1697, 1463, 1421, 1381, 1304, 1249, 1198, 1157, 1110, 1076, 1037, 1019, 985, 836, 779, 738, 674, 663 cm$^{-1}$; $^1$H NMR (600 MHz, C$_6$D$_6$) δ=6.7 (s, 1H), 6.4 (s, 1H), 5.45 (dd, J=8.4, 3.6 Hz, 1H), 4.24 (dd, J=8.4, 3.6 Hz, 1H), 4.17 (d, J=9.0 Hz, 1H), 3.87-3.79 (m, 2H), 3.03 (dq, J=9.0, 7.2 Hz, 1H), 2.75 (ddd, J=12.0, 6.0, 6.0 Hz, 1H), 2.72 (dd, J=15.6, 8.4 Hz, 1H), 2.59 (dd, J=16.2, 3.0 Hz, 1H), 2.46 (ddd, J=12.0, 6.0, 6.0 Hz, 1H), 2.30 (s, 3H), 2.28-2.27 (m, 1H), 2.20 (s, 3H), 2.09-2.03 (m, 1H), 1.90-1.81 (m, 2H), 1.75-1.70 (m, 1H), 1.66-1.59 (m, 1H), 1.53-1.46 (m, 2H), 1.27 (dd, J=9.6, 3.0 Hz, 1H), 1.24-1.20 (m, 1H), 1.19 (d, J=6.6 Hz, 3H), 1.18 (s, 3H), 1.16 (s, 3H), 1.13 (d, J=7.0 Hz, 3H), 1.10-1.05 (m, 18H), 0.99 (s, 9H), 0.87 (s, 3H), 0.84-0.77 (m, 6H), 0.73-0.69 (m, 6H), 0.094 (s, 3H), 0.091 (s, 3H) ppm; $^{13}$C NMR (150 MHz, C$_6$D$_6$) δ=214.5, 170.7, 165.3, 153.7, 138.9, 120.5, 116.5, 80.1, 79.6, 75.9, 64.3, 54.9, 53.4, 50.1, 48.1, 43.3, 40.2, 37.4, 36.4, 35.4, 32.4, 26.2, 25.5, 23.6, 23.1, 20.1, 18.5, 17.6, 15.9, 15.6, 14.7, 7.42, 7.36, 5.95, 5.80, −5.12 ppm; HRMS (ESI) calcd for C$_{47}$H$_{89}$N$_2$O$_6$Si$_3$S$_2$ [M+H]$^+$ 925.5464, found 925.5454.

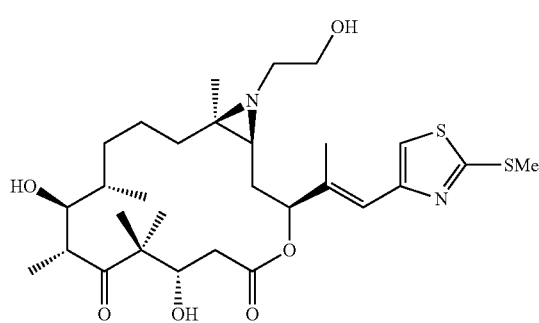

78

Epothilone 78:

To a stirred solution of protected epothilone 78a (30.0 mg, 0.032 mmol, 1.0 equiv.) in tetrahydrofuran (1.0 mL) at 0° C. was added hydrogen fluoride-pyridine complex (70% HF, 0.10 mL, 3.85 mmol, 120 equiv.). The reaction mixture was allowed to warm to 25° C. and stirred for 1 h. Then the reaction mixture was quenched with a saturated aqueous solution of sodium bicarbonate (5 mL), and the two phases were separated. The aqueous layer was extracted with ethyl acetate (3×5 mL), and the combined organic layers were dried with anhydrous sodium sulfate and concentrated in vacuo. The obtained residue was purified by flash column chromatography (silica gel, 5→20% methanol in ethyl acetate) to afford pure epothilone 78 (15.0 mg, 0.026 mmol, 79%) as a colorless oil. 78: R$_f$=0.41 (silica gel, 20% methanol in ethyl acetate); [α]$_D^{25}$=−16.3 (c=0.64, CH$_2$Cl$_2$); FT-IR (neat) v$_{max}$ 3373, 2927, 1729, 1685, 1654, 1559, 1460, 1452, 1424, 1259, 1149, 1037, 981, 881, 802, 735, 700 cm$^{-1}$; $^1$H NMR (600 MHz, C$_6$D$_6$) δ=6.71 (s, 1H), 6.47 (s, 1H), 5.55 (dd, J=4.2 Hz, 1H), 4.12 (dd, J=9.0, 3.0 Hz, 1H), 3.92-3.89 (m, 1H), 3.68-3.62 (m, 2H), 3.34 (ddd, J=13.8, 6.6, 6.6 Hz, 1H), 2.56-2.52 (m, 1H), 2.37-2.31 (m, 2H), 2.43-2.20 (m, 1H), 2.18 (s, 3H), 2.05 (s, 3H), 1.86-1.83 (m, 1H), 1.66 (ddd, J=15.6, 4.8, 4.8 Hz, 1H), 1.63-1.59 (m, 1H), 1.52-1.43 (m, 2H), 1.41-1.34 (m, 2H), 1.22 (ddd, J=13.8, 6.6, 6.6 Hz, 1H), 1.17 (s, 3H), 1.10 (d, J=7.0 Hz, 3H), 1.09-1.06 (m, 1H), 1.04 (d, J=7.0 Hz, 3H), 1.00-0.98 (m, 1H), 0.94 (s, 3H), 0.76 (s, 3H) ppm; $^{13}$C NMR (151 MHz, C$_6$D$_6$) δ=219.5, 170.9, 165.7, 153.6, 136.5, 118.6, 116.3, 76.8, 75.7, 63.8, 62.4, 55.7, 52.1, 47.0, 45.7, 42.3, 39.0, 35.2, 34.0, 30.8, 28.7, 25.4, 22.4, 21.8, 18.6, 16.2, 15.99, 15.98, 15.3 ppm; HRMS (ESI) calcd for C$_{29}$H$_{47}$N$_2$O$_6$S$_2$[M+H]$^+$ 583.2870, found 583.2861.

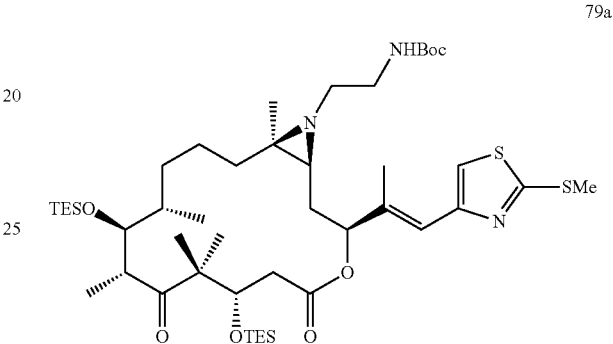

79a

Protected Epothilone 79a:

To a stirred solution of protected epothilone 79a (20.0 mg, 0.026 mmol, 1.0 equiv.) in dimethylformamide (0.3 mL) at 25° C. was added tert-butyl N-(2-bromoethyl) carbamate (62) (35.0 mg, 0.157 mmol, 6.0 equiv.), followed by potassium carbonate (18.0 mg, 0.130 mmol, 5.0 equiv.). The reaction mixture was heated to 75° C. and stirred for 12 h. The reaction mixture was then allowed to cool to 25° C., quenched with water (5 mL), and extracted with ethyl acetate (3×10 mL). The combined organic layers were dried with anhydrous sodium sulfate and concentrated in vacuo. The obtained residue was purified by flash column chromatography (silica gel, 10→40% methanol in ethyl acetate) to afford pure protected epothilone 79a (7.5 mg, 0.008 mmol, 32%) as a colorless oil, along with recovered 79a (7.0 mg, 0.009 mmol, 35%). 79a: R$_f$=0.34 (silica gel, 40% ethyl acetate in hexanes); [α]$_D^{25}$=−5.1 (c=0.75, CH$_2$Cl$_2$); FT-IR (neat) v$_{max}$ 3373, 2955, 2934, 2876, 1741, 1697, 1500, 1458, 1424, 1383, 1365, 1248, 1159, 1111, 1069, 1036, 1019, 985, 863, 837, 782, 739, 677 cm$^{-1}$; $^1$H NMR (600 MHz, C$_6$D$_6$) δ=6.64 (s, 1H), 6.47 (s, 1H), 5.37 (dd, J=8.4, 3.6 Hz, 1H), 5.02 (br s, 1H), 4.24 (dd, J=9.0, 3.6 Hz, 1H), 4.15 (d, J=9.0 Hz, 1H), 3.31 (dddd, J=12.6, 6.6, 6.6, 6.6 Hz, 1H), 3.21 (dddd, J=12.6, 6.0, 6.0, 6.0, Hz, 1H), 3.00 (ddd, J=14.4, 6.6, 6.6 Hz, 1H), 2.68 (dd, J=16.2, 8.4 Hz, 1H), 2.57 (dd, J=16.2, 3.6 Hz, 1H), 2.44-2.40 (m, 1H), 2.27 (s, 3H), 2.21 (s, 3H). 2.11-2.07 (m, 2H), 1.97-1.92 (m, 1H), 1.87-1.83 (m, 1H), 1.70-1.63 (m, 2H), 1.57-1.51 (m, 1H), 1.47 (s, 9H), 1.44-1.38 (m, 1H), 1.36-1.29 (m, 1H), 1.18 (d, J=6.6 Hz, 3H), 1.17 (s, 3H), 1.17-1.15 (m, 1H), 1.12 (d, J=6.6 Hz, 3H), 1.073 (t, J=8.4 Hz, 9H), 1.070 (t, J=8.4 Hz, 9H), 1.03-1.00 (m, 1H), 0.97 (s, 3H), 0.87 (s, 3H), 6.54 (m, 6H), 0.74-0.70 (m, 6H) ppm; $^{13}$C NMR (151 MHz, C$_6$D$_6$) δ=214.5, 170.6, 165.4, 155.9, 153.6, 138.7, 120.7, 116.6, 80.1, 79.4, 78.5, 75.8, 53.4, 51.7, 49.6, 48.0, 44.0, 41.5, 40.3, 37.3, 36.1, 34.9, 32.3, 28.5, 25.4, 23.6, 22.9, 20.2, 17.6, 15.9, 15.4, 14.7, 7.4, 7.3, 6.0, 5.8 ppm; HRMS (ESI) calcd for C$_{46}$H$_{84}$N$_3$O$_7$S$_2$Si$_2$ [M+H]$^+$ 910.5284, found 910.5293.

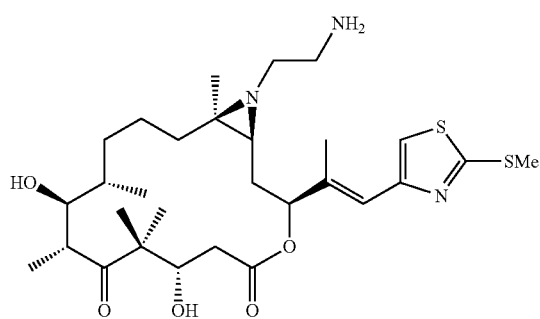

Epothilone 79:

To a stirred solution of protected epothilone 79a (6.0 mg, 0.007 mmol, 1.0 equiv.) in tetrahydrofuran (1.0 mL) at 0° C. was added hydrogen fluoride-pyridine complex (70% HF, 0.10 mL, 3.85 mmol, 500 equiv.). After 2 h, the reaction mixture was quenched with a saturated aqueous solution of sodium bicarbonate (5 mL) and allowed to warm to 25° C. The two phases were separated, the aqueous layer was extracted with ethyl acetate (3×5 mL), and the combined organic layers were dried with anhydrous sodium sulfate and concentrated in vacuo. The crude material was resuspended in dichloromethane (1.0 mL) and cooled to 0° C. Trifluoroacetic acid (0.05 mL, 0.65 mmol, 90 equiv.) was added, the reaction mixture was stirred for 1 h, and then allowed to warm to 25° C. The solvent was removed in vacuo, and the resulting residue was redissolved in ethyl acetate (15 mL). A saturated aqueous solution of sodium bicarbonate (5 mL) was added with stirring. After 10 min, the two phases were separated, and the organic layer was dried with anhydrous sodium sulfate and concentrated in vacuo. The obtained residue was purified by flash column chromatography (silica gel, 10→30% methanol in acetone) to afford pure epothilone 79 (2.5 mg, 0.004 mmol, 65%) as a colorless oil. 79: R$_f$=0.30 (silica gel, 30% methanol in acetone); $[α]^D_{25}$=−10.8 (c=0.25, CH$_2$Cl$_2$); FT-IR (neat) $ν_{max}$ 3366, 2929, 1729, 1686, 1565, 1421, 1370, 1338, 1252, 1149, 1037, 1008, 981, 881, 715 cm$^{-1}$; $^1$H NMR (600 MHz, CD$_2$Cl$_2$) δ=7.02 (s, 1H), 6.49 (s, 1H), 5.41 (dd, J=5.4, 5.4 Hz, 1H), 4.09 (dd, J=9.6, 3.0 Hz, 1H), 3.74 (dd, J=4.8, 4.8 Hz, 1H), 3.41 (s, 1H), 3.27 (ddd, J=12.0, 6.6, 6.6 Hz, 1H), 2.84-2.75 (m, 2H), 2.70 (s, 3H), 2.54-2.38 (m, 5H), 2.11 (s, 3H), 1.95-1.93 (m, 1H), 1.90-1.85 (m, 2H), 1.83-1.82 (m, 1H), 1.71-1.65 (m, 1H), 1.60-1.36 (m, 4H), 1.35 (s, 3H), 1.30-1.22 (m, 2H), 1.28 (s, 3H), 1.11 (d, J=6.6 Hz, 3H), 1.05 (s, 3H), 0.96 (d, J=6.6 Hz, 3H) ppm; $^{13}$C NMR (151 MHz, CD$_2$Cl$_2$) δ=206.7, 171.4, 165.9, 153.3, 138.0, 119.0, 116.4, 78.6, 75.4, 74.6, 70.4, 53.0, 50.8, 48.4, 44.3, 43.1, 39.6, 35.6, 32.3, 30.2, 28.2, 21.9, 20.9, 20.6, 17.6, 16.9, 16.1, 15.6, 14.0 ppm; HRMS (ESI) calcd for C$_{29}$H$_{48}$N$_3$O$_5$S$_2$[M+H]$^+$ 604.2849, found 604.2854.

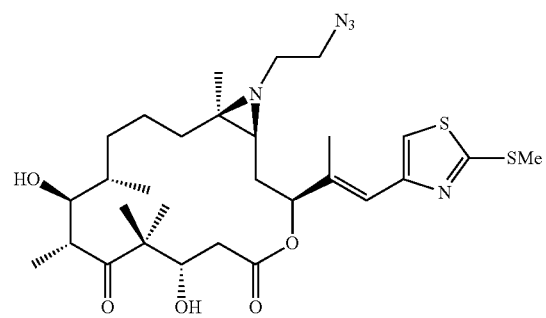

Epothilone 80:

To a stirred solution of epothilone 78 (12.8 mg, 0.022 mmol, 1.0 equiv.) in dichloromethane (1 mL) at 0° C. was added p-toluenesulfonic anhydride (35.8 mg, 0.11 mmol, 5.0 equiv.), followed by triethylamine (12.3 µL, 0.088 mmol, 4.0 equiv.) and 4-(dimethylamino)pyridine (2 mg, 0.016 mmol, 0.7 equiv.). After 30 min the reaction mixture was allowed to warm to 25° C., and stirred for an additional 15 min. The reaction mixture was quenched with methanol (0.5 mL) and water (10 mL). The two phases were separated, and the aqueous layer was extracted with ethyl acetate (3×5 mL). The combined organic layers were dried with anhydrous sodium sulfate and concentrated in vacuo. The obtained residue was filtered through silica gel, and washed with ethyl acetate. The filtrate was concentrated in vacuo. The crude tosylate was resuspended in dimethylformamide (0.5 mL) at 25° C., sodium azide (5.7 mg, 0.088 mmol, 4.0 equiv.) was added, and the reaction mixture was stirred for 17 h. Then the reaction mixture was quenched with water (5 mL) and extracted with ethyl acetate (3×5 mL). The combined organic layers were dried with anhydrous sodium sulfate and concentrated in vacuo. The obtained residue was purified by flash column chromatography (silica gel, 50→90% methanol in ethyl acetate) to afford pure epothilone 80 (5.3 mg, 0.009 mmol, 40%) as an amorphous solid. 80: R$_f$=0.35 (silica gel, ethyl acetate); $[α]^{25}_D$=−34.2 (c=0.55, CH$_2$Cl$_2$); FT-IR (neat) $ν_{max}$ 3432, 2929, 2101, 1731, 1687, 1554, 1423, 1384, 1263, 1148, 1036, 1009, 979, 881, 735 cm$^{-1}$; $^1$H NMR (600 MHz, CD$_2$Cl$_2$) δ=7.03 (s, 1H), 6.48 (s, 1H), 5.38 (dd, J=7.8, 3.6 Hz, 1H), 4.12-4.09 (m, 1H), 3.95 (br s, 1H), 3.74 (ddd, J=4.8, 4.8, 4.8 Hz, 1H), 3.44-3.37 (m, 2H), 3.26 (qd, J=6.6, 4.8 Hz, 1H), 2.70 (s, 3H), 2.67 (ddd, J=12.6, 6.0, 6.0 Hz, 1H), 2.59 (ddd, J=12.6, 6.6, 6.6 Hz, 1H), 2.49-2.45 (m, 2H), 2.39 (dd, J=15.0, 3.0 Hz, 1H), 2.13 (s, 3H), 2.01 (ddd, J=15.0, 4.2, 4.2 Hz, 1H), 1.82 (ddd, J=16.2, 7.8, 7.8 Hz, 1H), 1.71-1.65 (m, 1H), 1.51-1.41 (m, 4H), 1.35 (s, 3H), 1.30-1.28 (m, 1H), 1.26-1.22 (m, 1H), 1.16 (s, 3H), 1.12 (d, J=7.2 Hz, 3H), 1.05 (s, 3H), 0.97 (d, J=6.6 Hz, 3H) ppm; $^{13}$C NMR (151 MHz, CD$_2$Cl$_2$) δ=220.7, 171.2, 166.0, 153.1, 138.3, 119.3, 116.5, 78.8, 74.5, 74.2, 53.1, 52.3, 51.9, 49.0, 43.9, 43.8, 39.7, 35.9, 35.8, 32.7, 30.7, 22.0, 21.3, 20.3, 17.5, 16.9, 16.1, 15.4, 13.6 ppm; HRMS (ESI) calcd for C$_{29}$H$_{46}$N$_5$O$_5$S$_2$[M+H]$^+$ 608.2935, found 608.2933.

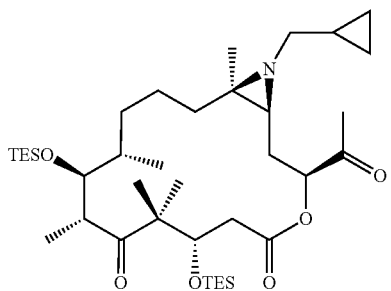

29a

Cyclopropylmethyl Aziridine 29a:

To a stirred solution of aziridine methyl ketone 29 (40.0 mg, 0.063 mmol, 1.0 equiv.) in dimethylformamide (0.4 mL) at 25° C. was added (bromomethyl)cyclopropane (50.6 mg, 0.375 mmol, 6.0 equiv.), followed by potassium carbonate (43.0 mg, 0.312 mmol, 5.0 equiv.). The reaction mixture was heated to 75° C. and stirred for 16 h. Then the reaction mixture was allowed to cool to 25° C. and quenched with water (10 mL). The mixture was extracted with ethyl acetate (3×5 mL), and the combined organic layers were dried with anhydrous sodium sulfate and concentrated in vacuo. The obtained residue was purified by flash column chromatography (silica gel, 10→40% ethyl acetate in hexanes) to afford pure cyclopropylmethyl aziridine 29a (40.0 mg, 0.058 mmol, 92%) as a pale yellow oil. 29a: $R_f$=0.23 (silica gel, 30% ethyl acetate in hexanes); $[\alpha]_D^{25}$=−6.5 (c=1.00, $CH_2Cl_2$); FT-IR (neat) $\nu_{max}$ 2952, 2918, 2877, 1747, 1732, 1696, 1460, 1414, 1381, 1308, 1284, 1239, 1197, 1158, 1109, 1070, 1042, 1010, 984, 941, 862, 835, 783, 725, 676 cm$^{-1}$; $^1$H NMR (600 MHz, $C_6D_6$) δ=4.93 (dd, J=9.0, 3.6 Hz, 1H), 4.19 (d, J=9.6 Hz, 1H), 4.06 (dd, J=7.8, 4.8 Hz, 1H), 2.85 (dq, J=9.6, 6.6 Hz, 1H), 2.72-2.71 (m, 2H), 2.60 (dd, J=12.0, 5.4 Hz, 1H), 2.11 (ddd, J=15.6, 3.0, 3.0 Hz, 1H), 1.98 (dd, J=12.0, 7.2 Hz, 1H), 1.85-1.76 (m, 2H), 1.77 (s, 3H), 1.73-1.56 (m, 3H), 1.48-1.35 (m, 2H), 1.26-1.22 (m, 1H), 1.21 (d, J=6.6 Hz, 3H), 1.16 (s, 3H), 1.10 (t, J=7.8 Hz, 9H), 1.08 (t, J=7.8 Hz, 9H), 1.04 (d, J=6.6 Hz, 3H), 1.03 (s, 3H), 0.99-0.92 (m, 2H), 0.86-0.77 (m, 6H), 0.74-0.70 (m, 6H), 0.68 (s, 3H), 0.45-0.42 (m, 2H), 0.22-0.16 (m, 2H) ppm; $^{13}$C NMR (151 MHz, $C_6D_6$) δ=213.9, 202.5, 171.8, 80.8, 78.2, 76.7, 56.7, 53.1, 50.1, 48.3, 43.2, 39.4, 36.9, 36.0, 31.6, 25.3, 25.1, 24.9, 23.0, 20.1, 17.8, 15.3, 12.0, 7.5, 7.3, 6.0, 5.8, 3.6, 3.4 ppm; HRMS (ESI) calcd for $C_{38}H_{72}NO_6Si_2$ [M+H]$^+$ 694.4893, found 694.4895.

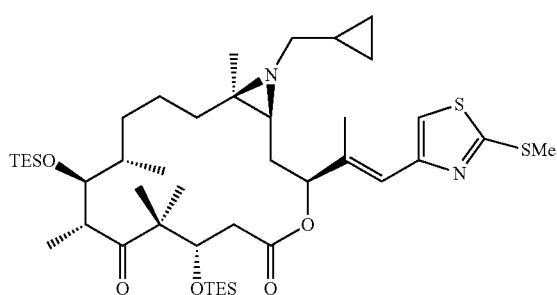

81a

Protected Epothilone 81a:

To a stirred solution of phosphonate 36 (150 mg, 0.533 mmol, 13 equiv.) in tetrahydrofuran (0.5 mL) at −78° C. was carefully added n-butyllithium (2.5 M hexanes, 0.17 mL, 0.425 mmol, 10 equiv.). After stirring for 20 min at the same temperature, a solution of cyclopropylmethyl aziridine 29a (28.7 mg, 0.041 mmol, 1.0 equiv.) in tetrahydrofuran (0.5 mL) was added. The reaction mixture was allowed to slowly warm to 10° C., stirred for an additional 1 h, and quenched with a saturated aqueous solution of ammonium chloride (10 mL). The two phases were separated, and the aqueous layer was extracted with ethyl acetate (3×5 mL). The combined organic layers were dried with anhydrous sodium sulfate and concentrated in vacuo. The obtained residue was purified by flash column chromatography (silica gel, 5→30% ethyl acetate in hexanes) to afford pure protected epothilone 81a (22.1 mg, 0.027 mmol, 65%) as a colorless oil. 81a: $R_f$=0.22 (silica gel, 20% ethyl acetate in hexanes); $[\alpha]_D^{25}$=+4.2 (c=1.00, $CH_2Cl_2$); FT-IR (neat) $\nu_{max}$ 2953, 2926, 2876, 1741, 1696, 1461, 1423, 1380, 1240, 1180, 1158, 1110, 1069, 1036, 1017, 985, 915, 863, 836, 782, 738, 674 cm$^{-1}$; $^1$H NMR (600 MHz, $C_6D_6$) δ=6.66 (s, 1H), 6.42 (s, 1H), 5.47 (dd, J=7.8, 3.6 Hz, 1H), 4.28 (dd, J=8.4, 3.6 Hz, 1H), 4.16 (d, J=9.0 Hz, 1H), 3.03 (dq, J=8.4, 6.6 Hz, 1H), 2.71 (dd, J=16.2, 8.4 Hz, 1H), 2.62-2.58 (m, 2H), 2.31-2.27 (m, 1H), 2.30 (s, 3H), 2.20 (s, 3H), 2.10 (ddd, J=15.0, 9.0, 9.0 Hz, 1H), 1.99 (dd, J=12.0, 7.2 Hz, 1H), 1.90-1.82 (m, 2H), 1.74-1.68 (m, 1H), 1.66-1.59 (m, 1H), 1.54-1.47 (m, 2H), 1.24-1.18 (m, 1H), 1.19 (d, J=6.6 Hz, 3H), 1.18 (s, 3H), 1.16-1.13 (m, 1H), 1.14 (d, J=6.6 Hz, 3H), 1.10 (s, 3H), 1.08 (t, J=7.8 Hz, 9H), 1.06 (t, J=7.8 Hz, 9H), 1.00-0.96 (m, 1H), 0.90 (s, 3H), 0.83-0.76 (m, 6H), 0.73-0.69 (m, 6H), 0.45-0.38 (m, 2H), 0.23-0.15 (m, 2H) ppm; $^{13}$C NMR (151 MHz, $C_6D_6$) δ=214.6, 170.7, 165.2, 153.7, 138.8, 120.6, 116.5, 79.7, 75.7, 56.9, 53.5, 49.5, 47.9, 43.5, 40.4, 37.5, 36.6, 35.2, 32.4, 30.2, 25.5, 23.6, 22.7, 20.1, 17.6, 15.9, 15.4, 14.6, 12.0, 7.43, 7.36, 5.9, 5.8, 3.6, 3.4 ppm; HRMS (ESI) calcd for $C_{43}H_{77}N_2O_5Si_2S_2$[M+H]$^+$ 821.4807, found 821.4789.

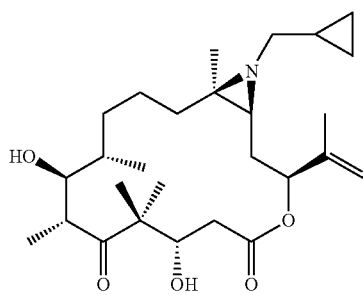

81

Epothilone 81:

To a stirred solution of protected epothilone 81a (18.0 mg, 0.022 mmol, 1.0 equiv.) in tetrahydrofuran (2.0 mL) at 0° C. was added hydrogen fluoride-pyridine complex (70% HF, 0.20 mL, 3.85 mmol, 175 equiv.). The reaction mixture was allowed to warm to 25° C., stirred for 3.5 h, and then quenched with a saturated aqueous solution of sodium bicarbonate (10 mL). The two phases were separated, and the aqueous layer was extracted with ethyl acetate (3×5 mL). The combined organic layers were dried with anhydrous sodium sulfate and concentrated in vacuo. The obtained residue was purified by flash column chromatography (silica gel, 1→5% methanol in ethyl acetate) to afford pure epothilone 81 (12.0 mg, 0.020 mmol, 92%) as a colorless oil. 81: $R_f$=0.39 (silica gel, 5% methanol in ethyl acetate); $[\alpha]_D^{25}$=−31.2 (c=1.00, $CH_2Cl_2$); FT-IR (neat) $\nu_{max}$ 3375, 2957, 2924, 2853, 1729, 1687, 1555, 1464, 1424, 1378, 1251, 1148, 1036, 1009, 981, 939, 882, 832, 734 cm$^{-1}$; $^1$H NMR (600 MHz, CD$_2$Cl$_2$) δ=7.01 (s, 1H), 6.48 (s, 1H), 5.44 (dd, J=4.8, 4.8 Hz, 1H), 4.09 (dd, J=10.2, 3.0 Hz, 1H), 3.73 (dd, J=4.8, 4.8 Hz, 1H), 3.32 (dq, J=6.6, 6.6 Hz, 1H), 2.70 (s, 3H), 2.48 (dd, J=13.8, 4.2 Hz, 1H), 2.41-2.37 (m, 1H), 2.40 (dd, J=13.8, 3.0 Hz, 1H), 2.30-2.26 (m, 1H), 2.12 (s, 3H), 1.92-1.90 (m, 2H), 1.76-1.66 (m, 2H), 1.56-1.38 (m, 4H), 1.37 (s, 3H), 1.33-1.27 (m, 2H), 1.24-1.22 (m, 1H), 1.13 (s, 3H), 1.11 (d, J=7.2 Hz, 3H), 1.04 (s, 3H), 0.96 (d, J=7.2 Hz, 3H) 0.53-0.45 (m, 2H), 0.20-0.16 (m, 1H), 0.11-0.08 (m, 1H) ppm; $^{13}$C NMR (151 MHz, CD$_2$Cl$_2$) δ=220.8, 171.6, 165.8, 153.3, 137.9, 118.9, 116.3, 78.1, 75.5, 57.9, 52.9, 48.2, 44.5, 43.2, 39.6, 35.5, 35.2, 32.0, 30.3, 23.0, 22.0, 21.3, 20.4, 17.7, 16.9, 16.3, 15.7, 14.1, 11.5, 4.2, 4.0 ppm; HRMS (ESI) calcd for C$_{31}$H$_{49}$N$_2$O$_5$S$_2$[M+H]$^+$ 593.3077, found 593.3063.

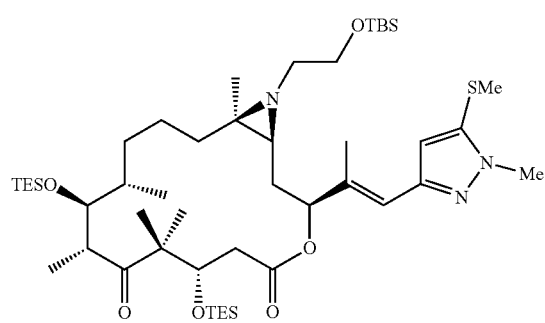

82a

Protected Epothilone 82a:

To a stirred solution of phosphonate 59 (350 mg, 0.906 mmol, 16 equiv.) in tetrahydrofuran (1.0 mL) at −78° C. was carefully added n-butyllithium (2.5 M hexanes, 0.29 mL, 0.725 mmol, 13 equiv.). After stirring for 45 min at the same temperature, a solution of methyl ketone 30 (45.0 mg, 0.056 mmol, 1.0 equiv.) in tetrahydrofuran (0.6 mL) was added. The reaction mixture was allowed to slowly warm to 25° C., stirred for an additional 2 h, and quenched with a saturated aqueous solution of ammonium chloride (10 mL). The two phases were separated, and the aqueous layer was extracted with ethyl acetate (3×5 mL). The combined organic layers were dried with anhydrous sodium sulfate and concentrated in vacuo. The obtained residue was purified by flash column chromatography (silica gel, 10→60% ethyl acetate in hexanes) to afford protected epothilone 82a (36.5 mg, 0.040 mmol, 70%, E:Z=1:1) as a colorless oil. 82a: R$_f$=0.32 (silica gel, 30% ethyl acetate in hexanes); [u]$_D^{25}$=−5.3 (c=1.00, CH$_2$Cl$_2$); FT-IR (neat) v$_{max}$ 2952, 2929, 2876, 2857, 1740, 1696, 1461, 1415, 1380, 1280, 1251, 1200, 1181, 1158, 1102, 1040, 1018, 1006, 984, 940, 916, 834, 812, 778, 733, 677 cm$^{-1}$; $^1$H NMR (600 MHz, C$_6$D$_6$) δ=6.80 (s, 1H), 6.78 (d, J=5.4 Hz, 1H), 6.37 (s, 1H), 6.30 (s, 1H), 6.28 (s, 1H), 5.49 (dd, J=8.4, 2.4 Hz, 1H), 4.24 (ddd, J=16.8, 8.4, 1.8 Hz, 2H), 4.18 (dd, J=8.4, 3.0 Hz, 2H), 3.90-3.78 (m, 4H), 3.46 (s, 3H), 3.42 (s, 3H), 3.10-3.02 (m, 2H), 2.85-2.81 (m, 1H), 2.76-2.68 (m, 3H), 2.62-2.55 (m, 3H), 2.47-2.43 (m, 2H), 3.29 (ddd, J=15.0, 4.2, 4.2 Hz, 1H), 2.26 (s, 3H), 2.20-2.15 (m, 1H), 2.10-2.03 (m, 1H), 1.90-1.85 (m, 4H), 1.89 (s, 3H), 1.82 (s, 3H), 1.78-1.71 (m, 3H), 1.76 (s, 3H), 1.66-1.47 (m, 7H), 1.21-1.13 (m, 28H), 1.10-1.03 (m, 36H), 0.99 (s, 9H), 0.98 (s, 9H), 0.93 (s, 3H), 0.85 (s, 3H), 0.83-0.78 (m, 6H), 0.77-0.70 (m, 18H), 0.090 (s, 3H), 0.088 (s, 3H), 0.082 (s, 3H), 0.074 (s, 3H) ppm; $^{13}$C NMR (151 MHz, C$_6$D$_6$) δ=214.5, 170.7, 148.8, 148.4, 138.5, 137.3, 136.0, 135.9, 119.7, 119.0, 110.2, 110.1, 80.4, 80.1, 79.5, 76.0, 75.8, 74.0, 64.4, 64.3, 55.3, 54.9, 53.5, 53.4, 50.6, 50.2, 48.2, 48.1, 43.4, 43.2, 40.2, 40.1, 37.4, 37.3, 36.6, 36.4, 36.2, 36.1, 35.6, 35.4, 32.3, 26.2, 25.5, 25.4, 23.8, 23.5, 23.2, 23.1, 20.3, 20.1, 19.1, 18.5, 18.4, 17.7, 17.6, 15.7, 15.6, 14.9, 7.4, 7.3, 7.2, 6.0, 5.9, 5.8, −5.1 ppm ($^1$H and $^{13}$C NMR were recorded as mixture); HRMS (ESI) calcd for C$_{48}$H$_{92}$N$_3$O$_6$Si$_3$S [M+H]$^+$ 922.6009, found 922.6010.

82

Epothilone 82:

To a stirred solution of protected epothilone 82a (8.0 mg, 0.009 mmol, 1.0 equiv.) in tetrahydrofuran (1.0 mL) at 0° C. was added hydrogen fluoride-pyridine complex (70% HF, 0.10 mL, 3.85 mmol, 428 equiv.). The reaction mixture was allowed to warm to 25° C., stirred for 5 h, and then quenched with a saturated aqueous solution of sodium bicarbonate (10 mL). The two phases were separated, and the aqueous layer was extracted with ethyl acetate (3×5 mL). The combined organic layers were dried with anhydrous sodium sulfate and concentrated in vacuo. The obtained residue was purified by flash column chromatography (silica gel, 5→20% methanol in ethyl acetate) to afford pure epothilone 82 (4.1 mg, 0.007 mmol, 81%) as a colorless oil. 82: R$_f$=0.28 (silica gel, 20% methanol in ethyl acetate); [α]$_D^{25}$=−20.0 (c=0.10, CH$_2$Cl$_2$); FT-IR (neat) v$_{max}$ 3367, 2922, 2852, 1727, 1687, 1555, 1462, 1378, 1334, 1274, 1261, 1148, 1057, 980, 885, 802, 764, 749, 671 cm$^{-1}$; $^1$H NMR (600 MHz, CD$_2$Cl$_2$) δ=6.40 (s, 1H), 6.33 (s, 1H), 6.31 (dd, J=8.4, 4.2 Hz, 1H), 6.21 (s, 1H), 6.15 (s, 1H), 5.43 (dd, J=4.8, 4.8 Hz, 1H), 4.05-4.02 (m, 2H), 3.85 (s, 3H), 3.84 (s, 3H), 3.77-3.73 (m, 2H), 3.68-3.60 (m, 4H), 3.31-3.26 (m, 1H), 3.24-3.20 (m, 1H), 2.76-2.73 (m, 1H), 2.65-2.61 (m, 1H), 2.59-2.55 (m, 1H), 2.53-2.46 (m, 3H), 2.44-2.37 (m, 3H), 2.41 (s, 6H), 2.06-2.02 (m, 1H), 1.94-1.92 (m, 1H), 1.90-1.82 (m, 2H), 1.87 (s, 3H), 1.70-1.64 (m, 2H), 1.56-1.42 (m, 8H), 1.37-1.30 (m, 5H), 1.34 (s, 3H), 1.33 (s, 3H), 1.14 (s, 6H), 1.20 (d, J=7.2 Hz, 6H), 1.07 (s, 3H), 1.03 (s, 3H), 0.97 (d, J=7.2 Hz, 3H), 0.96 (d, J=7.2 Hz, 3H) ppm; $^{13}$C NMR (151 MHz, CD$_2$Cl$_2$) δ=220.7, 171.3, 148.4, 147.9, 137.8, 137.0, 135.8, 119.0, 118.1, 109.6, 109.3, 77.8, 75.9, 75.0, 74.8, 73.9, 73.8, 62.4, 62.2, 60.6, 55.3, 54.7, 52.8, 52.7, 49.4, 48.2, 44.8, 44.6, 43.4, 39.7, 39.5, 36.9, 36.8, 36.0, 35.8, 35.5, 34.7, 32.9, 31.8, 31.1, 29.5, 21.9, 21.8, 21.4, 20.2, 19.9, 19.4, 19.1, 19.0, 17.6, 17.3, 16.5, 16.3, 15.7, 14.5, 13.2 ppm ($^1$H and $^{13}$C NMR were recorded as mixture); HRMS (ESI) calcd for $C_{30}H_{49}N_3O_6SNa$ [M+Na]$^+$ 602.3234, found 602.3235.

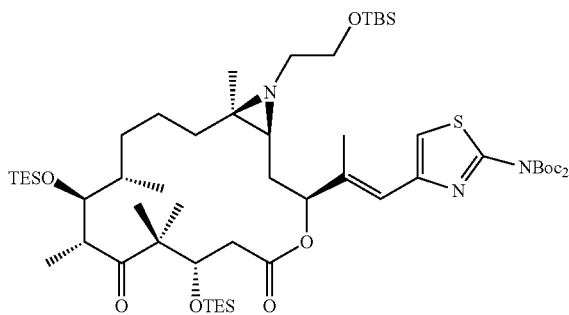

83a

Epothilone 83a:

To a stirred solution of phosphonate 64 (118 mg, 0.263 mmol, 14 equiv.) in tetrahydrofuran (1.0 mL) at −78° C. was carefully added sodium bis(trimethylsilyl)amide (1.0 M tetrahydrofuran, 0.26 mL, 0.263 mmol, 14 equiv.). After stirring for 30 min at the same temperature, a solution of methyl ketone 30 (15.0 mg, 0.019 mmol, 1.0 equiv.) in tetrahydrofuran (1.0 mL) was added. The reaction mixture was allowed to slowly warm to 0° C., stirred for an additional 3.5 h, and quenched with a saturated aqueous solution of ammonium chloride (10 mL). The two phases were separated, and the aqueous layer was extracted with ethyl acetate (3×5 mL). The combined organic layers were dried with anhydrous sodium sulfate and concentrated in vacuo. The obtained residue was purified by flash column chromatography (silica gel, 5→20% ethyl acetate in hexanes) to afford protected epothilone 83a (14.2 mg, 0.013 mmol, 69%) as a colorless oil. 83a: R$_f$=0.20 (silica gel, 10% ethyl acetate in hexanes); [α]$_D^{25}$=−7.5 (c=1.00, CH$_2$Cl$_2$); FT-IR (neat) ν$_{max}$ 2954, 2933, 2877, 2858, 1780, 1728, 1696, 1505, 1460, 1413, 1370, 1334, 1283, 1249, 1158, 1120, 1041, 1007, 984, 836, 806, 779, 738 cm$^{-1}$; $^1$H NMR (600 MHz, C$_6$D$_6$) δ=6.57 (s, 1H), 6.33 (s, 1H), 5.43 (dd, J=8.6, 2.8 Hz, 1H), 4.22 (dd, J=9.2, 2.6 Hz, 1H), 4.18 (d, J=9.0 Hz, 1H), 3.87-3.79 (m, 2H), 3.01 (dq, J=7.2, 7.2 Hz, 1H), 2.73 (ddd, J=12.0, 5.9, 5.9 Hz, 1H), 2.68 (dd, J=16.1, 9.3 Hz, 1H), 2.56 (dd, J=16.1, 2.9 Hz, 1H), 2.44 (ddd, J=12.0, 6.0, 6.0 Hz, 1H), 2.34 (s, 3H), 2.26-2.24 (m, 1H), 2.08-2.02 (m, 1H), 1.87-1.80 (m, 2H), 1.75-1.69 (m, 1H), 1.64-1.57 (m, 1H), 1.51-1.48 (m, 1H), 1.37 (s, 18H), 1.34-1.21 (m, 3H), 1.19 (d, J=6.9 Hz, 3H), 1.18 (s, 3H), 1.15 (s, 3H), 1.13 (d, J=6.9 Hz, 3H), 1.10-1.05 (m, 18H), 0.99 (s, 9H), 0.85 (s, 3H), 0.83-0.77 (m, 6H), 0.74-0.70 (m, 6H), 0.100 (s, 3H), 0.097 (s, 3H) ppm; $^{13}$C NMR (151 MHz, C$_6$D$_6$) δ=214.6, 170.7, 157.8, 150.0, 149.2, 138.3, 121.0, 114.4, 84.2, 80.2, 79.7, 75.9, 64.3, 55.0, 53.5, 50.3, 48.2, 43.4, 40.2, 37.5, 36.4, 35.4, 32.4, 27.7, 26.2, 25.5, 23.7, 23.3, 20.2, 18.6, 17.7, 15.7, 14.6, 7.5, 7.4, 6.0, 5.9, −5.1, ppm; HRMS (ESI) calcd for $C_{56}H_{103}N_3O_{10}Si_3S$ [M+H]$^+$ 1094.6745, found 1094.6742.

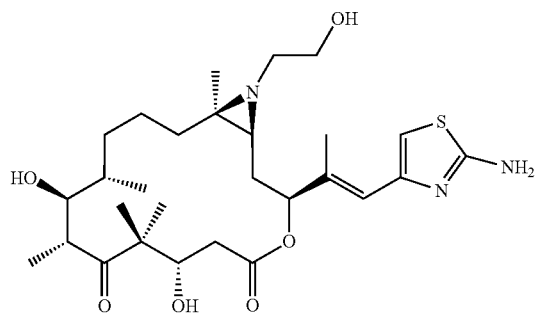

83

Epothilone 83:

To a stirred solution of protected epothilone 83a (10.0 mg, 0.009 mmol, 1.0 equiv.) in tetrahydrofuran (2.0 mL) at 0° C. was added hydrogen fluoride-pyridine complex (70% HF, 0.05 mL, 1.94 mmol, 215 equiv.). The reaction mixture was allowed to warm to 25° C. and stirred for an additional 5 h. Then the reaction mixture was quenched with a saturated aqueous solution of sodium bicarbonate (10 mL), and the two phases were separated. The aqueous layer was extracted with ethyl acetate (3×10 mL), and the combined organic layers were dried with anhydrous sodium sulfate and concentrated in vacuo. The crude material was resuspended in dichloromethane (1.0 mL) and cooled to 0° C. Trifluoroacetic acid (0.10 mL, 1.30 mmol, 144 equiv.) was added, the reaction mixture was stirred for 6 h, and then allowed to warm to 25° C. The solvent was removed in vacuo, and the resulting residue was redissolved in ethyl acetate (15 mL). A saturated aqueous solution of sodium bicarbonate (5 mL) was added with stirring. After 10 min, the two phases were separated, and the organic layer was dried with anhydrous sodium sulfate and concentrated in vacuo. The obtained residue was purified by flash column chromatography (silica gel, 10% methanol in dichloromethane) to afford pure epothilone 83 (4.0 mg, 0.007 mmol, 80%) as a colorless oil. 83: R$_f$=0.13 (silica gel, 10% methanol in dichloromethane); [α]$_D^{25}$=−16.7 (c=0.15, CH$_2$Cl$_2$); FT-IR (neat) ν$_{max}$ 3332, 2926, 2856, 1727, 1686, 1529, 1464, 1378, 1346, 1262, 1148, 1054, 1009, 982, 885, 875, 799, 735, 689 cm$^{-1}$; $^1$H NMR (600 MHz, CD$_2$Cl$_2$) δ=6.40 (s, 1H), 6.32 (s, 1H), 5.37 (dd, J=5.2, 5.2 Hz, 1H), 5.12 (br s, 2H), 4.07 (dd, J=10.1, 2.0 Hz, 1H), 3.73-3.70 (m, 4H), 3.26 (dq, J=7.2, 7.2 Hz, 1H), 2.74-2.64 (m, 2H), 2.47 (dd, J=13.9, 10.2 Hz, 1H), 2.35 (dd, J=13.9, 2.3 Hz, 1H), 2.06 (s, 3H), 2.03-1.98 (m, 3H), 1.72-1.66 (m, 1H), 1.55-1.41 (m, 5H), 1.34 (s, 3H), 1.32-1.27 (m, 3H), 1.21 (s, 3H), 1.11 (d, J=6.9 Hz, 3H), 1.03 (s, 3H), 0.96 (d, J=6.9 Hz, 3H) ppm; $^{13}$C NMR (151 MHz, CD$_2$Cl$_2$) δ=220.7, 171.3, 167.0, 148.8, 136.6, 119.7, 107.6, 78.0, 75.3, 74.4, 61.7, 54.8, 53.1, 44.3, 39.6, 35.6, 34.2, 32.3, 31.5, 30.1, 27.6, 23.1, 21.7, 20.6, 17.5, 16.7, 15.7, 14.3 ppm; HRMS (ESI) calcd for $C_{28}H_{45}N_3O_6S$ [M+Na]$^+$ 574.2921, found 574.2899.

Example 4—Biological Activity

Biological evaluation. The synthesized epothilone analogues were submitted to the NCI for testing against the NCI-60 human cancer cell line panel (Shoemaker, 2006). The N-Boc (5 and 6) and N-Teoc (7) protected analogues did not exhibit significant activity beyond the initial one dose test (10 μM) and, therefore, were not screened further. Compounds 8-14, however, having passed the initial one dose test, were subjected to duplicate five dose screens that revealed potent activities against a number of tumor cell lines, as highlighted in Table 1. Analogues 11 and 12 exhibited the strongest activities in this study, as demonstrated in Table 1.

TABLE 1

Selected NCI-60 Cytotoxicity Data [(GI$_{50}$, nM)$^a$ of 8-12, 14]$^b$

| Cell line | Compound | | | | | |
|---|---|---|---|---|---|---|
| | 8 | 9 | 10 | 11 | 12 | 14 |
| CCRF-CEM | 34.1 | 47.6 | 22.6 | 12.3 | 6.09 | 13.6 |
| HL-60(TB) | 15.8 | 7.88 | 17.2 | 7.36 | <5.00$^c$ | 14.1 |
| K-562 | 24.7 | 15.7 | 24.4 | 10.2 | <5.00 | 20.7 |
| MOLT-4 | 38.9 | 48.1 | 27.6 | 14.2 | <5.00 | 28.3 |
| RPMI-8226 | 21.3 | 11.1 | 17.8 | 9.98 | <5.00 | 19.6 |
| SR | 30.3 | NA$^d$ | 27.4 | 7.29 | <5.00 | 29.2 |
| A549/ATCC | 36.9 | 48.8 | 34.5 | 13.4 | 6.05 | 37.6 |
| HOP-92 | 146 | 183 | 80.7 | 16.1 | <5.00 | —$^e$ |
| NCI-H23 | 25.2 | 88.5 | 35.8 | 18.3 | 5.72 | 24.2 |
| NCI-H460 | 20.5 | 6.45 | 20.3 | 8.73 | <5.00 | 20.8 |
| COLO 205 | 18.6 | 14.7 | 20.4 | 8.48 | <5.00 | 18.2 |
| HCT-116 | 18.7 | 5.31 | 18.3 | 4.82 | <5.00 | 17.1 |
| HCT-15 | 26.7 | 22.0 | 32.5 | 11.0 | <5.00 | 22.6 |
| HT29 | 19.6 | 5.29 | 18.8 | 5.74 | <5.00 | 18.4 |
| KM12 | 19.2 | 5.25 | 20.6 | 9.16 | <5.00 | 17.7 |
| SW-620 | 25.0 | 5.40 | 24.5 | 6.23 | <5.00 | 23.6 |
| SF-539 | 19.0 | 24.8 | 15.8 | 9.55 | 9.41 | 26.2 |
| SNB-75 | 11.4 | NA | 16.4 | 5.75 | <5.00 | 11.7 |
| U251 | 35.6 | 38.1 | 30.8 | 14.6 | <5.00 | 36.2 |
| LOX IMVI | 23.6 | 25.0 | 31.3 | 10.3 | <5.00 | 23.1 |
| M14 | 19.2 | 13.7 | 18.0 | 4.88 | <5.00 | 18.7 |
| MDA-MB-435 | 8.09 | 2.08 | 9.56 | <3.25 | <5.00 | 8.35 |
| SK-MEL-5 | 20.0 | 22.1 | 21.9 | 10.1 | <5.00 | 18.0 |
| OVCAR-3 | 18.1 | 15.8 | 18.8 | 10.2 | <5.00 | 17.6 |
| A498 | 102 | 66.0 | 18.8 | 11.3 | <5.00 | 80.2 |
| RXF 393 | 38.4 | 40.7 | 39.6 | 14.0 | 9.39 | 30.6 |
| PC-3 | 30.4 | 32.2 | 34.3 | 12.7 | 9.75 | 25.8 |
| MCF7 | 15.2 | 3.65 | 17.7 | <3.25 | <5.00 | 14.0 |
| HS 578T | 44.0 | 36.4 | 31.6 | 7.10 | 5.51 | 37.2 |
| MDA-MB-468 | 39.2 | 23.1 | 23.4 | 10.6 | 7.22 | 20.9 |

$^a$GI$_{50}$ = the concentration that inhibits growth by 50%;
$^b$See FIG. 7 for complete NCI-60 results;
$^c$A less than (<) indicates the actual GI$_{50}$ is below the sensitivity threshold of the screen;
NA = Results not available;
$^e$A "—" indicates a GI$_{50}$ >100 nM.

In order to obtain further insights regarding the biological properties of the synthesized epothilone analogues (5-14) we investigated their ability to induce tubulin polymerization and growth inhibition against human breast (MCF-7) and ovarian (OVCAR-8) cancer cells. Epothilones A (epoA), B (epoB), C (epoC) and D (epoD), ixabepilone (Ixab), and paclitaxel (PTX) were tested in parallel for comparison purposes. As shown in Table 2, analogues 5-7 did not show significant activities in all three assays, whereas all other synthesized compounds (8-14) exhibited comparable or higher potencies to the naturally occurring epothilones, Ixab, and PTX. Analogues 11 and 12, were proven in this study as well to be highly potent, exhibiting stronger potencies than all the standard epothilones tested (epoA-D, Ixab) and PTX (see Table 2).

Structure-Activity Relationships.

The results of the biological evaluation of the synthesized analogues (5-14, FIG. 3) are consistent and provide further support to previously established structure-activity relationships within the epothilone class (Nicolaou et al., 2006; Altmann et al., 2000; Nicolaou et al., 2000; Nicolaou et al., 2003 and Alhamadsheh et al., 2008). The critical nature of a basic N-atom at a specific location of the side chain serving as a H-acceptor through H-bonding (with the protonated form of a histidine residue in β-tubulin) (Carlomagno et al., 2003; Nettles et al., 2004; Heinz et al., 2005 and Reese et al., 2007) and the steric tolerance of the side chain binding pocket are evident in the present series of compounds. Thus, loss of activity occurred with the three analogues equipped with bulky protecting groups on the side chain attached to the essential N-atom of their pyrazole moiety (i.e. 5-7, FIG. 3). All other analogues (i.e. 8-14, FIG. 3) exhibited strong activities except for 13, which demonstrated lower potencies against certain cell lines (e.g. MCF-7 and OVCAR-8, Table 2, as well as the NCI-60 human tumor cell line panel, Table 1). The significant loss of potency of compound 9 versus 8 (see Table 2) may be attributed to the electron withdrawing effect of the CF$_3$ group that weakens the H-bond accepting ability of the pyrazole N-atom involved in the docking of these molecules to their tubulin binding site. Compounds 11 and 12 proved to be the most potent as seen in Tables 1 and 2. Containing F-residues at the ortho position of the aniline moiety, these analogues enjoy the well-known benefits of fluorine as an enhancing element for bioactivity, (Manallack 2007 and Silverman 2004), while allowing for the H-bond between the crucial N-atom and the β-tubulin histidine, as opposed to the considerably less potent analogue 13, which may be suffering from steric interactions arising from the nearby trifluoromethyl group.

TABLE 2

Cytotoxicity and Tubulin Assembly Assays.

| compound | induction of tubulin assembly$^a$ (EC$_{50}$, µM ± SD)$^b$ | cytotoxicity (GI$_{50}$, nM ± SD)$^c$ | |
|---|---|---|---|
| | | MCF-7$^d$ | OVCAR-8$^e$ |
| EpoA | 16 ± 2 | 10 ± 2 | 11 ± 2 |
| EpoB | 3.5 ± 0.7 | 5.5 ± 0.7 | 3.5 ± 0.7 |
| EpoC | 18 ± 0.7 | 70 ± 10 | 110 ± 7 |
| EpoD | 18 ± 0 | 14 ± 1 | 13 ± 4 |
| Ixab | 4.5 ± 0.7 | 7.0 ± 1 | 35 ± 10 |
| PTX | — | 8.5 ± 0.7 | 6.5 ± 2 |
| 5 | >40 | 1,600 ± 500 | 900 ± 0 |
| 6 | >40 | 4,400 ± 900 | 1,200 ± 40 |
| 7 | >40 | 1,800 ± 700 | 1,300 ± 100 |
| 8 | 15 ± 4 | 10 ± 0 | 38 ± 10 |
| 9 | >40 | 900 ± 100 | 300 ± 0$^3$ |
| 10 | 8.0 ± 1 | 5.5 ± 0.7 | 23 ± 10 |
| 11 | 2.5 ± 0.5 | 3.0 ± 1 | 2.5 ± 0.4 |
| 12 | 7.8 ± 1 | 2.5 ± 0.7 | 1.8 ± 0.4 |
| 13 | >40 | 9.0 ± 1 | 35 ± 5 |
| 14 | 19 ± 1 | 14 ± 2 | 38 ± 10 |

$^a$In these experiments each 100 µL reaction mixture contained 1.0 mg/mL (10 µM) tubulin, 0.4M monosodium glutamate (taken from 2.0M stock solution adjusted to pH 6.6 with HCl, 0.5 mM MgCl$_2$, 2% (v/v) dimethyl sulfoxide, and varying compound concentrations. Incubation was for 30 min at room temperature (about 22° C.). Reaction mixtures were centrifuged for 10 min in an Eppendorf centrifuge at room temperature at 14,000 rpm. Protein was determined in 50 µL of the supernatant, using the Lowry assay, see Lin, et al., 1996;

$^b$EC50 = drug concentration yielding an unbound protein supernatant 50% that of controls;

$^c$Cell growth was evaluated using the standard NCI assay, the parameter measured with sulforhodamine B;

GI$_{50}$ = compound concentration that reduces cell growth by 50% after 96 h at 37° C.;

SD = standard deviation, a SD of 0 indicates that the same value was obtained in all three assays;

$^d$Human breast cancer cell line;

$^e$Ovarian cancer cell line.

TABLE 3

Cytotoxicity and tubulin binding assays of analogues 70-83.

| Structures | Enhancement of tubulin assembly[1] (EC50, uM) | Cytotoxicity (nM, ± SD)[2] | | | | |
|---|---|---|---|---|---|---|
| | | MCF-7 | OVCAR-8 | NCI/ADR-RES | MDA-MB-435 | SNB-75 |
| Epo A (1) | 14 ± 3 | 14 ± 4 | 20 ± 5 | 35 ± 5 | 15 ± 2 | 14 ± 3 |
| Epo B (2) | 3.8 ± 0.4 | 9.2 ± 2 | 11 ± 3 | 19 ± 4 | 5.3 ± 0.7 | 6.5 ± 2 |
| Paclitaxel | 5.0 ± 1 | 7.8 ± 2 | 10 ± 2 | 4,200 ± 1,000 | 4.0 ± 1 | 15 ± 0[3] |
| 70 | 19 | 2.0 ± 0 | 1.5 ± 0.7 | 35 ± 7 | —[4] | — |
| 71 | 18.2 | 3.0 ± 1 | 4.5 ± 0.7 | 55 ± 20 | — | — |
| 77 | 5.0 ± 1 | 4.0 ± 1 | 16 ± 4 | 8.8 ± 1 | 4.5 ± 0.5 | 11 ± 3 |
| 78 | 14 ± 3 | 28 ± 6 | 75 ± 10 | 55 ± 7 | 42 ± 5 | 60 ± 10 |
| 80 | 5.4 ± 0.6 | 13 ± 3 | 15 ± 0[4] | 3.2 ± 0.8 | 7.3 ± 2 | 22 ± 3 |
| 79 | 6.1 ± 0.1 | 14 ± 2 | 63 ± 3 | 70 ± 10 | 15 ± 4 | 23 ± 6 |
| 81 | 5.1 ± 0.4 | 18 ± 3 | 15 ± 2 | 18 ± 4 | 9.5 ± 2 | 16 ± 3 |
| 72 | >60 | 40 ± 7 | 38 ± 2 | 4,800 ± 400 | 12 ± 2 | 36 ± 5 |
| 83 | 13 ± 0.4 | 330 ± 40 | 290 ± 10 | 3,800 ± 300 | 220 ± 30 | 280 ± 30 |
| 75 | >60 | 65 ± 7 | 93 ± 20 | 2,800 ± 400 | 20 ± 3 | 130 ± 20 |
| 76 | 9.1 ± 1 | 15 ± 3 | 8.6 ± 1 | 45 ± 6 | 3.8 ± 0.7 | 50 ± 10 |
| 73 | >60 | 250 ± 40 | 170 ± 20 | 4,000 ± 1,000 | 30 ± 4 | 98 ± 10 |
| 74 | 7.9 ± 1 | 11 ± 1 | 23 ± 7 | 630 ± 80 | 3.5 ± 0.3 | 12 ± 3 |
| 82 | 4.6 ± 0.9 | 10 ± 1 | 78 ± 4 | 7.5 ± 2 | 12 ± 2 | 10 ± 2 |

[1]Assay as described in Lin, et al., 1996. In these experiments each 100 μL reaction mixture contained 1.0 mg/mL (10 μM) tubulin, 0.4M monosodium glutamate (taken from 2.0M stock solution adjusted to pH 6.6 with HCl, 0.5 mM MgCl$_2$, 2% (v/v) dimethyl sulfoxide, and varying compound concentrations. Incubation was for 30 min at room temperature (about 22° C.). Reaction mixtures were centrifuged for 10 min in an Eppendorf centrifuge at room temperature at 14,000 rpm. Protein was determined in 50 μL of the supernatant, using the Lowry assay.
[2]Cell growth was evaluated using the standard NCI assay, with protein the parameter measured with sulforhodamine B. The IC$_{50}$ is the compound concentration that reduces cell growth by 50% after 96 h at 37° C. The NCI/ADR-RES cell line is an isogenic clone of OVCAR-8 that overexpresses P-glycoprotein, resulting in multidrug resistance.
[3]A SD of 0 indicates that the same value was obtained in all assays.
[4]Data not available.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

V. REFERENCES

The following references, to the extent that they provide exemplary procedural or other details supplementary to those set forth herein, are specifically incorporated herein by reference:

Alhamadsheh et al., *Chem. Eur. J.*, 14: 570-581, 2008.
Altmann et al., *Bioorg. Med. Chem. Lett.*, 10: 2765-2768, 2000.
Altmann, et al., "The Epothilones: An Outstanding Family of Anti-Tumor Agents," In *Progess in the Chemistry of Organic Natural Products*, Eds. Kinghorn, Falk, and Kobayashi, Springer, New York, 2004.
Anderson, N. G., *Practical Process Research & Development—A Guide For Organic Chemists*, 2$^{nd}$ ed., Academic Press, New York, 2012.
Austin-Ward and Villaseca, *Rev. Med Chil.*, 126(7):838-45, 1998.
Barclay et al. (eds.), The Leucocyte Antigen Facts Book, 1993, Academic Press.
Bellamy and Ou, *Tet. Lett.*, 25: 839-842, 1984.
Bode and Carreira, *J. Am. Chem. Soc.*, 123:3611-3612, 2001.
Bukowski et al., *Clin. Cancer Res.*, 4(10):2337-47, 1998.
Burkly et al.: TWEAKing tissue remodeling by a multifunctional cytokine: role of TWEAK/Fn14 pathway in health and disease. *Cytokine* 40:1-16 (2007).
Campbell et al., *Cancer Res.*, 51(19):5329-5338 1991.
Carlomagno et al., *Angew. Chem. Int. Ed.*, 42, 2511-2515, 2003.
Christodoulides et al., *Microbiology*, 144(Pt 11):3027-37, 1998.
Davidson et al., *J. Immunother.*, 21(5):389-98, 1998.
Ermolenko and Potier, *Tet. Lett.*, 43:2895-2898, 2002.
Hammick and Voaden, *J. Chem. Soc.*, 3303, 1961.
Hanibuchi et al., *Int. J. Cancer*, 78(4):480-485, 1998.
Heinz et al., *Angew. Chem. Int. Ed.*, 44: 1298-1301, 2005.
Hellstrand et al., *Acta Oncol.*, 37(4):347-353, 1998.
Höfle, et al., *Angew. Chem. Int. Ed.*, 35:1567-1569, 2004.
Hui and Hashimoto, *Infect. Immun.*, 66(11):5329-36, 1998.
Izgu and Hoye, *Tet. Lett.*, 53, 4938-4941, 2012.
Ju et al., *Gene Ther.*, 7(19):1672-1679, 2000.
Keck, et al., *J. Org. Chem.*, 73:9675-9691, 2008.
Lee, et al., *J. Am. Chem. Soc.*, 123:5249, 2001.
Lin, et al., *Cancer Chemother. Pharmacol.*, 38:136-140, 1996.
Manallack, *Perspect. Med Chem.*, 1, 25-38, 2007.
*March's Advanced Organic Chemistry: Reactions, Mechanisms, and Structure*, 2007.
Martin and Thomas, *Tet. Lett.*, 42:8378-8377, 2001.
Masuda and Okutani, *Tetrahedron*, 30:409, 1974.
May and Grieco, *Chem. Commun.*, 1597-1598, 1998.
Mitchell et al., *Ann. NY Acad Sci.*, 690:153-166, 1993.
Mitchell et al., *J. Clin. Oncol.*, 8(5):856-869, 1990.

Meng, et al., *J. Am. Chem. Soc.*, 119:10073-10092, 1997.
Morton et al., *Arch. Surg.*, 127:392-399, 1992.
Mulzer, et al., *Tet. Lett.*, 39:8633-8636, 1998.
Nechushtan et al., 1997
Nettles et al., *Science*, 305: 866-869, 2004.
Nicolaou et al., *Angew. Chem. Int. Ed.*, 42: 3515-3520, 2003.
Nicolaou et al., *Bioorg. Med Chem.*, 7: 665-697, 1990.
Nicolaou et al., *Chem. Biol.*, 7: 593-599, 2000.
Nicolaou et al., *Chem. Eur. J.*, 6: 2783-2800, 2000.
Nicolaou et al., *ChemMedChem.*, 1: 41-44, 2006.
Nicolaou, et al., *J. Am. Chem. Soc.*, 119:7960-7973, 1997a.
Nicolaou, et al., *J. Am. Chem. Soc.*, 119:7974-7991, 1997b.
Nicolaou, et al., *Angew. Chem. Int. Ed.*, 37:84, 1998.
Onda et al., *Cancer Res.*, 64:1419-1424, 2004.
PCT Publication No. 2008/121949
PCT Publication No. 2011/053435
PCT Publication No. 2014/087413
Pietras et al., *Oncogene*, 17(17):2235-49, 1998.
Pratt, *PhD Dissertation*, The Scripps Research Institute, 2008.
Qin et al., *Proc. Natl. Acad Sci. USA*, 95(24): 14411-14416, 1998.
Ravindranath and Morton, *Intern. Rev. Immunol.*, 7: 303-329, 1991.
Reese et al., *Angew. Chem. Int. Ed.*, 46: 1864-1868, 2007.
Remington's Pharmaceutical Sciences, 15$^{th}$ Ed., 1035-1038 and 1570-1580, 1990.
Remington's Pharmaceutical Sciences, 15$^{th}$ Ed., 3:624-652, 1990.
Rosenberg et al., *Ann. Surg.* 210(4):474-548, 1989.
Rosenberg et al., *N. Engl. J. Med*, 319:1676, 1988.
Sawada, et al., *J. Am. Chem. Soc.*, 122:10521-10532, 2000.
Schank et al., *Tetrahedron*, 50: 3721-3742, 1994.
Schinzer, et al., *Synlett*, 861-863, 1998.
Shoemaker, *Nat. Rev. Cancer*, 6: 813-823, 2006.
Shoji et al., *J. Am. Chem. Soc.*, 129:1456-1464, 2007.
Silverman, *The Organic Chemistry of Drug Design and Drug Action*, 2$^{nd}$ Ed.; Elsevier Academic Press: Burlington, Mass., 2004; pp. 62-64.
Sinha, et al., *Proc. Natl. Acad. Sci. USA*, 95:14603-14608, 1998.
Taylor and Chen, *Org. Lett.*, 3:2221-2224, 2001.
Thompson (ed.), 1994, The Cytokine Handbook, Academic Press, San Diego.
U.S. Pat. No. 5,739,169
U.S. Pat. No. 5,801,005
U.S. Pat. No. 5,824,311
U.S. Pat. No. 5,830,880
U.S. Pat. No. 5,846,945
U.S. Pat. No. 6,232,287
U.S. Pat. No. 6,528,481
U.S. Pat. No. 7,452,964
U.S. Pat. No. 7,671,010
U.S. Pat. No. 7,781,565
U.S. Pat. No. 8,450,278
U.S. Pat. No. 8,507,445
U.S. Patent Publication No. 2004/005647
U.S. Patent Publications No. 2006/0034925
U.S. Patent Publications No. 2006/0115537
U.S. Patent Publications No. 2006/0223114
U.S. Patent Publications No. 2006/0234299
U.S. Patent Publications No. 2007/0148095
U.S. Patent Publications No. 2012/0141550
U.S. Patent Publications No. 2013/0138032
U.S. Patent Publications No. 2014/0024610
Valluri, et al., *Org. Lett.*, 3:3607-3609, 2001.
Wang, et al., *Org. Lett.*, 14:6354-6357, 2012.
Weitman et al., *Cancer Res.*, 52(12):3396-3401, 1992b.
Weitman et al., *Cancer Res.*, 52(23):6708-6711, 1992a.
White, et al., *J. Org. Chem.*, 64:684-685, 1999.
Winkles JA: The TWEAK-Fn14 cytokine-receptor axis: discovery, biology and therapeutic targeting. *Nat Rev Drug Discov* 7:411-425 (2008).
Winthrop et al., *Clin. Cancer Res.*, 9:3845s-3853s, 2003.
WO 2012/003498A1
Xing and Ogata, *J. Org. Chem.*, 47, 3577-3581, 1982.
Zhou et al., *Mol Cancer Ther.* 10(7): 1276-88, 2011.

What is claimed is:

1. A compound of the formula:

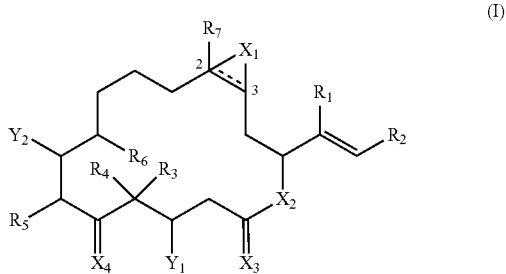

(I)

wherein:
$X_1$ is —O—;
$X_2$, $X_3$, and $X_4$ are each independently —O— or —$NR_b$—; wherein
$R_b$ is hydrogen or alkyl$_{(C\leq 8)}$, cycloalkyl$_{(C\leq 8)}$, alkanediyl$_{(C\leq 6)}$-cycloalkyl$_{(C\leq 8)}$, aralkyl$_{(C\leq 8)}$, or a substituted version of either of these groups;
$Y_1$ and $Y_2$ are each independently amino, hydroxy, or alkoxy$_{(C\leq 8)}$, aralkoxy$_{(C\leq 8)}$, acyloxy$_{(C\leq 8)}$, alkylamino$_{(C\leq 8)}$, dialkylamino$_{(C\leq 8)}$, amido$_{(C\leq 8)}$, or a substituted version of any of these groups, or —$OR_c$, wherein:
$R_c$ is a hydroxy protecting group;
$R_1$, $R_3$, $R_4$, $R_5$, $R_6$ and $R_7$ are each independently hydrogen or alkyl$_{(C\leq 12)}$, cycloalkyl$_{(C\leq 12)}$, alkenyl$_{(C\leq 12)}$, alkynyl$_{(C\leq 12)}$, aryl$_{(C\leq 12)}$, or a substituted version of any of these groups; and
$R_2$ is -heteroarenediyl$_{(C\leq 8)}$-$R_d$ or substituted -heteroarenediyl$_{(C\leq 8)}$-$R_d$; wherein:
the heteroarenediyl$_{(C\leq 8)}$ of $R_2$ is pyrazolyl, 3-trifluoromethylpyrazolyl, or 3-methylthiopyrazolyl; and
$R_d$ is substituted alkyl$_{(C\leq 12)}$; or aryl$_{(C\leq 12)}$, aralkyl$_{(C\leq 12)}$, heteroaryl$_{(C\leq 12)}$, heteroaralkyl$_{(C\leq 12)}$, or a substituted version of any one of these groups;
or a compound of the formula:

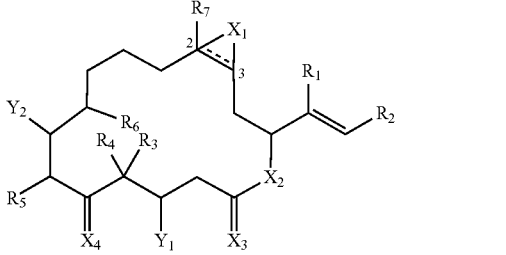

(IA)

wherein:
X$_1$ is absent or —NR$_a$—; wherein
R$_a$ is hydrogen or alkyl$_{(C\leq 8)}$, cycloalkyl$_{(C\leq 8)}$, alkanediyl$_{(C\leq 6)}$-cycloalkyl$_{(C\leq 8)}$, or a substituted version of either of these groups;
provided that when X$_1$ is absent, that the atoms to which it is attached are a part of a double bond; and provided that when the atoms to which it is attached are a part of a double bond, then X$_1$ is absent;
X$_2$, X$_3$, and X$_4$ are each independently —O— or —NR$_b$—; wherein
R$_b$ is hydrogen or alkyl$_{(C\leq 8)}$, cycloalkyl$_{(C\leq 8)}$, alkanediyl$_{(C\leq 6)}$-cycloalkyl$_{(C\leq 8)}$, aralkyl$_{(C\leq 8)}$, or a substituted version of either of these groups;
Y$_1$ and Y$_2$ are each independently amino, hydroxy, or alkoxy$_{(C\leq 8)}$, aralkoxy$_{(C\leq 8)}$, acyloxy$_{(C\leq 8)}$, alkylamino$_{(C\leq 8)}$, dialkylamino$_{(C\leq 8)}$, amido$_{(C\leq 8)}$, or a substituted version of any of these groups, or —OR$_c$, wherein:
R$_c$ is a hydroxy protecting group;
R$_1$, R$_3$, R$_4$, R$_5$, R$_6$ and R$_7$ are each independently hydrogen or alkyl$_{(C\leq 12)}$, cycloalkyl$_{(C\leq 12)}$, alkenyl$_{(C\leq 12)}$, alkynyl$_{(C\leq 12)}$, aryl$_{(C\leq 12)}$, or a substituted version of any of these groups;
R$_2$ is heteroaryl$_{(C\leq 12)}$, -heteroarenediyl$_{(C\leq 8)}$-R$_d$, or a substituted version of either of these groups; wherein:
R$_d$ is alkyl$_{(C\leq 12)}$, aryl$_{(C\leq 12)}$, aralkyl$_{(C\leq 12)}$, heteroaryl$_{(C\leq 12)}$, heteroaralkyl$_{(C\leq 12)}$, or a substituted version of either of these groups;
provided that R$_2$ is not 2-methyl-thiazolyl, 2-hydroxymethyl-thiazolyl, or N-2-methyl-3-methylthiopyrazolyl;
or a pharmaceutically acceptable salt thereof.

2. The compound of claim 1 further defined as:

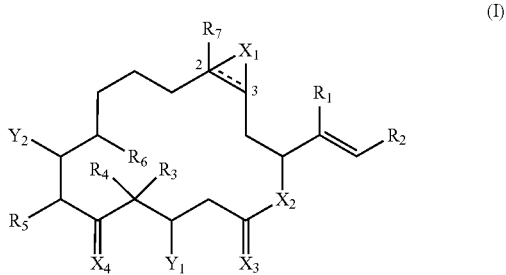

(I)

wherein:
X$_1$ is absent, —O— or —NR$_a$—; wherein
R$_a$ is hydrogen or alkyl$_{(C\leq 8)}$, cycloalkyl$_{(C\leq 8)}$, -alkanediyl$_{(C\leq 6)}$-cycloalkyl$_{(C\leq 8)}$, or a substituted version of either of these groups;
provided that when X$_1$ is absent, that the atoms to which it is attached are a part of a double bond; and provided that when the atoms to which it is attached are a part of a double bond, then X$_1$ is absent;
X$_2$, X$_3$, and X$_4$ are each independently —O— or —NR$_b$—; wherein
R$_b$ is hydrogen or alkyl$_{(C\leq 8)}$, cycloalkyl$_{(C\leq 8)}$, -alkanediyl$_{(C\leq 6)}$-cycloalkyl$_{(C\leq 8)}$, aralkyl$_{(C\leq 8)}$, or a substituted version of either of these groups;
Y$_1$ and Y$_2$ are each independently amino, hydroxy, or alkoxy$_{(C\leq 8)}$, aralkoxy$_{(C\leq 8)}$, acyloxy$_{(C\leq 8)}$, alkylamino$_{(C\leq 8)}$, dialkylamino$_{(C\leq 8)}$, amido$_{(C\leq 8)}$, or a substituted version of any of these groups, or —OR$_c$, wherein:
R$_c$ is a hydroxy protecting group;
R$_1$, R$_3$, R$_4$, R$_5$, R$_6$ and R$_7$ are each independently hydrogen or alkyl$_{(C\leq 12)}$, cycloalkyl$_{(C\leq 12)}$, alkenyl$_{(C\leq 12)}$, alkynyl$_{(C\leq 12)}$, aryl$_{(C\leq 12)}$, or a substituted version of any of these groups; and
R$_2$ is heteroaryl$_{(C\leq 12)}$, -heteroarenediyl$_{(C\leq 8)}$-R$_d$, or a substituted version of either of these groups; wherein:
R$_d$ is alkyl$_{(C\leq 12)}$, aryl$_{(C\leq 12)}$, or a substituted version of either of these groups;
provided that R$_2$ is not 2-methyl-thiazolyl, 2-hydroxymethyl-thiazolyl, or N-2-methyl-3-methylthiopyrazolyl;
or a pharmaceutically acceptable salt thereof.

3. The compound of claim 1 further defined as:

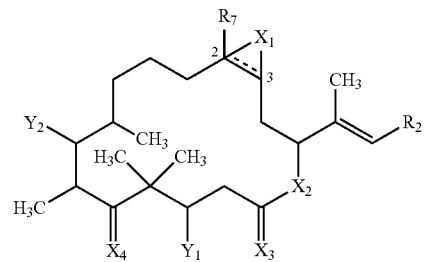

(II)

wherein:
X$_1$ is absent, —O— or —NR$_a$—; wherein
R$_a$ is hydrogen or alkyl$_{(C\leq 8)}$, cycloalkyl$_{(C\leq 8)}$, alkanediyl$_{(C\leq 6)}$-cycloalkyl$_{(C\leq 8)}$, or a substituted version of either of these groups;
provided that when X$_1$ is absent, that the atoms to which it is attached are a part of a double bond; and provided that when the atoms to which it is attached are a part of a double bond, then X$_1$ is absent;
X$_2$, X$_3$, and X$_4$ are each independently —O— or —NR$_b$—; wherein
R$_b$ is hydrogen or alkyl$_{(C\leq 8)}$, cycloalkyl$_{(C\leq 8)}$, alkanediyl$_{(C\leq 6)}$-cycloalkyl$_{(C\leq 8)}$, aralkyl$_{(C\leq 8)}$, or a substituted version of either of these groups;
Y$_1$ and Y$_2$ are each independently amino, hydroxy, or alkoxy$_{(C\leq 8)}$, aralkoxy$_{(C\leq 8)}$, acyloxy$_{(C\leq 8)}$, alkylamino$_{(C\leq 8)}$, dialkylamino$_{(C\leq 8)}$, amido$_{(C\leq 8)}$, or a substituted version of any of these groups, or —OR$_c$, wherein:
R$_c$ is a hydroxy protecting group;
R$_7$ is hydrogen or alkyl$_{(C\leq 12)}$, cycloalkyl$_{(C\leq 12)}$, alkenyl$_{(C\leq 12)}$, alkynyl$_{(C\leq 12)}$, aryl$_{(C\leq 12)}$, or a substituted version of any of these groups; and
R$_2$ is heteroaryl$_{(C\leq 12)}$, -heteroarenediyl$_{(C\leq 8)}$-R$_d$, or a substituted version of either of these groups; wherein:
R$_d$ is alkyl$_{(C\leq 12)}$, aryl$_{(C\leq 12)}$, aralkyl$_{(C\leq 12)}$, heteroaryl$_{(C\leq 12)}$, heteroaralkyl$_{(C\leq 12)}$, or a substituted version of either of these groups;
provided that R$_2$ is not 2-methyl-thiazolyl, 2-hydroxymethyl-thiazolyl, or N-2-methyl-3-methylthiopyrazolyl;
or a pharmaceutically acceptable salt thereof.

4. The compound of claim 1 further defined as:

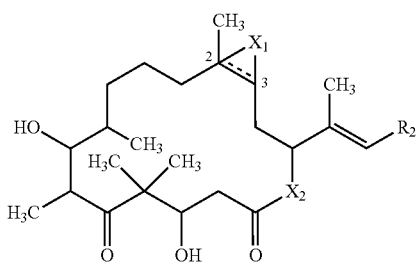
(V)

wherein:
X$_1$ is absent, —O— or —NR$_a$—; wherein
R$_a$ is hydrogen or alkyl$_{(C\leq8)}$, cycloalkyl$_{(C\leq8)}$, alkanediyl$_{(C\leq6)}$-cycloalkyl$_{(C\leq8)}$, or a substituted version of either of these groups;
provided that when X$_1$ is absent, that the atoms to which it is attached are a part of a double bond; and provided that when the atoms to which it is attached are a part of a double bond, then X$_1$ is absent;
X$_2$ is —O— or —NR$_b$—; wherein
R$_b$ is hydrogen or alkyl$_{(C\leq8)}$, cycloalkyl$_{(C\leq8)}$, alkanediyl$_{(C\leq6)}$-cycloalkyl$_{(C\leq8)}$, aralkyl$_{(C\leq8)}$, or a substituted version of either of these groups; and
R$_2$ is heteroaryl$_{(C\leq12)}$, -heteroarenediyl$_{(C\leq8)}$-R$_d$, or a substituted version of either of these groups; wherein:
R$_d$ is alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, or a substituted version of either of these groups;
provided that R$_2$ is not 2-methyl-thiazolyl, 2-hydroxymethyl-thiazolyl, or N-2-methyl-3-methylthiopyrazolyl;
or a pharmaceutically acceptable salt thereof.

5. The compound of claim 1 further defined as:

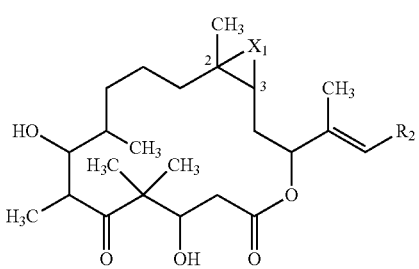
(VII)

wherein:
X$_1$ is —O— or —NR$_a$—; wherein
R$_a$ is hydrogen or alkyl$_{(C\leq8)}$, cycloalkyl$_{(C\leq8)}$, alkanediyl$_{(C\leq6)}$-cycloalkyl$_{(C\leq8)}$, or a substituted version of either of these groups;
R$_2$ is heteroaryl$_{(C\leq12)}$, -heteroarenediyl$_{(C\leq8)}$-R$_d$, or a substituted version of either of these groups; wherein:
R$_d$ is alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, or a substituted version of either of these groups;
provided that R$_2$ is not 2-methyl-thiazolyl, 2-hydroxymethyl-thiazolyl, or N-2-methyl-3-methylthiopyrazolyl;
or a pharmaceutically acceptable salt thereof.

6. The compound of claim 1, wherein R$_1$ is alkyl$_{(C\leq8)}$ or substituted alkyl$_{(C\leq8)}$.

7. The compound of claim 1, wherein R$_3$ is alkyl$_{(C\leq8)}$ or substituted alkyl$_{(C\leq8)}$, R$_4$ is alkyl$_{(C\leq8)}$ or substituted alkyl$_{(C\leq8)}$, R$_5$ is alkyl$_{(C\leq8)}$ or substituted alkyl$_{(C\leq8)}$, R$_6$ is alkyl$_{(C\leq8)}$ or substituted alkyl$_{(C\leq8)}$, or R$_7$ is alkyl$_{(C\leq8)}$ or substituted alkyl$_{(C\leq8)}$.

8. The compound of claim 1, wherein Y$_1$ is hydroxy or Y$_2$ is hydroxy and X$_2$ is O, X$_3$ is O, or X$_4$ is O.

9. The compound of claim 1, wherein R$_2$ is pyridinyl, benzothiazolyl, or R$_2$ is -heteroarenediyl$_{(C\leq8)}$-R$_d$, or a substituted version thereof; wherein: R$_d$ is alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, or a substituted version of either of these groups.

10. The compound of claim 9, wherein R$_d$ is alkyl$_{(C\leq12)}$ or substituted alkyl$_{(C\leq12)}$.

11. The compound of claim 1, wherein the compound is further defined as:

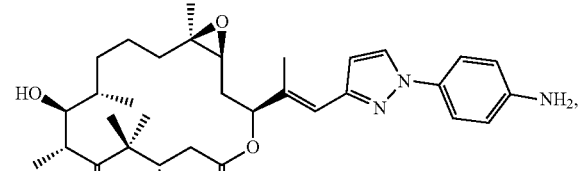

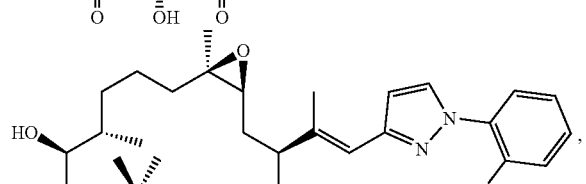

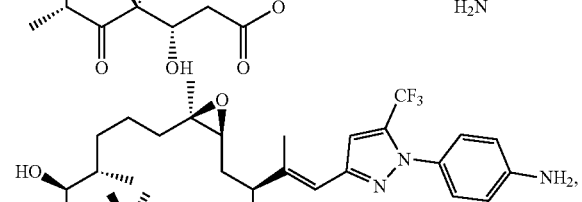

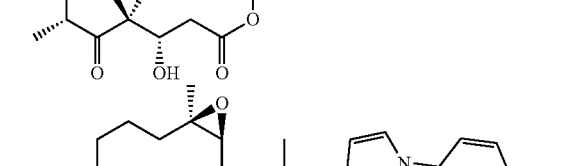

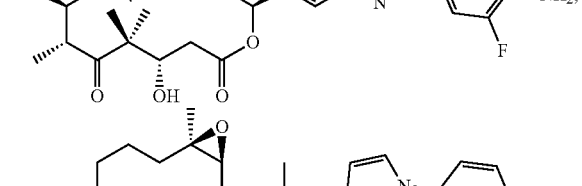

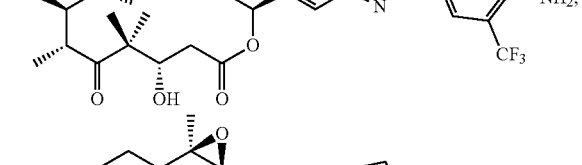

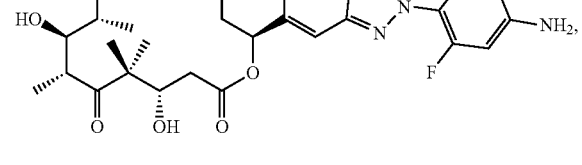

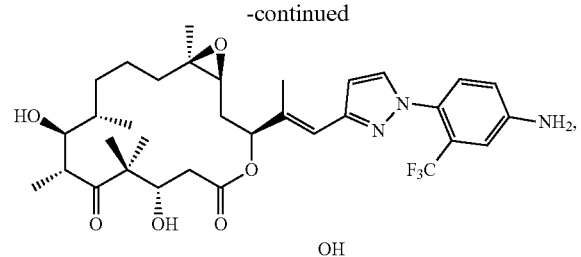
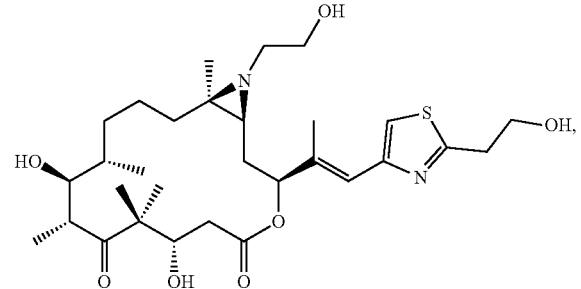
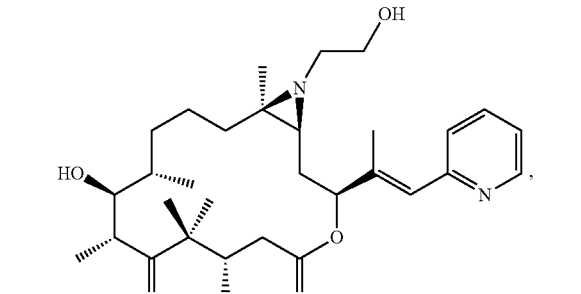
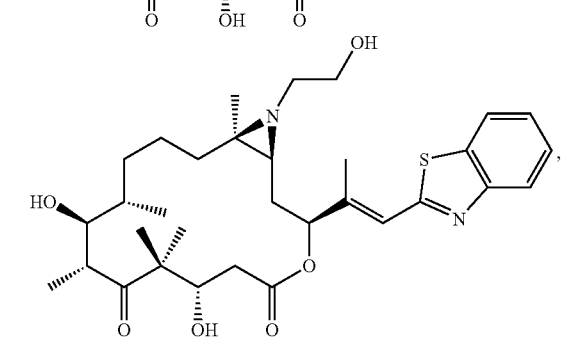
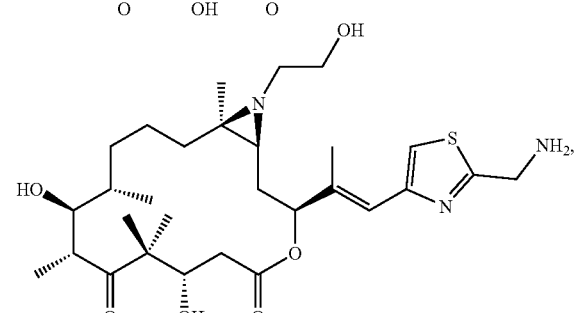
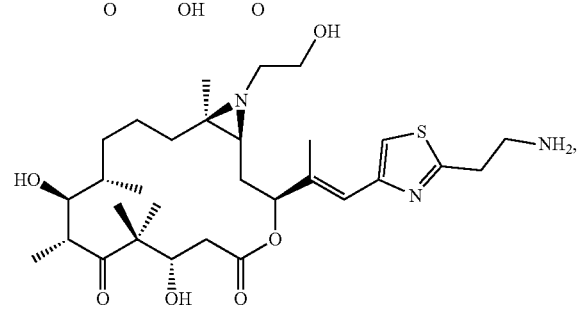
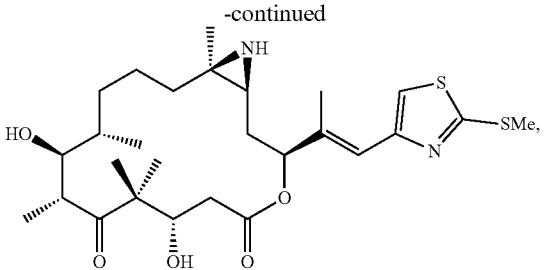
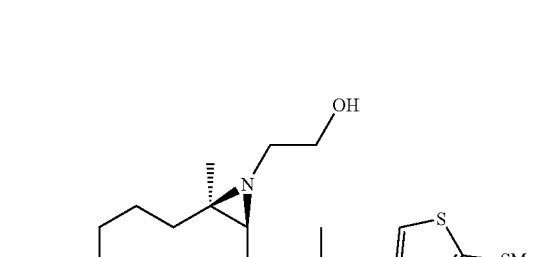
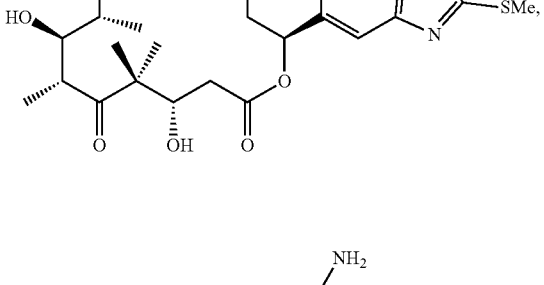
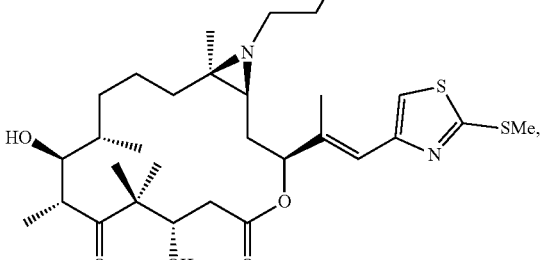
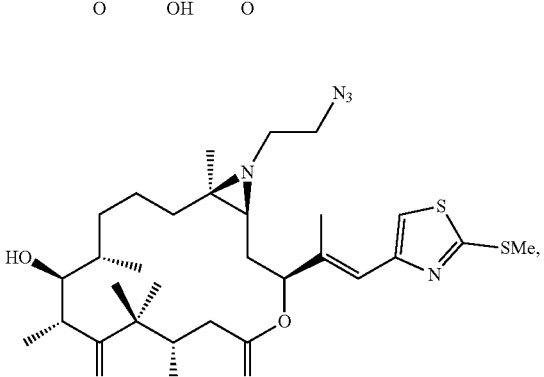
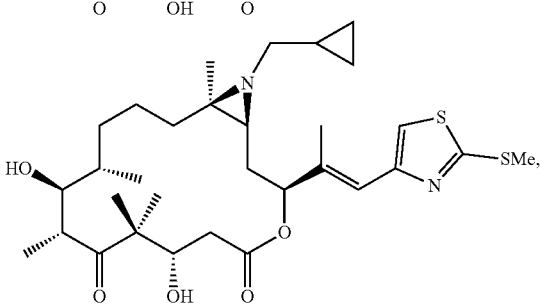

-continued

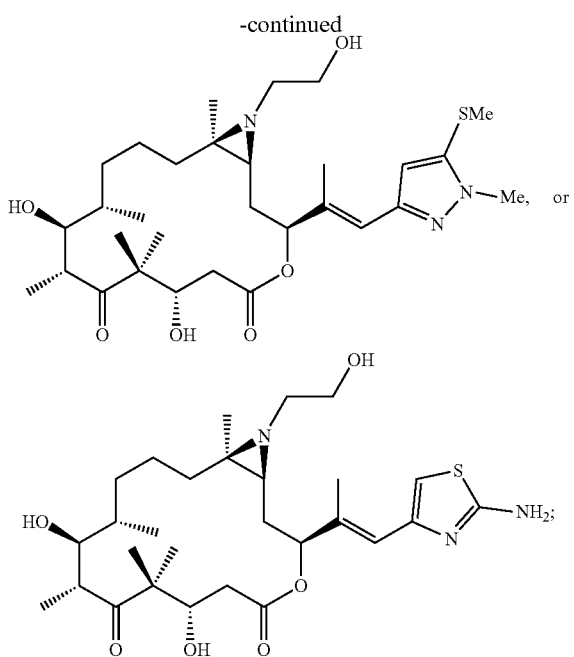

or a pharmaceutically acceptable salt thereof.

12. A pharmaceutical composition comprising:
(a) a compound of claim 1; and
(b) a pharmaceutically acceptable carrier.

13. A method of treating a disease or disorder, wherein the disease or disorder is a cancer from a carcinoma, sarcoma, lymphoma, leukemia, melanoma, mesothelioma, multiple myeloma, or seminoma or a cancer is of the bladder, blood, bone, brain, breast, central nervous system, cervix, colon, endometrium, esophagus, gall bladder, gastrointestinal tract, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid in a patient comprising administering to the patient in need thereof a therapeutically effective amount of a compound or composition of claim 1.

14. An antibody drug conjugate comprising:
(a) an antibody; and
(b) a compound of claim 1.

15. The antibody drug conjugate of claim 14, wherein the antibody and the compound are connected through a linker.

16. A method of preparing a compound of the formula:

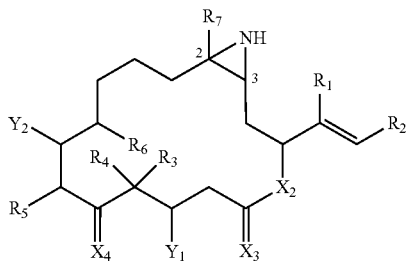

(XIII)

wherein:
$X_2$, $X_3$, and $X_4$ are each independently —O— or —$NR_b$—; wherein $R_b$ is hydrogen, a monovalent amine protecting group, or alkyl$_{(C \leq 8)}$, cycloalkyl$_{(C \leq 8)}$, -alkanediyl$_{(C \leq 6)}$-cycloalkyl$_{(C \leq 8)}$, aralkyl$_{(C \leq 8)}$, or a substituted version of either of these groups;

$Y_1$ and $Y_2$ are each independently amino, hydroxy, or alkoxy$_{(C \leq 8)}$, aralkoxy$_{(C \leq 8)}$, acyloxy$_{(C \leq 8)}$, alkylamino$_{(C \leq 8)}$, dialkylamino$_{(C \leq 8)}$, amido$_{(C \leq 8)}$, or a substituted version of any of these groups, or —$OR_c$, wherein:

$R_c$ is a hydroxy protecting group;

$R_1$, $R_3$, $R_4$, $R_5$, $R_6$ and $R_7$ are each independently hydrogen or alkyl$_{(C \leq 12)}$, cycloalkyl$_{(C \leq 12)}$, alkenyl$_{(C \leq 12)}$, alkynyl$_{(C \leq 12)}$, aryl$_{(C \leq 12)}$, or a substituted version of any of these groups; and $R_2$ is heteroaryl$_{(C \leq 12)}$, -heteroarenediyl$_{(C \leq 8)}$-$R_d$, or a substituted version of either of these groups; wherein:

$R_d$ is alkyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, or a substituted version of either of these groups;

comprising reacting a compound of the formula:

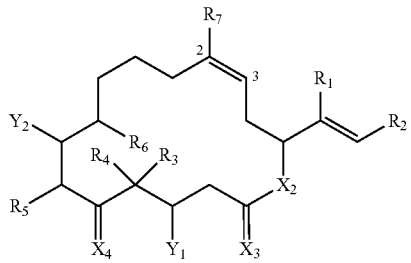

(XIV)

wherein:
$X_1$, $X_2$, $X_3$, $X_4$, $Y_1$, $Y_2$, $R_1$, $R_2$, $R_3$, $R_4$, $R_5$, $R_6$, and $R_7$ are as defined above; with O-(2,4-dinitrophenyl)hydroxylamine in the presence of a Rh catalyst.

17. A compound of the formula:

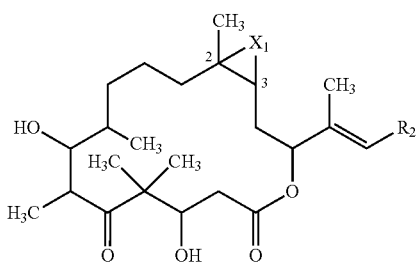

(VII)

wherein:
$X_1$ is —$NR_a$—; wherein
$R_a$ is hydrogen or alkyl$_{(C \leq 8)}$, cycloalkyl$_{(C \leq 8)}$, alkanediyl$_{(C \leq 6)}$-cycloalkyl$_{(C \leq 8)}$, or a substituted version of any one of these groups;

$R_2$ is heteroaryl$_{(C \leq 12)}$, -heteroarenediyl$_{(C \leq 8)}$-$R_d$, or a substituted version of either of these groups; wherein:

$R_d$ is alkyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, or a substituted version of either of these groups;

or a pharmaceutically acceptable salt thereof.

* * * * *